(12) United States Patent
Quinn et al.

(10) Patent No.: US 9,855,271 B2
(45) Date of Patent: Jan. 2, 2018

(54) QUINAZOLINONES AS BROMODOMAIN INHIBITORS

(71) Applicant: Zenith Epigenetics Ltd., Calgary (CA)

(72) Inventors: John Frederick Quinn, Albany, NY (US); Vladimir Khlebnikov, Edmonton (CA)

(73) Assignee: Zenith Epigenetics Ltd., Calgary, AB (CA)

( * ) Notice: Subject to any disclaimer, the term of this patent is extended or adjusted under 35 U.S.C. 154(b) by 0 days.

(21) Appl. No.: 14/908,898

(22) PCT Filed: Jul. 30, 2014

(86) PCT No.: PCT/IB2014/002510
§ 371 (c)(1),
(2) Date: Jan. 29, 2016

(87) PCT Pub. No.: WO2015/015318
PCT Pub. Date: Feb. 5, 2015

(65) Prior Publication Data
US 2016/0193218 A1 Jul. 7, 2016

Related U.S. Application Data

(60) Provisional application No. 61/860,403, filed on Jul. 31, 2013.

(51) Int. Cl.
| | | |
|---|---|---|
| *C07D 401/14* | (2006.01) | |
| *A61K 31/5377* | (2006.01) | |
| *C07D 401/04* | (2006.01) | |
| *C07D 401/12* | (2006.01) | |
| *C07D 405/12* | (2006.01) | |
| *C07D 239/91* | (2006.01) | |
| *C07D 471/04* | (2006.01) | |
| *A61K 31/517* | (2006.01) | |
| *A61K 45/06* | (2006.01) | |
| *C07D 403/12* | (2006.01) | |

(52) U.S. Cl.
CPC ........ *A61K 31/5377* (2013.01); *A61K 31/517* (2013.01); *A61K 45/06* (2013.01); *C07D 239/91* (2013.01); *C07D 401/04* (2013.01); *C07D 401/12* (2013.01); *C07D 401/14* (2013.01); *C07D 403/12* (2013.01); *C07D 405/12* (2013.01); *C07D 471/04* (2013.01)

(58) Field of Classification Search
CPC .................................................. C07D 401/14
See application file for complete search history.

(56) References Cited

U.S. PATENT DOCUMENTS

| | | |
|---|---|---|
| 5,565,469 A | 10/1996 | Mihm et al. |
| 6,380,235 B1 | 4/2002 | Zhang et al. |
| 8,053,440 B2 | 11/2011 | Hansen |
| 8,093,273 B2 | 1/2012 | Wong et al. |
| 8,691,747 B2 | 4/2014 | Kruidenier et al. |
| 8,697,725 B2 | 4/2014 | Demont et al. |
| 8,735,586 B2 | 5/2014 | Alonso et al. |
| 8,993,554 B2 | 3/2015 | Amans et al. |
| 9,029,395 B2 | 5/2015 | Amans et al. |
| 9,067,936 B2 | 6/2015 | Demont et al. |
| 9,073,878 B2 | 7/2015 | Fairfax et al. |
| 9,102,677 B2 | 8/2015 | Bailey et al. |
| 9,125,915 B2 | 9/2015 | Miyoshi et al. |
| 9,271,978 B2 | 3/2016 | Liu et al. |
| 9,278,940 B2 | 3/2016 | Fairfax et al. |
| 9,315,487 B2 | 4/2016 | Amans et al. |
| 9,321,765 B2 | 4/2016 | Gong |
| 9,388,161 B2 | 7/2016 | Bair et al. |
| 9,393,232 B2 | 7/2016 | Ren et al. |
| 9,422,281 B2 | 8/2016 | Bair et al. |
| 9,458,156 B2 | 10/2016 | Norris et al. |
| 9,598,367 B2 | 3/2017 | Liu et al. |
| 9,636,328 B2 | 5/2017 | Liu et al. |
| 9,662,311 B2 | 5/2017 | Liu et al. |

(Continued)

FOREIGN PATENT DOCUMENTS

| | | |
|---|---|---|
| CA | 2113361 A1 | 3/1993 |
| CA | 2195107 A1 | 2/1996 |

(Continued)

OTHER PUBLICATIONS

McMahon et al. (2000).*
Pinedo et al. (2000).*
Vippagunta et a. (2001).*
Aiello, R.J., et al., "Monocyte chemoattractant protein-1 accelerates atherosclerosis in apolipoprotein E-deficient mice" *Arterioscler Thromb. Vasc. Biol.* 19(6): 1518-25 (1999).
Alexandraki, K. et al., "Inflammatory process in type 2 diabetes: The role of cytokines" *Ann N Y Acad Sci*, 2006. 1084:89-117.

(Continued)

*Primary Examiner* — Paul V Ward
(74) *Attorney, Agent, or Firm* — Finnegan, Henderson, Farabow, Garrett & Dunner LLP

(57) ABSTRACT

The present disclosure relates to compounds, which are useful for inhibition of BET protein function by binding to bromodomains, and their use in therapy.

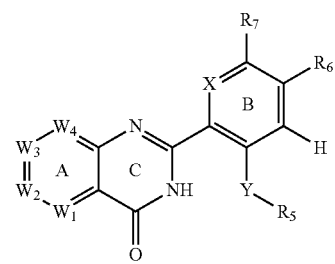

(I)

19 Claims, No Drawings

(56) References Cited

U.S. PATENT DOCUMENTS

| | | |
|---|---|---|
| 9,663,520 B2 | 5/2017 | Quinn et al. |
| 2002/0019395 A1 | 2/2002 | Zhu et al. |
| 2003/0036545 A1 | 2/2003 | Castelhano et al. |
| 2004/0044203 A1 | 3/2004 | Wittman et al. |
| 2004/0166137 A1 | 8/2004 | Lackey |
| 2005/0014812 A1 | 1/2005 | Hayashida et al. |
| 2005/0176775 A1 | 8/2005 | Devadas et al. |
| 2005/0176858 A1 | 8/2005 | Nohara et al. |
| 2007/0134161 A1 | 6/2007 | Brown |
| 2007/0213323 A1 | 9/2007 | Imogai et al. |
| 2007/0275984 A1 | 11/2007 | Imogai et al. |
| 2008/0015196 A1 | 1/2008 | Doller et al. |
| 2008/0188467 A1 | 8/2008 | Wong et al. |
| 2009/0312353 A1 | 12/2009 | Messersmith et al. |
| 2010/0063104 A1 | 3/2010 | Nakai et al. |
| 2010/0234354 A1 | 9/2010 | Dorsch et al. |
| 2010/0267714 A1 | 10/2010 | Jorgensen et al. |
| 2011/0070297 A1 | 3/2011 | Cao et al. |
| 2011/0136819 A1 | 6/2011 | Dorsch et al. |
| 2011/0136834 A1 | 6/2011 | Critchley et al. |
| 2011/0257181 A1 | 10/2011 | Stieber et al. |
| 2012/0004261 A1 | 1/2012 | Jorgensen et al. |
| 2012/0028912 A1 | 2/2012 | Zhou et al. |
| 2012/0157428 A1 | 6/2012 | Albrecht et al. |
| 2012/0208798 A1 | 8/2012 | Demont et al. |
| 2012/0208800 A1 | 8/2012 | Chung et al. |
| 2012/0208814 A1 | 8/2012 | Demont et al. |
| 2012/0220573 A1 | 8/2012 | Gosmini et al. |
| 2013/0085133 A1 | 4/2013 | Severson et al. |
| 2013/0143880 A1 | 6/2013 | Dudkin et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0031336 A1 | 1/2014 | Amans et al. |
| 2014/0045834 A1 | 2/2014 | Demont et al. |
| 2014/0140956 A1 | 5/2014 | Fairfax et al. |
| 2014/0142102 A1 | 5/2014 | Fairfax et al. |
| 2014/0162971 A1 | 6/2014 | Wang et al. |
| 2014/0171462 A1 | 6/2014 | Demont et al. |
| 2014/0179648 A1 | 6/2014 | Liu et al. |
| 2014/0256700 A1 | 9/2014 | Poss et al. |
| 2014/0256705 A1 | 9/2014 | Hasvold et al. |
| 2014/0256706 A1 | 9/2014 | Wang et al. |
| 2014/0256710 A1 | 9/2014 | Liu et al. |
| 2014/0275030 A1 | 9/2014 | Combs et al. |
| 2014/0275079 A1 | 9/2014 | Hasvold et al. |
| 2014/0296246 A1 | 10/2014 | Aktoudianakis et al. |
| 2014/0303121 A1 | 10/2014 | Zhang et al. |
| 2014/0336190 A1 | 11/2014 | Aktoudianakis et al. |
| 2014/0349990 A1 | 11/2014 | Blank et al. |
| 2015/0011540 A1 | 1/2015 | Combs et al. |
| 2015/0246919 A1 | 9/2015 | Engelhardt et al. |
| 2015/0344442 A1 | 12/2015 | Fairfax et al. |
| 2016/0130228 A1 | 5/2016 | Liu et al. |
| 2016/0137613 A1 | 5/2016 | Hansen |
| 2016/0145248 A1 | 5/2016 | Liu et al. |
| 2016/0159801 A1 | 6/2016 | Quinn et al. |
| 2016/0184273 A1 | 6/2016 | Liu et al. |
| 2017/0143731 A1 | 5/2017 | Liu et al. |
| 2017/0182029 A1 | 6/2017 | Liu et al. |

FOREIGN PATENT DOCUMENTS

| | | |
|---|---|---|
| CA | 2440211 A1 | 9/2002 |
| CA | 2818187 A1 | 6/2012 |
| CA | 2911408 A1 | 11/2014 |
| CA | 2915561 A1 | 1/2015 |
| CA | 2915622 A1 | 1/2015 |
| CA | 2915838 A1 | 1/2015 |
| CN | 1113235 A | 12/1995 |
| CN | 1636977 A | 7/2005 |
| CN | 1934092 A | 3/2007 |
| CN | 101061098 A | 10/2007 |
| CN | 101636386 A | 1/2010 |
| CN | 102731409 A | 10/2012 |
| EP | 0 195 947 A2 | 10/1986 |
| EP | 0 385 850 A2 | 9/1990 |
| EP | 0 556 789 A2 | 8/1993 |
| EP | 0 566 020 A1 | 10/1993 |
| EP | 1 944 311 A1 | 7/2008 |
| EP | 2 196 465 A1 | 6/2010 |
| EP | 2 390 250 A2 | 11/2011 |
| EP | 2 792 355 A1 | 10/2014 |
| WO | WO 96/33194 A1 | 10/1996 |
| WO | WO 00/34248 A1 | 6/2000 |
| WO | WO 00/66564 A1 | 11/2000 |
| WO | WO 01/55132 A1 | 8/2001 |
| WO | WO 02/067675 A2 | 9/2002 |
| WO | WO 02/076976 A2 | 10/2002 |
| WO | WO 02/078708 A1 | 10/2002 |
| WO | WO 2004/024897 A2 | 3/2004 |
| WO | WO 2004/078733 A1 | 9/2004 |
| WO | WO 2004/098494 A2 | 11/2004 |
| WO | WO2005/013950 A2 | 2/2005 |
| WO | WO 2005/075432 A1 | 8/2005 |
| WO | WO 2005/080380 A1 | 9/2005 |
| WO | WO 2005/090317 A1 | 9/2005 |
| WO | WO 2005/117876 A1 | 12/2005 |
| WO | WO 2006/030032 A1 | 3/2006 |
| WO | WO 2006/038734 A1 | 4/2006 |
| WO | WO 2006/119400 A2 | 11/2006 |
| WO | WO 2007/016525 A2 | 2/2007 |
| WO | WO 2007/063012 A1 | 6/2007 |
| WO | WO 2007/093901 A1 | 8/2007 |
| WO | WO 2008/054599 A2 | 5/2008 |
| WO | WO 2008/072784 A1 | 6/2008 |
| WO | WO 2009/006959 A1 | 1/2009 |
| WO | WO 2009/024221 A1 | 2/2009 |
| WO | WO 2009/043883 A1 | 4/2009 |
| WO | WO 2009/054790 A1 | 4/2009 |
| WO | WO 2009/099801 A1 | 8/2009 |
| WO | WO 2009/158258 A1 | 12/2009 |
| WO | WO 2010/068483 A2 | 6/2010 |
| WO | WO 2010/072296 A1 | 7/2010 |
| WO | WO 2010/077275 A1 | 7/2010 |
| WO | WO 2010/097368 A1 | 9/2010 |
| WO | WO 2010/104851 A1 | 9/2010 |
| WO | WO 2010/106436 A2 | 9/2010 |
| WO | WO 2010/123975 A1 | 10/2010 |
| WO | WO 2010/127976 A1 | 11/2010 |
| WO | WO 2011/054843 A1 | 5/2011 |
| WO | WO 2011/054846 A1 | 5/2011 |
| WO | WO 2011/143669 A2 | 11/2011 |
| WO | WO 2011/156626 A1 | 12/2011 |
| WO | WO 2011/159926 A1 | 12/2011 |
| WO | WO 2012/003576 A1 | 1/2012 |
| WO | WO 2012/009258 A2 | 1/2012 |
| WO | WO 2012/021382 A1 | 2/2012 |
| WO | WO 2012/040499 A2 | 3/2012 |
| WO | WO 2012/075456 A1 | 6/2012 |
| WO | WO 2012/143413 A1 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/064900 A1 | 5/2013 |
| WO | WO 2013/082429 A1 | 6/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/031928 A2 | 2/2014 |
| WO | WO 2014/043246 A1 | 3/2014 |
| WO | WO 2014/078257 A1 | 5/2014 |
| WO | WO 2014/095775 A1 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |

(56) References Cited

FOREIGN PATENT DOCUMENTS

| | | |
|---|---|---|
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/202578 A1 | 12/2014 |
| WO | WO 2015/002754 A2 | 1/2015 |
| WO | WO 2015/004533 A2 | 1/2015 |
| WO | WO 2015/004534 A2 | 1/2015 |
| WO | WO 2015/011084 A1 | 1/2015 |
| WO | WO 2015/013635 A2 | 1/2015 |
| WO | WO 2015/015318 A2 | 2/2015 |
| WO | WO 2015/086507 A1 | 6/2015 |
| WO | WO 2016/087936 A1 | 6/2016 |
| WO | WO 2016/087942 A1 | 6/2016 |
| WO | WO 2016/092375 A1 | 6/2016 |
| WO | WO 2016/097863 A1 | 6/2016 |
| WO | WO 2016/097870 A1 | 6/2016 |

OTHER PUBLICATIONS

Ambinter, "2(1H)-Pyridone, 1-[(4-chlorophenyl)methyl]-5-(1,3,4-oxadiazol-2-yl)-" Chemical Abstracts Record No. 1209999-95-0 [online], entered into STN Registry File Mar. 15, 2010.

Antonelli, A. et al., "Serum levels of proinflammatory cytokines interleukin-1 beta, interleukin-6, and tumor necrosis factor alpha in mixed cryoglobulinemia" *Arthritis Rheum*, 2009. 60(12):3841-7.

Aricha, R. et al., "Blocking of IL-6 suppresses experimental autoimmune myasthenia gravis" *J Autoimmun*, 2011. 36(2):135-41.

Arif, M. et al., "Protein lysine acetylation in cellular function and its role in cancer manifestation" *Biochim Biophys Acta*, 2010. 1799(10-12):702-16.

Ash, Z. and P. Emery, "The role of tocilizumab in the management of rheumatoid arthritis" *Expert Opin Biol Ther*, 2012. 12(9): 1277-89.

Bandukwala, H.S. et al., "Selective inhibition of CD4+ T-cell cytokine production and autoimmunity by BET protein and c-Myc inhibitors" *Proc Natl Acad Sci USA*, 2012. 109(36):14532-7.

Bandyopadhyay, K. et al., "Spermidinyl-CoA-based HAT inhibitors block DNA repair and provide cancer-specific chemo- and radiosensitization" *Cell Cycle*, 2009. 8(17):2779-88. (Author's manuscript, 19 pages).

Banerjee, C. et al., "BET bromodomain inhibition as a novel strategy for reactivation of HIV-1" *J Leukoc Biol*, 2012. 92(6):1147-54.

Baron, P. et al., "Production of IL-6 by human myoblasts stimulated with Abeta: relevance in the pathogenesis of IBM" *Neurology*, 2001. 57(9):1561-5.

Bartholomeeusen, K. et al., "BET bromodomain inhibition activates transcription via a transient release of P-TEFb from 7SK snRNP" JBC in Press, 2012. M112.410746, 16 pages. Final publication in: *J Biol Chem*, 287:36609-16.

Bassiouny, D.A. and O. Shaker, "Role of interleukin-17 in the pathogenesis of vitiligo" *Clin Exp Dermatol*, 2011. 36(3):292-7.

Bayraktaroğlu, T. et al., "Serum levels of tumor necrosis factor-alpha, interleukin-6 and interleukin-8 are not increased in dyspeptic patients with Helicobacter pylori-associated gastritis" *Mediators Inflamm*, 2004. 13(1):25-8.

Belanger, D.B. et al., "Discovery of imidazo[1,2-a]pyrazine-based Aurora kinase inhibitors" *Bioorg. Med. Chem. Lett.*, 20:5170-5174 (2010).

Belkina, A.C. and G.V. Denis, "BET domain co-regulators in obesity, inflammation and cancer" *Nat Rev Cancer*, 2012. 12(7):465-77.

Bellan, C. et al., "CDK9/CYCLIN T1 expression during normal lymphoid differentiation and malignant transformation" *J. Pathol.*, 2004. 203(4):946-52.

Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.

Berkovits, B.D. et al., "The testis-specific double bromodomain-containing protein BRDT forms a complex with multiple spliceosome components and is required for mRNA splicing and 3'-UTR truncation in round spermatids" *Nucleic Acids Res*, 2012. 40(15):7162-75.

Besnard, A.G. et al., "Inflammasome-IL-1-Th17 response in allergic lung inflammation" *J Mol Cell Biol*, 2012. 4(1):3-10.

Boring, L. et al., "Decreased lesion formation in CCR2-/- mice reveals a role for chemokines in the initiation of atherosclerosis" *Nature*, 1998. 394(6696):894-7.

Bradley, D.T. And S.E. Kountakis, "Role of interleukins and transforming growth factor-beta in chronic rhinosinusitis and nasal polyposis" *Laryngoscope*, 2005. 115(4):684-6.

Brennan, P., "Isoxazole Inhibitors of Bromodomains" presented at the *RSC Advances in Synthesis and Medicinal Chemistry Conference*, BioPark, Welwyn Garden City, UK, May 1, 2012 (46 pages).

Brodmerkel, C.M. et al., "Discovery and pharmacological characterization of a novel rodent-active CCR2 antagonist, INCB3344" *J Immunol*, 2005. 175(8):5370-8.

Brühl, H. et al., "Dual role of CCR2 during initiation and progression of collagen-induced arthritis: evidence for regulatory activity of CCR2+ T cells" *J Immunol*, 2004. 172(2):890-8.

Cannon, J.G., "Analog Design" in *Burger's Medicinal Chemistry and Drug Discovery. 5th Ed., vol. 1: Principles and Practice*. Manfred E. Wolff (ed.), John Wiley & Sons, Inc., New York, NY, 1995; Chapter 19, pp. 783-802.

Chaidos, A. et al., "Inhibition of bromodomain and extraterminal proteins (BET) as a potential therapeutic approach in haematological malignancies: emerging preclinical and clinical evidence" *Ther Adv Hematol*, 6(3):128-141 (2015).

ChemDiv, Inc. in Chemical Abstracts Record No. 1340694-11-8, Entered into the Registry File Nov. 4, 2011.

Chen, L. et al., "IL-17RA aptamer-mediated repression of IL-6 inhibits synovium inflammation in a murine model of osteoarthritis" *Osteoarthritis Cartilage*, 2011. 19(6):711-8.

Chevrel, G. et al., "Interleukin-17 increases the effects of IL-1 beta on muscle cells: arguments for the role of T cells in the pathogenesis of myositis" *J Neuroimmunol*, 2003. 137(1-2):125-33.

Chung, C.W. et al., "Bromodomains: a new target class for small molecule drug discovery" *Drug Discovery Today: Therapeutic Strategies* 9(2-3):e111-e120 (2012).

Chung, C.W. et al., "Discovery and characterization of small molecule inhibitors of the BET family bromodomains" *J Med Chem*, 2011. 54(11):3827-38.

Chung, C.W., "Small Molecule Bromodomain Inhibitors: Extending the Druggable Genome" *Progr. Med. Chem.*, 51:1-55 (2012).

Cid, J.M. et al., "Discovery of 1,5-Disubstituted Pyridones: A New Class of Positive Allosteric Modulators of the Metabotropic Glutamate 2 Receptor" *ACS Chem. Neurosci.* 1:788-795 (2010).

Clinical trials.gov, "A Study to Investigate the Safety, Pharmacokinetics, Pharmacodynamics, and Clinical Activity of GSK525762 in Subjects With NUT Midline Carcinoma (NMC) and Other Cancers" GlaxoSmithKline, Identifier NCT01587703, verified Dec. 2016 [online]. Retrieved from: https://clinicaltrials.gov/ct2/show/NCT01587703, on Dec. 28, 2016 (6 pages).

Costello, J.F. et al., "Cyclin-dependent kinase 6 (CDK6) amplification in human gliomas identified using two-dimensional separation of genomic DNA" *Cancer Res*, 1997. 57(7):1250-4.

D'Auria, L. et al., "Cytokines and bullous pemphigoid" *Eur Cytokine Netw*, 1999. 10(2):123-34.

Dawson, J. et al., "Targeting monocyte chemoattractant protein-1 signalling in disease" *Expert Opin Ther Targets*, 2003. 7(1):35-48.

Dawson, M.A. et al., "Inhibition of BET Recruitment to Chromatin as an Effective Treatment for MLL-fusion Leukaemia" *Nature*, 2011, 478:529-533.

De Falco, G. et al., "Cdk9 regulates neural differentiation and its expression correlates with the differentiation grade of neuroblastoma and PNET tumors" *Cancer Biol Ther*, 2005. 4(3):277-81.

(56) References Cited

OTHER PUBLICATIONS

De Lemos, J.A. et al., "Association between plasma levels of monocyte chemoattractant protein-1 and long-term clinical outcomes in patients with acute coronary syndromes" *Circulation*, 2003. 107(5):690-5.
De Paiva, C.S. et al., "IL-17 disrupts corneal barrier following desiccating stress" *Mucosal Immunol*, 2009. 2(3):243-53.
Degoma, E.M. and D.J. Rader, "Novel HDL-directed pharmacotherapeutic strategies" *Nat Rev Cardiol*, 2011. 8(5):266-77.
Delmore, J.E. et al., "BET bromodomain inhibition as a therapeutic strategy to target c-Myc" *Cell*, 2011. 146(6):904-17.
Deng, J. et al., "Th17 and Th1 T-cell responses in giant cell arteritis" *Circulation*, 2010. 121(7):906-15.
Denis, G.V. et al., "An emerging role for bromodomain-containing proteins in chromatin regulation and transcriptional control of adipogenesis" *FEBS Lett*, 2010. 584(15):3260-8. (Author manuscript, 21 pages).
Denis, G.V., "Bromodomain coactivators in cancer, obesity, type 2 diabetes, and inflammation" *Discov Med*, 2010. 10(55):489-99.
Deo, R. et al., "Association among plasma levels of monocyte chemoattractant protein-1, traditional cardiovascular risk factors, and subclinical atherosclerosis" *J Am Coll Cardiol*, 2004. 44(9): p. 1812-8.
Dias, P.M. and G. Banerjee, "The Role of Th17/IL-17 on Eosinophilic Inflammation" *J Autoimmun*, 2012. Article in Press: http://dx.doi.org/10.1016/j.jaut.2012.07.004, 12 pages.
Elliott, D.A. et al., "Apolipoproteins in the brain: implications for neurological and psychiatric disorders" *Clin Lipidol*, 2010. 51(4):555-573. (Author manuscript, 28 pages).
El-Osta, H.E. and R. Kurzrock, "Castleman's disease: from basic mechanisms to molecular therapeutics" *Oncologist*, 2011. 16(4):497-511.
European Patent Application No. 13864406.7, by Zenith Epigenetics Corp.: Extended European Search Report, including Search Opinion, dated Mar. 30, 2016 (6 pages).
European Patent Application No. 14822511.3, by Zenith Epigenetics Corp.: Extended European Search Report, including Search Opinion, dated Jan. 2, 2017 (7 pages).
European Patent Application No. 14832298.5, by Zenith Epigenetics Corp.: Extended European Search Report, including Search Opinion, dated Nov. 11, 2016 (6 pages).
European Patent No. EP 0 385 850 A2: Machine English translation; retrieved from ProQuest Dialog, on Aug. 15, 2016; 68 pages.
European Patent No. EP 0 556 789 A2: Machine English translation; retrieved from ProQuest Dialog, on Aug. 15, 2016; 59 pages.
Fife, B.T. et al., "CC chemokine receptor 2 is critical for induction of experimental autoimmune encephalomyelitis" *J Exp Med*, 2000. 192(6):899-905.
Figueroa-Vega, N. et al., "Increased circulating pro-inflammatory cytokines and Th17 lymphocytes in Hashimoto's thyroiditis" *J Clin Endocrinol Metab*, 2010. 95(2):953-62.
Filippakopoulos, P. and S. Knapp, "Targeting bromodomains: epigenetic readers of lysine acetylation" *Nature Reviews*, 13:337-356 (2014).
Filippakopoulos, P. et al., "Selective Inhibition of BET Bromodomains", *Nature*, 2010, 468:1067-1073.
Fish, P.V. et al., "Identification of a chemical probe for bromo and extra C-terminal bromodomain inhibition through optimization of a fragment-derived hit" *J. Med. Chem*. 55:9831-9837 (2012).
Freireich, E.J. et al., "Quantitative comparison of toxicity of anticancer agents in mouse, rat, hamster, dog, monkey, and man" *Cancer Chemother Rep*, 50(4):219-244 (1966).
French, C.A., "NUT midline carcinoma" *Cancer Genet Cytogenet*, 2010. 203(1):16-20. (Author manuscript, 9 pages).
Fujioka, A. et al., "The analysis of mRNA expression of cytokines from skin lesions in Churg-Strauss syndrome" *J Dermatol*, 1998. 25(3):171-7.
Fujishima, S. et al., "Involvement of IL-17F via the induction of IL-6 in psoriasis" *Arch Dermatol Res*, 2010. 302(7):499-505.
Gagnon, D. et al., "Proteasomal degradation of the papillomavirus E2 protein is inhibited by overexpression of bromodomain-containing protein 4" *J Virol*, 2009. 83(9):4127-39.
Gaucher, J. et al., "Bromodomain-dependent stage-specific male genome programming by Brdt" *EMBO J*, 2012. 31(19):3809-20.
Gharbi et al., "Exploring the specificity of the PI3k family inhibitor LY294002" *Biochem. J*. 404:15-21 (2007).
Gloddek, B. et al., "Pharmacological influence on inner ear endothelial cells in relation to the pathogenesis of sensorineural hearing loss" *Adv Otorhinolaryngol*, 2002. 59:75-83.
Gong, J-H. et al., "An antagonist of monocyte chemoattractant protein 1 (MCP-1) inhibits arthritis in the MRL-Ipr mouse model" *J Exp Med*, 1997. 186(1):131-7.
Gong, J-H. et al., "Post-onset inhibition of murine arthritis using combined chemokine antagonist therapy" *Rheumatology*, 2004. 43(1):39-42.
González-Serrano, M.E. et al., "Increased Pro-inflammatory Cytokine Production After Lipopolysaccharide Stimulation in Patients with X-linked Agammaglobulinemia" *J Clin Immunol*, 2012. 32(5):967-74.
Gosling, J. et al., "MCP-1 deficiency reduces susceptibility to atherosclerosis in mice that overexpress human apolipoprotein B" *J Clin Invest*, 1999. 103(6):773-8.
Graber, J.J. et al., "Interleukin-17 in transverse myelitis and multiple sclerosis" *J Neuroimmunol*, 2008. 196(1-2):124-32.
Greenwald, R.J. et al., "E mµ-BRD2 transgenic mice develop B-cell lymphoma and leukemia" *Blood*, 2004. 103(4):1475-84.
Grunwald, C. et al., "Expression of multiple epigenetically regulated cancer/germline genes in nonsmall cell lung cancer" *Int J Cancer*, 2006. 118(10):2522-8.
Gu, L. et al., "Absence of monocyte chemoattractant protein-1 reduces atherosclerosis in low density lipoprotein receptor-deficient mice" *Mol Cell*, 1998. 2(2):275-81.
Gu, Y. et al., "Interleukin (IL)-17 promotes macrophages to produce IL-8, IL-6 and tumour necrosis factor-alpha in aplastic anaemia" *Br J Haematol*, 2008. 142(1):109-14.
Harada, K. et al., "Periductal interleukin-17 production in association with biliary innate immunity contributes to the pathogenesis of cholangiopathy in primary biliary cirrhosis" *Clin Exp Immunol*, 2009. 157(2):261-70.
Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest Ophthalmol Vis Sci*, 2011. 52(6):3264-71.
Hay et al., "The design and synthesis of 5- and 6-isoxazolylbenzimidazoles as selective inhibitors of the BET bromodomains" *Med. Chem. Commun*. 4:140-144 (2013).
Hay, D.A. et al., "Discovery and Optimization of Small-Molecule Ligands for the CBP/p300 Bromodomains" *J. Am. Chem. Soc*. 136:9308-9319 (2014).
Hewings et al., "3,5-Dimethylisoxazoles Act as Acetyl-lysine-mimetic Bromodomain Ligands" *J. Med. Chem*. 54:6761-6770 (2011).
Hewings et al., "3,5-Dimethylisoxazoles inhibit the bromodomain-histone protein-protein interaction" *243rd National Spring Meeting of the American-Chemical-Society (Symposium on Ionic Liquids—Science and Applications)*, San Diego, CA. General Poster Session, Mar. 28, 2012, Poster 326 Abstract [online]. Retrieved from: http://acselb-529643017.us-west-2.elb.amazonaws.com/chem/243nm/program/view.php?pub_num=326&par=MEDI.
Hewings et al., "Optimization of 3,5-Dimethylisoxazole Derivatives as Potent Bromodomain Ligands" *J. Med. Chem*. 56:3217-3227 (2013).
Hewings et al., "Progress in the development and application of small molecule inhibitors of bromodomain-acetyl-lysine interactions" *J. Med. Chem*. 55:9393-9413 (2012).
Hintermann, S. et al., "Identification of a series of highly potent activators of the Nurr 1 signaling pathway" *Bioorg Med Chem Lett*, 17:193-196 (2007).
Hohki, S. et al., "Blockade of interleukin-6 signaling suppresses experimental autoimmune uveoretinitis by the inhibition of inflammatory Th17 responses" *Exp Eye Res*, 2010. 91(2):162-70.

(56) References Cited

OTHER PUBLICATIONS

Hölttä, V. et al., "IL-23/IL-17 immunity as a hallmark of Crohn's disease" *Inflamm Bowel Dis*, 2008. 14(9):1175-84.
Hoshino, I. and H. Matsubara, "Recent advances in histone deacetylase targeted cancer therapy" *Surg Today*, 2010. 40(9):809-15.
Huang, D. et al., "Absence of monocyte chemoattractant protein 1 in mice leads to decreased local macrophage recruitment and antigen-specific T helper cell type 1 immune response in experimental autoimmune encephalomyelitis" *J Exp Med*, 2001. 193(6):713-26.
Içöz, S. et al., "Enhanced IL-6 production in aquaporin-4 antibody positive neuromyelitis optica patients" *Int J Neurosci*, 2010. 120(1):71-5.
International Search Report and Written Opinion issued in International Application No. PCT/IB2013/000968: Date of Mailing: Sep. 13, 2013.
International Search Report and Written Opinion issued in International Application No. PCT/IB2013/001026; Date of Mailing: Sep. 30, 2013.
International Search Report and Written Opinion issued in International Application No. PCT/IB2013/001232; Date of Mailing: Sep. 6, 2013.
International Search Report and Written Opinion issued in International Application No. PCT/IB2013/003122; Date of Mailing: Jul. 9, 2014.
International Search Report and Written Opinion issued in International Application No. PCT/IB2013/003126: Date of Mailing: Jun. 26, 2014.
International Search Report and Written Opinion issued in International Application No. PCT/IB2013/003202; Date of Mailing: Jul. 17, 2014.
International Search Report and Written Opinion issued in International Application No. PCT/IB2014/002238: Date of Mailing: Apr. 23, 2015.
International Search Report and Written Opinion issued in International Application No. PCT/IB2014/002240; Date of Mailing: Mar. 10, 2015.
International Search Report and Written Opinion issued in International Application No. PCT/IB2014/002510; Date of Mailing: Apr. 15, 2015.
International Search Report and Written Opinion issued in International Application No. PCT/IB2015/002429; Date of Mailing: Apr. 13, 2016.
International Search Report and Written Opinion issued in International Application No. PCT/IB2015/002462; Date of Mailing: Apr. 13, 2016.
International Search Report and Written Opinion issued in International Application No. PCT/IB2015/002479; Date of Mailing: Apr. 21, 2016.
International Search Report and Written Opinion issued in International Application No. PCT/IB2015/002490; Date of Mailing: Apr. 1, 2016.
International Search Report and Written Opinion issued in International Application No. PCT/IB2015/002522: Date of Mailing: Apr. 13, 2016.
International Search Report and Written Opinion issued in International Application No. PCT/US2014/043423; Date of Mailing: Jan. 12, 2005.
Ishizu, T. et al., "CSF cytokine and chemokine profiles in acute disseminated encephalomyelitis" *J Neuroimmunol*, 2006. 175(1-2):52-58.
Ito, Y. et al., "Pathogenic significance of interleukin-6 in a patient with antiglomerular basement membrane antibody-induced glomerulonephritis with multinucleated giant cells" *Am J Kidney Dis*, 1995. 26(1):72-9.
Jadidi-Niaragh, F. and A. Mirshafiey, "Th17 cell, the new player of neuroinflammatory process in multiple sclerosis" *Scand J Immunol*, 2011. 74(1):1-13.

Jahagirdar, R. et al., "An Orally Bioavailable Small Molecule RVX-297 Significantly Decreases Disease in a Mouse Model of Multiple Sclerosis" (Poster Presentation). World Congress of Inflammation, Paris, France, 2011, 1 page.
Jen, H-Y. et al., "Increased serum interleukin-17 and peripheral Th17 cells in children with acute Henoch-Schonlein purpura" *Pediatr Allergy Immunol*, 2011. 22(8):862-8.
Jia, S., et al., "The T helper type 17/regulatory T cell imbalance in patients with acute Kawasaki disease" *Clin Exp Immunol*, 2010. 162(1):131-7.
Johnson, R.B. et al., "Interleukin-11 and IL-17 and the pathogenesis of periodontal disease" *J Periodontol*, 2004. 75(1):37-43.
Kahawita, I.P. and D.N. Lockwood, "Towards understanding the pathology of erythema nodosum leprosum" *Trans R Soc Trop Med Hyg*, 2008. 102(4):329-37.
Kallen, K.J. et al., "New developments in IL-6 dependent biology and therapy: where do we stand and what are the options?" *Expert Opin Investig Drugs*, 1999. 8(9):1327-49.
Kaplanski, G. et al., "Jarisch-Herxheimer reaction complicating the treatment of chronic Q fever endocarditis: elevated TNFalpha and IL-6 serum levels" *J Infect*, 1998. 37(1):83-4.
Kappel, L.W. et al., "IL-17 contributes to CD4-mediated graft-versus-host disease" *Blood*, 2009. 113(4):945-52.
Katsifis, G.E. et al., "Systemic and local interleukin-17 and linked cytokines associated with Sjogren's syndrome immunopathogenesis" *Am J Pathol*, 2009. 175(3):1167-77.
Kawai, M. et al., "Sustained response to tocilizumab, anti-interleukin-6 receptor antibody, in two patients with refractory relapsing polychondritis" *Rheumatology*, 2009. 48(3):318-9.
Kawakami, T. et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis" *Am J Gastroenterol*, 2009. 104(9):2363-4.
Kawakami, T. et al., "Serum levels of interleukin-6 in patients with cutaneous polyarteritis nodosa" *Acta Derm Venereol*, 2012. 92(3):322-3.
Kelly, P.N. and A. Strasser, "The role of Bcl-2 and its pro-survival relatives in tumourigenesis and cancer therapy" *Cell Death Differ*, 2011. 18(9):1414-24.
Kim, S.E. et al., "Increased serum interleukin-17 in Graves' ophthalmopathy" *Graefes Arch Clin Exp Ophthalmol*, 2012. 250(10):1521-6.
Kimura, A. and T. Kishimoto, "IL-6: regulator of Treg/Th17 balance" *Eur J Immunol*, 2010. 40(7):1830-5.
Koch, A.E. et al., "Enhanced production of monocyte chemoattractant protein-1 in rheumatoid arthritis" *J Clin Invest*, 1992. 90(3):772-9.
Kyburz, D. and M. Corr, "Th17 cells generated in the absence of TGF-beta induce experimental allergic encephalitis upon adoptive transfer" *Expert Rev Clin Immunol*, 2011. 7(3):283-5.
Lahdenperä, A.I. et al., "Up-regulation of small intestinal interleukin-17 immunity in untreated coeliac disease but not in potential coeliac disease or in type 1 diabetes" *Clin Exp Immunol*, 2012.167(2):226-34.
Lamale, L.M. et al., "Interleukin-6, histamine, and methylhistamine as diagnostic markers for interstitial cystitis" *Urology*, 2006. 68(4):702-6.
Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi: 10.1016/j.bmcl.2012.02.041. Final publication as: Seal, J. et al., "Identification of a novel series of BET family bromodomain inhibitors: binding mode and profile of I-BET151 (GSK1210151A)" *Bioorg Med Chem Lett*, 2012. 22(8):2968-72.
Latifi, S.Q. et al., "Persistent elevation of serum interleukin-6 in intraabdominal sepsis identifies those with prolonged length of stay" *J Pediatr Surg*, 2004. 39(10):1548-52.
Lee, D.K. et al., "Androgen receptor interacts with the positive elongation factor P-TEFb and enhances the efficiency of transcriptional elongation" *J Biol Chem*, 2001. 276(13):9978-84.

(56) References Cited

OTHER PUBLICATIONS

Li, Z., et al., "The BET bromodomain inhibitor JQ1 activates HIV latency through antagonizing Brd4 inhibition of Tat-transactivation" *Nucleic Acids Res Advance Access*, 2012. DOI:10.1093/nar/gks976, 11 pages.
Lin, F.J. et al., "Imbalance of regulatory T cells to Th17 cells in IgA nephropathy" *Scand J Clin Lab Invest*, 2012. 72(3):221-9.
Linhares, U.C. et al., "The Ex Vivo Production of IL-6 and IL-21 by CD4(+) T Cells is Directly Associated with Neurological Disability in Neuromyelitis Optica Patients" *J Clin Immunol*, 2012, DOI 10.1007/s10875-012-9780-2, 11 pages.
Lopez-Robles, E. et al., "TNFalpha and IL-6 are mediators in the blistering process of pemphigus" *Int J Dermatol*, 2001. 40(3):185-8.
Lu, M.O. and J. Zhu, "The role of cytokines in Guillain-Barre syndrome" *J Neurol*, 2011. 258(4):533-48.
Ma, D. et al., "Profile of Th17 cytokines (IL-17, TGF-beta, IL-6) and Th1 cytokine (IFN-gamma) in patients with immune thrombocytopenic purpura" *Ann Hematol*, 2008. 87(11):899-904.
Mahad, D.J. and R.M. Ransohoff, "The role of MCP-1 (CCL2) and CCR2 in multiple sclerosis and experimental autoimmune encephalomyelitis (EAE)" *Semin Immunol*, 2003. 15(1):23-32.
Matzuk, M.M. et al., "Small-Molecule Inhibition of BRDT for Male Contraception" *Cell*, 2012. 150(4):673-684, with supplemental pp. S1-S8.
McKeown, M. et al., "Biased Multicomponent Reactions to Develop Novel Bromodomain Inhibitors" *J Med Chem*, 57:9019-9027 (2014).
McKinley, L. et al., "TH17 cells mediate steroid-resistant airway inflammation and airway hyperresponsiveness in mice" *J Immunol*, 2008. 181(6):4089-97.
Medina-Franco, J.L. et al., "Pyridin-2(1H)-ones: A Promising Class of HIV-f1 Non-nucleoside Reverse Transcriptase Inhibitors" *ChemMedChem*, 2:1141-1147 (2007).
Mendrzyk, F. et al., "Genomic and protein expression profiling identifies CDK6 as novel independent prognostic marker in medulloblastoma" *J Clin Oncol*, 2005. 23(34):8853-62.
Mertz, Jennifer A., "Targeting MYC Dependence in Cancer by Inhibiting BET Bromodomains", *PNAS*, 2011, 108(40):16669-16674.
Min, C.K. et al., "Cutaneous leucoclastic vasculitis (LV) following bortezomib therapy in a myeloma patient; association with pro-inflammatory cytokines" *Eur J Haematol*, 2006. 76(3):265-8.
Mirguet, O. et al., "From ApoA1 upregulation to BET family bromodomain inhibition: discovery of I-BET151" *Bioorg Med Chem Lett*, Article in Press, 2012. doi: 10.1016/j.bmcl.2012.01.125, 5 pages. Final publication in vol. 22, No. 8, pp. 2963-2967.
Mitsuyama, K. et al., "STAT3 activation via interleukin 6 trans-signalling contributes to ileitis in SAMP1/Yit mice" *Gut*, 2006. 55(9):1263-9.
Miyazaki, et al. "Intravenous Injection of Rabbit Apolipoprotein A-I Inhibits the Progression of Atherosclerosis in Cholesterol-Fed Rabbits" *Arterioscler. Thromb. Vasc. Biol.* 15: 1882-1888 (1995).
Mok, M.Y. et al., "The relation of interleukin 17 (IL-17) and IL-23 to Th1/Th2 cytokines and disease activity in systemic lupus erythematosus" *J Rheumatol*, 2010. 37(10):2046-52.
Morin, R.D. et al., "Frequent mutation of histone-modifying genes in non-Hodgkin lymphoma" *Nature*, 2011. 476(7360):298-303. (Author manuscript, 17 pages).
Mudter, J. and M.F. Neurath, "IL-6 signaling in inflammatory bowel disease: pathophysiological role and clinical relevance" *Inflamm Bowel Dis*, 2007. 13(8):1016-23.
Muller Kobold, A.C. et al., "In vitro up-regulation of E-selectin and induction of interleukin-6 in endothelial cells by autoantibodies in Wegener's granulomatosis and microscopic polyangiitis" *Clin Exp Rheumatol*, 1999. 17(4):433-40.
Muller, S. et al., "Bromodomains as therapeutic targets" *Expert Rev Mol Med*, 2011. 13: e29, 21 pages.
Nakahama, H. et al., "Distinct responses of interleukin-6 and other laboratory parameters to treatment in a patient with Wegener's granulomatosis" *Intern Med*, 1993. 32(2):189-92.

Narayana, B.L. et al., "Synthesis of New 2-Substituted Pyrido[2,3-d]pyrimidine-4(1H)-ones and Their Antibacterial Activity" *Eur. J. Med. Chem.* 44(3):1369-1376 (2009).
Nelken, N.A. et al., "Monocyte chemoattractant protein-1 in human atheromatous plaques" *J Clin Invest*, 1991. 88(4):1121-7.
Ni, J. et al., "Involvement of Interleukin-17A in Pancreatic Damage in Rat Experimental Acute Necrotizing Pancreatitis" *Inflammation*, 2012. [online] DOI: 10.1007/s10753-012-9519-5, published Sep. 19, 2012 (13 pages).
Nicodeme et al., "Suppression of inflammation by a synthetic histone mimic" *Nature* 468:1119-1123 (2010).
Niu, J. and P.E. Kolattukudy, "Role of MCP-1 in cardiovascular disease: molecular mechanisms and clinical implications" *Clin Sci*, 2009. 117(3):95-109.
Ooi, J.D. et al, "Review: T helper 17 cells: their role in glomerulonephritis" *Nephrology*, 2010. 15(5):513-21.
Ortiz-Lucas, M. et al., "Irritable bowel syndrome immune hypothesis. Part two: the role of cytokines" *Rev Esp Enferm Dig*, 2010. 102(12):711-7.
Ott, C.J. et al., "BET bromodomain inhibition targets both c-Myc and IL7R in high-risk acute lymphoblastic leukemia" *Blood*, 2012. 120(14):2843-52.
Pakrashi, S.C. "4-Quinazolinones. II. Self-condensation of anthranilamide" *J Org Chem*, 36(5):642-645 (1971).
Palermo, R.D. et al., RNA polymerase II stalling promotes nucleosome occlusion and pTEFb recruitment to drive immortalization by Epstein-Barr virus. *PLoS Pathog*, 2011. 7(10): e1002334, 15 pages.
Paquet, P. and G.E. Pierard, "Interleukin-6 and the skin" *Int Arch Allergy immunol*, 1996. 109(4):308-17.
Peserico, A. and C. Simone, "Physical and functional HAT/HDAC interplay regulates protein acetylation balance" *J Biomed Biotechnol*, 2011. 371832, 10 pages.
Poreba, E. et al., "Epigenetic mechanisms in virus-induced tumorigenesis" *Clin Epigenetics*, 2011. 2(2):233-47.
Prabakaran, K. et al., "Iridium bromide catalysed, ultrasound-assisted, region-selective synthesis of ethyl-5-(trifluoromethyl)-1-(3-substituted-isoguinolin-I-yl)-1H-pyrazole-4-carboxylates", *Res. Chem. Intermed.*, 38:429-441 (2012).
Prinjha, R.K. et al., "Place your BETs: the therapeutic potential of bromodomains" *Trends Pharmacol Sci*, 2012. 33(3):146-53.
Radstake, T.R. et al., "The pronounced Th17 profile in systemic sclerosis (SSc) together with intracellular expression of TGFbeta and IFNgamma distinguishes SSc phenotypes" *PLoS One*, 2009. 4(6):e5903. 9 pages.
Ramsay, R.G. and T.J. Gonda, "MYB function in normal and cancer cells" *Nat Rev Cancer*, 2008. 8(7):523-34.
Raychaudhuri, S.P. et al., "IL-17 receptor and its functional significance in psoriatic arthritis" *Mol Cell Biochem*, 2012. 359(1-2):419-29.
Rhodus, N.L. et al., "Proinflammatory cytokine levels in saliva before and after treatment of (erosive) oral lichen planus with dexamethasone" *Oral Dis*, 2006. 12(2):112-6.
Rodriguez, R.M. et al., "Aberrant epigenetic regulation of bromodomain BRD4 in human colon cancer" *J Mol Med*, 2012. 90(5):587-95.
Roger, V.L. et al., "Heart disease and stroke statistics—2012 update: a report from the American Heart Association" *Circulation*, 2012. 125(1):3-e220.
Ruden, M. and N. Puri, "Novel anticancer therapeutics targeting telomerase" *Cancer Treat Rev*, 2012. Article in Press: http://dx.doi.org/10.1016/j.ctrv.2012.06.007, 13 pages.
Rudloff, U. and Y. Samuels, "TYRO3-mediated regulation of MITF: a novel target in melanoma?" *Pigment Cell Melanoma Res*, 2010. 23(1):9-11.
Sanchez, R. and M.M. Zhou, "The role of human bromodomains in chromatin biology and gene transcription" *Curr Opin Drug Discov Devel*, 2009. 12(5):659-65. (Author manuscript, 12 pages.).
Scanlan, M.J. et al., "Expression of cancer-testis antigens in lung cancer: definition of bromodomain testis-specific gene (BRDT) as a new CT gene, CT9" *Cancer Lett*, 2000. 150(2):155-64.

(56) References Cited

OTHER PUBLICATIONS

Seal, J. et al., "Identification of a novel series of BET family bromodomain inhibitors: Binding mode and profile of I-BET151(GSK121051A)" *Bioorg. Med. Chem. Lett.*, 22:2968-2972 (2012).

Segura, M.F. et al., "BRD4 is a novel therapeutic target in melanoma" Poster Presentation, AACR 103rd Annual Meeting, Mar. 31-Apr. 4, 2012 in Chicago, IL. *Cancer Research*, 2012. 72(8), Supplement 1, Abstract 2185.

Shang, E. et al., "The first bromodomain of Brdt, a testis-specific member of the BET sub-family of double-bromodomain-containing proteins, is essential for male germ cell differentiation" *Development*, 2007. 134(19):3507-15.

Shibuya, M. et al., "Successful treatment with tocilizumab in a case of Cogan's syndrome complicated with aortitis" *Mod Rheumatol*, 2012, online: DOI 10.1007/s10165-012-0691-0, 5 pages.

Simmons, E.M. et al., "Plasma cytokine levels predict mortality in patients with acute renal failure" *Kidney Int*, 2004. 65(4):1357-65.

Simone, C. and A. Giordano, "Abrogation of signal-dependent activation of the cdk9/cyclin T2a complex in human RD rhabdomyosarcoma cells" *Cell Death Differ*, 2007. 14(1):192-5.

Soltesz, P. et al., "Immunological features of primary anti-phospholipid syndrome in connection with endothelial dysfunction" *Rheumatology*, 2008. 47(11):1628-34.

Stenman, G. et al., "New tricks from an old oncogene: gene fusion and copy number alterations of MYB in human cancer" *Cell Cycle*, 2010. 9(15):2986-95.

Sun, Y. et al., "MMP-9 and IL-6 are potential biomarkers for disease activity in Takayasu's arteritis" *Int J Cardiol*, 2012. 156(2):236-8.

Tang, X. et al., "Assessment of Brd4 inhibition in idiopathic pulmonary fibrosis lung fibroblasts and in vivo models of lung fibrosis" *Am. J. Pathol.*, 183(2):470-479 (2013).

Taylan, A. et al., "Evaluation of the T helper 17 axis in ankylosing spondylitis" *Rheumatol Int*, 2012. 32(8):2511-5.

Tong, W.G. et al., "Phase I and pharmacologic study of SNS-032, a potent and selective Cdk2, 7, and 9 inhibitor, in patients with advanced chronic lymphocytic leukemia and multiple myeloma" *J Clin Oncol*, 2010. 28(18):3015-22.

Traves, S.L. and L.E. Donnelly, "Th17 cells in airway diseases" *Curr. Mol. Med.*, 2008. 8(5):416-26.

Uchida, T. et al., "Antitumor effect of bcl-2 antisense phosphorothioate oligodeoxynucleotides on human renal-cell carcinoma cells in vitro and in mice" *Mel Urol*, 2001. 5(2):71-8.

Urano, W. et al., "The inflammatory process in the mechanism of decreased serum uric acid concentrations during acute gouty arthritis" *J Rheumatol*, 2002. 29(9):1950-3.

Utsunomiya, I. et al., "Preparation of Alkyl-Substituted Indoles in the Benzene Portion. Part 13. Enantiospecific Synthesis of Mitosene Analogues Related to FFR 900482 and FR 66979" *Chem Pharm Bull*, 43(1):37-48.

Velisek, L. et al., "GABAergic neuron deficit as an idiopathic generalized epilepsy mechanism: the role of BRD2 haploinsufficiency in juvenile myoclonic epilepsy" *PLoS One*, 2011. 6(8): e23656, 8 pages.

Vernarecci, S. et al., "Tuning acetylated chromatin with HAT inhibitors: a novel tool for therapy" *Epigenetics*, 2010. 5(2): p. 105-11.

Vidal, B. et al., "Discovery and Characterization of 4'-(2-Furyl)-N-pyridin-3-yl-4,5'-bipyrimidin-2'-amine (LAS38096), a Potent, Selective, and Efficacious $A_{2B}$ Adenosine Receptor Antagonist" *J. Med. Chem.* 50:2732-2736 (2007).

Vidler, L.R. et al., "Discovery of Novel Small-Molecule Inhibitors of BRD4 Using Structure-Based Virtual Screening" *J Med Chem*, 56:8073-8088 (2013).

Vita, M. and M. Henriksson, "The Myc oncoprotein as a therapeutic target for human cancer" *Semin Cancer Biol*, 2006. 16(4):318-30.

Voitenko et al., "Esters of o-(4-oxo-3,4-dihydro-2-quinazolinyl)benzoic acid and 5,11-dihydroisoindolo[2,1-a]quinazolinone-5 derivatives as β-cyclodextrin modifiers" *Dopovidi Natsional'noi Akademli Nauk Uraini (Reports of the National Academy of Sciences of Ukraine)*, 8:132-138 (2005) English abstract on p. 132.

Wang, F. et al., "Brd2 disruption in mice causes severe obesity without Type 2 diabetes" *Biochem J*, 2010. 425(1): p. 71-83, with supplemental online material, 2 pages.

Wang, G. et al., "Increased cyclin-dependent kinase 6 expression in bladder cancer" *Oncol Lett*, 2012. 4(1): p. 43-46.

Wang, S. and P.M. Fischer, "Cyclin-dependent kinase 9: a key transcriptional regulator and potential drug target in oncology, virology and cardiology" *Trends Pharmacol Sci*, 2008. 29(6):302-13.

Watson, J.D., "Curing 'incurable' cancer" *Cancer Discov*, 2011. 1(6):477-80.

Wu, S.Y. and C.M. Chiang, "The double bromodomain-containing chromatin adaptor Brd4 and transcriptional regulation" *J Biol Chem*, 2007. 282(18):13141-5.

Xing, W. et al., "Discovery of novel 2,6-disubstituted pyridazinone derivatives as acetylcholinesterase inhibitors" *Eur. J. Med. Chem.* 63:95-103 (2013).

Xu, L. et al., "Critical role of Th17 cells in development of autoimmune hemolytic anemia" *Exp Hematol*, 2012. Article in Press: http://dx.doi.org/10.1016/j.exphern.2012.08.008, 15 pages.

Yamaguchi, M. et al., "Novel Antiasthmatic Agents with Dual Activities of Thromboxane $A_2$ Synthetase Inhibition and Bronchodilation. 2. 4-(3-Pyridyl)-1(2H)-phthalazinones" *J. Med. Chem.*, 36:4061-4068 (1993).

Yamashita, T. et al., "IL-6-mediated Th17 differentiation through RORγt is essential for the initiation of experimental autoimmune myocarditis" *Cardiovasc Res*, 2011. 91(4):640-8.

Yoshii, T. et al., "Local levels of interleukin-1beta, -4, -6 and tumor necrosis factor alpha in an experimental model of murine osteomyelitis due to *Staphylococcus aureus*" *Cytokine*, 2002. 19(2):59-65.

Yoshimura, T. et al., "Involvement of Th17 cells and the effect of anti-IL-6 therapy in autoimmune uveitis" *Rheumatology*, 48(4):347-354 (2009).

You, J. et al., "Kaposi's sarcoma-associated herpesvirus latency-associated nuclear antigen interacts with bromodomain protein Brd4 on host mitotic chromosomes" *J Virol*, 2006. 80(18):8909-19.

Yu et al., "Discovery of Highly Potent and Selective α4β2-Nicotinic Acetylcholine Receptor (nAChR) Partial Agonists Containing an Isoxazolylpyridine Ether Scaffold that Demonstrate Antidepressant-like Activity" *J Med Chem*, 55:9997-10009 (2012).

Yu et al., "Toll-Like Receptor 7 Agonists: Chemical Feature Based Pharmacophore Identification and Molecular Docking Studies" *PLoS ONE* 8(3):e56514, doi:10.1371/journal.pone.0056514 (2013).

Zhang, G. et al., "Down-regulation of NF-kappaB Transcriptional Activity in HIVassociated Kidney Disease by BRD4 Inhibition" *JBC Papers in Press*, 2012. M112.359505 with supplement, 38 pages. Final publication in: *J Biol Chem*, 287(34):28840-51.

Zhang, W.S. et al., "Bromodomain-Containing-Protein 4 (BRD4) Regulates RNA Polymerase II Serine 2 Phosphorylation in Human CD4+ T Cells" JBC Papers in Press, 2012. M112.413047, 30 pages. Final publication in: *J Biol Chem*, 287:43137-55.

Zhao, L. et al., "Interleukin-17 contributes to the pathogenesis of autoimmune hepatitis through inducing hepatic interleukin-6 expression" *PLoS One*, 2011. 6(4):e18909, 8 pages.

Zhou, M. et al., "Bromodomain protein Brd4 regulates human immunodeficiency virus transcription through phosphorylation of CDK9 at threonine 29" *J Virol*, 2009. 83(2):1036-44.

Zhu, J. et al., "Reactivation of Latent HIV-1 by Inhibition of BRD4" *Cell Rep*, 2012. 2:1-10, with supplemental pp. S1-S7.

Zuber, J. et al., "RNAi screen identifies Brd4 as a therapeutic target in acute myeloid leukaemia" *Nature*, 2011. 478(7370):524-8.

Chemical Abstracts Service, 'Registry' File, RN 1348682-08-5; STN Database [online]. Entry Date: Dec. 4, 2011 (1 page).

Chemical Abstracts Service, 'Registry' File, RN 1349387-93-4; STN Database [online]. Entry Date: Dec. 6, 2011 (1 page).

European Patent Application No. 14820520.6, by Zenith Epigenetics Corp.; Extended European Search Report, including Search Opinion, dated Feb. 8, 2017 (9 pages).

(56) References Cited

OTHER PUBLICATIONS

European Patent Application No. 14822480.1, by Zenith Epigenetics Corp.; Extended European Search Report, including Search Opinion, dated Jan. 4, 2017 (10 pages).
Hankovszky, H.O. et al., "Synthesis and reaction of ortho-fluoronitriaryl nitroxides. Novel versatile synthons and reagents for spin-labelling studies" Can J Chem, 67:1392-1400 (1989).
International Search Report and Written Opinion issued in International Application No. PCT/IB2016/001874; dated Apr. 25, 2016.

* cited by examiner

QUINAZOLINONES AS BROMODOMAIN INHIBITORS

CROSS-REFERENCE TO RELATED PATENT APPLICATIONS

This application is a U.S. national stage of International Patent Application No. PCT/IB2014/002510, filed Jul. 30, 2014, which claims the benefit of priority to U.S. Provisional Application No. 61/860,403, filed Jul. 31, 2013, all of which are incorporated herein by reference in their entirety.

The invention provides novel compounds, pharmaceutical compositions containing such compounds, and their use in prevention and treatment of diseases and conditions associated with bromodomain and extra terminal domain (BET) proteins.

Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs). A. Peserico and C. Simone, "Physical and functional HAT/HDAC interplay regulates protein acetylation balance," *J Biomed Biotechnol* 2011:371832 (2011). Small molecule inhibitors of HDACs and HATs are being investigated as cancer therapy. I. Hoshino and H. Matsubara, "Recent advances in histone deacetylase targeted cancer therapy" *Surg Today* 40(9):809-15 (2010); S. Vernarecci et al., "Tuning acetylated chromatin with HAT inhibitors: a novel tool for therapy" *Epigenetics* 5(2): 105-11 (2010); K. Bandyopadhyay et al., "Spermidinyl-CoA-based HAT inhibitors block DNA repair and provide cancer-specific chemo- and radiosensitization," *Cell Cycle* 8(17):2779-88 (2009); M. Arif et al., "Protein lysine acetylation in cellular function and its role in cancer manifestation," *Biochim Biophys Acta* 1799(10-12):702-16 (2010). Histone acetylation controls gene expression by recruiting protein complexes that bind directly to acetylated lysine via bromodomains. R. Sanchez and M. Zhou, "The role of human bromodomains in chromatin biology and gene transcription," *Curr Opin Drug Discov Devel* 12(5):659-65 (2009). One such family, the bromodomain and extra terminal domain (BET) proteins, comprises Brd2, Brd3, Brd4, and BrdT, each of which contains two bromodomains in tandem that can independently bind to acetylated lysines, as reviewed in S. Wu and C. Chiang, "The double bromodomain-containing chromatin adaptor Brd4 and transcriptional regulation," *J Biol Chem* 282(18):13141-5 (2007).

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis. A. Belkina and G. Denis, "BET domain co-regulators in obesity, inflammation and cancer," *Nat Rev Cancer* 12(7):465-77 (2012). BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections. R. Prinjha et al., "Place your BETs: the therapeutic potential of bromodomains," *Trends Pharmacol Sci* 33(3): 146-53 (2012).

Autoimmune diseases, which are often chronic and debilitating, are a result of a dysregulated immune response, which leads the body to attack its own cells, tissues, and organs. Pro-inflammatory cytokines including IL-1$\beta$, TNF-$\alpha$, L-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy. A. Kimura and T. Kishimoto, "IL-6: regulator of Treg/Th17 balance," *Eur J Immunol* 40(7): 1830-5 (2010). BET inhibitors are expected to have anti-inflammatory and immunomodulatory properties. A. Belkina and G. Denis, *Nat Rev Cancer* 12(7):465-77 (2012); R. Prinjha et al., *Trends Pharmacol Sci* 33(3): 146-53 (2012). BET inhibitors have been shown to have a broad spectrum of anti-inflammatory effects in vitro including the ability to decrease expression of pro-inflammatory cytokines such as IL-1$\beta$, MCP-1, TNF-$\alpha$, and IL-6 in activated immune cells. O. Mirguet et al., "From ApoA1 upregulation to BET family bromodomain inhibition: discovery of I-BET151," *Bioorg Med Chem Lett* 22(8):2963-7 (2012); E. Nicodeme et al., "Suppression of inflammation by a synthetic histone mimic," *Nature* 468 (7327):1119-23 (2010); J. Seal et al., "Identification of a novel series of BET family bromodomain inhibitors: binding mode and profile of I-BET151 (GSK 1210151A)," *Bioorg Med Chem Lett* 22(8):2968-72 (2012). The mechanism for these anti-inflammatory effects may involve BET inhibitor disruption of Brd4 co-activation of NF-$\kappa$B-regulated pro-inflammatory cytokines and/or displacement of BET proteins from cytokine promoters, including IL-6. E. Nicodeme et al., *Nature* 468(7327):1119-23 (2010); G. Zhang et al., "Down-regulation of NF-kappaB Transcriptional Activity in HIV associated Kidney Disease by BRD4 Inhibition," *J Biol Chem*, 287(34):8840-51 (2012); M. Zhou et al., "Bromodomain protein Brd4 regulates human immunodeficiency virus transcription through phosphorylation of CDK9 at threonine 29." *J Virol* 83(2):1036-44 (2009). In addition, because Brd4 is involved in T-cell lineage differentiation, BET inhibitors may be useful in inflammatory disorders characterized by specific programs of T cell differentiation. W. Zhang et al., "Bromodomain-Containing-Protein 4 (BRD4) Regulates RNA Polymerase II Serine 2 Phosphorylation in Human CD4+ T Cells," *J Biol Chem* (2012).

The anti-inflammatory and immunomodulatory effects of BET inhibition have also been confirmed in vivo. A BET inhibitor prevented endotoxin- or bacterial sepsis-induced death and cecal ligation puncture-induced death in mice, suggesting utility for BET inhibitors in sepsis and acute inflammatory disorders. E. Nicodeme et al., *Nature* 468 (7327): 1119-23 (2010). A BET inhibitor has been shown to ameliorate inflammation and kidney injury in HIV-1 transgenic mice, an animal model for HIV-associated nephropathy, in part through inhibition of Brd4 interaction with NF-kappaB. G. Zhang, et al., *J Biol Chem* 287(34):8840-51 (2012). The utility of BET inhibition in autoimmune disease was demonstrated in a mouse model of multiple sclerosis, where BET inhibition resulted in abrogation of clinical signs of disease, in part, through inhibition of IL-6 and IL-17. R. Jahagirdar et al., "An Orally Bioavailable Small Molecule RVX-297 Significantly Decreases Disease in a Mouse Model of Multiple Sclerosis," *World Congress of Inflammation* Paris, France (2011). These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells. H. Bandukwala et al., "Selective inhibition of CD4+ T-cell cytokine production and autoimmunity by BET protein and c-Myc inhibitors," *Proc Natl Acad Sci USA* 109(36): 14532-7 (2012).

BET inhibitors may be useful in the treatment of a variety of chronic autoimmune inflammatory conditions. Thus, one aspect of the invention provides compounds, compositions, and methods for treating autoimmune and/or inflammatory diseases by administering one or more compounds of the invention or pharmaceutical compositions comprising one or more of those compounds. Examples of autoimmune and inflammatory diseases, disorders, and syndromes that may be treated using the compounds and methods of the invention include but are not limited to, inflammatory pelvic disease, urethritis, skin sunburn, sinusitis, pneumonitis, encephalitis, meningitis, myocarditis, nephritis (G. Zhang et al., *J Biol Chem* 287(34):8840-51 (2012)), osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis (R. Prinjha et al., *Trends Pharmacol Sci* 33(3): 146-53 (2012)), Sjogren's disease, tissue graft rejection, hyperacute rejection of transplanted organs, asthma, allergic rhinitis, chronic obstructive pulmonary disease (COPD)), autoimmune polyglandular disease (also known as autoimmune polyglandular syndrome), autoimmune alopecia, pernicious anemia, glomerulonephritis, dermatomyositis, multiple sclerosis (H. Bandukwala et al., *Proc Natl Acad Sci USA* 109(36): 14532-7 (2012)), scleroderma, vasculitis, autoimmune hemolytic and thrombocytopenic states, (Goodpasture's syndrome, atherosclerosis, Addison's disease, Parkinson's disease, Alzheimer's disease, Type I diabetes (A. Belkina and G. Denis, *Nat Rev Cancer* 12(7): 465-77 (2012)), septic shock ((G. Zhang et al *J Biol Chem* 287(34):8840-51 (2012)), systemic lupus erythematosus (SLE) (R. Prinjha et al, *Trends Pharmacol Sci* 33(3):146-53 (2012)), rheumatoid arthritis (G. Denis "Bromodomain coactivators in cancer, obesity, type 2 diabetes, and inflammation," *Discov Med* 10(55):489-99 (2010)), psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions. Thus, one aspect of the invention provides compounds, compositions, and methods for treating inflammatory conditions including but not limited to, acute gout, giant cell arteritis, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock (E. Nicodeme et al., *Nature* 468(7327):1119-23 (2010)), systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus. A. Belkina and G. Denis, *Nat Rev Cancer* 12(7):465-77 (2012). Thus, one aspect of the invention provides compounds, compositions, and methods for treating these inflammatory responses to infections with bacteria, viruses, fungi, parasites, and their toxins described herein.

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs. J. Watson "Curing 'incurable' cancer," *Cancer Discov* 1(6):477-80 (2011); R. Morin et al., "Frequent mutation of histone-modifying genes in non-Hodgkin lymphoma" *Nature* 476 (7360):298-303 (2011).

One aspect of the invention provides compounds, compositions, and methods for treating human cancer, including, but not limited to, cancers that result from aberrant translocation or overexpression of BET proteins (e.g., NUT midline carcinoma (NMC) (C. French "NUT midline carcinoma," *Cancer Genet Cytogenet* 203(1):16-20 (2010) and B-cell lymphoma (R. Greenwald et al., "E mu-BRD2 transgenic mice develop B-cell lymphoma and leukemia," *Blood* 103(4):1475-84 (2004)). NMC tumor cell growth is driven by a translocation of the Brd4 or Brd3 gene to the nutlin 1 gene. P. Filippakopoulos et al., "Selective inhibition of BET bromodomains," *Nature* 468(7327):1067-73 (2010). BET inhibition has demonstrated potent antitumor activity in murine xenograft models of NMC, a rare but lethal form of cancer. The present disclosure provides a method for treating human cancers, including, but not limited to, cancers dependent on a member of the myc family of oncoproteins including c-myc, MYCN, and L-myc. M. Vita and M. Henriksson, "The Myc oncoprotein as a therapeutic target for human cancer," *Semin Cancer Biol* 16(4):318-30 (2006). These cancers include Burkitt's lymphoma, acute myelogenous leukemia, multiple mycloma, and aggressive human medulloblastoma. M. Vita and M. Henriksson, *Semin Cancer Biol* 16(4):318-30 (2006). Cancers in which c-myc is overexpressed may be particularly susceptible to BET protein inhibition; it has been shown that treatment of tumors that have activation of c-myc with a BET inhibitor resulted in tumor regression through inactivation of c-myc transcription. M. Dawson et al., Inhibition of BET recruitment to chromatin as an effective treatment for MLL-fusion leukaemia. Nature, 2011. 478(7370): p. 529-33; J. Delmore et al., "BET bromodomain inhibition as a therapeutic strategy to target c-Myc," *Cell* 146(6):904-17 (2010); J. Mertz et al., "Targeting MYC dependence in cancer by inhibiting BET bromodomains," *Proc Natl Acad Sci USA* 108(40):16669-74 (2011); C. Ott et al., "BET bromodomain inhibition targets both c-Myc and IL7R in highrisk acute lymphoblastic leukemia," *Blood* 120(14):2843-52 (2012); J. Zuber et al., "RNAi screen identifies Brd4 as a therapeutic target in acute myeloid leukaemia," *Nature* 478(7370):524-8 (2011).

Embodiments of the invention include methods for treating human cancers that rely on BET proteins and pTEFb (Cdk9/CyclinT) to regulate oncogenes (S. Wang, and P. Fischer, "Cyclin-dependent kinase 9: a key transcriptional regulator and potential drug target in oncology, virology and cardiology," *Trends Pharmacol Sci* 29(6):302-13 (2008)), and cancers that can be treated by inducing apoptosis or senescence by inhibiting Bcl2, cyclin-dependent kinase 6 (CDK6) (M. Dawson et al., *Nature* 478 (7370):529-33 (2011)), or human telomerase reverse transcriptase (hTERT). J. Delmore et al., *Cell* 146(6):904-17 (2010); M. Ruden and N. Puri, "Novel anticancer therapeutics targeting telomerase," *Cancer Treat Rev* (2012).

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia (M. Dawson et al., *Nature* 478(7370):529-33 (2011); J. Mertz, et al., *Proc Natl Acad Sci USA* 108(40): 16669-74 (2011); J. Zuber et al., *Nature* 478(7370):524-8 (2011)), adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia (C. Ott et al., *Blood* 120(14):2843-52 (2012)), B-cell chronic lymphocytic leukemia, B-cell prolymphocytic leukemia, B-cell lymphoma (R. Greenwald et al., *Blood* 103(4):1475-84 (2004)), basal cell carcinoma, biliary tract cancer, bladder cancer, blastoma, bone cancer, Brenner tumor, Brown tumor, Burkitt's lymphoma (J. Mertz et al., *Proc Natl Acad Sci USA* 108(40):16669-74 (2011)), breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia (Mertz, J. A., et al., *Proc Natl Acad Sci USA* 108(40):16669-74 (2011)), chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma (M. Segura et al., "BRD4 is a novel therapeutic target in melanoma," *Cancer Research* 72(8):Supplement 1 (2012)), meningioma, Merkel cell cancer, mesothelioma, metastatic urothelial carcinoma, mixed Mullerian tumor, mixed lineage leukemia (M. Dawson et al., *Nature* 478(7370):529-33 (2011)), mucinous tumor, multiple myeloma (J. Delmore et al., *Cell* 146(6):904-17 (2010)), muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma (P. Filippakopoulos et al., *Nature* 468(7327):1067-73 (2010)), ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. Thus, one aspect of the inventions provides compounds, compositions, and methods for treating such cancers.

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. X. Tang et al., "Assessment of Brd4 Inhibition in Idiopathic Pulmonary Fibrosis Lung Fibroblasts and in Vivo Models of Lung Fibrosis," *Am J Pathology* in press (2013). Thus, one aspect of the invention provides compounds, compositions, and methods for treating such benign proliferative and fibrotic disorders.

Cardiovascular disease (CVD) is the leading cause of mortality and morbidity in the United States. V. Roger et al., "Heart disease and stroke statistics—2012 update: a report from the American Heart Association," *Circulation* 125(1): e2-e220 (2012). Atherosclerosis, an underlying cause of CVD, is a multifactorial disease characterized by dyslipidemia and inflammation. BET inhibitors are expected to be efficacious in atherosclerosis and associated conditions because of aforementioned anti-inflammatory effects as well as ability to increase transcription of ApoA-I, the major constituent of HDL. O. Mirguet et al., *Bioorg Med Chem Lett* 22(8):2963-7 (2012); C. Chung et al., "Discovery and characterization of small molecule inhibitors of the BET family bromodomains," *J Med Chem* 54(11):3827-38 (2011). Accordingly, one aspect of the invention provides compounds, compositions, and methods for treating cardiovascular disease, including but not limited to atherosclerosis.

Up-regulation of ApoA-I is considered to be a useful strategy in treatment of atherosclerosis and CVD. E. Degoma and D. Rader, "Novel HDL-directed pharmacotherapeutic strategies," *Nat Rev Cardiol* 8(5):266-77 (2011) BET inhibitors have been shown to increase ApoA-I transcription and protein expression. O. Mirguet et al., *Bioorg Med Chem Left* 22(8):2963-7 (2012); C. Chung et al., *J Med Chem* 54(11):3827-38 (2011). It has also been shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-I and HDL such as hypercholesterolemia, dyslipidemia, atherosclerosis (E. Degoma and D. Rader, *Nat Rev Cardiol* 8(5):266-77 (2011)), and Alzheimer's disease and other neurological disorders. D. Elliott et al., "Apolipoproteins in the brain: implications for neurological and psychiatric disorders," *Clin Lipidol* 51(4): 555-573 (2010). Thus, one aspect of the invention provides compounds, compositions, and methods for treating cardiovascular disorders by upregulation of ApoA-1.

BET inhibitors may be useful in the prevention and treatment of conditions associated with ischemia-reperfusion injury such as, but not limited to, myocardial infarction, stroke, acute coronary syndromes (R. Prinjha et al. *Trends Pharmacol Sci* 33(3):146-53 (2012)), renal reperfusion injury, organ transplantation, coronary artery bypass grafting, cardio-pulmonary bypass procedures, hypertension, pulmonary, renal, hepatic, gastro-intestinal, or peripheral limb embolism. Accordingly, one aspect of the invention provides compounds, compositions, and methods for prevention and treatment of conditions described herein that are associated with ischemia-reperfusion injury.

Obesity-associated inflammation is a hallmark of type II diabetes, insulin resistance, and other metabolic disorders. A. Belkina and G. Denis, *Nat Rev Cancer* 12(7):465-77 (2012); G. Denis *Discov Med* 10(55):489-99 (2010). Consistent with the ability of BET inhibitors to inhibit inflammation, gene disruption of Brd2 in mice ablates inflammation and protects animals from obesity-induced insulin resistance. F. Wang et al., "Brd2 disruption in mice causes severe obesity without Type 2 diabetes," *Biochem J* 425(1): 71-83 (2010). It has been shown that Brd2 interacts with PPARγ and opposes its transcriptional function. Knockdown of Brd2 in vitro promotes transcription of PPARγ-regulated networks, including those controlling adipogenesis. G. Denis et al., "An emerging role for bromodomain-containing proteins in chromatin regulation and transcriptional control of adipogenesis," *FEBS Lett* 584(15):3260-8 (2010). In addition Brd2 is highly expressed in pancreatic β-cells and regulates proliferation and insulin transcription. F. Wang et al., *Biochem J* 425(1):71-83 (2010). Taken together, the combined effects of BET inhibitors on inflammation and metabolism decrease insulin resistance and may be useful in the treatment of pre-diabetic and type II diabetic individuals as well as patients with other metabolic complications. A. Belkina and G. Denis *Nat Rev Cancer* 12(7):465-77 (2012). Accordingly, one aspect of the invention provides compounds, compositions, and methods for treatment and prevention of metabolic disorders, including but not limited to obesity-associated inflammation, type II diabetes, and insulin resistance.

Host-encoded BET proteins have been shown to be important for transcriptional activation and repression of viral promoters. Brd4 interacts with the E2 protein of human papilloma virus (HPV) to enable E2 mediated transcription of E2-target genes. D. Gagnon et al., "Proteasomal degradation of the papillomavirus E2 protein is inhibited by overexpression of bromodomain-containing protein 4," *J Virol* 83(9):4127-39 (2009). Similarly, Brd2, Brd3, and Brd4 all bind to latent nuclear antigen 1 (LANA1), encoded by Kaposi's sarcoma-associated herpes virus (KSHV), promoting LANA1-dependent proliferation of KSHV-infected cells. J. You et al., "Kaposi's sarcoma-associated herpesvirus latency-associated nuclear antigen interacts with bromodomain protein Brd4 on host mitotic chromosomes," *J Virol* 80(18):8909-19 (2006). A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies. R. Palermo et al., "RNA polymerase II stalling promotes nucleosome occlusion and pTEFb recruitment to drive immortalization by Epstein-Barr virus," *PLoS Pathog* 7(10):e1002334 (2011). Also, a BET inhibitor reactivated HIV in models of latent T cell infection and latent monocyte infection, potentially allowing for viral eradication by complementary anti-retroviral therapy. J. Zhu et al., "Reactivation of Latent HIV-1 by Inhibition of BRD4," *Cell Rep* (2012); C. Banerjee et al., "BET bromodomain inhibition as a novel strategy for reactivation of HIV-1," *J Leukoc Biol* (2012); K. Bartholomeeusen et al., "BET bromodomain inhibition activates transcription via a transient release of P-TEFb from 7SK snRNP," *J Biol Chem* (2012); Z. Li et al., "The BET bromodomain inhibitor JQ1 activates HIV latency through antagonizing Brd4 inhibition of Tat-transactivation," *Nucleic Acids Res* (2012).

BET inhibitors may be useful in the prevention and treatment of episome-based DNA viruses including, but not limited to, human papillomavirus, herpes virus, Epstein-Barr virus, human immunodeficiency virus (A. Belkina and G. Denis, *Nat Rev Cancer* 12(7):465-77 (2012)), adenovirus, poxvirus, hepatitis B virus, and hepatitis C virus. Thus, the invention also provides compounds, compositions, and methods for treatment and prevention of episome-based DNA virus infections described herein.

Some central nervous system (CNS) diseases are characterized by disorders in epigenetic processes. Brd2 haploinsufficiency has been linked to neuronal deficits and epilepsy. L. Velisek et al., "GABAergic neuron deficit as an idiopathic generalized epilepsy mechanism: the role of BRD2 haploinsufficiency in juvenile myoclonic epilepsy," *PLoS One* 6(8): e23656 (2011) SNPs in various bromodomain-containing proteins have also been linked to mental disorders including schizophrenia and bipolar disorders. R. Prinjha et al., *Trends Pharmacol Sci* 33(3):146-53 (2012). In addition, the ability of BET inhibitors to increase ApoA-I transcription may make BET inhibitors useful in Alzheimer's disease therapy considering the suggested relationship between increased ApoA-I and Alzheimer's disease and other neurological disorders. D. Elliott et al., *Clin Lipidol* 51(4):555-573 (2010). Accordingly, one aspect of the invention provides compounds, compositions, and methods for treating such CNS diseases and disorders.

BRDT is the testis-specific member of the BET protein family which is essential for chromatin remodeling during spermatogenesis. J. Gaucher et al., "Bromodomain-dependent stage-specific male genome programming by Brdt," *EMBO J* 31(19):3809-20 (2012); E. Shang et al., "The first bromodomain of Brdt, a testis-specific member of the BET sub-family of double-bromodomain-containing proteins, is essential for male germ cell differentiation," *Development* 134(19):3507-15 (2007). Genetic depletion of BRDT or inhibition of BRDT interaction with acetylated histones by a BET inhibitor resulted in a contraceptive effect in mice, which was reversible when small molecule BET inhibitors were used. M. Matzuk et al., "Small-Molecule Inhibition of BRDT for Male Contraception," *Cell* 150(4): 673-684 (2012); B. Berkovits et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012). These data suggest potential utility of BET inhibitors as a novel and efficacious approach to male contraception. Thus, another aspect of the invention provides compounds, compositions, and methods for male contraception.

Monocyte chemotactic protein-1 (MCP-1, CCL2) plays an important role in cardiovascular disease. J. Niu and P. Kolattukudy, "Role of MCP-1 in cardiovascular disease: molecular mechanisms and clinical implications," *Clin Sci (Lond)* 117(3):95-109 (2009). MCP-1, by its chemotactic activity, regulates recruitment of monocytes from the arterial lumen to the subendothelial space, where they develop into macrophage foam cells, and initiate the formation of fatty streaks which can develop into atherosclerotic plaque. J. Dawson et al., "Targeting monocyte chemoattractant protein-1 signalling in disease," *Expert Opin Ther Targets* 7(1):35-48 (2003). The critical role of MCP-1 (and its cognate receptor CCR2) in the development of atherosclerosis has been examined in various transgenic and knockout mouse models on a hyperlipidemic background. L. Boring et al., "Decreased lesion formation in CCR2–/– mice reveals a role for chemokines in the initiation of atherosclerosis," *Nature* 394(6696):894-7 (1998); J. Gosling et al., "MCP-1 deficiency reduces susceptibility to atherosclerosis in mice that overexpress human apolipoprotein B," *J Clin Invest* 103(6):773-8 (1999); L. Gu et al., "Absence of monocyte chemoattractant protein-1 reduces atherosclerosis in low density lipoprotein receptor-deficient mice," *Mol Cell* 2(2): 275-81 (1998); R. Aiello et al., "Monocyte chemoattractant protein-1 accelerates atherosclerosis in apolipoprotein E-deficient mice," *Arterioscler Thromb Vase Biol* 19(6):1518-25 (1999). These reports demonstrate that abrogation of MCP-1 signaling results in decreased macrophage infiltration to the arterial wall and decreased atherosclerotic lesion development.

The association between MCP-1 and cardiovascular disease in humans is well-established. J. Niu and P. Kolattukudy, *Clin Sci (Lond)* 117(3):95-109 (2009). MCP-1 and its receptor are overexpressed by endothelial cells, smooth muscle cells, and infiltrating monocytes/macrophages in human atherosclerotic plaque. N. Nelken et al., "Monocyte chemoattractant protein-1 in human atheromatous plaques," *J Clin Invest* 88(4): 1121-7 (1991). Moreover, elevated circulating levels of MCP-1 are positively correlated with most cardiovascular risk factors, measures of coronary atherosclerosis burden, and the incidence of coronary heart disease (CHD). R. Deo et al., "Association among plasma levels of monocyte chemoattractant protein-1, traditional cardiovascular risk factors, and subclinical atherosclerosis," *J Am Coll Cardiol* 44(9):1812-8 (2004). CHD patients with among the highest levels of MCP-1 are those with acute coronary syndrome (ACS). J. de Lemos et al., "Association between plasma levels of monocyte chemoattractant protein-1 and long-term clinical outcomes in patients with acute coronary syndromes," *Circulation* 107(5):690-5 (2003). In addition to playing a role in the underlying inflammation associated with CHD, MCP-1 has been shown to be involved in plaque rupture, ischemic/reperfusion injury, restenosis, and heart transplant rejection. J. Niu and P. Kolattukudy, *Clin Sci (Lond)* 117(3):95-109 (2009).

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients. A. Koch et al., "Enhanced production of monocyte chemoattractant protein-1 in rheumatoid arthritis," *J Clin Invest* 90(3):772-9 (1992). Blockade of MCP-1 and MCP-1 signaling in animal models of RA have also shown the importance of MCP-1 to macrophage accumulation and proinflammatory cytokine expression associated with RA. C. Brodmerkel et al., "Discovery and pharmacological characterization of a novel rodent-active CCR2 antagonist, INCB3344," *J Immunol* 175(8):5370-8 (2005); H. Bruhl et al., "Dual role of CCR2 during initiation and progression of collagen-induced arthritis: evidence for regulatory activity of CCR2+ T cells," *J Immunol* 172(2):890-8 (2004); J. Gong et al., "An antagonist of monocyte chemoattractant protein 1 (MCP-1) inhibits arthritis in the MRL-lpr mouse model," *J Exp Med* 186(1): 131-7 (1997); 65. J. Gong et al., "Post-onset inhibition of murine arthritis using combined chemokine antagonist therapy," *Rheumatology* (Oxford 43(1): 39-42 (2004).

Overexpression of MCP-1, in the brain, cerebrospinal fluid (CSF), and blood, has also been associated with chronic and acute MS in humans. D. Mahad and R. Ransohoff, "The role of MCP-1 (CCL2) and CCR2 in multiple sclerosis and experimental autoimmune encephalomyelitis (EAE)," *Semin Immunol* 15(1):23-32 (2003). MCP-1 is overexpressed by a variety of cell types in the brain during disease progression and contributes to the infiltration of macrophages and lymphocytes which mediate the tissue damage associated with MS. Genetic depletion of MCP-1 or CCR2 in the experimental autoimmune encephalomyelitis (EAE) mouse model, a model resembling human MS, results in resistance to disease, primarily because of decreased macrophage infiltration to the CNS. B. Fife et al., "CC chemokine receptor 2 is critical for induction of experimental autoimmune encephalomyelitis," *J Exp Med* 192(6):899-905 (2000); D. Huang et al., "Absence of monocyte chemoattractant protein 1 in mice leads to decreased local macrophage recruitment and antigen-specific T helper cell type 1 immune response in experimental autoimmune encephalomyelitis," *J Exp Med* 193(6):713-26 (2001).

Preclinical data have suggested that small- and large-molecule inhibitors of MCP-1 and CCR2 have potential as therapeutic agents in inflammatory and autoimmune indications. Thus, one aspect of the invention provides compounds, compositions, and methods for treating cardiovascular, inflammatory, and autoimmune conditions associated with MCP-1 and CCR2.

Accordingly, the invention provides compounds that are useful for inhibition of BET protein function by binding to bromodomains, pharmaceutical compositions comprising one or more of those compounds, and use of these compounds or compositions in the treatment and prevention of diseases and conditions, including, but not limited to, cancer, autoimmune, and cardiovascular diseases.

The first aspect of the invention includes compounds of Formula I and methods of administering a therapeutically effective amount of those compounds to a mammal (e.g., a human) in need thereof:

Formula I or a stereoisomer, tautomer, pharmaceutically acceptable salt, or hydrate thereof,
wherein:
$W_1$ is selected from N and $CR_1$;
$W_2$ is selected from N and $CR_2$;
$W_3$ is selected from N and $CR_3$;
$W_4$ is selected from N and $CR_4$;
X is selected from N and CH;
Y is selected from —S(O)—, —C(O)—, —NH—, —NHCH$_2$—, —NHCH$_2$CH$_2$—, and —NHCH$_2$CH$_2$CH$_2$—, with the nitrogen attached to the B ring, and one or more hydrogens may be optionally substituted with alkyl($C_1$-$C_3$), halogen, hydroxyl, or amino;
$R_1$, $R_2$, $R_3$, and $R_4$ are independently selected from hydrogen, alkyl, alkenyl, alkynyl, alkoxy, amino such as, e.g., aminoalkyl, aryloxy, aryl, hydroxyl, and halogen;
two adjacent substituents selected from $R_1$, $R_2$, $R_3$, and $R_4$ may be connected in a 5- or 6-membered ring to form a bicyclic carbocycle or bicyclic heterocycle;
$R_5$ is selected from amino, 5- and 6-membered carbocycles and heterocycles;
$R_6$ is selected from hydrogen, alkoxy, alkyl, halogen, aminoalkyl, and thioalkyl; and
$R_7$ is selected from hydrogen, alkyl, alkoxy, thioalkyl, aminoalkyl, and halogen.

Another aspect of the invention includes compounds of Formula Ia and methods of administering a therapeutically effective amount of those compounds to a mammal (e.g., a human) in need thereof:

Formula Ia or a stereoisomer, tautomer, pharmaceutically acceptable salt, or hydrate thereof,
wherein:
X is selected from N and CH;
Y is selected from —S(O)—, —C(O)—, —NH—, —NHCH$_2$—, —NHCH$_2$CH$_2$—, and —NHCH$_2$CH$_2$CH$_2$—, with the nitrogen attached to the B ring, and one or more hydrogens may be optionally substituted with alkyl($C_1$-$C_3$), halogen, hydroxyl, or amino;
$R_1$ and $R_3$ are independently selected from hydrogen, alkyl, alkenyl, alkynyl, alkoxy, amino such as, e.g., aminoalkyl, aryloxy, aryl, hydroxyl, and halogen;
$R_5$ is selected from amino, aminoalkyl, 5- and 6-membered carbocycles and heterocycles optionally substituted with halogen, amino, amide, alkyl($C_1$-$C_6$), or alkoxy($C_1$-$C_6$) for example, the structures where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH;
$R_6$ is selected from hydrogen, alkoxy, alkyl, halogen, aminoalkyl, and thioalkyl; and
$R_7$ is selected from hydrogen, alkyl, alkoxy, thioalkyl, aminoalkyl, and halogen.

In another aspect of the invention, a pharmaceutical composition comprising a compound of Formula I or Formula Ia, or a pharmaceutically acceptable salt thereof and one or more pharmaceutically acceptable carriers, diluents or excipients is provided.

In yet another aspect of the invention there is provided a compound of Formula I or Formula Ia, or a pharmaceutically acceptable salt thereof for use in therapy, in particular in the treatment of diseases or conditions for which a bromodomain inhibitor is indicated.

In yet another aspect of the invention there is provided a compound of Formula I or Formula Ia, or a pharmaceutically acceptable salt thereof in the manufacture of a medicament for the treatment of diseases or conditions for which a bromodomain inhibitor is indicated.

Definitions

As used in the present specification, the following words, phrases and symbols are generally intended to have the meanings as set forth below, except to the extent that the context in which they are used indicates otherwise. The following abbreviations and terms have the indicated meanings throughout.

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically. e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as ($C_1$-$C_8$)alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as ($C_1$-$C_8$)alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_8$)alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —$NR_aC(O)(R_b)$— or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —NR$_d$R$_e$ or —N(R$_d$)R$_e$—, where R$_d$ and R$_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of R$_d$ and R$_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of R$_d$ or R$_e$ is an alkyl group. In some embodiments Rd and Re each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "(C$_6$)aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "(C$_6$)arylalkyl."

The term "carbamate" as used herein refers to the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of R$_g$, R$_h$ and R$_i$ are independently selected from aryl or heteroaryl, such as pyridine, pyridazine, pyrimidine, and pyrazine).

The term "carbocycle" as used herein refers to an aryl or cycloalkyl group.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "(C$_3$-C$_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, filmaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—R$_j$—, —R$_k$C(O)O—R$_j$—, or —R$_k$C(O)O—, where O is not bound to hydrogen, and R$_j$ and R$_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. R$_k$ can be a hydrogen atom, but R$_j$ cannot be a hydrogen atom. The ester may be cyclic, for example the carbon atom and R$_j$, the oxygen atom and R$_k$, or R$_j$ and R$_k$ may be joined to form a 3- to 12-membered ring. Exemplary esters include, but are not limited to, alkyl esters wherein at least one of Rj or Rk is alkyl, such as —O—C(O)-alkyl, —C(O)—O-alkyl-, and -alkyl-C(O)—O-alkyl-. Exemplary esters also include aryl or heteroaryl esters, e.g. wherein at least one of Rj or Rk is a heteroaryl group such as pyridine, pyridazine, pyrimidine and pyrazine, such as a nicotinate ester. Exemplary esters also include reverse esters having the structure —R$_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$) or —R$_n$—C(O)—R$_o$—. The ketone can be attached to another group through R$_n$ or R$_o$. R$_n$ or R$_o$ can be alkyl, alkenyl, alkynyl, cycloalkyl, heterocyclyl or aryl, or R$_n$ or R$_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S-alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{1-8}$ alkyl, alkenyl or alkynyl; $C_{1-6}$ aryl, $C_{2-5}$ heteroaryl; $C_{37}$ cycloalkyl; $C_{1-8}$ alkoxy; $C_6$ aryloxy; —CN; —OH; oxo; halo, carboxy; amino, such as —NH($C_{1-8}$ alkyl), —N($C_{1-8}$ alkyl)$_2$, —NH(($C_6$)aryl), or —N(($C_6$)aryl)$_2$; formyl; ketones, such as —CO($C_{1-8}$ alkyl), —CO(($C_6$ aryl))$_2$ aryl) esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

EXEMPLARY EMBODIMENTS OF THE INVENTION

In certain aspects, the invention is directed to a compound according to Formula I:

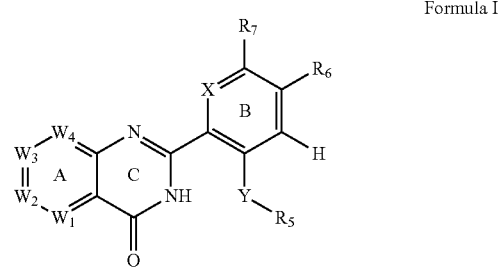

Formula I or a stereoisomer, tautomer, pharmaceutically acceptable salt, or hydrate thereof, wherein:
  $W_1$ is selected from N and $CR_1$;
  $W_2$ is selected from N and $CR_2$;
  $W_3$ is selected from N and $CR_3$;
  $W_4$ is selected from N and $CR_4$;
  X is selected from N and CH;
  Y is selected from —S(O)—, —C(O)—, —NH—, —NHCH$_2$—, —NHCH$_2$CH$_2$—, and —NHCH$_2$CH$_2$CH$_2$—, with the nitrogen attached to the B ring, and one or more hydrogens may be optionally substituted with alkyl($C_1$-$C_3$), halogen, hydroxyl, or amino;
  $R_1$, $R_2$, $R_3$, and $R_4$ are independently selected from hydrogen, alkyl, alkenyl, alkynyl, alkoxy, amino (such as, e.g., aminoalkyl), aryloxy, aryl, hydroxyl, and halogen;
  two adjacent substituents selected from $R_1$, $R_2$, $R_3$, and $R_4$ may be connected in a 5- or 6-membered ring to form a bicyclic carbocycle or bicyclic heterocycle;
  $R_5$ is selected from amino and 5- and 6-membered carbocycles and heterocycles;
  $R_6$ is selected from hydrogen, alkoxy, alkyl, halogen, aminoalkyl, and thioalkyl; and
  $R_7$ is selected from hydrogen, alkyl, alkoxy, thioalkyl, aminoalkyl, and halogen.

Another aspect of the invention is directed to a compound according to Formula Ia:

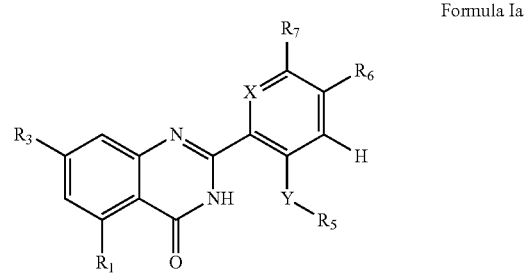

Formula Ia or a stereoisomer, tautomer, pharmaceutically acceptable salt, or hydrate thereof, wherein:

X is selected from N and CH;

Y is selected from —S(O)—, —C(O)—, —NH—, —NHCH$_2$—, —NHCH$_2$CH$_2$—, and —NHCH$_2$CH$_2$CH$_2$—, with the nitrogen attached to the B ring, and one or more hydrogens may be optionally substituted with alkyl(C$_1$-C$_3$), halogen, hydroxyl, or amino;

R$_1$ and R$_3$ are independently selected from hydrogen, alkyl, alkenyl, alkynyl, alkoxy, amino such as, e.g., aminoalkyl, aryloxy, aryl, hydroxyl, and halogen;

R$_5$ is selected from amino, aminoalkyl, 5- and 6-membered carbocycles and heterocycles optionally substituted with halogen, amino, amide, alkyl(C$_1$-C$_6$), or alkoxy(C$_1$-C$_6$) for example, the structures

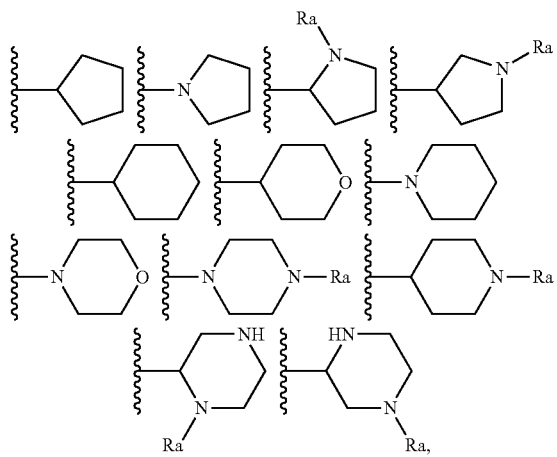

where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH;

R$_6$ is selected from hydrogen, alkoxy, alkyl, halogen, aminoalkyl, and thioalkyl; and R$_7$ is selected from hydrogen, alkyl, alkoxy, thioalkyl, aminoalkyl, and halogen.

In some embodiments of a compound of Formula I, each of R$_1$, R$_2$, R$_3$, and R$_4$, if present, are independently selected from hydrogen, alkyl, alkoxy, amino, and halogen.

In some embodiments of a compound of Formula Ia, each of R$_1$ and R$_3$ are independently selected from hydrogen, alkyl, alkoxy, amino, and halogen.

In some embodiments of a compound of Formula I, each of R$_1$, R$_2$, R$_3$, and R$_4$, if present, are independently selected from hydrogen, alkyl, and alkoxy, each of which may be optionally substituted with hydroxyl, amino, or halogen.

In some embodiments of a compound of Formula Ia, each of R$_1$ and R$_3$ are independently selected from hydrogen, alkyl, and alkoxy, each of which may be optionally substituted with hydroxyl, amino, or halogen.

In some embodiments of a compound of Formula I, each of R$_1$, R$_2$, R$_3$, and R$_4$, if present, is independently selected from aryl and aryloxy, each of which may be optionally substituted with halogen, alkoxy, or amino.

In some embodiments of a compound of Formula Ia, each of R$_1$ and R$_3$ are independently selected from aryl and aryloxy, each of which may be optionally substituted with halogen, alkoxy, or amino.

In certain embodiments of a compound of Formula I, W$_1$ is CR$_1$, W$_3$ is CR$_3$, and R$_1$ and R$_3$ are each independently an alkoxy group, for example methoxy, ethoxy, isopropoxy, and propoxy.

In certain embodiments of a compound of Formula Ia, R$_1$ and R$_3$ are each independently an alkoxy group, for example methoxy, ethoxy, isopropoxy, and propoxy.

In other embodiments of a compound of Formula I, W$_1$ is CR$_1$, W$_2$ is CR$_2$, W$_3$ is CR$_3$, W$_4$ is CR$_4$, and R$_1$ and R$_3$ are each alkoxy and R$_2$ and R$_4$ are each hydrogen.

In other embodiments of a compound of Formula I, W$_1$ is CR$_1$, W$_2$ is CR$_2$, W$_3$ is N, W$_4$ is CR$_4$, and R$_1$ and R$_3$ are each alkoxy and R$_2$ is hydrogen.

In other embodiments of a compound of Formula I, W$_1$ is CR$_1$, W$_2$ is CR$_2$, W$_3$ is CR$_3$, W$_4$ is CR$_4$, and R$_1$ and R$_3$ are each methoxy and R$_2$ and R$_4$ are each hydrogen.

In other embodiments of a compound of Formula Ia, R$_1$ and R$_3$ are each methoxy.

In other embodiments of a compound of Formula I, W$_1$ is CR$_1$, W$_2$ is CR$_2$, W$_3$ is CR$_3$, W$_4$ is CR$_4$, R$_1$ is methoxy, R$_3$ is amino or aminoalkyl, and R$_2$ and R$_4$ are each hydrogen.

In other embodiments of a compound of Formula Ia, R$_1$ is methoxy and R$_3$ is amino or aminoalkyl.

In some embodiments of a compound of Formula I or Formula Ia, R$_5$ is aminoalkyl.

In some embodiments of a compound of Formula I or Formula Ia, Y is selected from —NH—, —NHCH$_2$—, —NHCH$_2$CH$_2$—, and —NHCH$_2$CH$_2$CH$_2$—, with the nitrogen attached to the B ring, and one or more hydrogens may be optionally substituted with F, Me, OMe, and Cl.

In certain embodiments of a compound of Formula I or Formula Ia, Y is —NH—.

In certain embodiments of a compound of Formula I or Formula Ia, X is N.

In certain embodiments of a compound of Formula I or Formula Ia, X is CH.

In some embodiments of a compound of Formula I or Formula Ia, R$_5$ is selected from amino, aminoalkyl, and 5- and 6-membered carbocycles and heterocycles optionally substituted with halogen, amino, urea, ester, carbamate, amide, alkyl(C$_1$-C$_6$); alkoxy(C$_1$-C$_6$), and aryl.

In some embodiments of a compound of Formula I or Formula Ia, R$_5$ is selected from —NHRa and 5- and 6-membered carbocycles and heterocycles optionally substituted with halogen, amino, urea, ester, carbamate, amide, alkyl (C$_1$-C$_6$), alkoxy(C$_1$-C$_6$), or aryl, for example, the structures

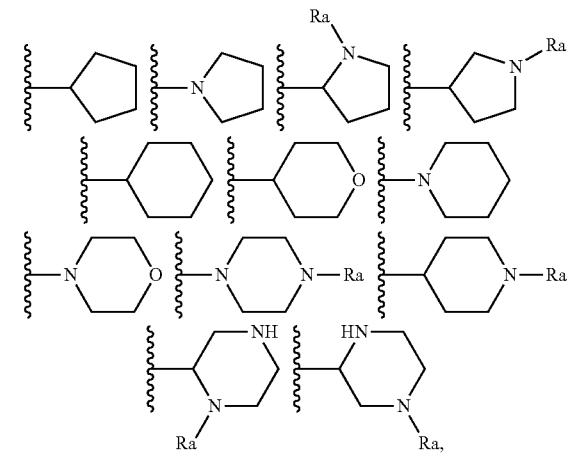

where Ra is selected from hydrogen, alkyl, alkenyl, aryl, —C(O)Alkyl(C$_1$-C$_4$), —C(O)Amino, —C(O)Oalkyl(C$_1$-C$_4$), and benzyl.

In some embodiments of a compound of Formula I or Formula Ia, R$_5$ is selected from —NHRa and 5- and 6-membered carbocycles and heterocycles optionally substituted with halogen, amino, amide, alkyl(C$_1$-C$_6$), or alkoxy(C$_1$-C$_6$) for example, the structures

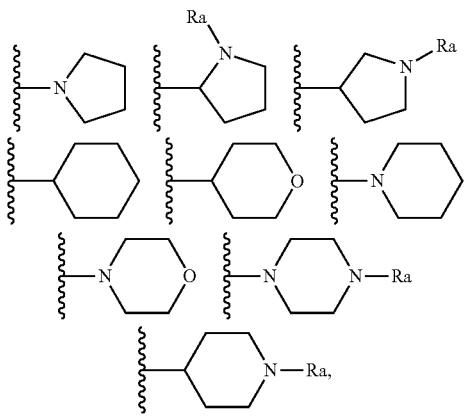

where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH.

In some embodiments of a compound of Formula I or Formula Ia, R$_6$ is selected from hydrogen, alkyl, alkoxy, aminoalkyl, and thioalkyl, each of which may be optionally substituted with halogen, amino, hydroxyl, or alkoxy.

In some embodiments of a compound of Formula I or Formula Ia, R$_6$ is selected from hydrogen, methyl, methoxy, ethoxy, and alkoxy optionally substituted with a hydroxyl or amino.

In some embodiments of a compound of Formula I or Formula Ia, R$_6$ is selected from hydrogen, methyl, and methoxy.

In a selected embodiment of a compound of Formula I or Formula Ia, R$_b$ is selected from groups represented by Formula II:

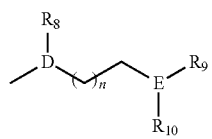

wherein:
D and E are independently selected from O, N, and S;
R$_8$ is selected from hydrogen and alkyl, and R$_8$ is present only if D is N;
R$_9$ and R$_{10}$ are independently selected from hydrogen, alkyl, and cycloalkyl, and only one of R$_9$ and R$_{10}$ is present if E is O or S;
R$_9$ and R$_{10}$ may be connected to form a carbocycle or a heterocycle containing one or more heteroatoms; and
n is selected from 1, 2, and 3.

In some embodiments of a compound of Formula I or Formula Ia, D is O and E is N;
n is 1; and
R$_9$ and R$_{10}$ are independently selected from hydrogen, alkyl, and carbocycle.

In certain embodiments of a compound of Formula I or Formula Ia, R$_6$ is selected from:

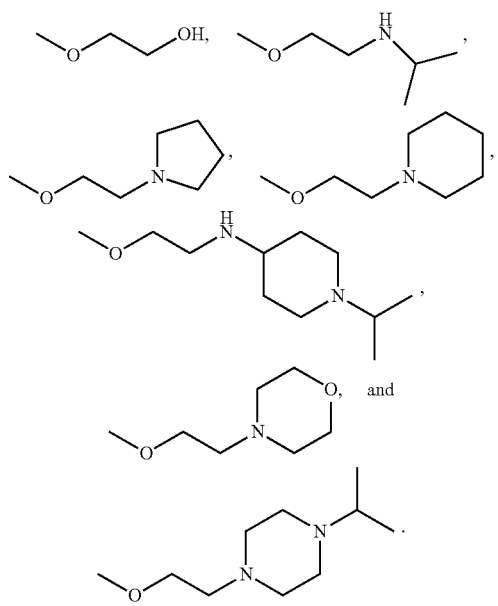

In some embodiments of a compound of Formula I or Formula Ia, R, is selected from hydrogen, methoxy, ethoxy, propoxy, isopropoxy, methyl, ethyl, propyl, isopropyl, and —OCF$_3$.

In some embodiments of a compound of Formula I,
W$_1$ is CR$_1$;
W$_2$ is CR$_2$;
W$_3$ is CR$_3$;
W$_4$ is CR$_4$;
R$_1$ and R$_3$ are each alkoxy;
R$_2$ and R$_4$ are each hydrogen;
Y is selected from —NH—, —NHCH$_2$—, —NHCH$_2$CH$_2$—, and —NHCH$_2$CH$_2$CH$_2$—, with the nitrogen attached to the B ring;
R$_5$ is selected from —NHRa and 5- or 6-membered carbocycle or heterocycles selected from

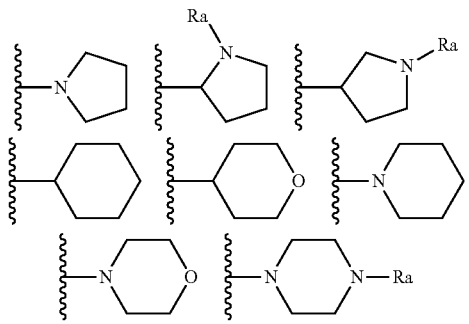

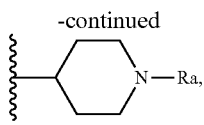

where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH; and R$_6$ is selected from hydrogen, methyl, methoxy, ethoxy, and alkoxy optionally substituted with a hydroxyl or amino.

In some embodiments of a compound of Formula Ia,

R$_1$ and R$_3$ are each alkoxy;

Y is selected from —NH—, —NHCH$_2$—, —NHCH$_2$CH$_2$—, and —NHCH$_2$CH$_2$CH$_2$—, with the nitrogen attached to the B ring;

R$_5$ is selected from —NHRa and 5- or 6-membered carbocycle or heterocycles selected from

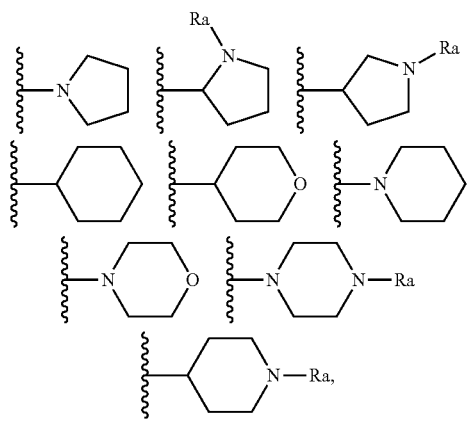

where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH; and R$_6$ is selected from hydrogen, methyl, methoxy, ethoxy, and alkoxy optionally substituted with a hydroxyl or amino.

In some embodiments of a compound of Formula I,

W$_1$ is CR$_1$;

W$_2$ is CR$_2$;

W$_3$ is CR$_3$;

W$_4$ is CR$_4$;

R$_1$ is alkoxy;

R$_3$ is amino or aminoalkyl;

R$_2$ and R$_4$ are each hydrogen;

Y is selected from —NH—, —NHCH$_2$—, —NHCH$_2$CH$_2$—, and —NHCH$_2$CH$_2$CH$_2$—, with the nitrogen attached to the B ring;

R$_5$ is selected from —NHRa and 5- or 6-membered carbocycle or heterocycles selected from

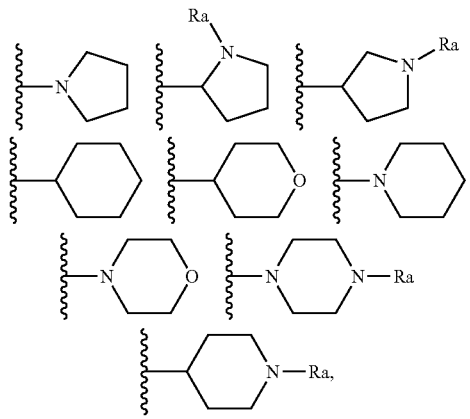

where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH; and R$_6$ is selected from hydrogen, methyl, methoxy, ethoxy, and alkoxy optionally substituted with a hydroxyl or amino.

In some embodiments of a compound of Formula Ia,

R$_1$ is alkoxy;

R$_3$ is amino or aminoalkyl;

Y is selected from —NH—, —NHCH$_2$—, —NHCH$_2$CH$_2$—, and —NHCH$_2$CH$_2$CH$_2$—, with the nitrogen attached to the B ring;

R$_5$ is selected from —NHRa and 5- or 6-membered carbocycle or heterocycles selected from

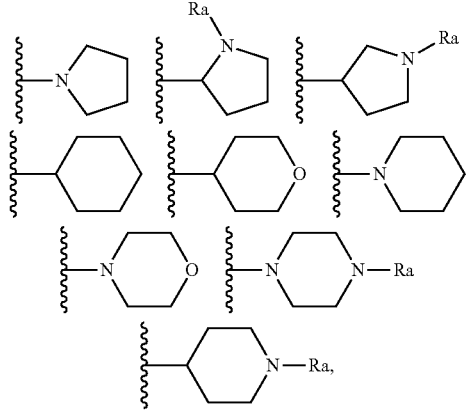

where Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$amino, and —CH$_2$CH$_2$C(Me)$_2$OH; and R$_6$ is selected from hydrogen, methyl, methoxy, ethoxy, and alkoxy optionally substituted with a hydroxyl or amino.

In some embodiments, the compound is selected from:

5,7-Dimethoxy-2-(4-methoxy-2-((1-methylpiperidin-4-yl)amino)phenyl)-quinazolin-4(3H)-one;

5,7-Dimethoxy-2-(4-methoxy-2-(4-methylpiperazine-1-carbonyl)phenyl)quinazolin-4(3H)-one;

2-(2-((1-isopropylpiperidin-4-yl)amino)-4-methoxyphenyl)-5,7-dimethoxyquinazolin-4(3H)-one;
5,7-Dimethoxy-2-(4-methoxy-2-((1-methylpyrrolidin-3-yl)amino)phenyl)quinazolin-4(3H)-one;
5,7-Dimethoxy-2-(4-methoxy-2-(methyl(1-methylpiperidin-4-yl)amino)phenyl) quinazolin-4(3H)-one;
5,7-Dimethoxy-2-(4-methoxy-2-(((1-methylpiperidin-4-yl)methyl)amino)phenyl) quinazolin-4(3H)-one;
5,7-Dimethoxy-2-(4-methoxy-2-(((1-methylpyrrolidin-3-yl)methyl)amino)phenyl)-quinazolin-4(3H)-one;
2-(2-((2-(Isopropylamino)ethyl)amino)-4-methoxyphenyl)-5,7-dimethoxyquinazolin-4(3H)-one;
5,7-dimethoxy-2-(4-Methoxy-2-((tetrahydro-2H-pyran-4-yl)amino)-phenyl)quinazolin-4(3H)-one;
2-(2-((1-Isopropylpiperidin-4-yl)amino)phenyl)-5,7-dimethoxyquinazolin-4(3H)-one;
5,7-Dimethoxy-2-(4-methoxy-2-((2-(pyrrolidin-1-yl)ethyl)amino)phenyl)quinazolin-4(3H)-one;
5,7-Dimethoxy-2-(4-methoxy-2-((2-(piperidin-1-yl)ethyl)amino)phenyl)quinazolin-4(3H)-one;
5,7-Dimethoxy-2-(4-methoxy-2-((3-morpholinopropyl)amino)-phenyl)quinazolin-4(3H)-one;
5,7-Dimethoxy-2-(4-methoxy-2-((2-morpholinoethyl)amino)phenyl)-quinazolin-4(3H)-one;
5,7-Dimethoxy-2-(4-methoxy-2-((3-(pyrrolidin-1-yl)propyl)amino)phenyl)quinazolin-4(3H)-one;
2-(2-(((1-Isopropylpyrrolidin-3-yl)methyl)amino)-4-methoxyphenyl)-5,7-dimethoxyquinazolin-4(3H)-one;
2-(2-(((1-Isopropylpyrrolidin-2-yl)methyl)amino)-4-methoxyphenyl)-5,7-dimethoxyquinazolin-4(3H)-one;
2-(3-((1-Isopropylpiperidin-4-yl)amino)pyridin-2-yl)-5,7-dimethoxyquinazolin-4(3H)-one;
2-(2-((1-Isobutyrylpiperidin-4-yl)amino)-4-methoxyphenyl)-5,7-dimethoxyquinazolin-4(3H)-one;
2-(2-((3-(Isopropylamino)propyl)amino)-4-methoxyphenyl)-5,7-dimethoxyquinazolin-4(3H)-one;
5,7-Dimethoxy-2-(4-methoxy-2-((3-(methylpiperazin-1-yl)propyl)amino)-phenylquinazolin-4(3H)-one;
2-(2-((2-(4-Isopropylpiperazin-1-yl)ethyl)amino)-4-methoxyphenyl)-5,7-dimethoxyquinazolin-4(3H)-one;
5,7-Dimethoxy-2-[4-methoxy-2-(I-methylpiperidin-4-yl-sulfinyl)phenyl]quinazolin-4(3H)-one;
5,7-Dimethoxy-2-(4-methoxy-2-((2-(piperazin-1-ylethyl)amino)phenyl)quinazolin-4(3H)-one;
5,7-Dimethoxy-2-(4-methoxy-2-((2-(4-methylpiperazin-1-yl)ethyl)amino)phenyl)-quinazolin-4(3H)-one;
2-(2-((1-Isopropylpiperidin-4-yl)amino)-5-methoxyphenyl)-5,7-dimethoxyquinazolin-4(3H)-one;
2-(3-((1-Isopropylpiperidin-4-yl)amino)phenyl)-5,7-dimethoxyquinazolin-4(3H)-one;
5,7-Dimethoxy-2-(4-methoxy-2-[3-(piperazin-1-yl)propylamino]phenyl)quinazolin-4(3H)-one;
2-(2-((4,4-Dimethylcyclohexyl)amino)-4-methoxyphenyl)-5,7-dimethoxyquinazolin-4(3H)-one;
2-(3-((1-Isopropylpiperidin-4-yl)amino)-5-methoxypyridin-2-yl)-5,7-dimethoxyquinazolin-4(3H)-one;
2-(2-(((trans-4-(2-Hydroxypropan-2-yl)cyclohexyl)amino)-4-methoxyphenyl)-5,7-dimethoxyquinazolin-4(3H)-one;
2-(3-((1-isobutyrylpiperidin-4-yl)amino)-5-methoxypyridin-2-yl)-5,7-dimethoxyquinazolin-4(3H)-one;
2-(4-Chloro-2-((1-isopropylpiperidin-4-yl)amino)phenyl)-5,7-dimethoxyquinazolin-4(3H)-one;
2-(4-Chloro-2-((1-isobutyrylpiperidin-4-yl)amino)phenyl)-5,7-dimethoxyquinazolin-4(3H)-one;
2-(2-((1-Benzylpiperidin-4-yl)amino)-4-methoxyphenyl)-5,7-dimethoxyquinazolin-4(3H)-one;
2-(-((1-Isobutyrylpiperidin-4-yl)amino)pyridin-2-yl)-5,7-dimethoxyquinazolin-4(3H)-one;
2-(3-((1-Acetylpiperidin-4-yl)amino)pyridine-2-yl)-5,7-dimethoxyquinazolin-4(3H)-one;
N-(cis-4-((2-(5,7-Dimethoxy-4-oxo-3,4-dihydroquinazolin-2-yl)-5-methoxypyridin-3-yl)amino)cyclohexyl)isobutyramide;
2-(2-((1-Acetylpiperidin-4-yl)amino)-4-methoxyphenyl)-5,7-dimethoxyquinazolin-4(3H)-one;
5,7-Dimethoxy-2-(5-methoxy-3-((1-methylpiperidin-4-yl)amino)pyridin-2-yl)quinazolin-4(3H)-one;
5,7-Dimethoxy-2-(3-(((1-methylpyrrolidin-3-yl)methyl)amino)pyridin-2-yl)quinazolin-4(3H)-one;
4-((2-(5,7-Dimethoxy-4-oxo-3,4-dihydroquinazolin-2-yl)pyridin-3-yl)amino)-N,N-dimethylpiperidine-1-carboxamide;
2-(3-((3-(Isopropylamino)propyl)amino)pyridin-2-yl)-5,7-dimethoxyquinazolin-4(3H)-one;
5,7-Dimethoxy-2-(3-((1-dimethylpiperidin-4-yl)amino)pyridine-2-yl)quinazolin-4(3H)-one;
cis-4-((2-(5,7-Dimethoxy-4-oxo-3,4-dihydroquinazolin-2-yl)-5-methoxypyridin-3-yl)amino)-N-isopropylcyclohexane-1-carboxamide;
5,7-Dimethoxy-2-(3-((1-(2,2,2-trifluoroacetyl)piperidin-4-yl)amino)pyridin-2-yl)quinazolin-4(3H)-one;
4-((2-(5,7-Dimethoxy-4-oxo-3,4-dihydroquinazolin-2-yl)pyridin-3-yl)amino)-N-isopropylpiperidine-1-carboxamide;
5,7-Dimethoxy-2-(3-((1-pivaloylpiperidin-4-yl)amino)pyridin-2-yl)quinazolin-4(3H)-one;
5,7-Dimethoxy-2-(3-((2-morpholinoethyl)amino)pyridine-2-yl)quinazolin-4(3H)-one;
2-(3-((1-Isopropylpiperidin-4-yl)amino)-5-(2-((1-isopropylpiperidin-4-yl)amino)ethoxy)pyridin-2-yl)-5,7-dimethoxyquinazolin-4(3H)-one;
2-(4-((2-(5,7-Dimethoxy-4-oxo-3,4-dimethoxyquinazolin-2-yl)pyridin-3-yl)amino)piperidin-1-yl)-N,N-dimethyl-2-oxoacetamide;
4-((2-(5,7-dimethoxy-4-oxo-3,4-dihydroquinazolin-2-yl)pyridin-3-yl)amino)-N-ethylpiperidine-1-carboxamide;
cis-4-((2-(5,7-Dimethoxy-4-oxo-3,4-dimethoxyquinazolin-2-yl)pyridin-3-yl)amino)-N,N-dimethylcyclohexane-1-carboxamide;
4-((2-(5,7-Dimethoxy-4-oxo-3,4-dimethoxyquinazolin-2-yl)pyridin-3-yl)amino)piperidine-1-carboxamide;
Methyl-2-(4-((2-(5,7-Dimethoxy-4-oxo-3,4-dihydroquinazolin-2-yl)pyridin-3-yl)amino)piperidin-1-yl)-2-oxoacetate;
N-(2-((2-(5,7-Dimethoxy-4-oxo-3,4-dihydroquinazolin-2-yl)pyridin-3-yl)amino)ethyl)isobutyramide;
N-(3-((2-(5,7-Dimethoxy-4-oxo-3,4-dihydroquinazolin-2-yl)pyridin-3-yl)amino)propyl)isobutyramide;
2-(3-((1-Isopropylpiperidin-4-yl)amino)pyridin-2-yl)-5-methoxypyrido[3,4-d]pyrimidin-4(3H)-one;
2-(3-((1-(2-Hydroxy-2-methylpropyl)piperidin-4-yl)amino)pyridin-2-yl)-5,7-dimethoxyquinazolin-4(3H)-one;
2-(3-((1-(2-hydroxypropanoyl)piperidin-4-yl)amino)pyridin-2-yl)-5,7-dimethoxyquinazolin-4(3H)-one;
2-(3-((1-Isopropylpiperidin-4-yl)amino)pyridin-2-yl)-5-methoxy-7-((4-methoxybenzyl)amino)quinazolin-4(3H)-one;
2-[5-(2-Hydroxyethoxy)-3-(1-isopropylpiperidin-4-ylamino)pyridin-2-yl]-5,7-dimethoxyquinazolin-4(3H)-one;
cis-4-((2-(5,7-Dimethoxy-4-oxo-3,4-dihydroquinazolin-2-yl)pyridin-3-yl)amino)-N-isopropylcyclohexane-1-carboxamide;

2-[5-(2-Hydroxyethoxy)-3-(1-isobutyroylpiperidin-4-ylamino)pyridin-2-yl]-5,7-dimethoxyquinazolin-4(3H)-one;

7-amino-2-(3-((1-Isopropylpiperidin-4-yl)amino)pyridin-2-yl)-5-methoxyquinazolin-4(3H)-one;

2-{3-(1-Isopropylpiperidin-4-ylamino)-5-[2-(pyrrolidin-1-yl)ethoxy]pyridin-2-yl}-5,7-dimethoxyquinazolin-4(3H)-one;

2-{5-[2-(Isopropylamino)ethoxy]-3-(1-isopropylpiperidin-4-ylamino)pyridin-2-yl}-5,7-dimethoxyquinazolin-4(3H)-one;

2-(3-((1-(1-Hydroxy-2-methylpropan-2-yl)piperidin-4-yl)amino)pyridin-2-yl)-5,7-dimethoxyquinazolin-4(3H)-one; and 7-(Ethylamino)-2-(3-((1-isopropylpiperidin-4-yl)amino)pyridin-2-yl)-5,7-dimethoxyquinazolin-4(3H)-one;

or a stereoisomer, tautomer, pharmaceutically acceptable salt, or hydrate thereof.

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formula I or Formula Ia.

In one embodiment, because of potent effects of BET inhibitors in vitro on IL-6 and IL-17 transcription, BET inhibitor compounds of Formula I or Formula Ia may be used as therapeutics for inflammatory disorders in which IL-6 and/or IL-17 have been implicated in disease. The following autoimmune diseases are amenable to therapeutic use of BET inhibition by administration of a compound of Formula I or Formula Ia or a stereoisomer, tautomer, pharmaceutically acceptable salt, or hydrate thereof because of a prominent role of IL-6 and/or IL-17: Acute Disseminated Encephalomyelitis (T. Ishizu et al., "CSF cytokine and chemokine profiles in acute disseminated encephalomyelitis," *J Neuroimmunol* 175(1-2): 52-8 (2006)), Agammaglobulinemia (M. Gonzalez-Serrano, et al., "Increased Pro-inflammatory Cytokine Production After Lipopolysaccharide Stimulation in Patients with X-linked Agammaglobulinemia," *J Clin Immunol* 32(5):967-74 (2012)), Allergic Disease (L. McKinley et al., "TH17 cells mediate steroid-resistant airway inflammation and airway hyperresponsiveness in mice," *J Immunol* 181(6):4089-97 (2008)), Ankylosing spondylitis (A. Taylan et al., "Evaluation of the T helper 17 axis in ankylosing spondylitis," *Rheumatol Int* 32(8):2511-5 (2012)), Anti-GBM/Anti-TBM nephritis (Y. Ito et al., "Pathogenic significance of interleukin-6 in a patient with antiglomerular basement membrane antibody-induced glomerulonephritis with multinucleated giant cells," *Am J Kidney Dis* 26(1):72-9 (1995)), Anti-phospholipid syndrome (P. Soltesz et al., "Immunological features of primary anti-phospholipid syndrome in connection with endothelial dysfunction," *Rheumatology* (Oxford) 47(11):1628-34 (2008)), Autoimmune aplastic anemia (Y. Gu et al., "Interleukin (IL)-17 promotes macrophages to produce IL-8, IL-6 and tumour necrosis factor-alpha in aplastic anaemia," *Br J Haematol* 142(1):109-14 (2008)), Autoimmune hepatitis (L. Zhao et al., "Interleukin-17 contributes to the pathogenesis of autoimmune hepatitis through inducing hepatic interleukin-6 expression," *PLoS One* 6(4): e18909 (2011)), Autoimmune inner ear disease (B. Gloddek et al., "Pharmacological influence on inner ear endothelial cells in relation to the pathogenesis of sensorineural hearing loss," *Adv Otorhinolaryngol* 59:75-83 (2002)), Autoimmune myocarditis (T. Yamashita et al., "IL-6-mediated Th17 differentiation through RORgammat is essential for the initiation of experimental autoimmune myocarditis," *Cardiovasc Res* 91(4):640-8 (2011)), Autoimmune pancreatitis (J. Ni et al., "Involvement of Interleukin-17A in Pancreatic Damage in Rat Experimental Acute Necrotizing Pancreatitis," *Inflammation* (2012)), Autoimmune retinopathy (S. Hohki et al., "Blockade of interleukin-6 signaling suppresses experimental autoimmune uveoretinitis by the inhibition of inflammatory Th17 responses," *Exp Eye Res* 91(2):162-70 (2010)), Autoimmune thrombocytopenic purpura (D. Ma et al., "Profile of Th7 cytokines (IL-17, TGF-beta, IL-6) and Th1 cytokine (IFN-gamma) in patients with immune thrombocytopenic purpura," *Ann Hematol* 87(11):899-904 (2008)), Behcet's Disease (T. Yoshimura et al., "Involvement of Th17 cells and the effect of anti-IL-6 therapy in autoimmune uveitis," *Rheumatology* (Oxford) 48(4):347-54 (2009)), Bullous pemphigoid (L. D'Auria et al., "Cytokines and bullous pemphigoid," *Eur Cytokine Netw* 10(2):123-34 (1999)), Castleman's Disease (H. El-Osta and R. Kurzrock, "Castleman's disease: from basic mechanisms to molecular therapeutics," *Oncologist* 16(4):497-511 (2011)), Celiac Disease (A. Lahdenpera et al., "Up-regulation of small intestinal interleukin-17 immunity in untreated coeliac disease but not in potential coeliac disease or in type I diabetes," *Clin Exp Immunol* 167(2):226-34 (2012)), Churg-Strauss syndrome (A. Fujioka et al., "The analysis of mRNA expression of cytokines from skin lesions in Churg-Strauss syndrome," *J Dermatol* 25(3):171-7 (1998)), Crohn's Disease (V. Holtta et al., "IL-23/IL-17 immunity as a hallmark of Crohn's disease," *Inflamm Bowel Dis* 14(9):1175-84 (2008)), Cogan's syndrome (M. Shibuya et al., "Successful treatment with tocilizumab in a case of Cogan's syndrome complicated with aortitis," *Mod Rheumatol* (2012)), Dry eye syndrome (C. De Paiva et al., "IL-17 disrupts corneal barrier following desiccating stress," *Mucosal Immunol* 2(3):243-53 (2009)), Essential mixed cryoglobulinemia (A. Antonelli et al., "Serum levels of proinflammatory cytokines interleukin-1beta, interleukin-6, and tumor necrosis factor alpha in mixed cryoglobulinemnia," *Arthritis Rheum* 60(12):3841-7 (2009)), Dermatomyositis (G. Chevrel et al., "Interleukin-17 increases the effects of IL-1 beta on muscle cells: arguments for the role of T cells in the pathogenesis of myositis," *J Neuroimmunol* 137(1-2):125-33 (2003)), Devic's Disease (U. Linhares et al., "The Ex Vivo Production of IL-6 and IL-21 by CD4(+) T Cells is Directly Associated with Neurological Disability in Neuromyelitis Optica Patients," *J Clin Immunol* (2012)), Encephalitis (D. Kyburz and M. Corr. "Th17 cells generated in the absence of TGF-beta induce experimental allergic encephalitis upon adoptive transfer," *Expert Rev Clin Immunol* 7(3):283-5 (2011)), Eosinophlic esophagitis (P. Dias and G. Banerjee, "The Role of Th17/IL-17 on Eosinophilic Inflammation," *J Autoimmun* (2012)), Eosinophilic fasciitis (P. Dias and G. Banerjee, *J Autoimmun* (2012)), Erythema nodosum (I. Kahawita and D. Lockwood, "Towards understanding the pathology of erythema nodosum leprosum," *Trans R Soc Trop Med Hyg* 102(4):329-37 (2008)), Giant cell arteritis (J. Deng et al., "Th17 and Th1 T-cell responses in giant cell arteritis," *Circulation* 121(7): 906-15 (2010)), Glomerulonephritis (J. Ooi et al., "Review: T helper 17 cells: their role in glomerulonephritis," *Nephrology* (Carlton) 15(5):513-21 (2010)), Goodpasture's syndrome (Y. Ito et al., "Pathogenic significance of interleukin-6 in a patient with antiglomerular basement membrane antibody-induced glomerulonephritis with multinucleated giant cells," *Am J Kidney Dis* 26(1):72-9 (1995)), Giranulomatosis with Polyangiitis (Wegener's) (H. Nakahama et al., "Distinct responses of interleukin-6 and other laboratory parameters to treatment in a patient with Wegener's granulomatosis," *Intern Med* 32(2):189-92 (1993)), Graves' Disease (S. Kim et al., "Increased serum interleukin-17 in Graves' ophthalmopathy," *Graefes Arch Clin Exp Ophthalmol* 250(10):1521-6 (2012)), Guillain-Barre syndrome (M. Lu and J. Zhu, "The role of cytokines in Guillain-Barre syndrome," *J Neurol* 258(4):533-48 (2011)), Hashimoto's thyroiditis (N. Figueroa-Vega et al., "Increased circulating pro-inflammatory cytokines and Th17 lymphocytes in Hashimoto's thyroiditis," *J Clin Endocrinol Metab* 95(2):953-62 (2009)), Hemolytic anemia (L. Xu et al., "Critical role of Th17 cells in development of autoimmune hemolytic anemia," *Exp Hematol* (2012)), Henoch-Schonlein purpura (H. Jen et al., "Increased serum interleukin-17 and peripheral Th17 cells in children with acute Henoch-Schonlein purpura," *Pediatr Allergy Immunol* 22(8):862-8 (2011)), IgA nephropathy (F. Lin et al., "Imbalance of regulatory T cells to Th17 cells in IgA nephropathy," *Scand J Clin Lab Invest* 72(3):221-9 (2012)), Inclusion body myositis (P. Baron et al., "Production of IL-6 by human myoblasts stimulated with Abeta: relevance in the pathogenesis of IBM," *Neurology* 57(9):1561-5 (2001)), Type I diabetes (A. Belkina and G. Denis, *Nat Rev Cancer* 12(7):465-77 (2012)), Interstitial cystitis (L. Lamale et al., "Interleukin-6, histamine, and methylhistamine as diagnostic markers for interstitial cystitis," *Urology* 68(4):702-6 (2006)), Kawasaki's Disease (S. Jia et al., "The T helper type 17/regulatory T cell imbalance in patients with acute Kawasaki disease," *Clin Exp Immunol* 162(1):131-7 (2010)), Leukocytoclastic vasculitis (Min, C. K., et al., "Cutaneous leucoclastic vasculitis (LV) following bortezomib therapy in a myeloma patient; association with pro-inflammatory cytokines," *Eur J Haematol* 76(3):265-8 (2006)), Lichen planus (N. Rhodus et al., "Proinflammatory cytokine levels in saliva before and after treatment of (erosive) oral lichen planus with dexamethasone," *Oral Dis* 12(2):112-6 (2006)), Lupus (SLE) (M. Mok et al., "The relation of interleukin 17 (IL-17) and IL-23 to Th1/Th2 cytokines and disease activity in systemic lupus erythematosus," *J Rheumatol* 37(10):2046-52 (2010)), Microscopic polyangitis (A. Muller Kobold et al., "In vitro up-regulation of E-selectin and induction of interleukin-6 in endothelial cells by autoantibodies in Wegener's granulomatosis and microscopic polyangiitis," *Clin Exp Rheumatol* 17(4):433-40 (1999)), Multiple sclerosis (F. Jadidi-Niaragh and A. Mirshafiey, "Th17 cell, the new player of neuroinflammatory process in multiple sclerosis," *Scand J Immunol* 74(1):1-13 (2011)), Myasthenia gravis (R. Aricha et al., "Blocking of IL-6 suppresses experimental autoimmune myasthenia gravis," *J Autoimmun* 36(2):135-41 (2011)), myositis (G. Chevrel et al., "Interleukin-17 increases the effects of IL-1 beta on muscle cells: arguments for the role of T cells in the pathogenesis of myositis," *J Neuroimmunol* 137(1-2):125-33 (2003)). Optic neuritis (S. Icoz et al., "Enhanced IL-6 production in aquaporin-4 antibody positive neuromyelitis optica patients," *Int J Neurosci* 120(1):71-5 (2010)), Pemphigus (E. Lopez-Robles et al., "TNFalpha and IL-6 are mediators in the blistering process of pemphigus," *Int J Dermatol* 40(3):185-8 (2001)), POEMS syndrome (K. Kallen et al., "New developments in IL-6 dependent biology and therapy: where do we stand and what are the options?" *Expert Opin Investig Drugs* 8(9):1327-49 (1999)), Polyarteritis nodosa (T. Kawakami et al., "Serum levels of interleukin-6 in patients with cutaneous polyarteritis nodosa," *Acta Derm Venereal* 92(3):322-3 (2012)), Primary biliary cirrhosis (K. Harada et al., "Periductal interleukin-17 production in association with biliary innate immunity contributes to the pathogenesis of cholangiopathy in primary biliary cirrhosis," *Clin Exp Immunol* 157(2):261-70 (2009)), Psoriasis (S. Fujishima et al., "Involvement of IL-17F via the induction of IL-6 in psoriasis," *Arch Dermatol Res* 302(7):499-505 (2010)). Psoriatic arthritis (S. Raychaudhuri et al., IL-17 receptor and its functional significance in psoriatic arthritis," *Mol Cell Biochem* 359(1-2):419-29 (2012)), Pyoderma gangrenosum (T. Kawakami et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis," *Am J Gastroenterol* 104(9):2363-4 (2009)), Relapsing polychondritis (M. Kawai et al., "Sustained response to tocilizumab, anti-interleukin-6 receptor antibody, in two patients with refractory relapsing polychondritis," *Rheumatology (Oxford)* 48(3):318-9 (2009)), Rheumatoid arthritis (Z. Ash and P. Emery, "The role of tocilizumab in the management of rheumatoid arthritis," *Expert Opin Biol Ther,* 12(9):1277-89 (2012)), Sarcoidosis (F. Belli et al., "Cytokines assay in peripheral blood and bronchoalveolar lavage in the diagnosis and staging of pulmonary granulomatous diseases," *Int J Immunopathol Pharmacol* 13(2):61-67 (2000)), Scleroderma (T. Radstake et al., "The pronounced Th17 profile in systemic sclerosis (SSc) together with intracellular expression of TGFbeta and IFNgamma distinguishes SSc phenotypes," *PLoS One,* 4(6): e5903 (2009)), Sjogren's syndrome (G. Katsifis et al., "*Systemic and local interleukin-17 and linked cytokines associated with Sjogren's syndrome immunopathogenesis,*" *Am J Pathol* 175(3):1167-77 (2009)), Takayasu's arteritis (Y. Sun et al., "MMP-9 and IL-6 are potential biomarkers for disease activity in Takayasu's arteritis," *Int J Cardiol* 156(2):236-8 (2012)), Transverse myelitis (J. Graber et al., "Interleukin-17 in transverse myelitis and multiple sclerosis," *J Neuroimmunol* 196(1-2):124-32 (2008)), Ulcerative colitis (J. Mudter and M. Neurath, "Il-6 signaling in inflammatory bowel disease: pathophysiological role and clinical relevance," *Inflamm Bowel Dis* 13(8):1016-23 (2007)), Uveitis (H. Haruta et al., "Blockade of interleukin-6 signaling suppresses not only th17 but also interphotoreceptor retinoid binding protein-specific Th1 by promoting regulatory T cells in experimental autoimmune uveoretinitis," *Invest Ophthalmol Vis Sci* 52(6):3264-71 (2011)), and Vitiligo (D. Bassiouny and O. Shaker, "Role of interleukin-17 in the pathogenesis of vitiligo," *Clin Exp Dermatol* 36(3):292-7 115. (2011)). Thus, the invention includes compounds of Formula I or Formula Ia, stereoisomers, tautomers, pharmaceutically acceptable salts, or hydrates thereof; pharmaceutical compositions comprising one or more of those compounds; and methods of using those compounds or compositions for treating these diseases.

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis (D. Bradley and S. Kountakis, "Role of interleukins and transforming growth factor-beta in chronic rhinosinusitis and nasal polyposis," *Laryngoscope* 115(4):684-6 (2005)), pneumonitis (Besnard, A. G., et al., "*Inflammasome-IL-1-Th17 response in allergic lung inflammation*" *J Mol Cell Biol* 4(1):3-10 (2012)), osteomyelitis (T. Yoshii et al., "Local levels of interleukin-1beta, -4, -6 and tumor necrosis factor alpha in an experimental model of murine osteomyelitis due to *staphylococcus aureus,*" *Cytokine* 19(2):59-65 2002), gastritis (T. Bayraktaroglu et al., "Serum levels of tumor necrosis factor-alpha, interleukin-6 and interleukin-8 are not increased in dyspeptic patients with *Helicobacter pylori*-associated gastritis,"

*Mediators Inflamm* 13(1):25-8 (2004)), enteritis (K. Mitsuyama et al., "STAT3 activation via interleukin 6 trans-signalling contributes to ileitis in SAMP1/Yit mice," *Gut* 55(9):1263-9. (2006)), gingivitis (R. Johnson et al., "Interleukin-11 and IL-17 and the pathogenesis of periodontal disease," *J Periodontol* 75(1):37-43 (2004)), appendicitis (S. Latifi et al., "Persistent elevation of serum interleukin-6 in intraabdominal sepsis identifies those with prolonged length of stay," *J Pediatr Surg* 39(10):1548-52 (2004)), irritable bowel syndrome (M. Ortiz-Lucas et al., "Irritable bowel syndrome immune hypothesis. Part two: the role of cytokines," *Rev Esp Enferm Dig* 102(12):711-7 (2010)), tissue graft rejection (L. Kappel et al., "IL-17 contributes to CD4-mediated graft-versus-host disease," *Blood* 113(4): 945-52 (2009)), chronic obstructive pulmonary disease (COPD) (S. Traves and L. Donnelly, "Th17 cells in airway diseases," *Curr Mol Med* 8(5):416-26 (2008)), septic shock (toxic shock syndrome, SIRS, bacterial sepsis, etc) (E. Nicodeme et al., *Nature* 468(7327):1119-23 (2010)), osteoarthritis (L. Chen et al., "IL-17RA aptamer-mediated repression of IL-6 inhibits synovium inflammation in a murine model of osteoarthritis." *Osteoarthritis Cartilage* 19(6):711-8 (2011)), acute gout (W. Urano et al., "The inflammatory process in the mechanism of decreased serum uric acid concentrations during acute gouty arthritis," *J Rheumatol* 29(9):1950-3 (2002)), acute lung injury (S. Traves and L. Donnelly, "Th17 cells in airway diseases," *Curr Mol Med* 8(5):416-26 (2008)), acute renal failure (E. Simmons et al., "Plasma cytokine levels predict mortality in patients with acute renal failure," *Kidney Int* 65(4):1357-65 (2004)), burns (P. Paquet and G. Pierard, "Interleukin-6 and the skin," *Int Arch Allergy Immunol* 109(4):308-17 (1996)), Herxheimer reaction (G. Kaplanski et al., "Jarisch-Herxheimer reaction complicating the treatment of chronic Q fever endocarditis: elevated TNFalpha and IL-6 serum levels," *J Infect* 37(1):83-4 (1998)), and SIRS associated with viral infections (A. Belkinaand G. Denis, *Nat Rev Cancer* 12(7):465-77 (2012)). Thus, the invention includes compounds of Formula I or Formula Ia, stereoisomers, tautomers, pharmaceutically acceptable salts, or hydrates thereof; pharmaceutical compositions comprising one or more of those compounds; and methods of using those compounds or compositions for treating these diseases.

In one embodiment, BET inhibitor compounds of Formula I or Formula Ia, stereoisomers, tautomers, pharmaceutically acceptable salts, or hydrates thereof, or compositions comprising one or more of those compounds may be used for treating rheumatoid arthritis (RA) and multiple sclerosis (MS). Strong proprietary data exist for the utility of BET inhibitors in preclinical models of RA and MS. R. Jahagirdar et al., "An Orally Bioavailable Small Molecule RVX-297 Significantly Decreases Disease in a Mouse Model of Multiple Sclerosis," *World Congress of Inflammation*, Paris, France (2011). Both RA and MS are characterized by a dysregulation of the IL-6 and IL-17 inflammatory pathways (A. Kimura and T. Kishimoto, "IL-6: regulator of Treg/Th17 balance," *Eur J Immunol* 40(7):1830-5 (2010)) and thus would be especially sensitive to BET inhibition. In another embodiment, BET inhibitor compounds of Formula I or Formula Ia may be used for treating sepsis and associated afflictions. BET inhibition has been shown to inhibit development of sepsis, in part, by inhibiting IL-6 expression, in preclinical models in both published (E. Nicodeme et al., *Nature* 468(7327):1119-23 (2010)) and proprietary data.

In one embodiment, BET inhibitor compounds of Formula I or Formula Ia, stereoisomers, tautomers, pharmaceutically acceptable salts, or hydrates thereof, or compositions comprising one or more of those compounds may be used to treat cancer. Cancers that have an overexpression, translocation, amplification, or rearrangement c-myc or other myc family oncoproteins (MYCN, L-myc) are particularly sensitive to BET inhibition. J. Delmore et al., *Cell* 146(6):904-17 (2010); J. Mertz et al., *Proc Natl Acad Sci USA* 108(40): 16669-74 (2011). These cancers include, but are not limited to, B-acute lymphocytic leukemia, Burkitt's lymphoma. Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma. M. Vita and M. Henriksson, *Semin Cancer Biol* 16(4):318-30 (2006).

In one embodiment, BET inhibitor compounds of Formula I or Formula Ia, stereoisomers, tautomers, pharmaceutically acceptable salts, or hydrates thereof, or compositions comprising one or more of those compounds may be used to treat cancers that result from an aberrant regulation (overexpression, translocation, etc) of BET proteins. These include, but are not limited to, NUT midline carcinoma (Brd3 or Brd4 translocation to nutlin 1 gene) (C. French *Cancer Genet Cytogenet* 203(1):16-20 (2010)), B-cell lymphoma (Brd2 overexpression) (R. Greenwald et al., *Blood* 103(4):1475-84 (2004)), non-small cell lung cancer (BrdT overexpression) (C. Grunwald et al., "Expression of multiple epigenetically regulated cancer/germline genes in nonsmall cell lung cancer," *Int J Cancer* 118(10):2522-8 (2006)), esophageal cancer and head and neck squamous cell carcinoma (BrdT overexpression) (M. Scanlan et al., "Expression of cancer-testis antigens in lung cancer: definition of bromodomain testis-specific gene (BRDT) as a new CT gene, CT9," *Cancer Lett* 150(2):55-64 (2000)), and colon cancer (Brd4) (R. Rodriguez et al., "Aberrant epigenetic regulation of bromodomain BRD4 in human colon cancer," *J Mol Med (Berl)* 90(5):587-95 (2012)).

In one embodiment, because BET inhibitors decrease Brd-dependent recruitment of pTEFb to genes involved in cell proliferation, BET inhibitor compounds of Formula I or Formula Ia, stereoisomers, tautomers, pharmaceutically acceptable salts, or hydrates thereof, or compositions comprising one or more of those compounds may be used to treat cancers that rely on pTEFb (Cdk9/cyclin T) and BET proteins to regulate oncogenes. These cancers include, but are not limited to, chronic lymphocytic leukemia and multiple myeloma (W. Tong et al., "Phase I and pharmacologic study of SNS-032, a potent and selective Cdk2, 7, and 9 inhibitor, in patients with advanced chronic lymphocytic leukemia and multiple myeloma," *J Clin Oncol* 28(18): 3015-22 (2010)), follicular lymphoma, diffuse large B cell lymphoma with germinal center phenotype, Burkitt's lymphoma, Hodgkin's lymphoma, follicular lymphomas and activated, anaplastic large cell lymphoma (C. Bellan et al., "CDK9/CYCLIN T1 expression during normal lymphoid differentiation and malignant transformation," *J Pathol* 203 (4):946-52 (2004)), neuroblastoma and primary neuroectodermal tumor (G. De Falco et al., "Cdk9 regulates neural differentiation and its expression correlates with the differentiation grade of neuroblastoma and PNET tumors," *Cancer Biol Ther* 4(3):277-81 (2005)), rhabdomyosarcoma (C. Simone and A. Giordano, "Abrogation of signal-dependent activation of the cdk9/cyclin T2a complex in human RD rhabdomyosarcoma cells," *Cell Death Differ* 14(1):192-5 (2007)), prostate cancer (D. Lee et al., "Androgen receptor interacts with the positive elongation factor P-TEFb and enhances the efficiency of transcriptional elongation," *J Biol Chem* 276(13):9978-84 (2001)), and breast cancer (K. Bartholomecusen et al., "BET bromodomain inhibition activates transcription via a transient release of P-TEFb from 7SK snRNP," *J Biol Chem* (2012)).

In one embodiment, BET inhibitor compounds of Formula I or Formula Ia, stereoisomers, tautomers, pharmaceutically acceptable salts, or hydrates thereof, or compositions comprising one or more of those compounds may be used to treat cancers in which BET-responsive genes, such as CDK6, Bcl2, TYRO3, MYB, and hTERT are up-regulated. M. Dawson et al., *Nature* 478(7370):529-33 (2011); J. Delmore et al., *Cell* 146(6):904-17 (2010). These cancers include, but are not limited to, pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma. M. Ruden and N. Puri, "Novel anticancer therapeutics targeting telomerase," *Cancer Treat Rev* (2012); P. Kelly and A. Strasser, "The role of Bcl-2 and its pro-survival relatives in tumourigenesis and cancer therapy" *Cell Death Differ* 18(9):1414-24 (2011); T. Uchida et al., "Antitumor effect of bcl-2 antisense phosphorothioate oligodeoxynucleotides on human renal-cell carcinoma cells in vitro and in mice," *Mol Urol* 5(2):71-8 (2001).

Published and proprietary data have shown direct effects of BET inhibition on cell proliferation in various cancers. In one embodiment, BET inhibitor compounds of Formula I or Formula Ia, stereoisomers, tautomers, pharmaceutically acceptable salts, or hydrates thereof, or compositions comprising one or more of those compounds may be used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), and non-Hodgkin's lymphoma. P. Filippakopoulos et al., *Nature* 468(7327):1067-73 (2010); M. Dawson et al., *Nature* 478(7370):529-33 (2011); Zuber, J., et al., "RNAi screen identifies Brd4 as a therapeutic target in acute myeloid leukaemia," *Nature* 478(7370):524-8 (2011); M. Segura, et al. *Cancer Research*. 72(8):Supplement 1 (2012). The compounds of the invention have a demonstrated BET inhibition effect on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formula I or Formula Ia, stereoisomers, tautomers, pharmaceutically acceptable salts, or hydrates thereof, or compositions comprising one or more of those compounds may be combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vernurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

In one embodiment, BET inhibitor compounds of Formula I or Formula Ia, stereoisomers, tautomers, pharmaceutically acceptable salts, or hydrates thereof, or compositions comprising one or more of those compounds may be used to treat benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. X. Tang et al., *Am J Pathology* in press (2013).

In one embodiment, because of their ability to up-regulate ApoA-1 transcription and protein expression (O. Mirguet et al., *Bioorg Med Chem Lett* 22(8):2963-7 (2012); C. Chung et al., *J Med Chem* 54(11):3827-38 (2011)), BET inhibitor compounds of Formula I or Formula Ia, stereoisomers, tautomers, pharmaceutically acceptable salts, or hydrates thereof, or compositions comprising one or more of those compounds may be used to treat cardiovascular diseases that are generally associated with including dyslipidemia, atherosclerosis, hypercholesterolemia, and metabolic syndrome (A. Belkina and G. Denis, *Nat Rev Cancer* 12(7):465-77 (2012); G. Denis *Discov Med* 10(55):489-99 (2010)). In another embodiment, BET inhibitor compounds of Formula I or Formula Ia may be used to treat non-cardiovascular disease characterized by deficits in ApoA-1, including Alzheimer's disease. D. Elliott et al., *Clin Lipidol* 51(4): 555-573 (2010).

In one embodiment, BET inhibitor compounds of Formula I or Formula Ia, stereoisomers, tautomers, pharmaceutically acceptable salts, or hydrates thereof, or compositions comprising one or more of those compounds may be used in patients with insulin resistance and type II diabetes. A. Belkina and G. Denis, *Nat Rev Cancer* 12(7):465-77 (2012); G. Denis *Discov Med* 10(55):489-99 (2010); F. Wang et al., *Biochem J* 425(1):71-83 (2010); G. Denis et al, *FEBS Lett* 584(15):3260-8 (2010). The anti-inflammatory effects of BET inhibition would have additional value in decreasing inflammation associated with diabetes and metabolic disease. K. Alexandraki et al., "Inflammatory process in type 2 diabetes: The role of cytokines," *Ann N Y Acad Sci* 1084: 89-117 (2006).

In one embodiment, because of their ability to down-regulate viral promoters, BET inhibitor compounds of Formula I or Formula Ia, stereoisomers, tautomers, pharmaceutically acceptable salts, or hydrates thereof, or compositions comprising one or more of those compounds may be used as therapeutics for cancers that are associated with viruses including Epstein-Barr Virus (EBV), hepatitis virus (HBV, HCV). Kaposi's sarcoma associated virus (KSHV), human papilloma virus (HPV), Merkel cell polyomavirus, and human cytomegalovirus (CMV). D. Gagnon et al., *J Virol* 83(9):4127-39 (2009); J. You et al., *J Virol* 80(18):8909-19 (2006); R. Palermo et al., "RNA polymerase II stalling promotes nucleosome occlusion and pTEFb recruitment to drive immortalization by Epstein-Barr virus," *PLoS Pathog* 7(10):e1002334 (2011); E. Poreba et al., "Epigenetic mechanisms in virus-induced tumorigenesis," *Clin Epigenetics* 2(2):233-47. 2011. In another embodiment, because of their ability to reactivate HIV-1 in models of latent T cell infection and latent monocyte infection, BET inhibitors could be used in combination with anti-retroviral therapeutics for treating HIV. J. Zhu, et al., *Cell Rep* (2012); C. Banerjee et al., *J Leukoc Biol* (2012); K. Bartholomeeusen et al., *J Biol Chem* (2012); Z. Li et al., *Nucleic Acids Res* (2012.)

In one embodiment, because of the role of epigenetic processes and bromodomain-containing proteins in neurological disorders, BET inhibitor compounds of Formula I or Formula Ia, stereoisomers, tautomers, pharmaceutically acceptable salts, or hydrates thereof, or compositions comprising one or more of those compounds may be used to treat diseases including, but not limited to, Alzheimer's disease, Parkinson's disease, Huntington disease, bipolar disorder, schizophrenia, Rubinstein-Taybi syndrome, and epilepsy. R. Prinjha et al., *Trends Pharmacol Sci* 33(3):146-53 (2012); S. Muller et al., "Bromodomains as therapeutic targets," *Expert Rev Mol Med* 13:e29 (2011).

In one embodiment, because of the effect of BRDT depletion or inhibition on spermatid development, BET inhibitor compounds of Formula I or Formula Ia, stereoisomers, tautomers, pharmaceutically acceptable salts, or hydrates thereof, or compositions comprising one or more of those compounds may be used as reversible, male contraceptive agents. M. Matzuk et al., "Small-Molecule Inhibition of BRDT for Male Contraception," *Cell* 150(4): p. 673-684 (2012); B. Berkovits et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012).

Pharmaceutical Compositions

Pharmaceutical compositions of the present disclosure comprise at least one compound of Formula I or Formula Ia, or a tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula I or Formula Ia or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I or Formula Ia or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and Table 1 for Equivalent Surface Area Dosage Factors).

TABLE 1

Equivalent Surface Area Dosage Factors:

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I or Formula Ia or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I or Formula Ia or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

EXAMPLES

Example 1: 5,7-Dimethoxy-2-(4-methoxy-2-((1-methylpiperidin-4-yl)amino)phenyl)-quinazolin-4(3H)-one

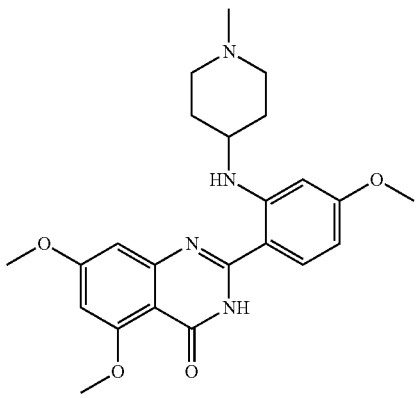

To a solution of 2-fluoro-4-methoxybenzaldehyde (5.0 g, 25.3 mmol) and 2-amino-4,6-dimethoxybenzamide (3.9 g, 25.3 mmol) in N,N-dimethylacetamide (100 mL) was added NaHSO$_3$ (58.5% SO$_2$ content, 6.8 g, 38.1 mmol) followed by p-toluenesulfonic acid monohydrate (0.97 g, 5.1 mmol). The resulting mixture was heated at 120° C. for 18 h. After that time the reaction was cooled to rt and poured onto ice. The precipitated solids were collected by filtration, washed with water and dried under vacuum to give 2-(2-fluoro-4-methoxyphenyl)-5,7-dimethoxyquinazolin-4(3H)-one (4.8 g, 57%) as an off-white solid: $^1$H NMR (400 MHz, DMSO-d$_6$) δ 11.89 (br s, 1H), 7.71 (t, J=8.6 Hz, 1H), 6.99 (dd, J=12.9, 2.3 Hz, 1H), 6.92 (dd, J=8.8, 2.5 Hz, 1H), 6.72 (d, J=2.3 Hz, 1H), 6.55 (d, J=2.3 Hz, 1H), 3.88 (s, 3H), 3.86 (s, 6H); ESI MS m/z 331 [M+H]$^+$.

To a suspension of 2-(2-fluoro-4-methoxyphenyl)-5,7-dimethoxyquinazolin-4(3H)-one (1.0 g, 3 mmol) and 1-methylpiperidin-4-amine (0.38 g, 3.3 mmol) in THF (25 mL) was added lithium bis(trimethylsilyl)amide (1 M in THF, 6 mL, 6 mmol). The reaction mixture was heated at reflux with stirring for 18 h. After that time a second portion of lithium bis(trimethylsilyl)amide (1 M in THF, 6 mL, 6 mmol) was added and reflux with stirring was continued for an additional 18 h. After that time the reaction was cooled to rt, diluted with cold water (25 mL) and concentrated under reduced pressure. The precipitated solids were collected by filtration and dried. The product was purified by flash column chromatography (silica gel, 99:1 dichloromethane/methanol to 90:10 dichloromethane/methanol) to give 5,7-dimethoxy-2-(4-methoxy-2-((1-methylpiperidin-4-yl)amino)phenyl)quinazolin-4(3H)-one (0.052 g, 4%) as an off-white solid: mp 252-253° C., $^1$H NMR (400 MHz, DMSO-d$_6$) δ 11.51 (br s, 1H), 9.50 (d, J=7.4 Hz, 1H), 7.83 (d, J=8.6 Hz, 1H), 6.58 (d, J=1.95 Hz, 1H), 6.51 (d, J=2.3 Hz, 1H), 6.16-6.26 (m, 2H), 3.89 (s, 3H), 3.85 (s, 3H), 3.79 (s, 3H), 3.48-3.61 (m, 1H), 2.55-2.66 (m, 2H), 2.24-2.37 (m, 2H), 2.20 (s, 3H), 1.93-2.02 (m, 2H), 1.52-1.66 (m, 2H); ESI MS m/z 425 [M+H]$^+$.

Example 2: 5,7-Dimethoxy-2-(4-methoxy-2-(4-methylpiperazine-1-carbonyl)phenyl) quinazolin-4(3H)-one

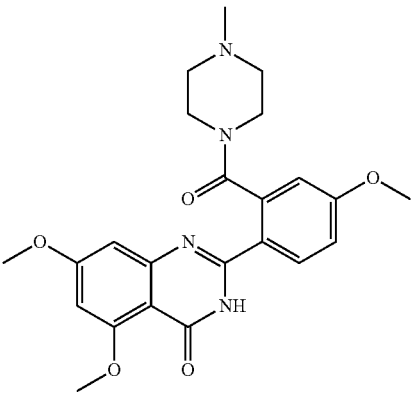

POCl$_3$ (1.02 g, 6.66 mmol) was added to a solution of 2-formyl-5-methoxybenzoic acid (1.0 g, 5.55 mmol) in anhydrous pyridine (20 mL) at 0° C. and stirred for 30 min. After that time 1-methyl piperazine (0.556 g, 5.55 mmol) was added. The reaction was allowed to warm to rt and stir for 16 h. After that time the reaction was concentrated under reduced pressure, diluted with water and made basic with aqueous Na$_2$CO$_3$. The mixture was extracted with ethyl acetate (3×200 mL). The combined organic layers were washed with saturated NaH—CO$_3$ solution, water, brine, dried over Na$_2$SO$_4$ and concentrated to give 4-methoxy-2-(4-methylpiperazine-1-carbonyl) benzaldehyde as yellow solid (1.0 g, 68%): $^1$H NMR (400 MHz, CDCl$_3$) δ 9.86 (s, 1H), 7.82 (d, J=8.6 Hz, 1H), 6.95 (dd, J=8.6, 1.95 Hz, 1H), 6.76 (d, J=2.3 Hz, 1H), 3.66-3.87 (m, 5H), 3.11-3.18 (m, 2H), 2.46 (br s, 2H), 2.16-2.28 (m, 5H).

To a solution of 4-methoxy-2-(4-methylpiperazine-1-carbonyl)benzaldehyde (1.0 g, 3.81 mmol) and 2-amino-4,6-dimethoxybenzamide (0.748 g, 3.81 mmol) in N,N-dimethyl acetamide (40 mL), were added NaHSO$_3$ (1.03 g, 5.72 mmol) and p-toluenesulfonic acid monohydrate (0.871 g, 4.58 mmol). The reaction was heated at 120° C. for 16 h. After that time the mixture was cooled to rt, concentrated under reduced pressure, diluted with water (100 mL) and made basic with Na$_2$CO$_3$. The water was removed by lyophilization and the residue was extracted with 3% methanol in dichloromethane (2×250 mL). The solvent was evaporated under reduced pressure and the residue was purified by flash column chromatography (silica gel, 97:3 dichloromethane/methanol) to give 5,7-dimethoxy-2-(4-methoxy-2-(4-methylpiperazine-1-carbonyl)phenyl)quinazolin-4(3H)-one as light yellow solid (0.140 g, 8%): mp 215° C. dec.; $^1$H NMR (400 MHz, CDCl$_3$) δ 9.84 (br s, 1H), 7.91 (d, J=8.6 Hz, 1H), 7.04 (dd, J=8.8, 2.5 Hz, 1H), 6.86 (d, J=2.3 Hz, 1H), 6.72 (d, J=2.3 Hz, 1H), 6.45 (d, J=1.95 Hz, 1H), 3.96 (s, 3H), 3.90 (s, 3H), 3.88 (s, 3H), 3.80 (br s, 2H), 3.23 (br s, 2H), 2.43 (br s, 2H), 2.19 (s, 3H), 1.67 (br s, 2H); ESI MS m/z 439 [M+H]$^+$.

Example 3: 2-(2-((1-isopropylpiperidin-4-yl)amino)-4-methoxyphenyl)-5,7-dimethoxyquinazolin-4(3H)-one

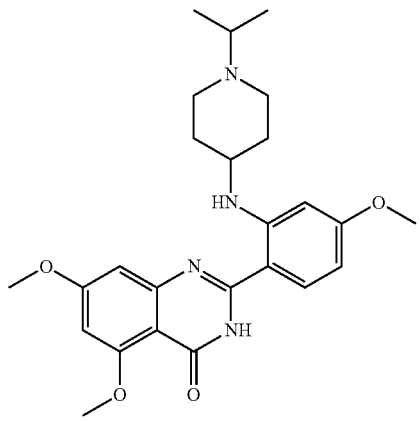

To a suspension of 2-(2-fluoro-4-methoxyphenyl)-5,7-dimethoxyquinazolin-4(3H)-one (0.660 g, 2 mmol) in anhydrous THF (20 mL) was added 1-isopropylpiperidin-4-amine (1.25 mL, 8 mmol) and lithium bis(trimethylsilyl)amide (1 M in THF, 10 mL, 10 mmol). The reaction was heated at reflux with stirring for 48 h. After that time a second portion of lithium bis(trimethylsilyl)amide (1 M in THF, 6 mL, 6 mmol) was added and reflux with stirring was continued for an additional 6 h. After that time the reaction was cooled to rt, diluted with cold water (3 mL) and concentrated under reduced pressure. The product was purified by flash column chromatography (silica gel, 97:3 dichloromethane/methanol then 97:3 dichloromethane/7 N ammonia in methanol) to give 2-(2-((1-isopropylpiperidin-4-yl)amino)-4-methoxyphenyl)-5,7-dimethoxyquinazolin-4(3H)-one (0.267 g, 30%) as an off-white solid: mp 248-250° C.; $^1$H NMR (400 MHz, DMSO-$d_6$) δ 11.49 (br s, 1H), 9.49 (d, J=7.4 Hz, 1H), 7.83 (d, J=8.6 Hz, 1H), 6.53-6.64 (m, 1H), 6.50 (s, 1H), 6.10-6.29 (m, 2H), 3.89 (s, 3H), 3.85 (s, 3H), 3.78 (s, 3H), 3.51 (br s, 1H), 2.63-2.76 (m, 3H), 2.42 (t, J=9.2 Hz, 2H), 1.97 (br s, 2H), 1.47-1.63 (m, 2H), 0.97 (d, J=6.25 Hz, 6H); ESI MS m/z 453 [M+H]$^+$.

Example 4: 5,7-Dimethoxy-2-(4-methoxy-2-((1-methylpyrrolidin-3-yl)amino)phenyl)quinazolin-4(3H)-one

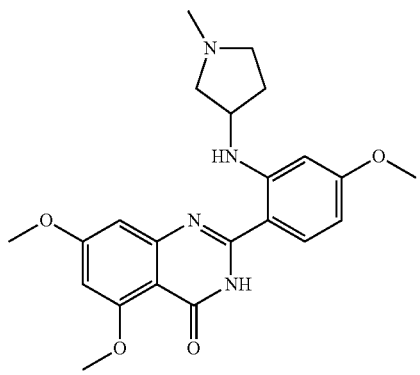

To a suspension of 2-(2-fluoro-4-methoxyphenyl)-5,7-dimethoxyquinazolin-4(3H)-one (0.660 g, 2 mmol) in anhydrous THF (25 mL) was added 1-methylpyrrolidine-3-amine dihydrochloride (1.03 g, 6 mmol) and lithium bis(trimethylsilyl)amide (1 M solution in THF, 18 mL, 18 mmol). The reaction was heated at reflux with stirring for 24 h. After that time the reaction was cooled to rt, diluted with cold water (5 mL) and concentrated under reduced pressure. The residue was dissolved in ethyl acetate (30 mL), diluted with water (30 mL) and stirred for 1 h. The precipitated solid was collected by filtration, washed with water then hexanes and air dried. The product was triturated (1:1, ethyl acetate/hexanes) to give 5,7-dimethoxy-2-(4-methoxy-2-(1-methylpyrrolidin-3-yl)phenyl)quinazolin-4(3H)-one (0.160 g, 20%) as an off-white solid: mp 214-215° C.; $^1$H NMR (400 MHz, DMSO-$d_6$) δ 9.85 (br s, 1H), 7.88 (d, J=9.0 Hz, 1H), 6.53 (d, J=1.95 Hz, 1H), 6.49 (s, 1H), 6.20 (dd, J=8.8, 2.15 Hz, 1H), 6.11 (s, 1H), 4.05 (br s, 1H), 3.89 (s, 3H), 3.84 (s, 3H), 3.79 (s, 3H), 2.69-2.82 (m, 2H), 2.55 (m, 1H), 2.33-2.41 (m, 2H), 2.32 (s, 3H), 1.59-1.68 (m, 1H); ESI MS m/z 411 [M+H]$^+$.

Example 5: 5,7-Dimethoxy-2-(4-methoxy-2-(methyl(1-methylpiperidin-4-yl)amino)phenyl)quinazolin-4(3H)-one

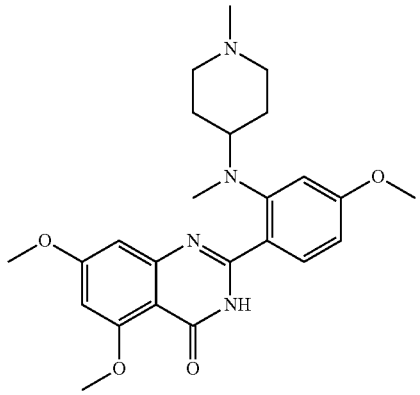

To a suspension of 2-(2-fluoro-4-methoxyphenyl)-5,7-dimethoxyquinazolin-4(3H)-one (0.660 g, 2 mmol) in anhydrous THF (20 mL) was added N,1-dimethylpiperidin-4-amine (0.50 g, 8 mmol) and lithium bis(trimethylsilyl)amide (1 M in THF, 6 mL, 6 mmol). The reaction was heated at reflux with stirring for 3 h. After that time a second portion of lithium bis(trimethylsilyl)amide (1 M in THF, 6 mL, 6 mmol) was added and reflux with stirring was continued for an additional 16 h. After that time the reaction was cooled to rt, diluted with cold water (5 mL) and concentrated under reduced pressure. The product was purified by flash column chromatography (silica gel, 97:3 dichloromethane/methanol then 97:3 dichloromethane/7N ammonia in methanol) to give 5,7-dimethoxy-2-(4-methoxy-2-(methyl(1-methylpiperidin-4-yl)amino)phenyl)quinazolin-4(3H)-one (0.362 g, 41%) as an off-white solid: mp 217-218° C.; $^1$H NMR (400 MHz, DMSO-$d_6$) δ 13.45 (s, 1H), 8.27 (d, J=9.0 Hz, 1H), 6.97 (d, J=2.3 Hz, 1H), 6.91 (dd, J=9.0, 2.3 Hz, 1H), 6.72 (d, J=1.95 Hz, 1H), 6.50 (d, J=2.3 Hz, 1H), 3.89 (s, 3H), 3.84 (s, 3H), 3.83 (s, 3H), 2.77-2.84 (m, 1H), 2.65-2.76 (m, 5H), 2.06 (s, 3H), 1.59-1.76 (m, 4H), 1.45-1.59 (m, 2H); ESI MS m/z 439 [M+H]$^+$.

Example 6: 5,7-Dimethoxy-2-(4-methoxy-2-(((1-methylpiperidin-4-yl)methyl)amino)phenyl)quinazolin-4(3H)-one

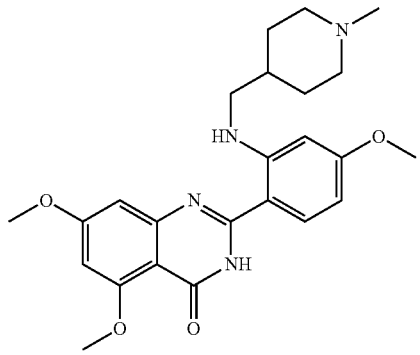

Lithium bis(trimethylsilyl)amide (1 M in THF, 11.2 mL, 11.2 mmol) was slowly added to a stirred suspension of 2-(2-fluoro-4-methoxyphenyl)-5,7-dimethoxyquinazolin-4(3H)-one (0.616 g, 1.86 mmol) and (1-methylpiperidin-4-yl)methanamine (0.956 g, 7.46 mmol) in anhydrous THF (20 mL). After the addition was complete, the reaction was heated to reflux with stirring for 24 h. After that time the reaction was cooled to rt, diluted with saturated aqueous NH$_4$Cl (15 mL) and concentrated under reduced pressure. The residue was suspended in water (25 mL), then saturated aqueous NaHCO$_3$ solution was added to adjust pH to about 8.5. The resulting suspension was stirred at rt for 30 min and the precipitated solid was collected by filtration, washed with water and air-dried. The product was purified by flash column chromatography (silica gel, 99:1 dichloromethane/7N ammonia in methanol to 97:3 dichloromethane/7N ammonia in methanol) to give 5,7-dimethoxy-2-(4-methoxy-2-(((1-methylpiperidin-4-yl)methyl)amino)phenyl)quinazolin-4(3H)-one (0.180 g, 22%) as a light yellow solid: mp 264-265° C.; $^1$H NMR (400 MHz, DMSO-d$_6$) δ 11.47 (br s, 1H), 9.63 (br s, 1H), 7.88 (d, J=9.0 Hz, 1H), 6.60 (d, J=1.95 Hz, 1H), 6.48 (d, J=1.95 Hz, 1H), 6.13-6.24 (m, 2H), 3.89 (s, 3H), 3.84 (s, 3H), 3.80 (s, 3H), 3.08-3.14 (m, 2H), 2.80-2.87 (m, 2H), 2.15 (s, 3H), 1.85-1.95 (m, 2H), 1.74-1.81 (m, 2H), 1.65-1.73 (m, 1H), 1.43-1.54 (m, 2H); ESI MS m/z 439 [M+H]$^+$.

Example 7: 5,7-Dimethoxy-2-(4-methoxy-2-((1-methylpyrrolidin-3-yl)methyl)amino)phenyl)-quinazolin-4(3H)-one

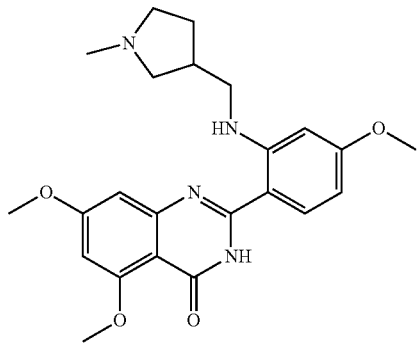

A 1 M solution of lithium hexamethyldisilazide in THF (10 mL, 10 mmol) was added in a single portion to a stirred suspension of 2-(2-fluoro-4-methoxyphenyl)-5,7-dimethoxyquinazolin-4(3H)-one (0.826 g, 2.5 mmol) and 1-methyl-3-aminomethylpyrrolidine (0.571 g, 5 mmol) in anhydrous THF (20 mL). The reaction mixture was stirred and heated to reflux for 19 h. After cooling to rt, the reaction mixture was quenched with a saturated aqueous solution of NH$_4$Cl (15 mL) and concentrated under reduced pressure to a volume of 20 mL. A solution of saturated aqueous NaHCO$_3$ (350 mL) was added and the mixture was extracted with chloroform (4×30 mL). The combined extracts were dried over MgSO$_4$, filtered and concentrated under reduced pressure to give a yellow solid. The product was purified by flash column chromatography (silica gel, 95:5 chloroform/methanol) followed by recrystallized from chloroform/hexanes to give 5,7-dimethoxy-2-(4-methoxy-2-(((1-methylpyrrolidin-3-yl)methyl)amino)phenyl)-quinazolin-4(3H)-one (0.367 g, 35%) as a yellow solid: mp 233-235° C.; $^1$H NMR (400 MHz, CDCl$_3$) δ 9.65 (br s, 1H), 9.23 (br s, 1H), 7.56 (d, J=9.2 Hz, 1H), 6.60 (d, J=2.4 Hz, 1H), 6.41 (d, J=2.4 Hz, 1H), 6.30 (dd, J=9.2, 2.4 Hz, 1H), 6.21 (d, J=2.4 Hz, 1H), 3.98 (s, 3H), 3.91 (s, 3H), 3.85 (s, 3H), 3.23-3.20 (m, 2H), 2.83-2.78 (m, 1H), 2.71-2.55 (m, 3H), 2.48-2.45 (m, 1H), 2.37 (s, 3H), 2.21-2.12 (m, 1H), 1.73-1.65 (m, 1H); ESI MS m/z 425 [M+H]$^+$.

Example 8: 2-(2-((2-(Isopropylamino)ethyl)amino)-4-methoxyphenyl)-5,7-dimethoxyquinazolin-4(3H)-one

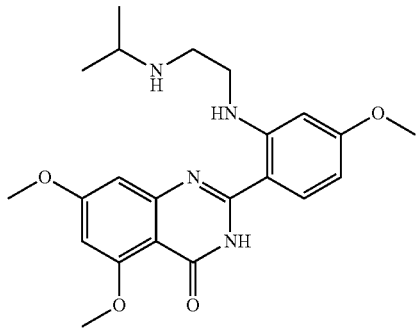

To a suspension of 2-(2-fluoro-4-methoxyphenyl)-5,7-dimethoxyquinazolin-4(3H)-one (0.660 g, 2 mmol) in anhydrous THF (20 mL) was added N$^1$-isopropylethane-1,2-diamine (1 mL, 8 mmol) and lithium bis(trimethylsilyl)amide (1 M in THF, 6 mL, 6 mmol). The reaction was heated at reflux with stirring for 16 h. After that time a second portion of lithium bis(trimethylsilyl)amide (1 M in THF, 6 mL, 6 mmol) was added and reflux with stirring was continued for an additional 16 h. After that time the reaction was cooled to rt, diluted with sat. NH$_4$Cl solution (6 mL) and concentrated under reduced pressure. The residue was treated with water (50 mL) and the resulting precipitate was collected by filtration, washed with water, dried and triturated with ethyl acetate to give 2-(2-((2-(isopropylamino)ethyl)amino)-4-methoxyphenyl)-5,7-dimethoxyquinazolin-4(3H)-one (0.387 g, 47%) as a yellow solid: mp 262-264°

C.; ¹H NMR (400 MHz, DMSO-d₆) δ 9.35 (t, J=5.3 Hz, 1H), 7.83 (d, J=9.0 Hz, 1H), 6.89 (s, 1H), 6.44-6.55 (m, 1H), 6.20-6.37 (m, 2H), 3.90 (s, 3H), 3.84 (s, 3H), 3.82 (s, 3H), 3.60 (br s, 2H), 3.23 (br s, 1H), 3.03-3.15 (m, 2H), 1.20 (d, J=6.25 Hz, 6H); ESI MS m/z 413 [M+H]⁺.

Example 9: 5,7-dimethoxy-2-(4-Methoxy-2-((tetrahydro-2H-pyran-4-yl)amino)-phenyl)quinazolin-4(3H)-one

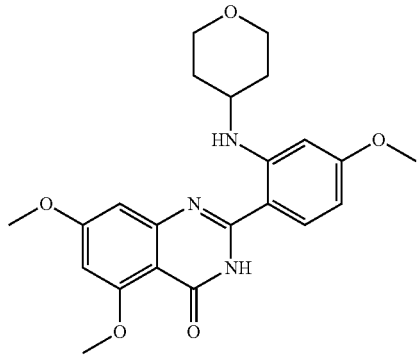

To a suspension of 2-(2-fluoro-4-methoxyphenyl)-5,7-dimethoxyquinazolin-4(3H)-one (0.66 g, 2 mmol) and tetrahydro-2H-pyran-4-amine (0.3 g, 3 mmol) in THF (50 mL) was added lithium bis(trimethylsilyl)amide (1 M in THF, 9 mL, 9 mmol). The reaction was heated at reflux with stirring for 18 h. After that time a second portion of lithium bis(trimethylsilyl)amide (1 M in THF, 9 mL, 9 mmol) was added and reflux with stirring was continued for an additional 18 h. After that time the reaction was cooled to rt, diluted with cold water (25 mL) and concentrated under reduced pressure. The precipitated solids were collected by filtration and dried. The product was purified by flash column chromatography (silica gel, 99:1 dichloromethane/methanol to 90:10 dichloromethane/methanol) to give 5,7-dimethoxy-2-(4-methoxy-2-((tetrahydro-2H-pyran-4-yl)amino)phenyl)quinazolin-4(3H)-one (0.12 g, 14%) as solid: mp 286-287° C.; ¹H NMR (400 MHz, CDCl₃) δ 9.48 (br s, 1H), 9.36 (d, J=7.0 Hz, 1H), 7.56 (dd, J=9.0, 2.7 Hz, 1H), 6.58 (d, J=1.95 Hz, 1H), 6.42 (d, J=2.3 Hz, 1H), 6.31 (dd, J=8.8, 2.5 Hz, 1H), 6.25 (d, J=2.3 Hz, 1H), 4.05 (dt, J=11.9, 4.0 Hz, 2H), 3.99 (s, 3H), 3.93 (s, 3H), 3.86 (s, 3H), 3.58-3.71 (m, 3H), 2.18-2.07 (m, 2H), 1.75-1.64 (m, 2H); ESI MS m/z 412 [M+H]⁺.

Example 10: 2-(2-((1-Isopropylpiperidin-4-yl)amino)phenyl)-5,7-dimethoxyquinazolin-4(3H)-one

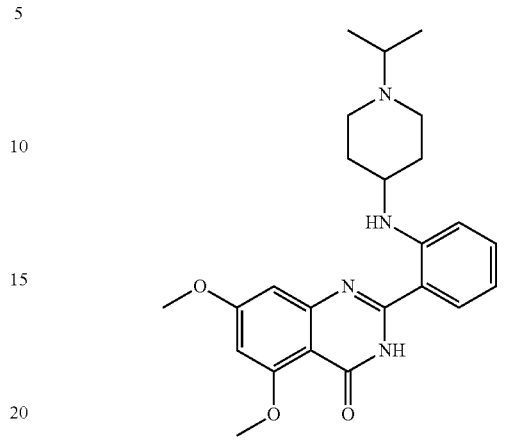

To a solution of 2-amino-4,6-dimethoxybenzamide (3.160 g, 16.1 mmol) and 2-fluorobenzaldehyde (2.0 g, 16.1 mmol) in N,N-dimethylacetamide (20 mL) was added sodium bisulfite (58.5% SO₂ content, 4.29 g, 24.2 mmol) followed by p-toluenesulfonic acid monohydrate (0.613 g, 3.2 mmol). The resulting mixture was heated at 120° C. for 17 h. After that time the reaction was cooled to rt and concentrated under reduced pressure. The residue was diluted with water (100 mL) and saturated aqueous NaHCO₃ was added to adjust the pH to 8. The resulting suspension was stirred for 30 min at rt and the precipitated dark orange solid was collected by filtration, washed with water and air-dried. The product was triturated with ethyl acetate to give 2-(2-fluorophenyl)-5,7-dimethoxyquinazolin-4(3H)-one (2.40 g, 50%) as an off-white solid: ¹H NMR (400 MHz, DMSO-d₆) δ 12.09 (br s, 1H), 7.70-7.78 (m, 1H), 7.54-7.65 (m, 1H), 7.30-7.41 (m, 2H), 6.74 (d, J=2.3 Hz, 1H), 6.58 (d, J=2.3 Hz, 1H), 3.88 (s, 3H), 3.86 (s, 3H); ESI MS m/z 301 [M+H]⁺.

Lithium bis(trimethylsilyl)amide (1 M in THF, 12 mL, 12 mmol) was slowly added to a stirred suspension of 2-(2-fluorophenyl)-5,7-dimethoxyquinazolin-4(3H)-one (0.600 g, 2 mmol) and 1-isopropylpiperidin-4-amine (1.14 g, 8 mmol) in anhydrous THF (20 mL). The reaction was heated to reflux with stirring for 40 h. After that time the reaction mixture was cooled to rt, diluted with saturated aqueous. NH₄Cl (5 mL), and concentrated under reduced pressure. The residue was diluted with water (20 mL) and the resulting suspension was stirred at rt for 30 min. The precipitated solid was collected by filtration, washed with water and air-dried. The product was purified by flash column chromatography (silica gel, 99:1 dichloromethane/7N ammonia in methanol to 97:3 dichloromethane/7N ammonia in methanol) to give 2-(2-((1-isopropylpiperidin-4-yl)amino)phenyl)-5,7-dimethoxyquinazolin-4(3H-one (0.230 g, 27%) as a yellow solid: mp 267-269° C.; ¹H NMR (400 MHz, CDCl₃) δ 9.53 (br s, 1H), 8.98 (d, J=7.4 Hz, 1H), 7.57 (d, J=8.2 Hz, 1H), 7.3 (m, 1H), 6.80 (d, J=8.6 Hz, 1H), 6.70 (m, 1H), 6.64 (d, J=2.3 Hz, 1H), 6.44 (d, J=2.3 Hz, 1H), 3.98 (s, 3H), 3.93 (s, 3H), 3.45-3.55 (m, 1H), 2.85-2.95 (m, 2H), 2.69-2.84 (m, 1H), 2.31-2.46 (m, 2H), 2.12-2.18 (m, 2H), 1.65-1.75 (m, 2H), 1.09 (d, J=6.2 Hz, 6H); ESI MS m/z 423 [M+H]⁺.

Example 11: 5,7-Dimethoxy-2-(4-methoxy-2-((2-(pyrrolidin-1-yl)ethyl)amino)phenyl)quinazolin-4(3H)-one

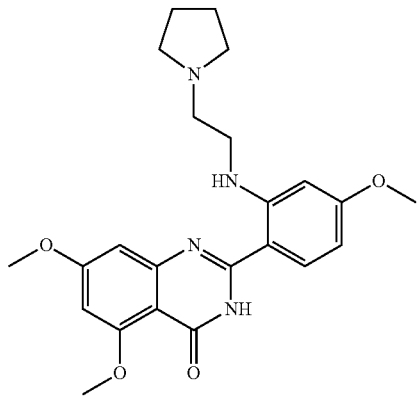

Lithium bis(trimethylsilyl)amide (1 M in THF, 6 mL, 6 mmol) was slowly added to a stirred suspension of 2-(2-fluoro-4-methoxyphenyl)-5,7-dimethoxyquinazolin-4(3H)-one (0.660 g, 2 mmol) and 2-(pyrrolidin-1-yl)ethan-1-amine (1.01 mL, 8 mmol) in anhydrous THF (20 mL). The reaction was heated at reflux with stirring for 16 h. After that time a second portion of lithium bis(trimethylsilyl)amide (1 M in THF, 6 mL, 6 mmol) was added and reflux with stirring was continued for an additional 16 h. After that time the reaction was cooled to rt, diluted with sat. NH$_4$Cl solution (6 mL) and concentrated under reduced pressure. The residue was treated with water (50 mL) and the precipitated solids were collected by filtration and dried. The product was triturated with ethyl acetate to give 5,7-dimethoxy-2-(4-methoxy-2-((2-(pyrrolidin-1-yl)ethyl)amino)phenyl)quinazolin-4(3H)-one (0.640 g, 75%) as a yellow solid: mp 226-228° C.; $^1$H NMR (400 MHz, CDCl$_3$) δ 9.10 (br s, 1H), 7.51 (d, J=8.6 Hz, 1H), 6.67 (d, J=1.95 Hz, 1H), 6.40 (d, J=1.95 Hz, 1H), 6.30 (dd, J=8.8, 2.15 Hz, 1H), 6.23 (d, J=1.95 Hz, 1H), 3.98 (s, 3H), 3.92 (s, 3H), 3.86 (s, 3H), 3.32-3.41 (m, 2H), 2.87 (t, J=6.25 Hz, 2H), 2.63 (br s, 4H), 1.81 (br s, 4H); ESI MS m/z 425 [M+H]$^+$.

Example 12: 5,7-Dimethoxy-2-(4-methoxy-2-((2-(piperidin-1-yl)ethyl)amino)-phenyl)quinazolin-4(3H)-one

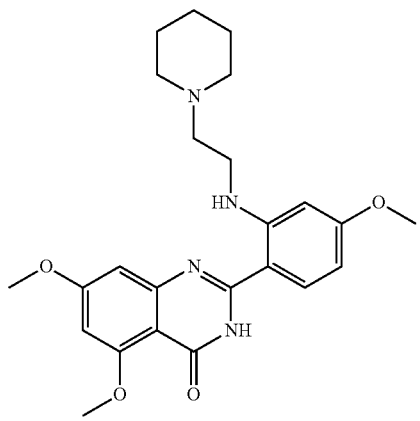

To a suspension of 2-(2-fluoro-4-methoxyphenyl)-5,7-dimethoxyquinazolin-4(3H)-one (0.50 g, 1.5 mmol) and 2-(piperidin-1-yl)ethan-1-amine (0.39 g, 3 mmol) in THF (50 mL) was added lithium bis(trimethylsilyl)amide (1 M in THF, 4.5 mL, 4.5 mmol). The reaction mixture was heated at reflux with stirring for 18 h. After that time a second portion of lithium bis(trimethylsilyl)amide (1 M in THF, 4.5 mL, 4.5 mmol) was added and reflux with stirring was continued for an additional 18 h. After that time the reaction was cooled to rt, diluted with cold water (25 mL) and concentrated under reduced pressure. The precipitated solids were collected by filtration and dried. The product was purified by flash column chromatography (silica gel, 99:1 dichloromethane/methanol to 90:10 dichloromethane/methanol) to give 5,7-dimethoxy-2-(4-methoxy-2-((2-(piperidin-1-yl)ethyl)amino)phenyl)quinazolin-4(3H)-one (0.16 g, 24%) as an off-white solid: mp 231-232° C.; $^1$H NMR (400 MHz, CDCl$_3$) δ 9.42 (br s, 1H), 8.87 (t, J=4.5 Hz, 1H), 7.50 (d, J=9.0 Hz, 1H), 6.71 (d, J=2.3 Hz, 1H), 6.41 (d, J=2.3 Hz, 1H), 6.30 (dd, J=8.6, 2.3 Hz, 1H), 6.23 (d, J=2.7 Hz, 1H), 3.98 (s, 3H), 3.92 (s, 3H), 3.85 (s, 3H), 3.28-3.39 (m, 2H), 2.71 (t, J=6.4 Hz, 2H), 2.48 (br s, 4H), 1.58 (quin. J=5.6 Hz, 4H), 1.37-1.48 (m, 2H); ESI MS m/z 439 [M+N]$^+$.

Example 13: 5,7-Dimethoxy-2-(4-methoxy-2-((3-morpholinopropyl)amino)-phenyl)quinazolin-4(3H)-one

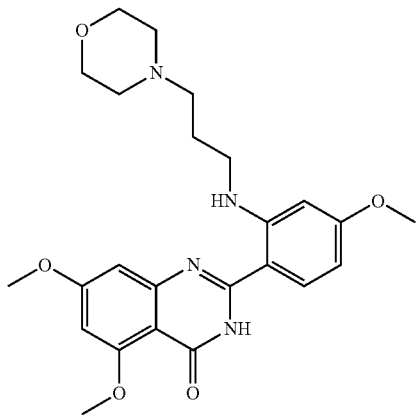

To a suspension of 2-(2-fluoro-4-methoxyphenyl)-5,7-dimethoxyquinazolin-4(3H)-one (0.50 g, 1.5 mmol) and 3-morpholinopropan-1-amine (0.39 g, 3 mmol) in THF (50 mL) was added lithium bis(trimethylsilyl)amide (1 M in THF, 4.5 mL, 4.5 mmol). The reaction mixture was heated at reflux with stirring for 18 h. After that time a second portion of lithium bis(trimethylsilyl)amide (1 M in THF, 4.5 mL, 4.5 mmol) was added and reflux with stirring was continued for an additional 18 h. After that time the reaction was cooled to rt, diluted with cold water (25 mL) and concentrated under reduced pressure. The precipitated solids were collected by filtration and dried. The product was purified by flash column chromatography (silica gel, 99:1 dichloromethane/methanol to 90:10 dichloromethane/methanol) to give 5,7-dimethoxy-2-(4-methoxy-2-((3-morpholinopropyl)amino)phenyl)quinazolin-4(3H)-one (0.16 g, 24%) as an off-white solid; mp 234-235° C.; $^1$H NMR (400 MHz, CDCl$_3$) δ 8.99 (br s, 1H), 8.93-8.97 (m, 1H), 7.41 (d, J=9.0 Hz, 1H), 6.61 (d, J=2.3 Hz, 1H), 6.42 (d, J=2.3 Hz, 1H), 6.30 (dd, J=9.0, 2.3 Hz, 1H), 6.25 (d, J=2.3 Hz, 1H), 3.98 (s, 3H), 3.92 (s, 3H), 3.86 (s, 3H), 3.69-3.74 (m, 4H), 3.28-3.35 (m, 2H), 2.54 (t, J=7.4 Hz, 2H), 2.44-2.50 (m, 4H), 1.91-1.98 (m, 2H); ESI MS m/z 455 [M+H]+.

Example 14: 5,7-Dimethoxy-2-(4-methoxy-2-((2-morpholinoethyl)amino)phenyl)-quinazolin-4(3H)-one

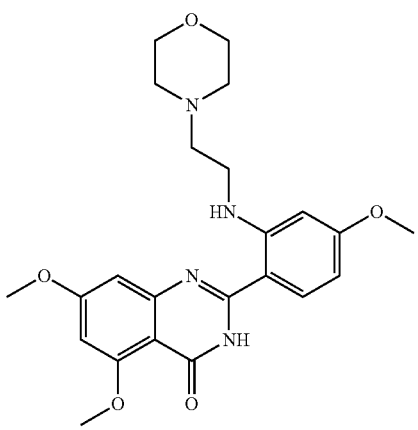

Lithium bis(trimethylsilyl)amide (1 M in THF, 6 mL, 6 mmol) was slowly added to a stirred suspension of 2-(2-fluoro-4-methoxyphenyl)-5,7-dimethoxyquinazolin-(4(3H)-one (0.660 g, 2 mmol) and 2-(morpholin-4-yl)ethanamine (0.780 g, 6 mmol) in anhydrous THF (25 mL). After the addition was complete, the reaction was heated to reflux with stirring for 3 h. After that time a second portion of lithium bis(trimethylsilyl)amide (1M in THF, 6 mL, 6 mmol) was added. Heating to reflux with stirring was continued for 16 h. After that time the reaction was cooled to rt, diluted with saturated aqueous NH4Cl (5 mL) and concentrated under reduced pressure. The residue was dissolved in ethyl acetate (20 mL), diluted with water (20 mL) and stirred for 1 h. The precipitated solid was collected by filtration, washed with water then hexanes and air dried. The product was purified by column chromatography (silica gel, 90:10 ethyl acdetate/methanol) to give 5,7-dimethoxy-2-(4-methoxy((2-morpholinoethyl)amino)phenylquinazolin-4(3H)-one (0.330 g, 38%) as a yellow solid: mp 239-240° C.; 1H NMR (400 MHz, CDCl3) δ 9.18 (br s, 1H), 8.87 (br s, 1H), 7.45 (d, J=9.0 Hz, 1H), 6.72 (d, J=2.3 Hz, 1H), 6.42 (d, J=1.95 Hz, 1H), 6.31 (dd, J=9.0, 2.3 Hz, 1H), 6.23 (d, J=2.3 Hz, 1H), 3.99 (s, 3H), 3.91 (s, 3H), 3.86 (s, 3H), 3.69-3.76 (m, 4H), 3.30-3.38 (m, 2H), 2.76 (t, J=6.2 Hz, 2H), 2.51-2.59 (m, 4H); ESI MS m/z 441 [M+H]+.

Example 15: 5,7-Dimethoxy-2-(4-methoxy-2-((3-(pyrrolidin-1-yl)propyl)amino)phenyl)quinazolin-4(3H)-one

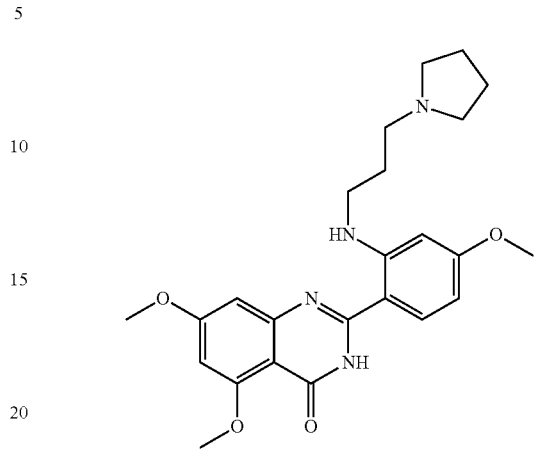

Lithium bis(trimethylsilyl)amide (1 M in THF, 12 mL, 12 mmol) was slowly added to a stirred suspension of 2-(2-fluoro-4-methoxyphenyl)-5,7-dimethoxyquinazolin-4(3H)-one (0.661 g, 2 mmol) and 3-(pyrrolidin-1-yl)propan-1-amine (1.030 g, 8 mmol) in anhydrous THF (20 mL). After the addition was complete the reaction was heated to reflux with stirring for 24 h. After that time, the reaction was cooled to rt, diluted with saturated aqueous solution of NH4Cl (10 mL), and concentrated under reduced pressure. The residue was dissolved in ethyl acetate (20 mL), diluted with water (20 mL) and stirred for 1 h. The precipitated solid was collected by filtration, washed with water then hexanes and air dried. The product was purified by column chromatography (silica gel, 99:1 dichloromethane/7N ammonia in methanol to 97:3 dichloromethane/7N ammonia in methanol) to give 5,7-dimethoxy-2-(4-methoxy-2-((3-(pyrrolidin-1-yl)propyl)amino)phenyl)quinazolin-4(3H)-one (0.220 g, 25%) as a yellow solid: 1H NMR (400 MHz, CDCl3) δ 9.33 (br s, 1H), 9.04 (br s, 1H), 7.49 (d, J=8.8 Hz, 1H), 6.62 (d, J=2.3 Hz, 1H), 6.41 (d, J=2.3 Hz, 1H), 6.29 (dd, J=8.8, 2.3 Hz, 1H), 6.23 (d, J=2.3 Hz, 1H), 3.98 (s, 3H), 3.92 (s, 3H), 3.85 (s, 3H), 3.31 (t, J=7.0 Hz, 2H), 2.62-2.68 (m, 2H), 2.48-2.56 (m, 4H), 1.99 (quin, J=7.0 Hz, 2H), 1.75-1.80 (m, 4H); ESI MS m/z 439 [M+H]+.

Example 16: 2-(2-(((1-Isopropylpyrrolidin-3-yl)methyl)amino)-4-methoxyphenyl)-5,7-dimethoxy-quinazolin-4(3H)-one

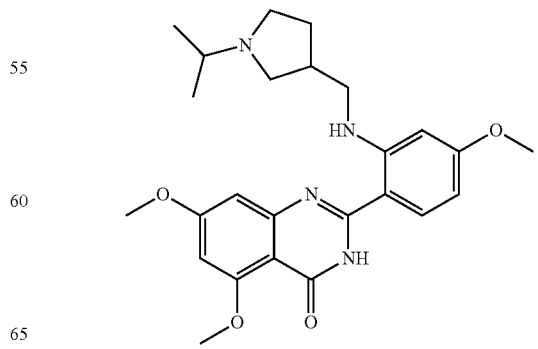

Lithium bis(trimethylsilyl)amide (1 M in THF, 6 mL, 6 mmol) was slowly added to a stirred suspension of 2-(2-fluoro-4-methoxyphenyl)-5,7-dimethoxyquinazolin-(4(3H)-one (0.660 g, 2 mmol) and (1-isopropylpyrrolidin-3-yl)methanamine (1.14 g, 8 mmol) in anhydrous THF (20 mL). After the addition was complete, the reaction was heated to reflux with stirring for 3 h. After that time a second portion of lithium bis(trimethylsilyl)amide (1M in THF, 6 mL, 6 mmol) was added. Heating to reflux with stirring was continued for 16 h. After that time the reaction was cooled to rt, diluted with saturated aqueous $NH_4Cl$ (6 mL) and concentrated under reduced pressure. The residue was diluted with water (50 mL) and the precipitated solid was collected by filtration, washed with water and dried. The resulting solids were triturated with ethyl acetate, then with 90:10 diethyl ether/methanol and dried under vacuum to give 2-(2-(((1-isopropylpyrrolidin-3-yl)methyl)amino)-4-methoxyphenyl)-5,7-dimethoxyquinazolin-4(3H)-one (0.347 g, 38%) as a pale orange solid: mp 228-230° C.; $^1$H NMR (400 MHz, $CDCl_3$) δ 9.50 (br s, 1H), 9.21 (br s, 1H), 7.53 (d, J=8.6 Hz, 1H), 6.59 (d, J=1.95 Hz, 1H), 6.40 (d, J=1.95 Hz, 1H), 6.30 (dd, J=8.8, 2.5 Hz, 1H), 6.21 (d, J=2.3 Hz, 1H), 3.98 (s, 3H), 3.90 (s, 3H), 3.86 (s, 3H), 3.16-3.25 (m, 2H), 3.01 (t, J=8.8 Hz, 1H), 2.55-2.80 (m, 3H), 2.30-2.45 (m, 2H), 2.10-2.23 (m, 1H), 1.62-1.74 (m, 1H), 1.12 (d, J=6.2 Hz, 6H); ESI MS m/z 453 $[M+H]^+$.

Example 17: 2-(2-(((1-Isopropylpyrrolidin-2-yl)methyl)amino)-4-methoxyphenyl)-5,7-dimethoxyquinazolin-4(3H)-one

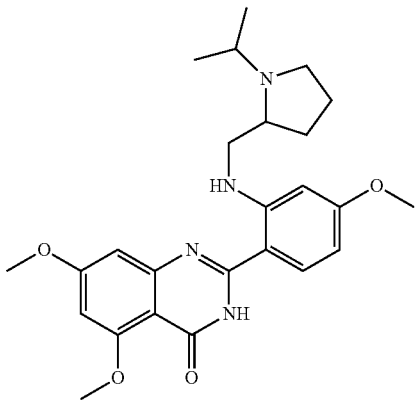

Lithium bis(trimethylsilyl)amide (1 M in THF, 12 mL, 12 mmol) was slowly added to a stirred suspension of 2-(2-fluoro-4-methoxyphenyl)-5,7-dimethoxyquinazolin-(4(3H)-one (0.660 g, 2 mmol) and (1-isopropylpyrrolidin-2-yl)methanamine (1.140 g, 8 mmol) in anhydrous THF (20 mL). After the addition was complete, the reaction was heated to reflux with stirring for 24 h. After that time the reaction was cooled to rt, diluted with saturated aqueous $NH_4Cl$ (10 mL) and concentrated under reduced pressure. The residue was diluted with water (20 mL) and the resulting suspension was stirred at rt for 30 min. The precipitated solid was collected by filtration, washed with water and dried. The product was purified by column chromatography (silica gel, 99:1 dichloromethane/7N ammonia in methanol to 97:3 dichloromethane/7N ammonia in methanol) to give 2-(2-(((1-isopropylpyrrolidin-2-yl)methyl)amino)-4-methoxyphenyl)-5,7-dimethoxyquinazolin-4(3H)-one (0.240 g, 27%) as a yellow solid: mp 207-209° C.; $^1$H NMR (400 MHz, $CDCl_3$) δ 9.33 (br s, 1H), 9.20 (br s, 1H), 7.49 (d, J=8.9 Hz, 1H), 6.67 (d, J=2.3 Hz, 1H), 6.40 (d, J=2.3 Hz, 1H), 6.29 (dd, J=8.9, 2.3 Hz, 1H), 6.22 (d, J=2.3 Hz, 1H), 3.98 (s, 3H), 3.91 (s, 3H), 3.85 (s, 3H), 3.15-3.30 (m, 2H), 2.99-3.12 (m, 3H), 2.53-2.61 (m, 1H), 1.68-1.97 (m, 4H), 1.16 (d, J=6.6 Hz, 3H), 1.02 (d, J=6.25 Hz, 3H); ESI MS m/z 453 $[M+H]^+$.

Example 18: 2-(3-((1-Isopropylpiperidin-4-yl)amino)pyridin-2-yl)-5,7-dimethoxyquinazolin-4(3H)-one

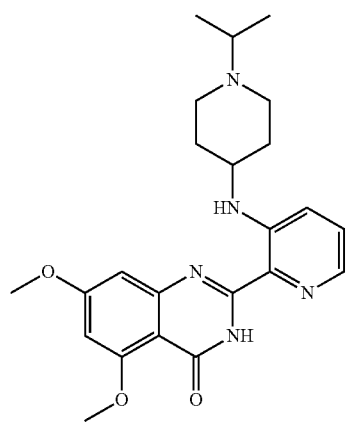 [SMILES: COc1cc(OC)c2c(=O)[nH]c(-c3ncccc3NC3CCN(C(C)C)CC3)nc2c1]

Lithium bis(trimethylsilyl)amide (1 M in THF, 3.2 mL, 3.2 mmol) was added to a stirred suspension of 2-(3-fluoropyridin-2-yl)-5,7-dimethoxyquinazolin-4(3H)-one (0.322 g, 1.07 mmol) and 1-isopropylpiperidin-4-amine (0.676 mL, 4.28 mmol) in anhydrous THF (10 mL). After the addition was complete, the reaction was heated to reflux with stirring for 1 h. After that time a second portion of lithium bis(trimethylsilyl)amide (1M in THF, 3.2 mL, 3.2 mmol) was added. Heating to reflux with stirring was continued for 2 h. After that time the reaction was cooled to rt, diluted with saturated aqueous $NH_4Cl$ (3 mL) and concentrated under reduced pressure. The residue was diluted with water (30 mL) and the precipitated solid was collected by filtration, washed with water and dried. The product was purified by flash column chromatography (silica gel, 97:3 dichloromethane/methanol then 97:3 dichloromethane/7 N ammonia in methanol) to give 2-(3-((1-isopropylpiperidin-4-yl)amino)pyridin-2-yl)-5,7-dimethoxyquinazolin-4(3H)-one (0.145 g, 32%) as a yellow solid: mp 170-172° C.; $^1$H NMR (400 MHz, $CDCl_3$) δ 10.92 (br s, 1H), 9.50 (d, J=7.8 Hz, 1H), 7.89 (d, J=4.3 Hz, 1H), 7.23 (dd, J=8.6, 4.3 Hz, 1H), 7.10 (d, J=8.6 Hz, 1H), 6.65 (d, J=2.3 Hz, 1H), 6.45 (d, J=2.3 Hz, 1H), 3.98 (s, 3H), 3.94 (s, 3H), 3.43-3.57 (m, 1H), 2.86-2.98 (m, 2H), 2.78 (sept, J=6.5 Hz, 1H), 2.42 (t, J=10.2 Hz, 2H), 2.09-2.21 (m, 2H), 1.61-1.83 (m, 2H), 1.10 (d, J=6.6 Hz, 6H); ESI MS m/z 424 $[M+H]^+$.

Example 19: 2-(2-((1-Isobutyrylpiperidin-4-yl)amino)-4-methoxyphenyl)-5,7-dimethoxyquinazolin-4(3H)-one

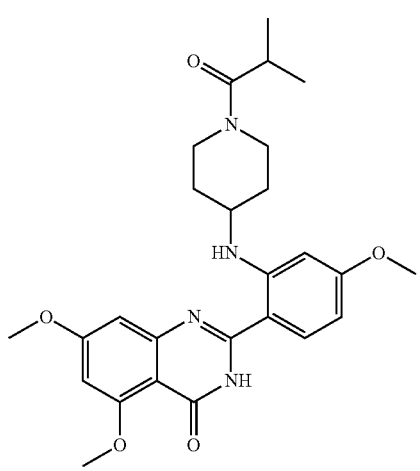

Lithium bis(trimethylsilyl)amide (1M in THF, 12.0 mL, 12.0 mmol) was added to a stirred suspension of 2-(2-fluoro-4-methoxyphenyl)-5,7-dimethoxyquinazolin-(4(3H)-one (0.660 g, 2.0 mmol) and 1-(4-aminopiperidin-1-yl)-2-methylpropan-1-one hydrochloride (1.240 g, 6.0 mmol) in anhydrous THF (20 mL). After the addition was complete, the reaction was heated to reflux with stirring for 3 h. After that time a second portion of lithium bis(trimethylsilyl)amide (1M in THF, 6.0 mL, 6.0 mmol) was added. Heating to reflux with stirring was continued for 16 h. After that time the reaction was cooled to rt, diluted with saturated aqueous $NH_4Cl$ (5.0 mL) and concentrated under reduced pressure. The residue was diluted with water (30 mL) and extracted with $CH_2Cl_2$ (2×30 mL). The combined organics were concentrated under reduced pressure and purified by flash column chromatography (silica gel, 90:10 ethyl acetate/methanol) followed by prep. HPCL to give 2-(2-((1-isobutyrylpiperidin-4-yl)amino)-4-methoxyphenyl)-5,7-dimethoxyquinazolin-4(3H)-one (0.090 g, 9%) as a yellow solid: $^1$H NMR (400 MHz, $CDCl_3$) δ 9.35 (br s, 1H), 9.19 (br s, 1H), 7.50 (d, J=8.6 Hz, 1H), 6.54 (s, 1H), 6.42 (s, 1H), 6.32 (d, J=8.6 Hz, 1H), 6.25 (br s, 1H), 4.27 (br s, 1H), 3.98 (s, 3H), 3.92 (s, 3H), 3.86 (s, 3H), 3.70 (br s, 1H), 3.23-3.43 (m, 2H), 2.84 (sept, J=6.2 Hz 1H), 2.07-2.20 (m, 2H), 1.59-1.71 (m, 2H), 1.14 (d, J=6.2 Hz, 6H); ESI MS m/z 481 $[M+H]^+$.

Example 20: 2-(2-((3-(Isopropylamino)propyl)amino)-4-methoxyphenyl)-5,7-dimethoxyquinazolin-4(3H)-one

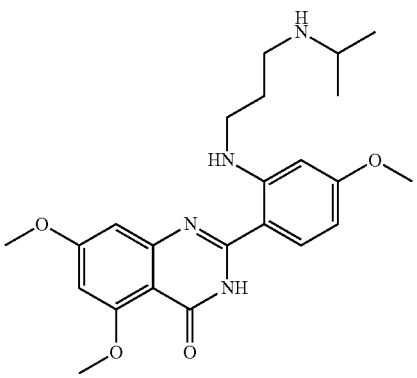

Lithium bis(trimethylsilyl)amide (1 M in THF, 6 mL, 6 mmol) was added to a stirred suspension of 2-(2-fluoro-4-methoxyphenyl)-5,7-dimethoxyquinazolin-4(3H)-one (0.660 g, 2 mmol) and $N^1$-isopropylpropane-1,3-diamine (1.35 mL, 8 mmol) in anhydrous THF (20 mL). After the addition was complete, the reaction was heated to reflux with stirring for 3 h. After that time a second portion of lithium bis(trimethylsilyl)amide (1M in THF, 6 mL, 6 mmol) was added. Heating to reflux with stirring was continued for 16 h. After that time the reaction was cooled to rt, diluted with saturated aqueous $NH_4Cl$ (6 mL) and concentrated under reduced pressure. The residue was diluted with water (50 mL) and the precipitated solid was collected by filtration, washed with water and dried. The product was purified by flash column chromatography (silica gel, 97:3 dichloromethane/methanol then 97:3 dichloromethane/7 N ammonia in methanol) to give 2-(2-((3-(isopropylamino)propyl)amino)-4-methoxyphenyl)-5,7-dimethoxyquinazolin-4(3H)-one (0.171 g, 20%) as a yellow solid: mp 208-210° C.; $^1$H NMR (400 MHz, DMSO-$d_6$) δ 7.83 (d, J=9.8 Hz, 1H), 6.61 (d, J=2.3 Hz, 1H), 6.49 (d, J=2.3 Hz, 1H), 6.16-6.24 (m, 2H), 3.89 (s, 3H), 3.85 (s, 3H), 3.80 (s, 3H), 3.50 (br s, 2H), 3.26 (t, J=6.6 Hz, 2H), 2.64-2.75 (m, 3H), 1.86-1.76 (m, 2H), 0.95 (d, J=5.9 Hz, 6H); ESI MS m/z 427 $[M+H]^+$.

Example 21: 5,7-Dimethoxy-2-(4-methoxy-2-((3-(methylpiperazin-1-yl)propyl)amino)-phenylquinazolin-4(3H)-one

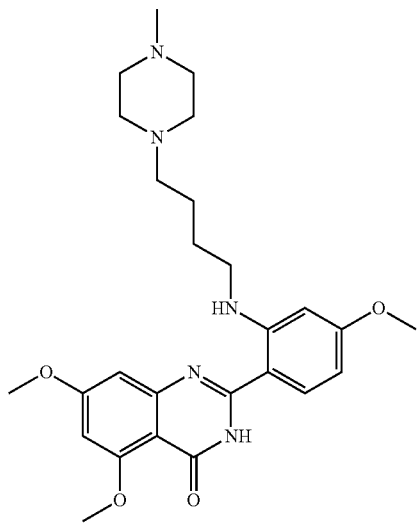

Lithium bis(trimethylsilyl)amide (1 M in THF, 6.0 mL, 6.0 mmol) was added to a stirred suspension of 2-(2-fluoro-4-methoxyphenyl)-5,7-dimethoxyquinazolin-(4(3H)-one (0.660 g, 2.0 mmol) and 3-(4-methylpiperazin-1-yl)propan-1-amine (0.942 g, 6.0 mmol) in anhydrous THF (25 mL). After the addition was complete, the reaction was heated to reflux with stirring for 3 h. After that time a second portion of lithium bis(trimethylsilyl)amide (1M in THF, 6.0 mL, 6.0 mmol) was added. Heating to reflux with stirring was continued for 16 h. After that time the reaction was cooled to rt, diluted with saturated aqueous $NH_4Cl$ (5.0 mL) and concentrated under reduced pressure. The residue was diluted with water (30 mL) and ethyl acetate (10 mL) and stirred for 1 h. The precipitated solids were collected by filtration, washed with water, then hexanes and air dried. The material was triturated with ethyl acetate (2×20 mL) and ether (2×20 mL) to give 5,7-dimethoxy-2-(4-methoxy-2-((3-(methylpiperazin-1-yl)propyl)amino)phenylquinazolin-4(3H)-one (0.440 g, 47%) as a light yellow solid: mp 220-222° C.; $^1$H NMR (400 MHz, $CDCl_3$) δ 9.00 (br s, 1H), 7.51 (d, J=8.8 Hz, 1H), 6.61 (d, J=2.3 Hz, 1H), 6.41 (d, J=1.9 Hz, 1H), 6.29 (dd, J=8.8, 1.9 Hz, 1H), 6.23 (d, J=2.3 Hz, 1H), 3.98 (s, 3H), 3.92 (s, 3H), 3.85 (s, 3H), 3.29 (t, J=6.5 Hz, 2H), 2.37-2.66 (m, 11H), 2.29 (s, 3H), 1.90-2.00 (m, 2H); ESI MS m/z 468 $[M+H]^+$.

Example 22: 2-(2-((2-(4-Isopropylpiperazin-1-yl)ethyl)amino)-4-methoxyphenyl)-5,7-dimethoxyquinazolin-4(3H)-one

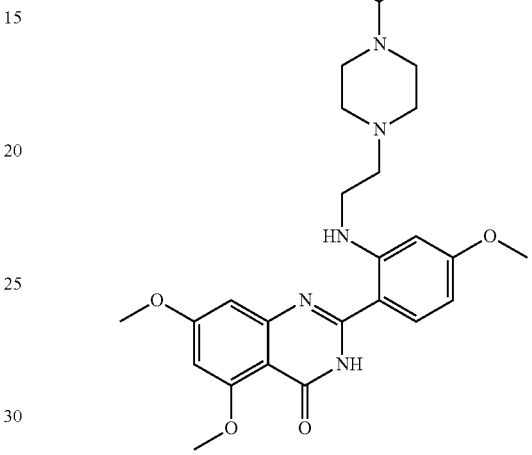

Lithium bis(trimethylsilyl)amide (1 M in THF, 4 mL, 4 mmol) was added to a stirred suspension of 2-(2-fluoro-4-methoxyphenyl)-5,7-dimethoxyquinazolin-4(3H)-one (0.660 g, 2 mmol) and 2-(4-isopropylpiperazin-1-yl)ethan-1-amine (1.02 g, 6 mmol) in anhydrous THF (20 mL). After the addition was complete, the reaction was heated to reflux with stirring for 3 h. After that time a second portion of lithium bis(trimethylsilyl)amide (1 M in THF, 4 mL, 4 mmol) was added. Heating to reflux with stirring was continued for 16 h. After that time the reaction was cooled to rt, diluted with saturated aqueous $NH_4Cl$ (6 mL) and concentrated under reduced pressure. The residue was diluted with water (50 mL) and the precipitated solid was collected by filtration, washed with water and dried. The solid was triturated with ethyl acetate followed by 90:10 diethyl ether/methanol and dried under vacuum to give 2-(2-((2-(4-isopropylpiperazin-1-yl)ethyl)amino)-4-methoxyphenyl)-5,7-dimethoxyquinazolin-4(3H)-one (0.776 g, 80%) as an off-white solid: mp 227-228° C.; $^1$H NMR (400 MHz, DMSO-$d_6$) δ 11.44 (br s, 1H), 9.29 (t, J=4.3 Hz, 1H), 7.80 (d, J=9.8 Hz, 1H), 6.72 (d, J=2.3 Hz, 1H), 6.51 (d, J=2.3 Hz, 1H), 6.15-6.26 (m, 2H), 3.88 (s, 3H), 3.85 (s, 3H), 3.80 (s, 3H), 3.33 (br s, 1H), 3.25 (q, J=5.1 Hz, 2H), 2.64 (t, J=5.7 Hz, 2H), 2.52-2.60 (m, 1H), 2.43 (br s, 8H), 0.90 (d, J=6.6 Hz, 6H); ESI MS m/z 482 $[M+H]^+$.

Example 23: 5,7-Dimethoxy-2-[4-methoxy-2-(1-methylpiperidin-4-ylsulfinyl)phenyl]quinazolin-4(3H)-one

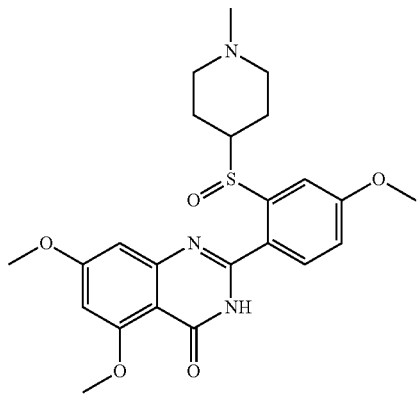

A mixture of 2-(2-fluoro-4-methoxyphenyl)-5,7-dimethoxyquinazolin-4(3H)-one (3.62 g, 11 mmol), 1-methylpiperidine-4-thiol (1.51 g, 11.5 mmol), $K_2CO_3$ (3.04 g, 22 mmol) and anhydrous DMSO (44 mL) was heated at 90° C. with stirring for 20 h. After that time the reaction was cooled to rt, diluted with $CHCl_3$ (150 mL) and washed with water (3×100 mL) and brine (100 mL), dried ($MgSO_4$) and concentrated under reduced pressure. The residue was triturated with diethyl ether (3×30 mL) and dried in vacuum to give 5,7-dimethoxy-2-[4-methoxy-2-(1-methylpiperidin-4-ylthio)phenyl]quinazolin-4(3H)-one (4.59 g, 95%) as an off-white solid: $^1$H NMR (400 MHz, $CDCl_3$) δ 11.40 (br s, 1H), 7.82 (d, J=8.8 Hz, 1H), 6.98 (d, J=2.4 Hz, 1H), 6.87 (dd, J=8.8, 2.4 Hz, 1H), 6.78 (d, J=2.4 Hz, 1H), 6.46 (d, J=2.4 Hz, 1H), 3.97 (s, 3H), 3.91 (s, 3H), 3.86 (s, 3H), 2.99-2.93 (m, 1H), 2.70-2.67 (m, 2H), 2.21 (s, 3H), 1.91-1.84 (m, 4H), 1.59-1.50 (m, 2H).

A solution of $NaIO_4$ (0.449 g, 2.1 mmol) in water (7 mL) was added dropwise to a stirred suspension of 5,7-dimethoxy-2-[4-methoxy-2-(1-methylpiperidin-4-ylthio)phenyl]quinazolin-4(3H)-one (0.883 g, 2 mmol) in methanol (20 mL). After the addition was complete the reaction was stirred for 18 h at rt. After that time the reaction was diluted with water (80 mL) and the precipitated solid collected by filtration, washed with water (4×30 mL) and dried. The product was purified by flash column chromatography (silica gel, 95:5 chloroform/methanol) to give 5,7-dimethoxy-2-[4-methoxy-2-(1-methylpiperidin-4-ylsulfinyl)phenyl]quinazolin-4(3H)-one (0.312 g, 34%) as a white solid: mp 263-265° C.; $^1$H NMR (400 MHz, $CDCl_3$) δ 7.93 (d, J=8.4 Hz, 1H), 7.74 (d, J=2.8 Hz, 1H), 7.13 (dd, J=8.4, 2.8 Hz, 1H), 6.65 (d, J=2.4 Hz, 1H), 6.49 (d, J=2.4 Hz, 1H), 3.99 (s, 3H), 3.97 (s, 3H), 3.93 (s, 3H), 3.48-3.40 (m, 1H), 3.06-2.93 (m, 2H), 2.24 (s, 3H), 2.21-1.87 (m, 5H), 1.36-1.33 (m, 1H); ESI MS m/z 458 [M+H]$^+$.

Example 24: 5,7-Dimethoxy-2-(4-methoxy-2-((2-(piperazin-1-yl)ethyl)amino)phenyl)quinazolin-4(3H)-one

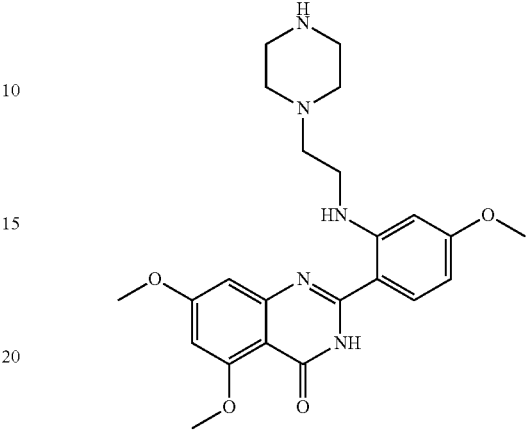

Lithium bis(trimethylsilyl)amide (1 M in THF, 6.0 mL, 6.0 mmol) was added slowly to a stirred suspension of 2-(2-fluoro-4-methoxyphenyl)-5,7-dimethoxyquinazolin-(4(3H)-one (0.660 g, 2.0 mmol) and tert-butyl 4-(2-aminoethyl)piperazine-1-carboxylate (0.916 g, 4.0 mmol) in anhydrous THF (25 mL). After the addition was complete, the reaction was heated to reflux with stirring for 1 h. After that time a second portion of lithium bis(trimethylsilyl)amide (1 M in THF, 4.0 mL, 4.0 mmol) was added. Heating to reflux with stirring was continued for 16 h. After that time the reaction was cooled to rt, diluted with saturated aqueous $NH_4Cl$ (5.0 mL) and concentrated under reduced pressure. The residue was diluted with water (40 mL) and stirred for 1 h. The precipitated solid was collected by filtration, washed with water and hexanes and air dried. The product was purified by flash column chromatography (silica gel, 99:1 ethyl acetate/methanol) to give tert-butyl 4-(2-((2-(5,7-dimethoxy-4-oxo-3,4-dihydroquinazolin-2-yl)-5-methoxyphenyl)amino)ethyl)piperazine-1-carboxylate (0.440 g, 41%) as an off-white solid: $^1$H NMR (400 MHz, $CDCl_3$) δ 9.06 (br s, 1H), 8.82 (br s, 1H), 7.43 (d, J=9.0 Hz, 1H), 6.68 (d, J=2.0 Hz, 1H), 6.42 (d, J=2.0 Hz, 1H), 6.31 (dd, J=8.8, 2.1 Hz, 1H), 6.22 (d, J=2.3 Hz, 1H), 3.99 (s, 3H), 3.89 (s, 3H), 3.86 (s, 3H), 3.44 (br s, 4H), 3.34 (q, J=5.5 Hz, 2H), 2.76 (t, J=6.1 Hz, 2H), 2.49 (br s, 4H), 1.45 (s, 9H); ESI MS m/z 540 [M+H]$^+$.

Trifluoroacetic acid (5.0 mL) was added dropwise to a suspension of tert-butyl 4-(2-((2-(5,7-dimethoxy-4-oxo-3,4-dihydroquinazolin-2-yl)-5-methoxyphenyl)amino)ethyl)piperazine-1-carboxylate (0.420 g, 0.78 mmol) in $CH_2Cl_2$ (20 mL). The reaction mixture was stirred at rt for 3 h. After that time the reaction was concentrated under reduced pressure and the residue diluted with ice-cold water (30 mL). The resulting mixture was made basic with solid $NaHCO_3$ and extracted with $CH_2Cl_2$ (3×30 mL). The combined organics were dried and concentrated to give a solid residue that was triturated (3×20 mL, 50:50 hexanes/diethyl ether) to give 5,7-dimethoxy-2-(4-methoxy-2-((2-(piperazin-1-yl)ethyl)amino)phenyl)quinazolin-4(3H)-one (0.230 g, 67%) as an off-white solid: mp 210-212° C.; $^1$H NMR (400 MHz, $CDCl_3$) δ 8.86-8.94 (m, 1H), 7.48 (d, J=8.6 Hz, 1H), 6.72 (d, J=2.3 Hz, 1H), 6.42 (d, J=2.3 Hz, 1H), 6.31 (dd, J=8.8, 2.1 Hz, 1H), 6.22 (d, J=2.3 Hz, 1H), 3.99 (s, 3H), 3.91 (s, 3H), 3.86 (s, 3H), 3.34 (q, J=5.9 Hz, 2H), 2.84-2.96 (m, 4H), 2.75 (t, J=6.3 Hz, 2H), 2.52 (br s, 4H); ESI MS m/z 440 [M+H]+.

Example 25: 5,7-Dimethoxy-2-(4-methoxy-2-((2-(4-methylpiperazin-1-yl)ethyl)amino)phenyl)-quinazolin-4(3H)-one

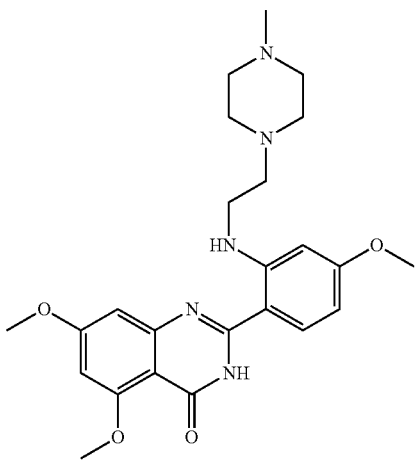

Lithium bis(trimethylsilyl)amide (1 M in THF, 4 mL, 4 mmol) was added to a stirred suspension of 2-(2-fluoro-4-methoxyphenyl)-5,7-dimethoxyquinazolin-4(3H)-one (0.660 g, 2 mmol) and 2-(4-methylpiperazin-1-yl)ethan-1-amine (0.86 g, 6 mmol) in anhydrous THF (20 mL). After the addition was complete, the reaction was heated to reflux with stirring for 3 h. After that time a second portion of lithium bis(trimethylsilyl)amide (1M in THF, 4 mL, 4 mmol) was added. Heating to reflux with stirring was continued for 16 h. After that time the reaction was cooled to rt, diluted with saturated aqueous NH4Cl (6 mL) and concentrated under reduced pressure. The residue was diluted with water (50 mL) and the precipitated solid was collected by filtration, washed with water and dried. The product was purified by flash column chromatography (silica gel, 96:4 dichloromethane/methanol then 96:4 dichloromethane/7 N ammonia in methanol) to give 5,7-dimethoxy-2-(4-methoxy-2-((2-(4-methylpiperazin-1-yl)ethyl)amino)phenyl)quinazolin-4(3H)-one (0.310 g, 34%) as pale yellow solid: mp 230-231° C.; 1H NMR (400 MHz, DMSO-d6) δ 11.46 (br s, 1H), 9.26 (t, J=4.3 Hz, 1H), 7.79 (d, J=9.4 Hz, 1H), 6.70 (d, J=1.95 Hz, 1H), 6.51 (d, J=1.95 Hz, 1H), 6.14-6.27 (m, 2H), 3.89 (s, 3H), 3.86 (s, 3H), 3.80 (s, 3H), 3.26 (q, J=5.1 Hz, 2H), 2.65 (t, J=5.9 Hz, 2H), 2.47 (br s, 4H), 2.32 (br s, 4H), 2.11 (s, 3H); ESI MS m/z 454 [M+H]+.

Example 26: 2-(2-((1-Isopropylpiperidin-4-yl)amino)-5-methoxyphenyl)-5,7-dimethoxyquinazolin-4(3H)-one

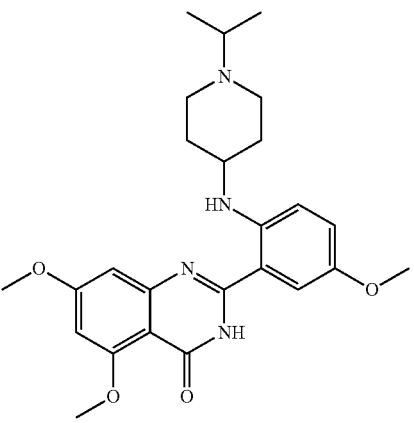

A mixture of 2-bromo-5-methoxybenzaldehyde (5.0 g, 23.3 mmol), propane-1,3-diol (2.13 g, 28.0 mmol) and para-toluenosulfonic acid monohydrate (0.10 g, 0.53 mmol) in anhydrous toluene (110 mL) was heated to reflux for 24 h with azeotropic removal of water using a Dean-Stark apparatus. After that time the reaction was cooled to rt, washed with 5% aqueous Na2CO3 solution (50 mL), dried over Na2SO4 and concentrated under reduced pressure. The product was purified by flash column chromatography (silica gel, 95:5 hexanes/ethyl acetate to 80:20 hexanes/ethyl acetate) to give 2-(2-bromo-5-methoxyphenyl)-1,3-dioxane (5.8 g, 91%) as a thick viscous liquid: 1H NMR (400 MHz, CDCl3) δ 7.40 (d, J=8.6 Hz, 1H), 7.24 (d, J=2.7 Hz, 1H), 6.77 (dd, J=8.8, 2.9 Hz, 1H), 5.72 (s, 1H), 4.27 (dd, J=11.3, 4.7 Hz, 2H), 4.03 (t, J=11.3 Hz, 2H), 3.81 (s, 3H), 2.18-2.32 (m, 1H), 1.44-1.48 (m, 1H).

A mixture of 2-(2-bromo-5-methoxyphenyl)-1,3-dioxane (5.1 g, 18.7 mmol), 1-isopropylpiperidin-4-amine (3.45 g, 24.38 mmol), 2,2'-bis(diphenylphosphino)-1,1'-binaphthyl (0.746 g, 1.2 mmol) and tris(dibenzylideneacetone)dipalladium(0) (0.366 g, 0.4 mmol) in anhydrous toluene (50 mL) was purged with nitrogen for 15 min. Sodium-tert-butoxide (3.24 g, 33.7 mmol) was added and the mixture was purged with nitrogen for an additional 5 min. The reaction mixture was heated at 110° C. for 18 h, then cooled to rt, diluted with ethyl acetate (100 mL) and filtered. The reaction was concentrated under reduced pressure and the residue was purified by flash column chromatography (silica gel, 90:10 ethyl acetate/methanol) to give N-(2-(1,3-dioxan-2-yl)-4-methoxyphenyl)-1-isopropylpiperidin-4-amine (4.5 g, 73%) as a thick viscous liquid: 1H NMR (400 MHz, CDCl3) δ 6.90 (d, J=2.7 Hz, 1H), 6.79 (dd, J=8.6, 2.7 Hz, 1H), 6.66 (d, J=8.6 Hz, 1H), 5.41 (s, 1H), 4.54 (br s, 1H), 4.25 (dd, J=11.1, 4.9 Hz, 2H), 3.91-4.02 (m, 2H), 3.74 (s, 3H), 3.31 (br s, 1H), 2.83 (d, J=11.3 Hz, 2H), 2.74 (dt, J=12.9, 6.4 Hz, 1H), 2.31 (t, J=10.4 Hz, 2H), 2.13-2.26 (m, 1H), 2.09 (br s, 1H), 1.42-1.60 (m, 3H), 1.06 (d, J=6.6 Hz, 6H); ESI MS m/z 335 [M+H]+.

A solution of HCl (2.5 M, 15 mL, 37.5 mmol) was slowly added to a vigorously stirred solution of N-(2-(1,3-dioxan-2-yl)-4-methoxyphenyl)-1-isopropylpiperidin-4-amine (1.5 g, 4.5 mmol) in methanol (15 mL) cooled to 0° C. The resulting mixture was allowed to warm to rt and stirred for 2 h. The majority of methanol was removed under reduced pressure and the residue was diluted with water (30 mL). The pH of the aqueous phase was adjusted to approx. 10 using solid $Na_2CO_3$. The mixture was extracted with ethyl acetate (2×50 mL). The combined organics were washed with brine, dried over $Na_2SO_4$, and concentrated under reduced pressure to give 2-((1-isopropylpiperidin-4-yl) amino)-5-methoxybenzaldehyde as a thick viscous gum (0.820 g, 65%): $^1$H NMR (400 MHz, $CDCl_3$) δ 9.78 (s, 1H), 8.14 (d, J=7.0 Hz, 1H), 7.06 (dd, J=9.2, 2.9 Hz, 1H), 7.0 (d, J=3.1 Hz, 1H), 6.69 (d, J=9.4 Hz, 1H), 3.79 (s, 3H), 3.44 (br s, 1H), 2.80-2.89 (m, 2H), 2.75 (br s, 1H), 2.35 (br s, 2H), 2.06 (br s, 2H), 1.62 (d, J=9.4 Hz, 2H), 1.07 (d, J=6.3 Hz, 6H); ESI MS m/z 277 [M+H]$^+$.

A mixture of 2-((1-isopropylpiperidin-4-yl)amino)-5-methoxybenzaldehyde (0.8 g, 2.9 mmol), 2-amino-4,6-dimethoxybenzamide (0.57 g, 2.9 mmol), sodium bisulfite (58.5% $SO_2$ content, 0.773 g, 4.5 mmol) and para-toluenosulfonic acid monohydrate (0.228 g, 1.2 mmol) in N,N-dimethylacetamide (15 mL) was stirred and heated at 120° C. for 20 h. After that time, the reaction mixture was cooled to rt and concentrated under reduced pressure. The residue was diluted with water (20 mL) and the pH was adjusted to approx. 10 with aqueous $Na_2CO_3$ solution. The mixture was extracted with $CH_2Cl_2$ (3×40 mL) and the combined organics were concentrated under reduced pressure. The product was purified by flash column chromatography (silica gel, 99:1 ethyl acetate/7N ammonia in methanol to 97:3 ethyl acetate/7N ammonia in methanol) followed by prep. HPLC to give 2-(2-((1-isopropylpiperidin-4-yl)amino)-5-methoxyphenyl)-5,7-dimethoxyquinazolin-4(3H)-one (0.043 g, 3%) as a yellow solid: $^1$H NMR (400 MHz, DMSO-d$_6$) δ 8.53-8.63 (m, 1H), 8.20 (br s, 1H), 7.34 (br s, 1H), 6.95 (d, J=7.4 Hz, 1H), 6.77 (d, J=9.0 Hz, 1H), 6.60 (s, 1H), 6.53 (s, 1H), 3.87 (s, 3H), 3.84 (s, 3H), 3.74 (s, 3H), 3.58-3.68 (m, 1H), 3.44 (br s, 1H), 2.73 (br s, 2H), 2.40 (br s, 2H), 1.93 (br s, 2H), 1.52 (br s, 2H), 0.95 (d, J=5.5 Hz, 6H); ESI MS m/z 453 [M+H]$^+$.

Example 27: 2-(3-((1-Isopropylpiperidin-4-yl) amino)phenyl)-5,7-dimethoxyquinazolin-4(3H)-one

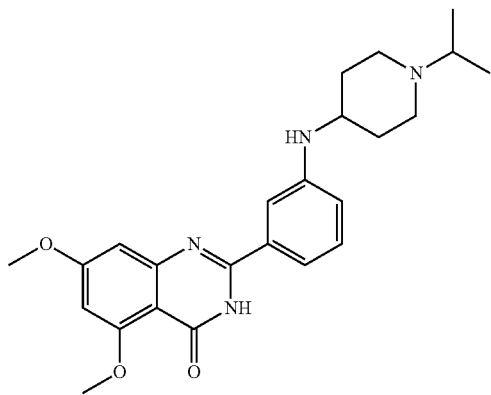 [SMILES: COc1cc(OC)c2c(=O)[nH]c(-c3cccc(NC4CCN(C(C)C)CC4)c3)nc2c1]

A mixture of 3-bromobenzaldehyde (10.0 g, 54.1 mmol), propane-1,3-diol (4.93 g, 64.9 mmol) and para-toluenosulfonic acid monohydrate (0.10 g, 0.53 mmol) in anhydrous toluene (100 mL) was heated to reflux for 24 h with azeotropic removal of water using a Dean-Stark apparatus. After that time the reaction was cooled to rt, washed with 5% aqueous $Na_2CO_3$ solution (50 mL), dried over $Na_2SO_4$ and concentrated under reduced pressure. The product was purified by flash column chromatography (silica gel, 95:5 hexanes/ethyl acetate to 90:10 hexanes/ethyl acetate) to give 2-(3-bromophenyl)-1,3-dioxane (11.5 g, 87%) as a light brown oil: $^1$H NMR (400 MHz, $CDCl_3$) δ 7.62-7.70 (m, 1H), 7.46 (ddd, J=8.1, 2.05, 1.2 Hz, 1H), 7.40 (d, J=7.8 Hz, 1H), 7.15-7.27 (m, 1H), 5.46 (s, 1H), 4.24-4.29 (m, 2H), 3.98 (t of d, J=12.11, 2.74 Hz, 2H), 2.11-2.33 (m, 1H), 1.39-1.51 (m, 1H).

A mixture of 2-(3-bromophenyl)-1,3-dioxane (5.0 g, 20.6 mmol), 1-isopropylpiperidin-4-amine (3) (4.39 g, 30.9 mmol), 2,2'-bis(diphenylphosphino)-1,1'-binaphthyl (1.28 g, 2.06 mmol) and tris(dibenzylideneacetone)dipalladium(0) (0.94 g, 1.03 mmol) in anhydrous toluene (60 mL) was purged with nitrogen for 15 min. Sodium-tert-butoxide (3.95 g, 41.1 mmol) was added and the mixture was purged with nitrogen for an additional 5 min. The reaction mixture was heated at 110° C. for 4 h, then cooled to rt, diluted with ethyl acetate (100 mL) and filtered. The reaction was concentrated under reduced pressure and the residue was purified by flash column chromatography (silica gel, 98:2 dichloromethane/methanol to 95:5 dichloromethane/methanol) to give N-(3-(1,3-dioxan-2-yl)phenyl)-1-isopropylpiperidin-4-amine (4.43 g, 71%) as an off-white solid: $^1$H NMR (400 MHz, $CDCl_3$) δ 7.12-7.16 (m, 1H), 6.76 (d, J=7.4 Hz, 1H), 6.72 (d, J=1.95 Hz, 1H), 6.56 (dd, J=7.4, 1.95 Hz, 1H), 5.42 (s, 1H), 4.26 (dd, J=11.1, 4.6 Hz, 2H), 3.96-4.05 (m, 2H), 3.52-3.54 (m, 1H), 3.24-3.37 (m, 1H), 2.82-2.85 (m, 2H), 2.65-2.79 (m, 1H), 2.13-2.34 (m, 3H), 2.03-2.08 (m, 2H), 1.33-1.52 (m, 3H), 1.05 (d, J=6.6 Hz, 6H); ESI MS m/z 305 [M+H]$^+$.

A solution of HCl (2N, 50 mL, 100 mmol) was added slowly to a vigorously stirred solution of N-(3-(1,3-dioxan-2-yl)phenyl)-1-isopropylpiperidin-4-amine (4.43 g, 14.6 mmol) in methanol (50 mL) cooled to 0° C. The resulting mixture was allowed to warm to rt and stirred for 17 h. The majority of methanol was removed under reduced pressure and the residue was diluted with water (30 mL). The pH of the aqueous phase was adjusted to approx. 10 using solid $Na_2CO_3$. The mixture was extracted with ethyl acetate (2×150 mL). The combined organics were washed with brine, dried over $Na_2SO_4$, and concentrated under reduced pressure. The product was triturated (50:50 diethyl ether/hexanes) to give 3-((1-isopropylpiperidin-4-yl)amino)benzaldehyde (0.90 g, 25%) as an off-white solid: $^1$H NMR (400 MHz, $CDCl_3$) δ 9.92 (s, 1H), 7.30-7.39 (m, 1H), 7.21 (d, J=7.8 Hz, 1H), 7.05 (br s, 1H), 6.85-6.94 (m, 1H), 3.92-4.05 (m, 1H), 3.54-3.68 (m, 1H), 3.39-3.57 (m, 3H), 2.67-2.94 (m, 2H), 2.32-2.49 (m, 1H), 2.13-2.33 (m, 3H), 1.46 (d, J=6.6 Hz, 6H); ESI MS m/z 247 [M+H]$^+$.

A mixture of 3-((1-isopropylpiperidin-4-yl)amino)benzaldehyde (0.450 g, 1.83 mmol), 2-amino-4,6-dimethoxybenzamide (0.287 g, 1.46 mmol), sodium bisulfite (58.5% $SO_2$ content, 0.487 g, 2.74 mmol) and para-toluenosulfonic acid monohydrate (0.174 g, 0.91 mmol) in N,N-dimethylacetamide (15 mL) was stirred and heated at 120° C. for 17 h. After that time, the reaction mixture was cooled to rt and concentrated under reduced pressure. Water (50 mL) was added and the resulting suspension was stirred for 30 min at rt. The precipitated solid was collected by filtration, washed with water and air-dried. The product was purified by flash column chromatography (silica gel, 99:1 ethyl acetate/7N ammonia in methanol to 97:3 ethyl acetate/7N ammonia in methanol) to give 2-(3-((1-isopropylpiperidin-4-yl)amino) phenyl)-5,7-dimethoxyquinazolin-4(3H)-one (0.310 g, 50%) as a white solid: mp 239-341° C.; $^1$H NMR (400 MHz, DMSO-d$_6$) 11.89 (br s, 1H), 7.24-7.36 (m, 2H), 7.09-7.23 (m, 1H), 6.76 (d, J=7.8 Hz, 1H), 6.70 (d, J=2.3 Hz, 1H), 6.53 (d, J=2.3 Hz, 1H), 5.70 (d, J=8.2 Hz, 1H), 3.89 (s, 3H), 3.85

(s, 3H), 3.26-3.37 (m, 1H), 2.65-2.81 (m, 3H), 2.20-2.29 (m, 2H), 1.75-1.94 (m, 2H), 1.28-1.41 (m, 2H), 0.98 (d, J=6.6 Hz, 6H); ESI MS m/z 423 [M+H]+.

Example 28: 5,7-Dimethoxy-2-(4-methoxy-2-[3-(piperazin-1-yl)propylamino]phenyl)quinazolin-4(3H)-one

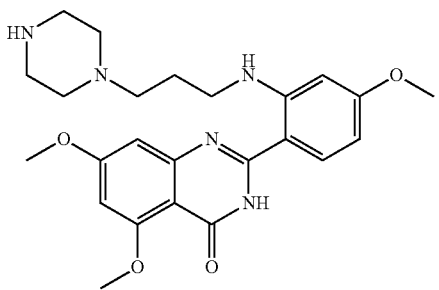

Lithium bis(trimethylsilyl)amide (1 M in THF, 10.3 mL, 10.3 mmol) was added to a stirred suspension of 2-(2-fluoro-4-methoxyphenyl)-5,7-dimethoxyquinazolin-4(3H)-one (0.679 g, 2.06 mmol) and 1-tert-butoxycarbonyl-4-(3-aminopropyl)piperazine (0.957 g, 3.93 mmol) in anhydrous THF (20 mL). After the addition was complete, the reaction was heated to reflux with stirring for 24 h. After that time the reaction was cooled to rt, diluted with saturated aqueous NH$_4$Cl (15 mL) and concentrated under reduced pressure. Saturated aqueous NaHCO$_3$ (50 mL) was added and the mixture was extracted with chloroform (4×30 mL). The combined organic layers were dried (MgSO$_4$) and concentrated under reduced pressure. The product was purified by flash column chromatography (silica gel, 98:2 chloroform/methanol) followed by recrystallization from chloroform/hexanes to give 5,7-dimethoxy-2-(4-methoxy-2-[3-(1-tert-butoxycarbonylpiperazin-4-yl)propylamino]phenyl)quinazolin-4(3H)-one (0.253 g, 22%) as a yellow solid: $^1$H NMR (400 MHz, CDCl$_3$) δ 9.50 (br s, 1H), 9.04 (br s, 1H), 7.54 (d, J=8.8 Hz, 1H), 6.60 (d, J=2.4 Hz, 1H), 6.41 (d, J=2.4 Hz, 1H), 6.30 (dd, J=8.8, 2.4 Hz, 1H), 6.23 (d, J=2.4 Hz, 1H), 3.98 (s, 3H), 3.92 (s, 3H), 3.86 (s, 3H), 3.44-3.42 (m, 4H), 3.33-3.29 (m, 2H), 2.56-2.53 (m, 2H), 2.41 (br s, 4H), 1.98-1.93 (m, 2H), 1.46 (s, 9H).

A solution of 5,7-dimethoxy-2-(4-methoxy-2-[3-(1-tert-butoxycarbonylpiperazin-4-yl)propylamino]phenyl)quinazolin-4(3H)-one (0.253 g, 0.46 mmol) in chloroform (10 mL) was added dropwise to a solution of HCl (1.0 g, 27.4 mmol) in methanol (18 mL) cooled to 0° C. After the addition was complete, the reaction was allowed to warm to rt and stir for 1 h. After that time the reaction was concentrated under reduced pressure and the residue was triturated with chloroform (4×30 mL). The product was then neutralized with saturated aqueous NaHCO$_3$ (20 mL) and extracted with chloroform (3×20 mL). The combined organic layers were dried (MgSO$_4$) and concentrated under reduced pressure. The product was purified by flash column chromatography (silica gel, 90:10 chloroform/methanol) to give 5,7-dimethoxy-2-(4-methoxy-2-[3-(piperazin-1-yl)propylamino]phenyl)quinazolin-4(3H)-one (0.091 g, 44%) as a yellow solid: mp 225-228° C.; $^1$H NMR (400 MHz, CDCl$_3$) δ 7.52 (d, J=9.2 Hz, 1H), 6.61 (d, J=2.0 Hz, 1H), 6.41 (d, J=2.4 Hz, 1H), 6.30 (dd, J=9.2, 2.0 Hz, 1H), 6.23 (d, J=2.0 Hz, 1H), 3.97 (s, 3H), 3.93 (s, 31H), 3.86 (s, 3H), 3.31-3.28 (m, 2H), 2.91-2.88 (m, 4H), 2.55-2.46 (m, 6H), 1.99-1.92 (m, 2H); ESI MS m/z 454 [M+H]+.

Example 29: 2-(2-((4,4-Dimethylcyclohexyl)amino)-4-methoxyphenyl)-5,7-dimethoxyquinazolin-4(3H)-one

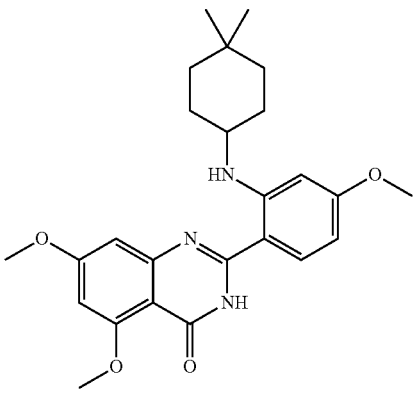

Lithium bis(trimethylsilyl)amide (1 M in THF, 6.0 mL, 6.0 mmol) was added to a stirred suspension of 2-(2-fluoro-4-methoxyphenyl)-5,7-dimethoxyquinazolin-4(3H)-one (0.661 g, 2 mmol) and 4,4-dimethylcyclohexan-1-amine (0.509 g, 4 mmol) in anhydrous THF (20 mL). After the addition was complete, the reaction was heated to reflux with stirring for 24 h. After that time the reaction was cooled to rt, diluted with saturated aqueous NH$_4$Cl (5 mL) and concentrated under reduced pressure. The residue was diluted with water (50 mL) and the resulting suspension was stirred at rt for 30 min. The precipitated solid was collected by filtration, washed with water and air-dried. The product was purified by column chromatography (silica gel, 99:1 dichloromethane/methanol to 97:3 dichloromethane/methanol), followed by preparative HPLC to give 2-(2-((4,4-dimethylcyclohexyl)amino)-4-methoxyphenyl)-5,7-dimethoxyquinazolin-4(3H)-one (0.060 g, 7%) as a light yellow solid: $^1$H NMR (400 MHz, CDCl$_3$) δ 9.23 (br s, 1H), 9.15 (br s, 1H), 7.45 (d, J=9.0 Hz, 1H), 6.65 (d, J=2.3 Hz, 1H), 6.41 (d, J=2.3 Hz, 1H), 6.22-6.29 (m, 2H), 3.98 (s, 3H), 3.91 (s, 3H), 3.85 (s, 3H), 3.41-3.50 (m, 1H), 1.88-1.98 (m, 2H), 1.48-1.67 (m, 4H), 1.29-1.39 (m, 2H), 0.99 (s, 3H), 0.98 (s, 3H); ESI MS m/z 438 [M+H]+.

Example 30: 2-(3-((1-Isopropylpiperidin-4-yl)amino)-5-methoxypyridin-2-yl)-5,7-dimethoxyquinazolin-4(3H)-one

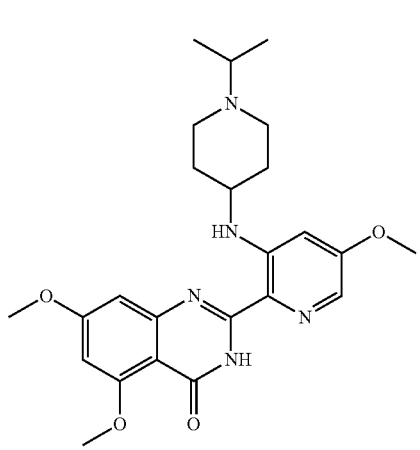

Lithium bis(trimethylsilyl)amide (1 M in THF, 1.0 mL, 1.0 mmol) was added to a stirred suspension of 2-(3-fluoro-5-methoxypyridin-2-yl)-5,7-dimethoxyquinazolin-4(3H)-one (0.166 g, 0.50 mmol) and 1-isopropylpiperidin-4-amine (0.24 mL, 1.50 mmol) in anhydrous THF (5 mL). After the addition was complete, the reaction was heated to reflux with stirring for 1 h. After that time a second portion of lithium bis(trimethylsilyl)amide (1 M in THF, 1.0 mL, 1.0 mmol) was added and reflux with stirring was continued for an additional 5 h. After that time the reaction was cooled to rt, diluted with saturated aqueous NH$_4$Cl (1 mL) and concentrated under reduced pressure. The product was purified by flash column chromatography (silica gel, 97:3 dichloromethane/methanol then 97:3 dichloromethane/7N ammonia in methanol) to give 2-(3-((1-isopropylpiperidin-4-yl)amino)-5-methoxypyridin-2-yl)-5,7-dimethoxyquinazolin-4(3H)-one (0.070 g, 31%) as a yellow solid: mp 207-208° C.; $^1$H NMR (400 MHz, CDCl$_3$) δ 10.71 (br s, 1H), 9.58 (d, J=7.8 Hz, 1H), 7.63 (d, J=2.3 Hz, 1H), 6.60 (d, J=2.3 Hz, 1H), 6.49 (d, J=2.3 Hz, 1H), 6.42 (d, J=2.3 Hz, 1H), 3.97 (s, 3H), 3.93 (s, 3H), 3.90 (s, 3H), 3.40-3.52 (m, 1H), 2.86-2.97 (m, 2H), 2.78 (sept, J=6.6 Hz, 1H), 2.43 (t, J=10.55 Hz, 2H), 2.10-2.20 (m, 2H), 1.68-1.83 (m, 2H), 1.10 (d, J=6.6 Hz, 6H); ESI MS m/z 454 [M+H]$^+$.

Example 31: 2-(2-(((trans-4-(2-Hydroxypropan-2-yl)cyclohexyl)amino)-4-methoxyphenyl)-5,7-dimethoxyquinazolin-4(3H)-one

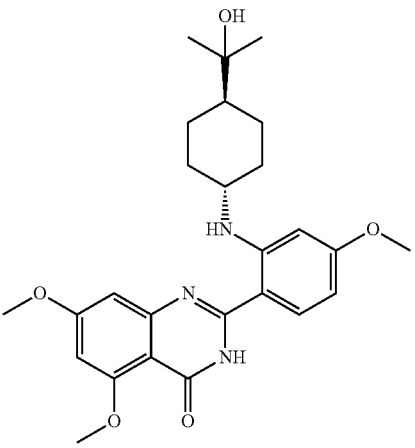

Lithium bis(trimethylsilyl)amide (1 M in THF, 7.2 mL, 7.2 mmol) was added to a stirred suspension of 2-(2-fluoro-4-methoxyphenyl)-5,7-dimethoxyquinazolin-4(3H)-one (0.400 g, 1.20 mmol) and 2-(trans-4-aminocyclohexyl)propan-2-ol (0.476 g, 3.03 mmol) in anhydrous THF (15 mL). After the addition was complete, the reaction was heated to reflux with stirring for 21 h. After that time the reaction was cooled to rt, diluted with saturated aqueous NH$_4$Cl (6 mL) and concentrated under reduced pressure. The residue was diluted with water (30 mL) and the resulting suspension was stirred at rt for 30 min. The precipitated solid was collected by filtration, washed with water and air-dried. The product was purified by flash column chromatography (silica gel, 99:1 dichloromethane/methanol to 97:3 dichloromethane/methanol) followed by recrystallization from chloroform/hexanes to give 2-(2-((trans-4-(2-hydroxypropan-2-yl)cyclohexyl)amino)-4-methoxyphenyl)-5,7-dimethoxyquinazolin-4(3H)-one (0.115 g, 20%) as a light yellow solid: mp: 253° C. dec.; $^1$H NMR (400 MHz, CDCl$_3$) δ 9.18 (br s, 1H), 9.14 (d, J=7.0 Hz, 1H), 7.46 (d, J=9.0 Hz, 1H), 6.58 (d, J=2.3 Hz, 1H), 6.41 (d, J=2.3 Hz, 1H), 6.22-6.30 (m, 2H), 3.98 (s, 3H), 3.93 (s, 3H), 3.85 (s, 3H), 3.25-3.33 (m, 1H), 2.29-2.37 (m, 2H), 1.93-1.99 (m, 2H), 1.24-1.46 (m, 6H), 1.23 (s, 6H); ESI MS m/z 468 [M+H]$^+$.

Example 32: 2-(3-((1-Isobutyrylpiperidin-4-yl)amino)-5-methoxypyridin-2-yl)-5,7-dimethoxyquinazolin-4(3H)-one

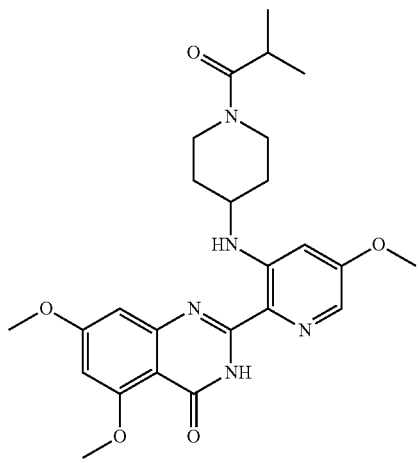

Lithium bis(trimethylsilyl)amide (1 M in THF, 2.4 mL, 2.4 mmol) was added to a stirred suspension of 2-(3-fluoro-5-methoxypyridin-2-yl)-5,7-dimethoxyquinazolin-4(3H)-one (0.155 g, 0.468 mmol) and 1-(4-aminopiperidin-1-yl)-2-methylpropan-1-one hydrochloride (0.290 g, 1.40 mmol) in anhydrous THF (5 mL). After the addition was complete, the reaction was heated to reflux with stirring for 1 h. After that time a second portion of lithium bis(trimethylsilyl)amide (1 M in THF, 0.9 mL, 0.9 mmol) was added and reflux with stirring was continued for an additional 5 h. After that time the reaction was cooled to rt, diluted with saturated aqueous NH$_4$Cl (1 mL) and concentrated under reduced pressure. The product was purified by flash column chromatography (silica gel, dichloromethane to 98:2 dichloromethane/methanol) followed by trituration with diethyl ether to give 2-(3-((1-isobutyrylpiperidin-4-yl)amino)-5-methoxypyridin-2-yl)-5,7-dimethoxyquinazolin-4(3H)-one (0.061 g, 27%) as a light yellow solid: mp 192-193° C.; $^1$H NMR (400 MHz, CDCl$_3$) 10.69 (s, 1H), 9.69 (d, J=7.0 Hz, 1H), 7.66 (d, J=2.3 Hz, 1H), 6.54 (d, J=2.3 Hz, 1H), 6.50 (d, J=2.3 Hz, 1H), 6.43 (d, J=1.95 Hz, 1H), 4.23-4.34 (m, 1H), 3.98 (s, 3H), 3.93 (s, 3H), 3.92 (s, 3H), 3.83-3.91 (m, 1H), 3.67-3.75 (m, 1H), 3.32-3.46 (m, 2H), 2.86 (sept, J=6.6 Hz, 1H), 2.06-2.21 (m, 2H), 1.59-1.79 (m, 2H), 1.16 (d, J=6.6 Hz, 6H); ESI MS m/z 482 [M+H]$^+$.

Example 33: 2-(4-Chloro-2-((1-isopropylpiperidin-4-yl)amino)phenyl)-5,7-dimethoxyquinazolin-4(3H)-one

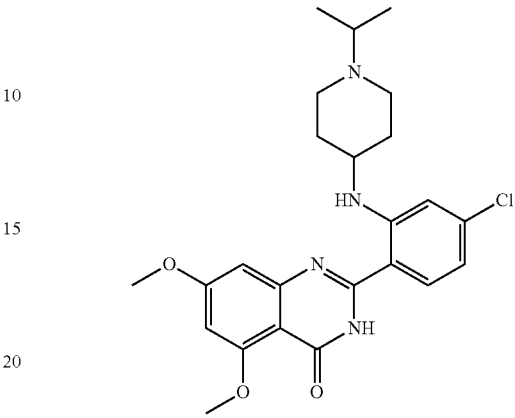

To a solution of 2-amino-4,6-dimethoxybenzamide (3.30 g, 17.0 mmol) and 4-chloro-2-fluorobenzaldehyde (3.0 g, 18.9 mmol) in N,N-dimethylacetamide (50 mL) was added NaHSO$_3$ (58.5% SO$_2$ content, 5.05 g, 28.4 mmol) and para-toluenosulfonic acid monohydrate (0.72 g, 3.8 mmol). The resulting mixture was heated at 120° C. for 17 h. After that time the reaction was cooled to rt, concentrated under reduced pressure, and diluted with water (100 mL). The resulting suspension was stirred for 30 min at rt and the precipitated yellow solids were collected by filtration, washed with water and air-dried. The product was purified by trituration (90:10 diethyl ether/methanol, 100 mL) to give 2-(4-chloro-2-fluorophenyl)-5,7-dimethoxyquinazolin-4(3H)-one (2.36 g, 43%) as an off-white solid: $^1$H NMR (400 MHz, DMSO-d$_6$) δ 12.15 (s, 1H), 7.77-7.79 (m, 1H), 7.65 (dd, J=10.2, 1.6 Hz, 1H), 7.45 (dd, J=8.2, 1.6 Hz, 1H), 6.75 (d, J=2.15 Hz, 1H), 6.59 (d, J=2.15 Hz, 1H), 3.88 (s, 3H), 3.86 (s, 3H): ESI MS m/z 335 [M+H]$^+$.

Lithium bis(trimethylsilyl)amide (1 M in THF, 12.0 mL, 12.0 mmol) was added to a stirred suspension of 2-(4-chloro-2-fluorophenyl)-5,7-dimethoxyquinazolin-4(3H)-one (0.650 g, 1.94 mmol) and 1-isopropylpiperidin-4-amine (0.854 g, 6.0 mmol) in anhydrous THF (20 mL). After the addition was complete, the reaction was heated to reflux with stirring for 6 h. After that time the reaction was cooled to rt, diluted with saturated aqueous NH$_4$Cl (10 mL) and concentrated under reduced pressure. The residue was diluted with water (50 mL) and the resulting suspension was stirred at rt for 30 min. The precipitated solid was collected by filtration, washed with water and air-dried. The product was purified by flash column chromatography (silica gel, 99:1 dichloromethane/7N ammonia in methanol to 97:3 dichloromethane/7N ammonia in methanol) to give 2-(4-chloro-2-((1-isopropylpiperidin-4-yl)amino)phenyl)-5,7-dimethoxyquinazolin-4(3H)-one (0.200 g, 22%) as a yellow solid: mp 265° C. dec.; $^1$H NMR (400 MHz, CDCl$_3$) δ 9.99 (br s, 1H), 9.23 (d, J=7.4 Hz, 1H), 7.59 (d, J=8.6 Hz, 1H), 6.74 (d, J=1.8 Hz, 1H), 6.66 (dd, J=8.6, 1.8 Hz, 1H), 6.62 (d, J=2.15 Hz, 1H), 6.45 (d, J=2.15 Hz, 1H), 3.99 (s, 3H), 3.94 (s, 3H), 3.41-3.47 (m, 1H), 2.86-2.94 (m, 2H), 2.72-2.81 (m, 1H), 2.35-2.46 (m, 2H), 2.11-2.19 (m, 2H), 1.61-1.75 (m, 2H), 1.08 (d, J=6.6 Hz, 6H); ESI MS m/z 457 and 459 [M+H]$^+$.

Example 34: 2-(4-Chloro-2-((1-isobutyrylpiperidin-4-yl)amino)phenyl)-5,7-dimethoxyquinazolin-4(3H)-one

Example 35: 2-(2-((1-Benzylpiperidin-4-yl)amino)-4-methoxyphenyl)-5,7-dimethoxyquinazolin-4(3H)-one

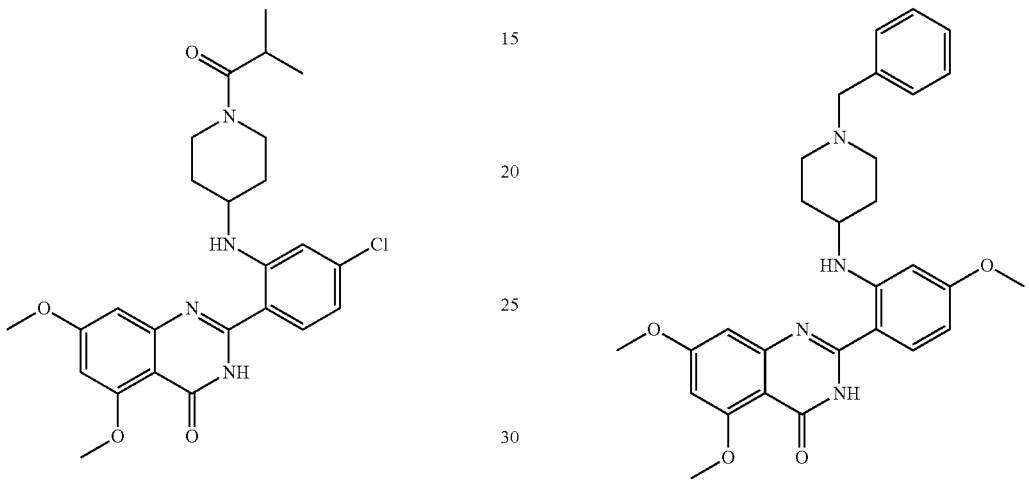

Lithium bis(trimethylsilyl)amide (1 M in THF, 16.0 mL, 16.0 mmol) was added to a stirred suspension of 2-(4-chloro-2-fluorophenyl)-5,7-dimethoxyquinazolin-4(3H)-one (0.660 g, 1.97 mmol) and 1-(4-aminopiperidin-1-yl)-2-methylpropan-1-one hydrochloride (1.22 g, 5.92 mmol) in anhydrous THF (20 mL). After the addition was complete, the reaction was heated to reflux with stirring for 6 h. After that time the reaction was cooled to rt, diluted with saturated aqueous NH$_4$Cl (10 mL) and concentrated under reduced pressure. The residue was diluted with water (50 mL) and the resulting suspension was stirred at rt for 30 min. The precipitated solid was collected by filtration, washed with water and air-dried. The product was purified by flash column chromatography (silica gel, 99:1 dichloromethane/methanol to 97:3 dichloromethane/methanol) to give 2-(4-chloro-2-((1-isobutyrylpiperidin-4-yl)amino)phenyl)-5,7-dimethoxyquinazolin-4(3H)-one (0.250 g, 26%) as a yellow solid: mp 281-283° C.; $^1$H NMR (400 MHz, CDCl$_3$) δ 10.70 (br s, 1H), 9.33 (d, J=7.0 Hz, 1H), 7.75 (d, J=8.2 Hz, 1H), 6.75 (d, J=1.95 Hz, 1H), 6.72 (dd, J=8.2, 1.95 Hz, 1H), 6.56 (d, J=2.15 Hz, 1H), 6.46 (d, J=2.15 Hz, 1H), 4.28-4.36 (m, 1H), 3.99 (s, 3H), 3.95 (m, 3H), 3.82-3.95 (m, 1H), 3.65-3.77 (m, 1H), 3.22-3.42 (m, 2H), 2.81-2.89 (m, 1H), 2.11-2.19 (m, 2H), 1.54-1.67 (m, 2H), 1.15 (d, J=6.7 Hz, 6H); ESI MS m/z 485 and 487 [M+H]$^+$.

Lithium bis(trimethylsilyl)amide (1 M in THF, 18 mL, 18 mmol) was added to a stirred suspension of 2-(2-fluoro-4-methoxyphenyl)-5,7-dimethoxyquinazolin-4(3H)-one (2.0 g, 6.0 mmol) and 1-benzylpiperidin-4-amine (2.28 g, 12.0 mmol) in anhydrous THF (100 mL). After the addition was complete, the reaction was heated to reflux with stirring for 72 h. After that time the reaction was cooled to rt, diluted with ice cold water (100 mL) and concentrated under reduced pressure. The resulting solids were collected by filtration, washed with water and dried. The product was purified by flash column chromatography (silica gel, 99:1 dichloromethane/methanol to 90:10 dichloromethane/methanol) to give 2-(2-((1-benzylpiperidin-4-yl)amino)-4-methoxyphenyl)-5,7-dimethoxyquinazolin-4(3H)-one (0.9 g, 30%) as a yellow solid: $^1$H NMR (400 MHz, DMSO-d$_6$) δ 11.50 (s, 1H), 9.50 (d, J=6.6 Hz, 1H), 7.82 (d, J=9.0 Hz, 1H), 7.27-7.36 (m, 5H), 6.59 (s, 1H), 6.51 (s, 1H), 6.21 (br s, 1H), 3.90 (s, 3H), 3.86 (s, 3H), 3.78 (s, 3H), 3.52-3.61 (m, 2H), 3.49 (s, 2H), 2.60-2.72 (m, 2H), 2.40 (br s, 2H), 1.93-2.05 (m, 2H), 1.51-1.66 (m, 2H); ESI MS m/z 501 [M+H]$^+$.

Example 36: 2-(-((1-Isobutyrylpiperidin-4-yl)amino)pyridin-2-yl)-5,7-dimethoxyquinazolin-4(3H)-one

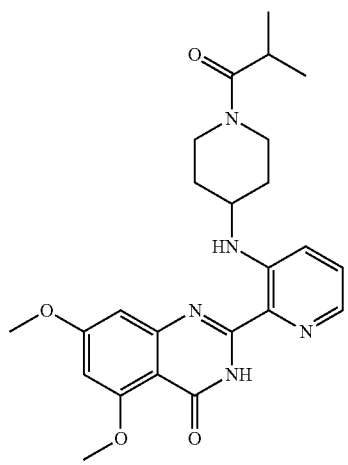 [SMILES: COc1cc(OC)c2c(=O)[nH]c(-c3ncccc3NC3CCN(C(=O)C(C)C)CC3)nc2c1]

Lithium bis(trimethylsilyl)amide (1 M in THF, 8 mL, 8 mmol) was added to a stirred suspension of 2-(3-fluoropyridin-2-yl)-5,7-dimethoxyquinazolin-4(3H)-one (0.390 g, 1.30 mmol) and 1-(4-aminopiperidin-1-yl)-2-methylpropan-1-one (0.828 g, 4.0 mmol) in anhydrous THF (15 mL). After the addition was complete, the reaction was heated to reflux with stirring for 1 h. After that time a second portion of lithium bis(trimethylsilyl)amide (1 M in THF, 4.0 mL, 4.0 mmol) was added and reflux with stirring was continued for an additional 18 h. After that time the reaction was cooled to rt, diluted with saturated aqueous $NH_4Cl$ (3.0 mL) and concentrated under reduced pressure. The residue was diluted with water (30 mL) and extracted with dichloromethane (2×30 mL). The combined organic layers were dried ($MgSO_4$) and concentrated under reduced pressure. The product was purified by flash column chromatography (silica gel, 90:10 ethyl acetate/methanol) followed by prep. HPLC to give 2-(-((1-isobutyrylpiperidin-4-yl)amino)pyridine-2-yl)-5,7-dimethoxyquinazolin-4(3H)-one (0.095 g, 16%) as a yellow solid: $^1$H NMR (400 MHz, CDCl$_3$) δ 10.92 (br s, 1H), 9.61 (d, J=6.6 Hz, 1H), 7.94 (d, J=3.5 Hz, 1H), 7.13 (d, J=8.6 Hz, 1H), 6.59 (d, J=2.0 Hz, 1H), 6.47 (s, 1H), 4.28-4.39 (m, 1H), 3.99 (s, 3H), 3.94 (s, 3H), 3.88 (br s, 1H), 3.75 (br s, 1H), 3.26-3.45 (m, 2H), 2.86 (sept, 6.6 Hz, 1H), 2.14 (br s, 2H), 1.58-1.77 (m, 2H), 1.16 (d, J=6.6 Hz, 6H); ESI MS m/z 452 [M+H]$^+$.

Example 37: 2-(3-((1-Acetylpiperidin-4-yl)amino)pyridine-2-yl)-5,7-dimethoxyquinazolin-4(3H)-one

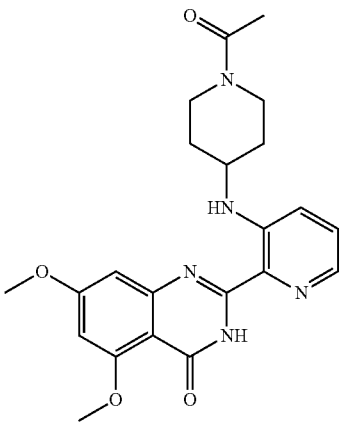 [SMILES: COc1cc(OC)c2c(=O)[nH]c(-c3ncccc3NC3CCN(C(C)=O)CC3)nc2c1]

A mixture of 2-(3-fluoropyridin-2-yl)-5,7-dimethoxyquinazolin-4(3H)-one (0.150 g, 0.5 mmol), 1-(4-aminopiperidin-1-yl)ethanone (0.142 g, 1.0 mmol) and $K_2CO_3$ (0.207 g, 1.5 mmol) in DMF (5.0 mL) was heated to 110° C. with stirring for 48 h. After that time the reaction mixture was cooled to rt and concentrated under reduced pressure. The residue was dissolved in $CH_2Cl_2$ (20 mL), washed with water (10 mL) then brine (10 mL), dried ($MgSO_4$) and concentrated under reduced pressure. The product was purified by flash column chromatography (silica gel, 90:10 ethyl acetate/methanol) to give 2-(3-((1-acetylpiperidin-4-yl)amino)pyridine-2-yl)-5,7-dimethoxyquinazolin-4(3H)-one (0.020 g, 10%) as a yellow solid: $^1$H NMR (400 MHz, CDCl$_3$) δ 10.90 (br s, 1H), 9.59 (d, J=7.0 Hz, 1H), 7.87-7.98 (m, 1H), 7.20-7.32 (m, 1H), 7.11 (d, J=8.6 Hz, 1H), 6.57 (s, 1H), 6.46 (s, 1H), 4.26-4.36 (m, 1H), 3.99 (s, 3H), 3.94 (s, 3H), 3.68-3.86 (m, 2H), 3.23-3.46 (m, 2H), 2.07-2.20 (m, 5H), 1.58-1.74 (m, 2H); ESI MS m/z 424 [M+H]$^+$.

Example 38: N-(cis-4-((2-(5,7-Dimethoxy-4-oxo-3,4-dihydroquinazolin-2-yl)-5-methoxypyridin-3-yl)amino)cyclohexyl)isobutyramide

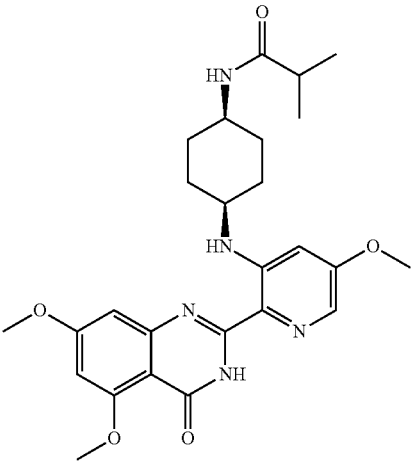

A solution of 5-bromo-2-chloro-3-fluoropyridine (8.90 g, 42.3 mmol) in anhydrous toluene (100 mL) was cooled to −78° C. A solution of n-butyl lithium (2.5 M solution in hexanes, 18.6 mL, 46.5 mmol) was added dropwise over a period of 15 min. After the addition was complete, the reaction was stirred at −78° C. for an additional 5 min. After that time trimethyl borate (5.6 mL, 50.7 mmol) was added dropwise at −78° C. over a period of 5 min. After the addition was complete, the reaction was stirred at −78° C. for an additional 15 min, then allowed to warm to rt and stirred for 16 h. The reaction mixture was cooled to 0° C. and aqueous NaOH solution (8 M, 60 mL) was added, followed by hydrogen peroxide (30 wt %, 40 mL). The mixture was stirred at rt for 2 h, then cooled to 0° C. and saturated aqueous sodium thiosulfate solution was added carefully until clear solution was obtained (about 40 mL). The resulting mixture was neutralized to pH1-7 using 1 N HCl and extracted with ethyl acetate (2×200 mL). The combined organics were washed with water then brine, dried ($Na_2SO_4$) and concentrated under reduced pressure to give 6-chloro-5-fluoropyridin-3-ol (5.61 g, 90%) as a brown solid: $^1$H NMR (DMSO-$d_6$) δ 10.79 (s, 1H), 7.86 (d, J=2.5 Hz, 1H), 7.33 (dd, J=10.2, 2.5 Hz, 1H).

A suspension of 6-chloro-5-fluoropyridin-3-ol (5.50 g, 37.2 mmol), methyl iodide (4.64 mL, 74.5 mmol) and potassium carbonate (10.3 g, 74.5 mmol) in acetone (300 mL) was heated to reflux with stirring for 16 h. After that time the reaction was cooled to rt and partitioned between water and ethyl acetate. The organic phase was separated, washed with water and brine, dried over $Na_2SO_4$, and concentrated under reduced pressure to give 2-chloro-3-fluoro-5-methoxypyridine (5.05 g, 84%) as a brown oil: $^1$H NMR (CDCl$_3$) δ 7.94 (d, J=2.7 Hz, 1H), 7.07 (dd, J=9.4, 2.7 Hz, 1H), 3.88 (s, 3H).

A solution of 2-chloro-3-fluoro-5-methoxypyridine (5.05 g, 31.2 mmol), triethylamine (13.0 mL, 93.6 mmol) and Pd(dppf)Cl$_2$ (1.14 g, 1.56 mmol) in methanol (150 mL) was purged with carbon monoxide three times and then heated in an autoclave with stirring at 110° C. for 6 h under a carbon monoxide atmosphere (200 psi). After that time, the mixture was cooled to rt, filtered through a pad of Celite and concentrated under reduced pressure. The product was purified by flash column chromatography (silica gel, 50:50 ethyl acetate/hexanes) to give methyl 3-fluoro-5-methoxypicolinate (4.52 g, 78%) as a white solid: $^1$H NMR (CDCl$_3$) δ 8.26 (d, J=2.3 Hz, 1H), 7.01 (dd, J=11.7, 2.3 Hz, 1H), 3.99 (s, 3H), 3.94 (s, 3H); ESI MS m/z 186 [M+H]$^+$.

A solution of 3-fluoro-5-methoxypicolinate (2.00 g, 10.8 mmol) in a mixture of anhydrous toluene (30 mL) and THF (25 mL) was cooled to −78° C. A solution of DIBAL-H (1.0 M in toluene, 32.4 mL, 32.4 mmol) was added dropwise at −70° C. over a period of 30 min and the resulting mixture was stirred at −70° C. for 30 min. The reaction was then allowed to warm to −5° C. over a period of 2 h and stirred at −5° C. for an additional 1 h. The mixture was cooled to −70° C. and isopropanol (10 mL) was carefully added followed by water (10 mL). The mixture was stirred at rt for 16 h and filtered through a pad of Celite. The solids were washed with CH$_2$Cl$_2$ and then ethyl acetate. The combined filtrates were concentrated under reduced pressure to give (3-fluoro-5-methoxypyridin-2-yl)methanol (1.68 g, 99%) as an off-white solid: $^1$H NMR (CDCl$_3$) δ 8.11 (s, 1H), 6.98 (dd, J=10.5, 2.3 Hz, 1H), 4.76 (d, J=5.3 Hz, 2H), 3.88 (s, 3H), 3.61 (t, J=5.3 Hz, 1H); ESI MS m/z 158 [M+H]$^+$.

A solution of (3-fluoro-5-methoxypyridin-2-yl)methanol (1.85 g, 11.8 mmol) and IBX (3.30 g, 11.8 mmol) in DMSO (20 mL) was stirred at rt for 2 h. After that time water (100 mL) was added and the precipitated solid was collected by filtration. The solid was washed with ethyl acetate (200 mL) and the filtrate was washed with brine, dried over $Na_2SO_4$ and concentrated under reduced pressure to give 3-fluoro-5-methoxypicolinaldehyde (1.66 g, 91%) as a pale yellow solid: $^1$H NMR (CDCl$_3$) δ 10.12 (s, 1H), 8.32 (d, J=1.6 Hz, 1H), 7.01 (dd, J=11.7, 2.3 Hz, 1H), 3.97 (s, 3H).

A solution of 3-fluoro-5-methoxypicolinaldehyde (1.57 g, 10.1 mmol), 2-amino-4,6-dimethoxybenzamide (1.99 g, 10.1 mmol), NaHSO$_3$ (58.5 wt %, 2.75 g, 15.2 mmol) and p-toluenesulfonic acid monohydrate (0.39 g, 2.02 mmol) in N,N-dimethyl acetamimde (30 mL) was stirred at 120° C. for 16 h. After that time the reaction was cooled to rt and concentrated under reduced pressure. Water was added and the precipitated solid was collected by filtration, washed with water, then diethyl ether and dried under reduced pressure. The product was purified by flash column chromatography (silica gel, 97:3 dichloromethane/methanol) followed by triturating (50:50 diethyl ether/ethyl acetate, 50 mL) to give 2-(3-fluoro-5-methoxypyridin-2-yl)-5,7-dimethoxyquinazolin-4(3H)-one (0.51 g, 15%) as a yellow solid: $^1$H NMR (CDCl$_3$) δ 10.42 (br s, 1H), 8.22 (d, J=2.3 Hz, 1H), 7.12 (dd, J=12.1, 2.3 Hz, 1H), 6.85 (d, J=2.3 Hz, 1H), 6.50 (d, J=2.3 Hz, 1H), 3.99 (s, 3H), 3.97 (s, 3H), 3.94 (s, 3H); ESI MS m/z 332 [M+H]$^+$.

Isobutyryl chloride (0.945 g, 8.87 mmol) was added dropwise to a vigorously stirred solution of tert-butyl (cis-4-aminocyclohexyl)carbamate (2.0 g, 9.33 mmol) and N,N-diisopropylethylamine (2.41 g, 18.66 mmol) in anhydrous dichloromethane (20 mL) at 0° C. After the addition was complete, the reaction mixture was allowed to warm to rt, stirred for 17 h and then diluted with ethyl acetate (300 mL). The organic phase was washed with 0.5M citric acid solution (50 mL), followed by saturated NaHCO$_3$ solution (50 mL) and brine, dried over $Na_2SO_4$ and concentrated under reduced pressure to give tert-butyl (cis-4-isobutyramidocyclohexyl)carbamate (2.5 g, 98%) as a white solid: $^1$H NMR (400 MHz, CDCl$_3$) δ 5.30-5.45 (m, 1H), 4.48-4.60 (m, 1H), 3.83-3.94 (m, 1H), 3.56-3.69 (m, 1H), 2.23-2.39 (m, 1H), 1.68-1.82 (m, 4H), 1.46-1.62 (m, 4H), 1.45 (s, 9H), 1.15 (d, J=7.0 Hz, 6H); ESI MS n/z 285 [M+H]$^+$.

Concentrated HCl (37%, 3.4 mL, 41 mmol) was added slowly to a stirred mixture of tert-butyl (cis-4-isobutyramidocyclohexyl)carbamate (2.33 g, 8.19 mmol) in methanol (50 mL) at 0° C. The reaction mixture was allowed to warm to rt and stirred for 17 h. After that time the reaction was concentrated under reduced pressure to give N-(cis-4-aminocyclohexyl)isobutyramide hydrochloride (1.83 g, >99%) as a white solid: $^1$H NMR (400 MHz, DMSO-$d_6$) δ 8.15 (br s, 3H), 7.57 (d, J=5.5 Hz, 1H), 3.63 (br s, 1H), 2.95-3.11 (m, 1H), 2.40-2.50 (m, 1H), 1.59-1.81 (m, 6H), 1.42-1.58 (m, 2H), 0.98 (d, J=6.6 Hz, 6H).

Lithium bis(trimethylsilyl)amide (1 M in THF, 12.1 mL, 12.1 mmol) was added to a stirred suspension of 2-(3-fluoro-5-methoxypyridin-2-yl)-5,7-dimethoxyquinazolin-4(3H)-one (0.402 g, 1.21 mmol) and N-(cis-4-aminocyclohexyl) isobutyramide hydrochloride (0.803 g, 3.64 mmol) in anhydrous THF (20 mL). After the addition was complete, the reaction was heated to reflux with stirring for 5 h. After that time the reaction was cooled to rt, diluted with saturated aqueous NH$_4$Cl (10 mL) and concentrated under reduced pressure. The residue was diluted with water (50 mL) and the resulting suspension was stirred at rt for 30 min. The precipitated solid was collected by filtration, washed with water and air-dried. The product was purified by flash column chromatography (silica gel, 99:1 dichloromethane/methanol to 97:3 dichloromethane/methanol) to give N-(cis- 4-((2-(5,7-dimethoxy-4-oxo-3,4-dimethoxyquinazolin-2-yl)-5-methoxypyridin-3-yl)amino)cyclohexyl)isobutyramide (0.160 g, 27%) as a yellow solid: mp 285° C. dec.; $^1$H NMR (400 MHz, DMSO-$d_6$) δ 10.56 (s, 1H), 9.72 (d, J=7.4 Hz, 1H), 7.74 (d, J=7.4 Hz, 1H), 7.64 (d, J=1.95 Hz, 1H), 6.72 (d, J=1.6 Hz, 1H), 6.66 (d, J=1.95 Hz, 1H), 6.55 (d, J=1.6 Hz, 1H), 3.89 (s, 6H), 3.78-3.86 (m, 4H), 3.62-3.74 (m, 1H), 2.28-2.42 (m, 1H), 1.83-1.93 (m, 2H), 1.71-1.81 (m, 4H), 1.51-1.66 (m, 2H), 0.97 (d, J=6.6 Hz, 6H); ESI MS m/z 494 [M+H]$^+$.

Example 39: 2-(2-((1-Acetylpiperidin-4-yl)amino)-4-methoxyphenyl)-5,7-dimethoxyquinazolin-4(3H)-one

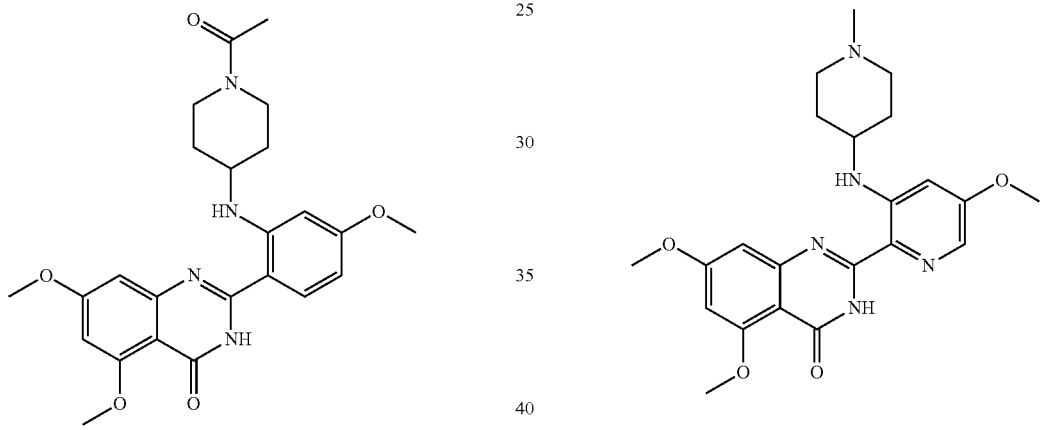

A mixture of 2-(2-((1-benzylpiperidin-4-yl)amino)-4-methoxyphenyl)-5,7-dimethoxyquinazolin-4(3H)-one (3.9 g, mmol) and Pd/C (6 g, 10% Pd, wet) in THF (25 mL) and ethanol (25 mL) was hydrogenated at rt under hydrogen pressure (50 psi) for 18 h. After that time, the mixture was filtered through celite and concentrated under reduced pressure. The product was purified by flash column chromatography (silica gel, 99:1 dichloromethane/methanol to 90:10 dichloromethane/methanol) to give 5,7-dimethoxy-2-(4-methoxy-2-(piperidin-4-ylamino)phenyl)quinazolin-4(3H)-one (0.55 g, 17%): $^1$H NMR (400 MHz, DMSO-$d_6$) δ 9.57 (br s, 1H), 7.83 (d, J=9.0 Hz, 1H), 6.52 (d, J=9.0 Hz, 21-1), 6.16-6.25 (m, 2H), 3.89 (s, 3H), 3.85 (s, 3H), 3.78 (s, 3H), 3.52-3.64 (m, 1H), 3.40-3.45 (m, 1H), 2.91-3.00 (m, 2H), 2.61-2.71 (m, 2H), 1.89-2.00 (m, 2H), 1.35-1.49 (m, 2H).

Acetic anhydride (0.0248 g) was added at 0° C. to a solution of 5,7-dimethoxy-2-(4-methoxy-2-(piperidin-4-ylamino)phenyl)quinazolin-4(3H)-one (0.100 g, 0.24 mmol) and triethylamine (0.243 g, 2.4 mmol) in dichloromethane (25 mL). The reaction was allowed to warm to rt and then stirred for 30 min. After that time the reaction was concentrated under reduced pressure and the product was purified by flash column chromatography (silica gel, 99:1 dichloromethane/methanol to 90:10 dichloromethane/methanol) to give 2-(2-((1-acetylpiperidin-4-yl)amino)-4-methoxyphenyl)-5,7-dimethoxyquinazolin-4(3H)-one (0.10 g, 92%) as white solid: $^1$H NMR (400 MHz, DMSO-$d_6$) δ 11.51 (s, 1H), 9.50 (d, J=7.4 Hz, 1H), 7.83 (d, J=8.6 Hz, 1H), 6.47-6.56 (m, 2H), 6.30 (s, 1H), 6.18-6.26 (m, 1H), 3.94-4.06 (m, 1H), 3.88 (s, 3H), 3.85 (s, 3H), 3.80 (s, 3H), 3.65-3.77 (m, 2H), 3.37-3.45 (m, 1H), 3.09-3.21 (m, 1H), 2.02 (s, 3H), 1.93-1.99 (m, 2H), 1.34-1.47 (m, 1H), 1.48-1.62 (m, 1H); ESI MS m/z 453 [M+H]$^+$.

Example 40: 5,7-Dimethoxy-2-(5-methoxy-3-((1-methylpiperidin-4-yl)amino)pyridin-2-yl)quinazolin-4(3H)-one Lithium bis(trimethylsilyl)amide (1 M in THF, 6.0 mL, 6.0 mmol) was added to a stirred suspension of 2-(3-fluoro-5-methoxypyridin-2-yl)-5,7-dimethoxyquinazolin-4(3H)-one (0.331 g, 1.0 mmol) and 1-methylpiperidin-4-amine (0.343 g, 3.0 mmol) in anhydrous THF (20 mL). After the addition was complete, the reaction was heated to reflux with stirring for 5 h. After that time the reaction was cooled to rt, diluted with saturated aqueous NH$_4$Cl (10 mL) and concentrated under reduced pressure. The residue was diluted with water (40 mL) and the resulting suspension was stirred at rt for 20 min. The precipitated solid was collected by filtration, washed with water and air-dried. The product was purified by flash column chromatography (silica gel, 99:1 dichloromethane/7N ammonia in methanol to 98:2 dichloromethane/7N ammonia in methanol) followed by trituration with methanol to give 5,7-dimethoxy-2-(5-methoxy-3-((1-methylpiperidin-4-yl)amino)pyridin-2-yl)quinazolin-4(3H)-one (0.080 g, 19%) as an off-white solid: mp 191-193° C.; $^1$H NMR (400 MHz, DMSO-$d_6$) δ 10.55 (s, 1H), 9.55 (d, J=7.0 Hz, 1H), 7.65 (d, J=2.3 Hz, 1H), 6.76 (d, J=2.3 Hz, 1H), 6.66 (d, J=2.15 Hz, 1H), 6.55 (d, J=2.15 Hz, 1H), 3.91 (s, 3H), 3.90 (s, 3H), 3.85 (s, 3H), 3.67-3.77 (m, 1H), 2.55-2.64 (m, 2H), 2.28-2.38 (m, 2H), 2.22 (s, 3H), 1.93-2.03 (m, 2H), 1.59-1.69 (m, 2H); ESI MS m/z 426 [M+H]$^+$.

Example 41: 5,7-Dimethoxy-2-(3-(((1-methylpyrrolidin-3-yl)methyl)amino)pyridin-2-yl)quinazolin-4(3H)-one

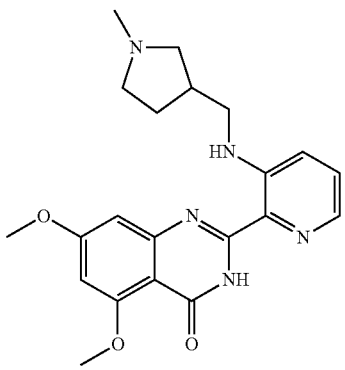 [SMILES: COc1cc(OC)c2c(=O)[nH]c(-c3ncccc3NCC3CCN(C)C3)nc2c1]

Lithium bis(trimethylsilyl)amide (1 M in THF, 5.6 mL, 5.6 mmol) was added to a stirred suspension of 2-(3-fluoropyridin-2-yl)-5,7-dimethoxyquinazolin-4(3H)-one (0.420 g, 1.39 mmol) and (1-methylpyrrolidin-3-yl)methanamine (0.478 g, 4.18 mmol) in anhydrous THF (20 mL). After the addition was complete, the reaction was heated to reflux with stirring for 3 h. After that time the reaction was cooled to rt, diluted with saturated aqueous NH$_4$Cl (5 mL) and concentrated under reduced pressure. The product was purified by flash column chromatography (silica gel, 99:1 dichloromethane/7N ammonia in methanol to 97:3 dichloromethane/7N ammonia in methanol) to give 5,7-dimethoxy-2-(3-(((1-methylpyrrolidin-3-yl)methyl)amino)pyridin-2-yl)quinazolin-4(3H)-one (0.160 g, 29%) as a yellow solid: mp 157-159° C.; $^1$H NMR (400 MHz, CDCl$_3$) δ 10.90 (br s, 1H), 9.43 (br s, 1H), 7.89-7.93 (m, 1H), 7.22-7.29 (m, 1H), 7.10 (d, J=7.8 Hz, 1H), 6.65 (d, J=1.95 Hz, 1H), 6.46 (d, J=1.95 Hz, 1H), 3.98 (s, 3H), 3.93 (s, 3H), 3.25-3.30 (m, 2H), 2.76-2.83 (m, 1H), 2.54-2.75 (m, 3H), 2.49 (dd, J=8.8, 5.3 Hz, 1H), 2.39 (s, 3H), 2.12-2.23 (m, 1H), 1.65-1.75 (m, 1H); ESI MS m/z 396 [M+H]$^+$.

Example 42: 4-((2-(5,7-Dimethoxy-4-oxo-3,4-dihydroquinazolin-2-yl)pyridin-3-yl)amino)-N,N-dimethylpiperidine-1-carboxamide

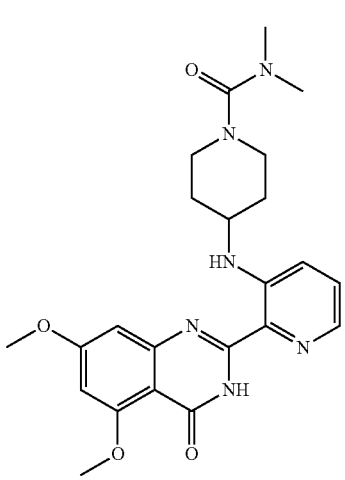 [SMILES: COc1cc(OC)c2c(=O)[nH]c(-c3ncccc3NC3CCN(C(=O)N(C)C)CC3)nc2c1]

Lithium bis(trimethylsilyl)amide (1 M in THF, 3.5 mL, 3.5 mmol) was added to a stirred suspension of 2-(3-fluoropyridin-2-yl)-5,7-dimethoxyquinazolin-4(3H)-one (0.352 g, 1.17 mmol) and 4-amino-N,N-dimethylpiperidine-1-carboxamide (0.500 g, 2.92 mmol) in anhydrous THF (20 mL). After the addition was complete, the reaction was heated to reflux with stirring for 6 h. After that time the reaction was cooled to rt, diluted with saturated aqueous NH$_4$Cl (5 mL) and concentrated under reduced pressure. The residue was diluted with water (30 mL) and the resulting suspension was stirred at rt for 30 min. The precipitated solid was collected by filtration, washed with water and air-dried. The product was purified by flash column chromatography (silica gel, 99:1 dichloromethane/methanol to 97:3 dichloromethane/methanol) to give 4-((2-(5,7-dimethoxy-4-oxo-3,4-dihydroquinazolin-2-yl)pyridin-3-yl)amino)-N,N-dimethylpiperidine-1-carboxamide (0.180 g, 34%) as a yellow solid: mp 195-197° C.; $^1$H NMR (400 MHz, CDCl$_3$) δ 10.91 (br s, 1H), 9.59 (d, J=7.4 Hz, 1H), 7.90-7.94 (m, 1H), 7.24-7.27 (m, 1H), 7.12 (d, J=8.2 Hz, 1H), 6.65 (d, J=2.15 Hz, 1H), 6.46 (d, J=2.15 Hz, 1H), 3.99 (s, 3H), 3.95 (s, 3H), 3.61-3.71 (m, 3H), 3.09-3.18 (m, 2H), 2.86 (s, 6H), 2.08-2.17 (m, 2H), 1.65-1.76 (m, 2H); ESI MS m/z 453 [M+H]$^+$.

Example 43: 2-(3-((3-(Isopropylamino)propyl)amino)pyridin-2-yl)-5,7-dimethoxyquinazolin-4(3H)-one

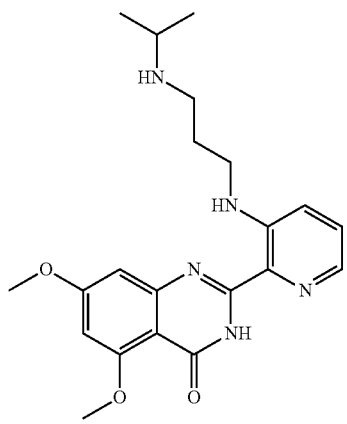 [SMILES: COc1cc(OC)c2c(=O)[nH]c(-c3ncccc3NCCCNC(C)C)nc2c1]

Lithium bis(trimethylsilyl)amide (1 M in THF, 3.6 mL, 3.6 mmol) was added to a stirred suspension of 2-(3-fluoropyridin-2-yl)-5,7-dimethoxyquinazolin-4(3H)-one (0.361 g, 1.20 mmol) and N$^1$-isopropylpropane-1,3-diamine (0.50 mL, 3.60 mmol) in anhydrous THF (20 mL). After the addition was complete, the reaction was heated to reflux with stirring for 2 h. After that time a second portion of lithium bis(trimethylsilyl)amide (1 M in THF, 1.2 mL, 1.2 mmol) was added and reflux with stirring was continued for an additional 2 h. After that time the reaction was cooled to rt, diluted with saturated aqueous NH$_4$Cl (3 mL) and concentrated under reduced pressure. The product was purified by flash column chromatography (silica gel, 97:3 dichloromethane/methanol then 97:3 dichloromethane/7N ammonia in methanol) to give 2-(3-((3-(isopropylamino)propyl)amino)pyridin-2-yl)-5,7-dimethoxyquinazolin-4(3H)-one (0.229 g, 48%) as a yellow solid: mp 121-122° C.; $^1$H NMR (400 MHz, CDCl$_3$) δ 9.32 (t, J=4.7 Hz, 1H), 7.90 (d, J=3.1 Hz, 1H), 7.21-7.27 (m, 1H), 7.12 (d, J=8.6 Hz, 1H), 6.65 (d, J=2.3 Hz, 1H), 6.45 (d, J=2.3 Hz, 1H), 3.99 (s, 3H), 3.94 (s, 3H), 3.33-3.42 (m, 2H), 2.78-2.88 (m, 3H), 1.92-2.00 (m, 2H), 1.07 (d, J=6.25 Hz, 6H); ESI MS m/z 398 [M+H]+.

Example 44: 5,7-Dimethoxy-2-(3-((1-methylpiperidin-4-yl)amino)pyridine-2-yl)quinazolin-4(3H)-one

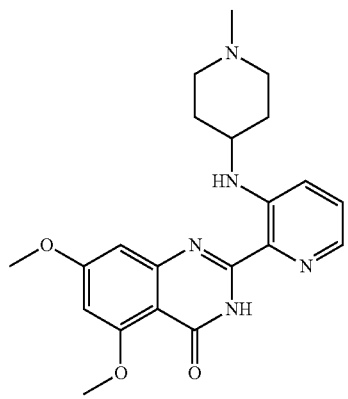 [SMILES: COc1cc(OC)c2c(=O)[nH]c(-c3ncccc3NC3CCN(C)CC3)nc2c1]

Lithium bis(trimethylsilyl)amide (1 M in THF, 4.0 mL, 4.0 mmol) was added to a stirred suspension of 2-(3-fluoropyridin-2-yl)-5,7-dimethoxyquinazolin-4(3H)-one (0.350 g, 1.16 mmol) and 1-methylpiperidine-4-amine (0.400 g, 3.5 mmol) in anhydrous THF (15 mL). After the addition was complete, the reaction was heated to reflux with stirring for 1 h. After that time a second portion of lithium bis(trimethylsilyl)amide (1 M in THF, 3.0 mL, 3.0 mmol) was added and reflux with stirring was continued for an additional 18 h. After that time the reaction was cooled to rt, diluted with saturated aqueous NH4Cl (3 mL) and concentrated under reduced pressure. The product was purified by flash column chromatography (silica gel, 97:3 dichloromethane/methanol then 97:3 dichloromethane/7N ammonia in methanol) to give 5,7-dimethoxy-2-(3-((1-methylpiperidin-4-yl)amino)pyridine-2-yl)quinazolin-4 (3H)-one (0.100 g, 22%) as a yellow solid: mp 186-188° C.; 1H NMR (CDCl3) δ 10.91 (br s, 1H), 9.55 (d, J=7.4 Hz, 1H), 7.89 (d, J=4.3 Hz, 1H), 7.19-7.27 (m, 1H), 7.11 (d, J=8.2 Hz, 1H), 6.65 (s, 1H), 6.46 (s, 1H), 3.98 (s, 3H), 3.93 (s, 3H), 3.53 (br s, 1H), 2.83 (br s, 2H), 2.36 (s, 3H), 2.31 (br s, 2H), 2.08-2.18 (m, 2H), 1.70-1.82 (m, 2H); ESI MS m/z 396 [M+H]+.

Example 45: cis-4-((2-(5,7-Dimethoxy-4-oxo-3,4-dihydroquinazolin-2-yl)-5-methoxypyridin-3-yl)amino)-N-isopropylcyclohexane-1-carboxamide

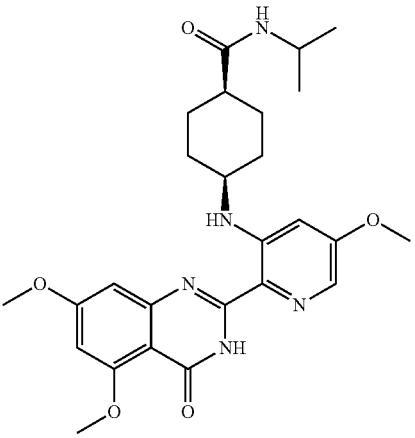

1-Ethyl-3-(3-dimethylaminopropyl)carbodiimide (2.10 g, 11.0 mmol) was added to a solution of cis-4[(tert-butoxycarbonyl)amino]cyclohexanecarboxylic acid (2.43 g, 10 mmol) and hydroxybenzotriazole (1.44 g, 11.0 mmol) in DMF (30 mL) and the reaction was stirred at rt for 20 min. After that time, isopropylamine (4.2 mL, 50 mmol) was added and the reaction mixture was stirred at rt for 18 h. After that time the reaction was concentrated under reduced pressure and the residue dissolved in CHCl3 (80 mL). The organic phase was washed with aqueous saturated NaHCO3 (2×40 mL) then brine (2×40 mL), dried (Na2SO4) and concentrated under reduced pressure to give tert-butyl-cis-(4-(isopropylcarbamoyl)cyclohexyl)carbamate (1.9 g, 67%) as an off-white solid: 1H NMR (400 MHz, CDCl3) δ 5.29 (br s, 1H), 4.76 (br s, 1H), 4.08 (dq, J=13.9, 6.7 Hz, 1H), 3.75 (br s, 1H), 2.04-2.14 (m, 1H), 1.72-1.81 (m, 2H), 1.65-1.72 (m, 4H), 1.54-1.65 (m, 2H), 1.44 (s, 9H), 1.14 (d, J=6.3 Hz, 6H).

Conc. HCl (4.0 mL, 40 mmol) was added to a solution of tert-butyl-cis-(4-(isopropylcarbamoyl)cyclohexyl)carbamate (1.9 g, 6.7 mmol) in methanol (30 mL) and the reaction was stirred at rt for 18 h. After that time the reaction was concentrated under reduced pressure to give cis-4-amino-N-isopropylcyclohexane-1-carboxamide hydrochloride (1.4 g, 95%) as an off-white solid: 1H NMR (400 MHz, DMSO-d6) δ 8.10 (br s, 3H), 7.62 (d, J=7.8 Hz, 1H), 3.80 (dq, J=13.6, 6.7 Hz, 1H), 3.09 (br s, 1H), 2.11-2.27 (m, 1H), 1.78-1.92 (m, 2H), 1.58-1.77 (m, 4H), 1.40-1.52 (m, 2H), 1.01 (d, J=6.6 Hz, 6H); ESI MS m/z 185 [M+H]+.

Lithium bis(trimethylsilyl)amide (1 M in THF, 6.0 mL, 6.0 mmol) was added to a stirred suspension of 2-(3-fluoro-5-methoxypyridin-2-yl)-5,7-dimethoxyquinazolin-4(3H)-one (0.400 g, 1.2 mmol) and cis-4-amino-N-isopropylcyclohexanecarboxamide hydrochloride (1.10 g, 5.0 mmol) in anhydrous THF (15 mL). After the addition was complete, the reaction was heated to reflux with stirring for 1 h. After that time a second portion of lithium bis(trimethylsilyl)amide (1 M in THF, 3.3 mL, 3.3 mmol) was added and reflux with stirring was continued for an additional 5 h. After that time the reaction was cooled to rt, diluted with saturated aqueous NH4Cl (3 mL) and concentrated under reduced pressure. The product was purified by flash column chromatography (silica gel, 97:3 dichloromethane/methanol)

then triturated with methanol to give cis-4-((2-(5,7-dimethoxy-4-oxo-3,4-dihydroquinazolin-2-yl)-5-methoxypyridin-3-yl)amino)-N-isopropylcyclohexane-1-carboxamide (0.025 g, 4%) as a light yellow solid: $^1$H NMR (400 MHz, CDCl$_3$) δ 10.72 (br s, 1H), 9.82 (d, J=7.8 Hz, 1H), 7.63 (s, 1H), 6.89 (s, 1H), 6.49 (s, 1H), 6.42 (s, 1H), 5.22 (d, J=7.0 Hz, 1H), 3.99-4.12 (m, 1H), 3.96 (s, 6H), 3.90 (s, 3H), 3.84 (br s, 1H), 3.49 (d, J=5.8 Hz, 1H), 2.14-2.24 (m, 1H), 1.92-2.09 (m, 4H), 1.81-1.91 (m, 2H), 1.64-1.78 (m, 2H), 1.08 (d, J=6.6 Hz, 6H); ESI MS m/z 496 [M+H]$^+$.

Example 46: 5,7-Dimethoxy-2-(3-((1-(2,2,2-trifluoroacetyl)piperidin-4-yl)amino)pyridin-2-yl)quinazolin-4(3H)-one

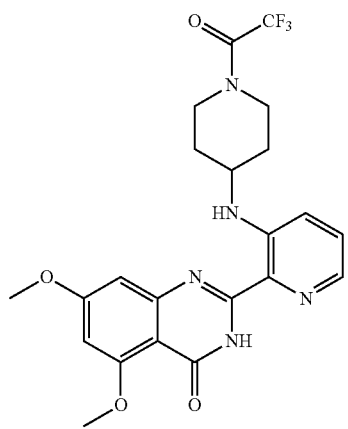 [SMILES: COc1cc(OC)c2c(=O)[nH]c(-c3ncccc3NC3CCN(C(=O)C(F)(F)F)CC3)nc2c1]

A suspension of 2-(3-fluoropyridin-2-yl)-5,7-dimethoxyquinazolin-4(3H)-one (1.0 g, 3.3 mmol), 1-benzylpiperidin-4-amine (1.25 g, 6.6 mmol), lithium bis(trimethylsilyl)amide (13.2 mL, 13.2 mmol) and THF (25 mL) was heated at 70° C. in a sealed tube for 3 h. After this time, the reaction was cooled to rt, quenched with cold water (100 mL) and concentrated under reduced pressure. The precipitated solid was collected by filtration, washed with water and air-dried. The product was purified by flash column chromatography (silica gel, dichloromethane to 70:30 dichloromethane/methanol) to give 2-(3-((1-benzylpiperidin-4-yl)amino)pyridin-2-yl)-5,7-dimethoxyquinazolin-4(3H)-one (0.92 g, 60%) as a yellow solid: $^1$H NMR (400 MHz, DMSO-d$_6$) δ 10.80 (d, J=1.6 Hz, 1H), 9.34-9.47 (m, 1H), 7.93 (d, J=1.95 Hz, 1H), 7.37-7.43 (m, 2H), 7.29-7.37 (m, 4H), 7.21-7.28 (m, 1H), 6.73 (s, 1H), 6.61 (s, 1H), 3.94 (s, 3H), 3.87 (s, 3H), 3.59-3.73 (m, 1H), 3.51 (s, 2H), 2.61-2.77 (m, 2H), 2.26-2.40 (m, 2H), 1.88-2.08 (m, 2H), 1.56-1.72 (m, 2H); ESI MS m/z 472 [M+H]$^+$.

A mixture of 2-(3-((1-benzylpiperidin-4-yl)amino)pyridin-2-yl)-5,7-dimethoxyquinazolin-4(3H)-one (0.7 g, 1.5 mmol) and Pd/C (2.1 g, 10% Pd, wet) in THF (20 mL) and ethanol (10 mL) was hydrogenated at rt under hydrogen pressure (50 psi) for 18 h. After that time, the mixture was filtered through celite and concentrated under reduced pressure. The product was purified by flash column chromatography (silica gel, dichloromethane to 70:30 dichloromethane/methanol) to give 5,7-dimethoxy-2-(3-(piperidin-4-ylamino)pyridin-2-yl)quinazolin-4(3H)-one (0.20 g, 35%) as a yellow solid: $^1$H NMR (400 MHz, DMSO-d$_6$) δ 9.43 (d, J=7.4 Hz, 1H), 7.92 (s, 1H), 7.38 (s, 2H), 6.66 (s, 1H), 6.60 (s, 1H), 3.93 (s, 3H), 3.87 (s, 3H), 3.58-3.73 (m, 1H), 3.14-3.26 (m, 1H), 2.90-3.06 (m, 2H), 2.59-2.76 (m, 2H), 1.88-2.06 (m, 2H), 1.39-1.58 (m, 2H); ESI MS m/z 382.1 [M+H]$^+$.

Trifluoroacetic anhydride (0.032 g, 0.15 mmol was added to a solution of 5,7-dimethoxy-2-(3-(piperidin-4-ylamino)pyridin-2-yl)quinazolin-4(3H)-one (0.070 g, 0.18 mmol) and triethylamine (0.182 g, 1.8 mmol) in THF (15 mL) at 0° C. The resulting mixture was allowed to warm to rt and stirred for 30 min. After that time the mixture was concentrated under reduced pressure. The product was purified by flash column chromatography (silica gel, dichloromethane to 70:30 dichloromethane/methanol) to give 5,7-dimethoxy-2-(3-((1-(2,2,2-trifluoroacetyl)piperidin-4-yl)amino)pyridin-2-yl)quinazolin-4(3H)-one (0.032 g, 39%) as a light yellow solid: mp 218-219° C.; $^1$H NMR (400 MHz, DMSO-d$_6$) δ 10.79 (br s, 1H), 9.40 (d, J=7.4 Hz, 1H), 7.94 (d, J=3.5 Hz, 1H), 7.33-7.54 (m, 2H), 6.70 (s, 1H), 6.57 (s, 1H), 4.04-4.20 (m, 1H), 3.89 (s, 3H), 3.77-3.87 (m, 3H), 3.44-3.57 (m, 2H), 3.08-3.25 (m, 2H), 2.03-2.19 (m, 2H), 1.54-1.75 (m, 2H); ESI MS m/z 478 [M+H]$^+$.

Example 47: 4-((2-(5,7-Dimethoxy-4-oxo-3,4-dihydroquinazolin-2-yl)pyridin-3-yl)amino)-N-isopropylpiperidine-1-carboxamide

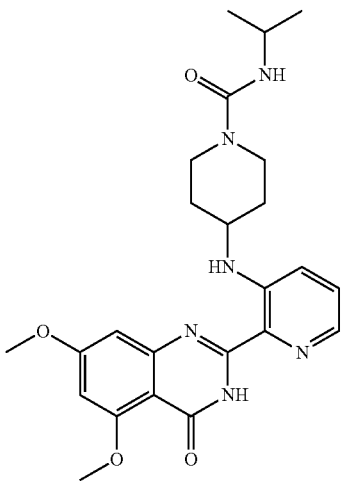 [SMILES: COc1cc(OC)c2c(=O)[nH]c(-c3ncccc3NC3CCN(C(=O)NC(C)C)CC3)nc2c1]

2-Isocyanatopropane (0.016 g, 0.18 mmol) was added to a solution of 5,7-dimethoxy-2-(3-(piperidin-4-ylamino)pyridin-2-yl)quinazolin-4(3H)-one (0.070 g, 0.18 mmol) and triethylamine (0.182 g, 1.8 mmol) in THF (15 mL) at 0° C. The resulting mixture was allowed to warm to rt and stirred for 30 min. After that time the mixture was concentrated under reduced pressure. The product was purified by flash column chromatography (silica gel, dichloromethane to 70:30 dichloromethane/methanol) to give 4-((2-(5,7-dimethoxy-4-oxo-3,4-dihydroquinazolin-2-yl)pyridin-3-yl)amino)-N-isopropylpiperidine-1-carboxamide (0.060 g, 71%) as a light yellow solid: mp 198-199° C.; $^1$H NMR (400 MHz, DMSO-d$_6$) δ 10.77 (br s, 1H), 9.39 (d, J=8.2 Hz, 1H), 7.92 (d, J=2.7 Hz, 1H), 7.32-7.50 (m, 2H), 6.64 (s, 1H), 6.57 (s, 1H), 6.21 (d, J=7.4 Hz, 1H), 3.89 (s, 3H), 3.84 (s, 3H), 3.69-3.80 (m, 4H), 3.00-3.14 (m, 2H), 1.88-2.00 (m, 2H), 1.38-1.55 (m, 2H), 1.03 (d, J=6.3 Hz, 6H); ESI MS m/467 [M+H]$^+$.

Example 48: 5,7-Dimethoxy-2-(3-((1-pivaloylpiperidin-4-yl)amino)pyridin-2-yl)quinazolin-4(3H)-one

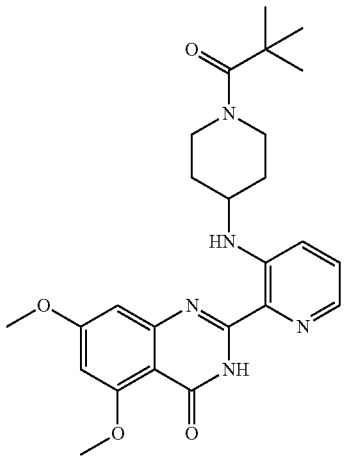 [SMILES: COc1cc(OC)c2c(=O)[nH]c(-c3ncccc3NC3CCN(C(=O)C(C)(C)C)CC3)nc2c1]

Pivaloyl chloride (0.016 g, 0.13 mmol) was added to a solution of 5,7-dimethoxy-2-(3-(piperidin-4-ylamino)pyridin-2-yl)quinazolin-4(3H)-one (0.050 g, 0.13 mmol) and triethylamine (0.131 g, 1.3 mmol) in THF (15 mL) at 0° C. The reaction was allowed to warm to rt and stirred for 30 min. After that time the mixture was concentrated under reduced pressure. The product was purified by flash column chromatography (silica gel, dichloromethane to 70:30 dichloromethane/methanol) to give 5,7-dimethoxy-2-(3-((1-pivaloylpiperidin-4-yl)amino)pyridin-2-yl)quinazolin-4 (3H)-one (0.044 g, 72%) as a yellow solid: mp 209-210° C.; $^{1}$H NMR (400 MHz, DMSO-$d_6$) δ 10.77 (br s, 1H), 9.43 (d, J=7.4 Hz, 1H), 7.92 (d, J=1.6 Hz, 1H), 7.35-7.48 (m, 2H), 6.64 (s, 1H), 6.57 (s, 1H), 3.95-4.07 (m, 2H), 3.88 (s, 3H), 3.84-3.87 (m, 1H), 3.84 (s, 3H), 3.24-3.27 (m, 2H), 1.93-2.07 (m, 2H), 1.43-1.56 (m, 2H), 1.19 (s, 9H); ESI MS m/z 466 [M+H]$^{+}$.

Example 49: 5,7-Dimethoxy-2-(3-((2-morpholinoethyl)amino)pyridine-2-yl)quinazolin-4(3H)-one

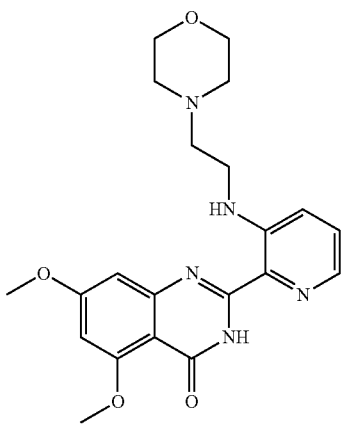 [SMILES: COc1cc(OC)c2c(=O)[nH]c(-c3ncccc3NCCN3CCOCC3)nc2c1]

Lithium bis(trimethylsilyl)amide (1 M in THF, 5.0 mL, 5.0 mmol) was added to a stirred suspension of 2-(3-fluoropyridin-2-yl)-5,7-dimethoxyquinazolin-4(3H)-one (0.400 g, 1.33 mmol) and 2-(morpholin-4-yl)ethanamine (0.520 g, 4.0 mmol) in anhydrous THF (15 mL). After the addition was complete, the reaction was heated to reflux with stirring for 1 h. After that time a second portion of lithium bis(trimethylsilyl)amide (1 M in THF, 3.0 mL, 3.0 mmol) was added and reflux with stirring was continued for an additional 18 h. After that time the reaction was cooled to rt, diluted with saturated aqueous NH$_4$Cl (3 mL) and concentrated under reduced pressure. The product was purified by flash column chromatography (silica gel, 97:3 dichloromethane/methanol) followed by recrystallization from chloroform/hexanes to give 5,7-dimethoxy-2-(3-((2-morpholinoethyl)amino)pyridine-2-yl)quinazolin-4(3H)-one (0.110 g, 20%) as a yellow solid: mp 168-170° C.; $^{1}$H NMR (CDCl$_3$) δ 10.91 (br s, 1H), 9.38 (br s, 1H), 7.93 (d, J=3.5 Hz, 1H), 7.29 (br s, 1H), 7.10 (d, J=8.2 Hz, 1H), 6.75 (s, 1H), 6.44-6.51 (m, 1H), 4.00 (s, 3H), 3.93 (s, 3H), 3.74-3.80 (m, 4H), 3.40 (q, J=5.6 Hz, 2H), 2.80 (t, J=6.0 Hz, 2H), 2.59 (br s, 4H); ESI MS m/z 412 [M+H]$^{+}$.

Example 50: 2-(3-((1-Isopropylpiperidin-4-yl)amino)-5-(2-((1-isopropylpiperidin-4-yl)amino)ethoxy)pyridin-2-yl)-5,7-dimethoxyquinazolin-4(3H)-one

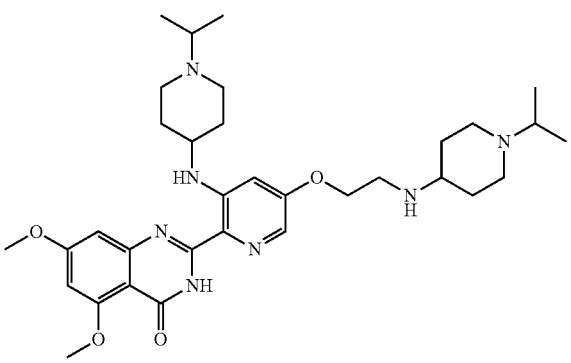 [SMILES: COc1cc(OC)c2c(=O)[nH]c(-c3ncc(OCCNC4CCN(C(C)C)CC4)cc3NC3CCN(C(C)C)CC3)nc2c1]

Butyllithium (1.6 M in hexanes, 82 mL, 130 mmol) was added dropwise to a suspension of 3-bromo-6-chloro-5-fluoropyridine (25.0 g, 119 mmol) in anhydrous toluene (280 mL) cooled to −78° C. After the addition was complete the reaction was stirred for 10 min. After that time, trimethyl borate (14.82 g, 143 mmol) was added dropwise while maintaining the temperature at −78° C. After the addition was complete, the reaction was allowed to warm to rt and stirring was continued for 17 h. After that time the reaction was re-cooled to −5° C. and carefully treated with 8N NaOH solution (18 mL) followed by 30% hydrogen peroxide (37.6 g, 1105 mmol). The reaction was warmed to rt and stirred an additional 2 h. After that time the reaction was re-cooled to 10° C. and carefully quenched with sat. Na$_2$S$_2$O$_3$ (60 mL). The organic phase was reserved. The aqueous phase was extracted with ethyl acetate (3×150 mL). The combined organics were washed with sat. NaCl (200 mL), dried (MgSO$_4$), filtered and concentrated under reduced pressure. This product was triturated with hexanes (3×100 mL) and dried to give 6-chloro-5-fluoropyridin-3-ol (14.2 g, 80%) as a white solid: $^{1}$H NMR (400 MHz, DMSO-$d_6$) δ 10.78 (br s, 1H), 7.86 (d, J=2.4 Hz, 1H), 7.32 (dd, J=10.4, 2.4 Hz, 1H).

A suspension of K$_2$CO$_3$ (19.8 g, 143 mmol), 6-chloro-5-fluoropyridin-3-ol (14.1 g, 95 mmol) and 2-tert-butyldimethylsilyloxyethyl bromide (25.1 g, 105 mmol) in anhydrous DMF (120 mL) was stirred at rt for 65 h. After that time the reaction mixture was diluted with ethyl acetate (200 mL), washed with water (4×100 mL), dried (MgSO$_4$) and concentrated under reduced pressure to give 5-(2-((tert-butyldimethylsilyl)oxy)ethoxy)-2-chloro-3-fluoropyridine (26.3 g, 90%) as a yellow solid: $^1$H NMR (400 MHz, CDCl$_3$) δ 7.94 (d, J=2.6 Hz, 1H), 7.11 (dd, J=9.5, 2.6 Hz, 1H), 4.10 (t, J=4.8 Hz, 2H), 3.98 (t, J=4.8 Hz, 2H), 0.90 (s, 9H), 0.09 (s, 6H).

A mixture of 5-[2-(tert-butyldimethylsilyloxy)ethoxy]-2-chloro-3-fluoropyridine (11.6 g, 38 mmol), Pd(dppf)Cl$_2$ (1.39 g, 1.9 mmol) and triethylamine (11.5 g, 114 mmol) in methanol (200 mL) was placed under a CO atmosphere (200 psi) and heated with stirring at 90° C. for 4 h. After that time the reaction was cooled to rt, filtered through a pad of celite and concentrated under reduced pressure. The product was suspended in diethyl ether (600 mL), filtered through a pad of silica gel and concentrated under reduced pressure to give methyl 5-(2-((tert-butyldimethylsilyl)oxy)ethoxy)-3-fluoropicolinate (11.6 g, 94%) as a white solid: $^1$H NMR (400 MHz, CDCl$_3$) δ 8.26 (d, J=2.4 Hz, 1H), 7.07 (dd, J=11.7, 2.4 Hz, 1H), 4.17 (t, J=4.4 Hz, 2H), 4.00 (t, J=4.4 Hz, 2H), 3.99 (s, 3H), 0.89 (s, 9H), 0.09 (s, 6H).

Sodium borohydride (7.57 g, 200 mmol) was added portionwise to a suspension of methyl 5-[2-(tert-butyldimethylsilyloxy)ethoxy]-3-fluoropicolinate (16.47 g, 50 mmol) in ethanol (135 mL) cooled to 10° C. and stirred for 15 h. After that time the reaction was concentrated under reduced pressure and dissolved in ethyl acetate (300 mL). The solution was washed with water (2×100 mL), sat. NaHCO$_3$ (100 mL) and sat. NaCl (100 mL), dried (MgSO$_4$) and concentrated under reduced pressure to give (5-(2-((tert-butyldimethylsilyl)oxy)ethoxy)-3-fluoropyridin-2-yl)methanol (14.91 g, 98%) as a white solid: $^1$H NMR (400 MHz, CDCl$_3$) δ 8.12 (d, J=2.4 Hz, 1H), 7.02 (dd, J=11.2, 2.4 Hz, 1H), 4.77-4.75 (m, 2H), 4.10 (t, J=4.8 Hz, 2H), 3.98 (t, J=4.8 Hz, 2H), 3.57 (t, J=4.8 Hz, 2H), 0.90 (s, 9H), 0.10 (s, 6H).

2-Iodoxybenzoic acid (18.0 g, 64 mmol) was added in one portion to a solution of (5-(2-((tert-butyldimethylsilyl)oxy)ethoxy)-3-fluoropyridin-2-yl)methanol (14.91 g, 50 mmol) in DMSO (82 mL) and stirred at rt for 18 h. After that time the reaction was diluted with water (500 mL). The precipitated solids were collected by filtration and washed with water (2×200 mL) and air-dried. The solids were triturated with diethyl ether (3×200 mL) to remove the product. The combined ether extracts were washed with sat. NaHCO$_3$ (100 mL), sat. NaCl (100 mL), dried (MgSO$_4$) and concentrated under reduced pressure to give 5-(2-(tert-butyldimethylsilyloxy)ethoxy)-3-fluoropicolinaldehyde (11.36 g, 77%) as a white crystalline solid: $^1$H NMR (400 MHz, CDCl$_3$) δ 10.12 (s, 1H), 8.32 (d, J=2.4 Hz, 1H), 7.07 (dd, J=11.8, 2.4 Hz, 1H), 4.20 (t, J=5.2 Hz, 2H), 4.02 (t, J=5.2 Hz, 2H), 0.90 (s, 91H), 0.09 (s, 6H).

A suspension of 2-amino-4,6-dimethoxybenzamide (7.37 g, 37.9 mmol) and 5-(2-(tert-butyldimethylsilyloxy)ethoxy)-3-fluoropicolinaldehyde (11.36 g, 38 mmol) in nitrobenzene (77 mL) was heated to 137° C. with stirring for 24 h. After that time, the reaction was cooled to rt and diluted with hexanes (600 mL). The dark tar-like precipitate was separated and purified by flash column chromatography (silica gel, 85:15 dichloromethane/ethyl acetate) to give 2-[5-(2-(tert-butyldimethylsilyloxy) ethoxy)-3-fluoropyridin-2-yl)-5,7-dimethoxyquinazolin-4(3H)-one (4.26 g, 24%) as a yellow solid: $^1$H NMR (400 MHz, CDCl$_3$) δ 10.43 (s, 1H), 8.22 (d, J=2.4 Hz, 1H), 7.17 (dd, J=12.4, 2.4 Hz, 1H), 6.85 (d, J=2.4 Hz, 1H), 6.49 (d, J=2.4 Hz, 1H), 4.20 (t, J=4.8 Hz, 2H), 4.02 (t, J=4.8 Hz, 2H), 3.99 (s, 3H), 3.94 (s, 3H), 0.91 (s, 9H), 0.11 (s, 6H).

Triethylamine trihydrofluoride (4.33 g, 26.9 mmol) was added in one portion to a suspension of 2-[5-(2-(tert-butyldimethylsilyloxy)ethoxy]-3-fluoropyridin-2-yl)-5,7-dimethoxyquinazolin-4(3H)-one (4.26 g, 8.96 mmol) in anhydrous THF (85 mL) and stirred at rt for 14 h. After that time the reaction was concentrated under reduced pressure and the solid was treated with saturated aqueous solution of NaHCO$_3$ (100 mL). The precipitated solids were collected by filtration and washed with water (3×100 mL), diethyl ether (3×100 mL) and dried to give 2-3-fluoro-5-(2-hydroxyethoxy)pyridin-2-yl)-5,7-dimethoxyquinazolin-4(3H)-one (3.15 g, 97%) as a yellow solid: $^1$H NMR (400 MHz, DMSO-d$_6$) δ 11.37 (s, 1H), 8.29 (s, 1H), 7.63 (d, J=11.5 Hz, 1H), 6.70 (s, 1H), 6.56 (s, 1H), 4.99 (t, J=4.6 Hz, 1H), 4.18 (t, J=4.6 Hz, 2H), 3.87 (s, 3H), 3.83 (s, 3H), 3.74 (q, J=4.6 Hz, 2H).

Phosphorus tribromide (4.72 g, 17.4 mmol) was added in one portion to a suspension of 2-(3-fluoro-5-(2-hydroxyethoxy)pyridin-2-yl)-5,7-dimethoxyquinazolin-4(3H)-one (3.15 g, 8.7 mmol) in anhydrous DMF (66 mL) and heated at 60° C. with stirring for 1 h. After that time the reaction was cooled to rt and concentrated under reduced pressure. The solids were dissolved in chloroform (130 mL) and the solution was washed with sat. NaHCO$_3$ (220 mL), dried (MgSO$_4$) and concentrated under reduced pressure. The product was triturated with diethyl ether (3×30 mL) and dried to give 2-(3-fluoro-5-(2-bromoethoxy)pyridin-2-yl)-5,7-dimethoxyquinazolin-4(3H)-one (3.41 g, 92%) as a yellow solid: $^1$H NMR (400 MHz, CDCl$_3$) δ 10.40 (s, 1H), 8.24 (d, J=2.4 Hz, 1H), 7.15 (dd, J=12.4, 2.4 Hz, 1H), 6.86 (d, J=2.4 Hz, 1H), 6.50 (d, J=2.4 Hz, 1H), 4.44 (t, J=5.6 Hz, 2H), 3.99 (s, 3H), 3.94 (s, 3H), 3.71 (t, J=5.6 Hz, 2H).

1-Isopropyl-4-aminopiperidine (0.711 g, 5 mmol) was added in one portion to a suspension of 2-(3-fluoro-5-(2-bromoethoxy)pyridin-2-yl)-5,7-dimethoxyquinazolin-4 (3H)-one (0.212 g, 0.5 mmol) in anhydrous DMSO (2 mL) and heated at 80° C. with stirring for 17 h. After that time the reaction was cooled to rt, diluted with chloroform (15 mL), washed with sat. NaHCO$_3$ (20 mL), water (2×15 mL), dried (MgSO$_4$) and concentrated under reduced pressure. The product was triturated (diethyl ether, 3×5 mL) and dried to give 2-(3-((1-isopropylpiperidin-4-yl)amino)-5-(2-((1-isopropylpiperidin-4-yl)amino)ethoxy)pyridin-2-yl)-5,7-dimethoxyquinazolin-4(3H)-one (0.252 g, 83%) as a yellow solid: $^1$H NMR (400 MHz, CDCl$_3$) δ 9.57 (d, J=7.2 Hz, 1H), 7.62 (d, J=2.0 Hz, 1H), 6.60 (d, J=2.0 Hz, 1H), 6.50 (d, J=2.0 Hz, 1H), 6.41 (d, J=2.0 Hz, 1H), 4.16 (t, J=4.8 Hz, 2H), 3.97 (s, 3H), 3.93 (s, 3H), 3.44 (br s, 1H), 3.07 (t, J=4.8 Hz, 2H), 2.91-2.70 (m, 6H), 2.54-2.40 (m, 3H), 2.21-2.13 (m, 4H), 1.96-1.93 (m, 2H), 1.78-1.74 (m, 3H), 1.45-1.37 (m, 2H), 1.10 (d, J=6.4 Hz, 6H), 1.04 (d, J=6.4 Hz, 6H); ESI MS m/z 608 [M+H]$^+$.

Example 51: 2-(4-((2-(5,7-Dimethoxy-4-oxo-3,4-dihydroquinazolin-2-yl)pyridin-3-yl)amino)piperidin-1-yl)-N,N-dimethyl-2-oxoacetamide

Example 52: 4-((2-(5,7-dimethoxy-4-oxo-3,4-dihydroquinazolin-2-yl)pyridin-3-yl)amino)-N-ethylpiperidine-1-carboxamide

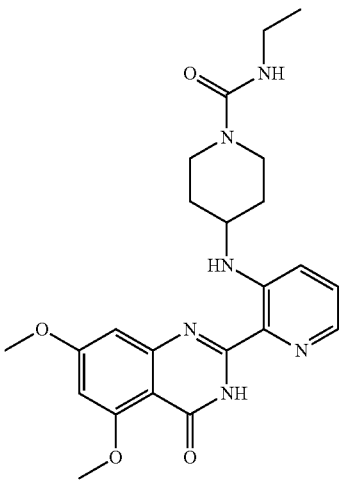

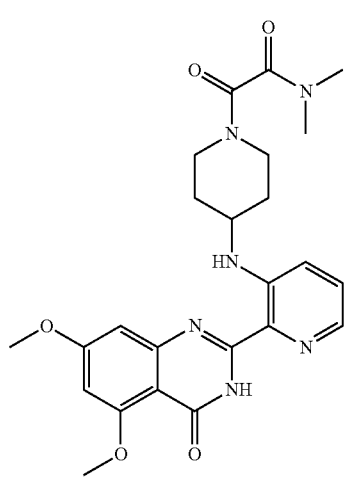

Ethyl isocyanate (0.016 g, 0.18 mmol) was added to an ice-cold solution of 5,7-dimethoxy-2-(3-(piperidin-4-ylamino)pyridin-2-yl)quinazolin-4(3H)-one (0.070 g, 0.18 mmol) and triethylamine (0.182 g, 1.8 mmol) in THF (15 mL). The reaction was allowed to warm to rt and stirred for 30 min. After that time the reaction was concentrated under reduced pressure and the product was purified by flash column chromatography (silica gel, dichloromethane to 70:30 dichloromethane/methanol) to give 4-((2-(5,7-dimethoxy-4-oxo-3,4-dihydroquinazolin-2-yl)pyridin-3-yl)amino)-N-ethylpiperidine-1-carboxamide (0.060 g, 78%) as yellow solid: mp 151-152° C.; $^1$H NMR (400 MHz, DMSO-$d_6$) 10.80 (br s, 1H), 9.42 (d, J=7.4 Hz, 1H), 7.95 (br s, 1H), 7.38-7.48 (m, 2H), 6.66 (s, 1H), 6.60 (s, 1H), 6.51-6.56 (m, 1H), 3.91 (s, 3H), 3.86 (s, 3H), 3.73-3.82 (m, 3H), 3.00-3.16 (m, 4H), 1.91-2.02 (m, 2H), 1.43-1.57 (m, 2H), 1.01 (t, J=7.2 Hz, 3H); ESI MS m/z 453 [M+H]$^+$.

Example 53: cis-4-((2-(5,7-Dimethoxy-4-oxo-3,4-dihydroquinazolin-2-yl)pyridin-3-yl)amino)-N,N-dimethylcyclohexane-1-carboxamide

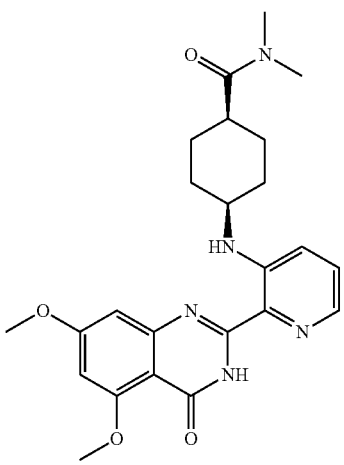 [SMILES: COc1cc(OC)c2c(=O)[nH]c(-c3ncccc3N[C@H]3CC[C@@H](C(=O)N(C)C)CC3)nc2c1]

N,N'-dicyclohexylcarbodiimide (0.081 g, 0.39 mmol) was added at room temperature to a solution of 2-(dimethylamino)-2-oxoacetic acid (0.046 g, 0.39 mmol) in DMF (15 mL), followed by 1-hydroxy-1H-benzotriazole (0.053 g, 0.39 mmol). The reaction was stirred for 1 h and then 5,7-dimethoxy-2-(3-(piperidin-4-ylamino)pyridin-2-yl)quinazolin-4(3H)-one (0.050 g, 0.13 mmol) was added. The reaction was then stirred at rt for 16 h, concentrated under reduced pressure and the product was purified by flash column chromatography (silica gel, dichloromethane to 70:30 dichloromethane/methanol) to give 2-(4-((2-(5,7-dimethoxy-4-oxo-3,4-dihydroquinazolin-2-yl)pyridin-3-yl)amino)piperidin-1-yl)-N,N-dimethyl-2-oxoacetamide (0.015 g, 24%) as yellow solid: mp 261-262° C.; $^1$H NMR (400 MHz, DMSO-$d_6$) δ 10.78 (br s, 1H), 9.41 (d, J=7.4 Hz, 1H), 7.95 (br s, 1H), 7.37-7.49 (m, 2H), 6.67 (s, 1H), 6.59 (s, 1H), 4.04-4.14 (m, 1H), 3.90 (s, 3H), 3.84 (s, 3H), 3.43-3.52 (m, 2H), 3.15-3.24 (m, 2H), 2.91 (s, 3H), 2.86 (s, 3H), 2.00-2.12 (m, 2H), 1.48-1.65 (m, 2H); ESI MS m/z 479 [M+H]$^+$.

1-Ethyl-3-(3-dimethylaminopropyl)carbodiimide (2.10 g, 11.0 mmol) was added to a solution of cis-4-[(tert-butoxycarbonyl)amino]cyclohexanecarboxylic acid (2.43 g, 10 mmol) and hydroxybenzotriazole (1.436 g, 11.0 mmol) in DMF (30 mL). The reaction was stirred at rt for 20 min. After that time dimethylamine (2 M solution in THF, 25 ml, 50 mmol) was added and the reaction mixture was stirred at rt for 18 h. After that time the reaction was concentrated under reduced pressure and the residue was dissolved in chloroform (80 mL). The organics were washed with sat. NaHCO$_3$ (2×40 mL), sat. NaCl (2×40 mL), dried (Na$_2$SO$_4$) and concentrated under reduced pressure to give tert-butyl-cis-(4-(dimethylcarbamoyl)cyclohexyl)carbamate (2.2 g, 82%) as an off-white solid: $^1$H NMR (400 MHz, CDCl$_3$) δ 4.82 (br s, 1H), 3.81 (br s, 1H), 3.04 (s, 3H), 2.94 (s, 3H), 2.52-2.63 (m, 1H), 1.74-1.86 (m, 2H), 1.64-1.77 (m, 2H), 1.51-1.64 (m, 4H), 1.44 (s, 9H).

Concentrated hydrochloric acid (4.0 mL, 40 mmol) was added to a solution of tert-butyl-cis-(4-(dimethylcarbamoyl)cyclohexyl)carbamate (2.2 g, 6.7 mmol) in methanol (30 mL) and stirred at rt for 18 h. After this time the reaction was concentrated under reduced pressure and dried to give cis-4-amino-N,N-dimethylcyclohexane-1-carboxamide hydrochloride (1.6 g, 95%) as an off-white solid: $^1$H NMR (400 MHz, DMSO-d$_6$) δ 8.08 (br s, 3H), 3.18 (br s, 1H), 2.99 (s, 3H), 2.80 (s, 3H), 2.73 (br s, 1H), 1.76-1.87 (m, 2H), 1.71 (dd, J=9.4, 4.3 Hz, 4H), 1.44-1.57 (m, 2H); ESI MS m/z 171 [M+H]$^+$.

Lithium bis(trimethylsilyl)amide (1 M in THF, 8.0 mL, 8.0 mmol) was added to a stirred suspension of 2-(3-fluoropyridin-2-yl)-5,7-dimethoxyquinazolin-4(3H)-one (0.400 g, 1.33 mmol) and cis-4-amino-N,N-dimethylcyclohexane-1-carboxamide hydrochloride (0.826 g, 4.0 mmol) in anhydrous THF (15 mL). After the addition was complete, the reaction was heated to reflux with stirring for 1 h. After that time a second portion of lithium bis(trimethylsilyl)amide (1 M in THF, 4.0 mL, 4.0 mmol) was added and reflux with stirring was continued for an additional 15 h. After that time the reaction was cooled to rt, diluted with saturated aqueous NH$_4$Cl (3 mL) and concentrated under reduced pressure. The product was purified by flash column chromatography (silica gel, 97:3 chloroform/methanol) followed by recrystallization from chloroform/hexanes to give cis-4-((2-(5,7-dimethoxy-4-oxo-3,4-dihydroquinazolin-2-yl)pyridin-3-yl)amino)-N,N-dimethylcyclohexane-1-carboxamide (0.075 g, 13%) as a light yellow solid: mp. 276-278° C.; $^1$H NMR (400 MHz, CDCl$_3$) δ 10.93 (br s, 1H), 9.80 (d, J=8.2 Hz, 1H), 7.87 (d, J=3.5 Hz, 1H), 7.22 (dd, J=8.6, 3.9 Hz, 1H), 7.05-7.17 (m, 2H), 6.46 (s, 1H), 4.04 (s, 3H), 3.97 (s, 3H), 3.91 (br s, 1H), 3.08 (s, 3H), 2.92 (s, 3H), 2.60-2.72 (m, 1H), 1.96-2.18 (m, 4H), 1.65-1.83 (m, 4H); ESI MS m/z 452 [M+H]$^+$.

Example 54: 4-((2-(5,7-Dimethoxy-4-oxo-3,4-dihydroquinazolin-2-yl)pyridin-3-yl)amino)piperidine-1-carboxamide

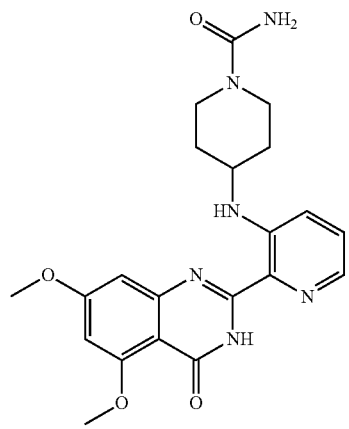 [SMILES: COc1cc(OC)c2c(=O)[nH]c(-c3ncccc3NC3CCN(C(N)=O)CC3)nc2c1]

Trimethylsilyl isocyanate (1.0 mL) was added to a solution of 5,7-dimethoxy-2-(3-(piperidin-4-ylamino)pyridin-2-yl)quinazolin-4(3H)-one (0.050 g, 0.13 mmol) and triethyl amine (1.0 mL) in THF (15 mL) cooled to 0° C. The reaction was allowed to warm to rt and stirred 16 h. After that time the reaction was concentrated under reduced pressure and the product was purified by flash column chromatography (silica gel, dichloromethane to 70:30 dichloromethane/methanol) to give 4-((2-(5,7-dimethoxy-4-oxo-3,4-dihydroquinazolin-2-yl)pyridin-3-yl)amino)piperidine-1-carboxamide (0.025 g, 45%) as yellow solid: mp 265-266° C.; $^1$H NMR (400 MHz, DMSO-d$_6$) δ 10.75 (br s, 1H), 9.39 (d, J=7.4 Hz, 1H), 7.92 (br s, 1H), 7.35-7.45 (m, 2H), 6.63 (s, 1H), 6.57 (s, 1H), 5.97 (br s, 2H), 3.89 (s, 3H), 3.84 (s, 3H), 3.67-3.80 (m, 3H), 3.03-3.16 (m, 2H), 1.87-2.01 (m, 2H), 1.40-1.54 (m, 2H); ESI MS m/z 425 [M+H]$^+$.

Example 55: Methyl-2-(4-((2-(5,7-dimethoxy-4-oxo-3,4-dihydroquinazolin-2-yl)pyridin-3-yl)amino)piperidin-1-yl)-2-oxoacetate

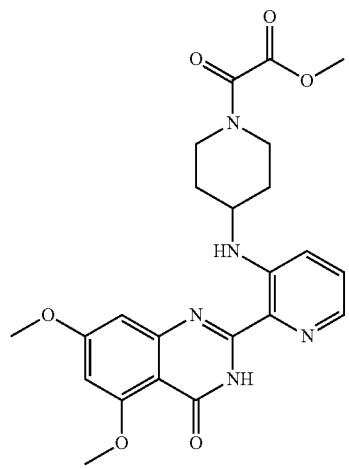

Methyl-2-chloro-2-oxoacetate (0.022 g, 0.183 mmol) was added to a solution of 5,7-dimethoxy-2-(3-(piperidin-4- ylamino)pyridin-2-yl)quinazolin-4(3H)-one (0.070 g, 0.183 mmol) and triethyl amine (0.182 g, 1.8 mmol) in THF (25 mL) cooled to 0° C. The reaction was allowed to warm to rt and stirred 30 min. After that time the reaction was concentrated under reduced pressure and the product was purified by flash column chromatography (silica gel, dichloromethane to 70:30 dichloromethane/methanol) to give methyl-2-(4-((2-(5,7-dimethoxy-4-oxo-3,4-dihydroquinazolin-2-yl)pyridin-3-yl)amino)piperidin-1-yl)-2-oxoacetate (0.044 g, 72%) as yellow solid: mp 165-166° C.; $^1$H NMR (400 MHz, DMSO-$d_6$) δ 10.79 (s, 1H), 9.38 (d, J=7.8 Hz, 1H), 7.94 (dd, J=3.9, 1.1 Hz 1H), 7.37-7.48 (m, 2H), 6.69 (d, J=1.9 Hz, 1H), 6.57 (d, J=1.9 Hz, 1H), 4.01-4.11 (m, 1H), 3.90 (s, 3H), 3.84 (s, 3H), 3.80 (s, 3H), 3.51-3.62 (m, 1H), 3.14-3.25 (m, 2H), 1.99-2.11 (m, 2H), 1.48-1.66 (m, 2H); ESI MS m/z 466 [M+H]$^+$.

Example 56: N-(2-((2-(5,7-Dimethoxy-4-oxo-3,4-dihydroquinazolin-2-yl)pyridin-3-yl)amino)ethyl)isobutyramide

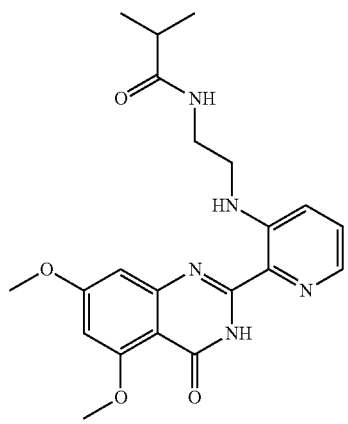 [SMILES: COc1cc(OC)c2c(=O)[nH]c(-c3ncccc3NCCNC(=O)C(C)C)nc2c1]

Lithium bis(trimethylsilyl)amide (1 M in THF, 10.0 mL, 10.0 mmol) was added to a stirred suspension of 2-(3-fluoropyridin-2-yl)-5,7-dimethoxyquinazolin-4(3H)-one (0.300 g, 0.99 mmol) and N-(2-aminoethyl)isobutyramide hydrochloride (0.498 g, 2.99 mmol in anhydrous THF (20 mL). After the addition was complete, the reaction was heated to reflux with stirring for 17 h. After that time the reaction was cooled to rt, diluted with saturated aqueous NH$_4$Cl (10 mL) and concentrated under reduced pressure. The residue was diluted with water (30 mL) and the resulting suspension was stirred at rt for 30 min. The precipitated solid was collected by filtration, washed with water and air-dried. The product was purified by flash column chromatography (silica gel, 97:3 dichloromethane/methanol) followed by recrystallization from chloroform/hexanes to give N-(2-((2-(5,7-dimethoxy-4-oxo-3,4-dihydroquinazolin-2-yl)pyridin-3-yl)amino)ethyl)isobutyramide (0.102 g, 25%) as a yellow solid: mp 235-237° C.; $^1$H NMR (400 MHz, CDCl$_3$) δ 10.80 (s, 1H), 9.34 (t, J=5.6 Hz, 1H), 7.84 (dd, J=4.3, 1.2 Hz, 1H), 7.19-7.25 (m, 1H), 7.12-7.18 (m, 1H), 6.70 (d, J=2.3 Hz, 1H), 6.35 (d, J=2.3 Hz, 1H), 6.25 (t, J=5.6 Hz, 1H), 3.96 (s, 3H), 3.93 (s, 3H), 3.61-3.67 (m, 2H), 3.46-3.52 (m, 2H), 2.47 (sept, J=6.7, 1H), 1.17 (d, J=6.7 Hz, 6H); ESI MS m/z 412 [M+H]$^+$.

Example 57: N-(3-((2-(5,7-Dimethoxy-4-oxo-3,4-dihydroquinazolin-2-yl)pyridin-3-yl)amino)propyl)isobutyramide

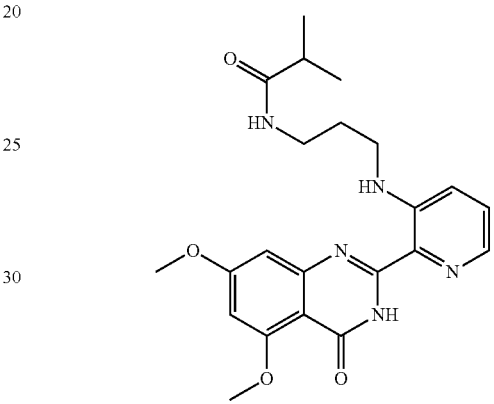

Lithium bis(trimethylsilyl)amide (1 M in THF, 9.6 mL, 9.6 mmol) was added to a stirred suspension of 2-(3-fluoropyridin-2-yl)-5,7-dimethoxyquinazolin-4(3H)-one (0.361 g, 1.20 mmol) and N-(3-aminopropyl)isobutyramide (0.65 g, 3.60 mmol) in anhydrous THF (20 mL). After the addition was complete, the reaction was heated to reflux with stirring for 1 h. After that time a second portion of lithium bis(trimethylsilyl)amide (1 M in THF, 2.4 mL, 2.4 mmol) was added and reflux with stirring was continued for an additional 2 h. After that time the reaction was cooled to rt, diluted with saturated aqueous NH$_4$Cl (5 mL) and concentrated under reduced pressure. The residue was diluted with water (30 mL) and the resulting suspension was stirred at rt for 30 min. The precipitated solid was collected by filtration, washed with water and air-dried. The product was purified by flash column chromatography (silica gel, dichloromethane to 97:3 dichloromethane/methanol) followed by trituration (90:10 diethyl ether/methanol) to give N-(3-((2-(5,7-dimethoxy-4-oxo-3,4-dihydroquinazolin-2-yl)pyridin-3-yl)amino)propyl)isobutyramide (0.207 g, 40%) as a yellow solid: mp 230-231° C.; $^1$H NMR (400 MHz, DMSO-$d_6$) δ 10.76 (s, 1H), 9.38 (t, J=5.7 Hz, 1H), 7.93 (dd, J=4.3, 1.2 Hz, 1H), 7.87 (t, J=5.7 I-Hz, 1H), 7.41 (dd, J=8.6, 3.9 Hz, 1H), 7.33 (dd, J=8, 1.2 Hz, 1H), 7.10 (d, J=2.3 Hz, 1H), 6.57 (d, J=2.3 Hz, 1H), 3.94 (s, 3H), 3.85 (s, 3H), 3.28-3.36 (m, 2H), 3.25 (q, J=6.6 Hz, 2H), 2.37 (sept, J=6.6 Hz, 1H), 1.70-1.80 (m, 2H), 1.02 (d, J=6.6 Hz, 6H); ESI MS m/z 426 [M+H]$^+$.

Example 58: 2-(3-((1-Isopropylpiperidin-4-yl)amino)pyridin-2-yl)-5-methoxypyrido[3,4-d]pyrimidin-4(3H)-one

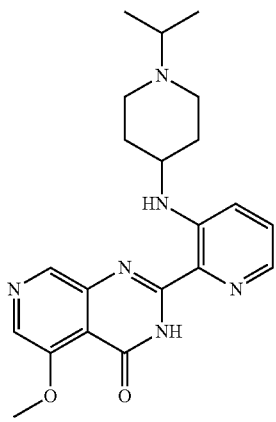 [SMILES: COc1cncc2nc(-c3ncccc3NC3CCN(C(C)C)CC3)[nH]c(=O)c12]

Lithium bis(trimethylsilyl)amide (1 M in THF, 2.0 mL, 2.0 mmol) was added to a suspension of 2-(3-fluoropyridin-2-yl)-5-methoxypyrido[3,4-d]pyrimidin-4(3H)-one (0.103 g, 0.37 mmol) and 1-isopropylpiperidin-4-amine (0.142 g, 1.0 mmol) in anhydrous THF (10 mL). After the addition was complete, the reaction was heated to in a sealed tube at 70° C. for 3 h. After that time the reaction was cooled to rt, diluted with ice-cold water (50 mL) and concentrated under reduced pressure. The product was purified by flash column chromatography (silica gel, 99:1 dichloromethane/methanol to 90:10 dichloromethane/methanol) to give 2-(3-((1-isopropylpiperidin-4-yl)amino)pyridin-2-yl)-5-methoxypyrido[3,4-d]pyrimidin-4(3H)-one (0.025 g, 17%) as a yellow solid: mp 237-238° C.; $^1$H NMR (400 MHz, DMSO-d$_6$) δ 11.32 (br s, 1H), 9.32 (d, J=8.2 Hz, 1H), 8.67 (s, 1H), 8.40 (s, 1H), 7.98 (br s, 1H), 7.45 (d, J=2.3 Hz, 2H), 4.01 (s, 3H), 3.63-3.86 (m, 1H), 2.72-3.17 (m, 5H), 2.01-2.23 (m, 2H), 1.58-1.89 (m, 2H), 1.0 (d, J=7.0 Hz, 6H); ESI MS m/z 395 [M+H]$^+$.

Example 59: 2-(3-((1-(2-Hydroxy-2-methylpropyl)piperidin-4-yl)amino)pyridin-2-yl)-5,7-dimethoxyquinazolin-4(3H)-one

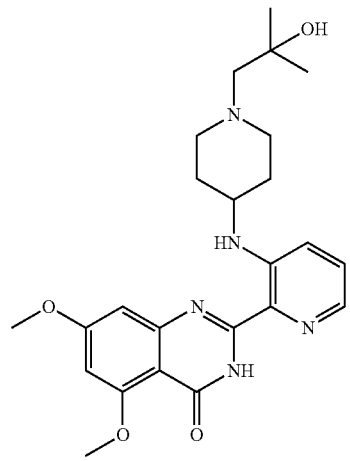 [SMILES: COc1cc(OC)c2c(=O)[nH]c(-c3ncccc3NC3CCN(CC(C)(C)O)CC3)nc2c1]

A solution of 5,7-dimethoxy-2-(3-(piperidin-4-ylamino)pyridin-2-yl)quinazolin-4(3H)-one (0.050 g, 0.13 mmol) and 2,2-dimethyloxirane (0.047 g, 0.65 mmol) in ethanol (3 mL) was heated to 140° C. with stirring in a sealed tube for 1.5 h using microwave radiation. After that time the reaction was cooled to rt, concentrated under reduced pressure and the product was purified by flash column chromatography (silica gel, dichloromethane to 70:30 dichloromethane/methanol) to give 2-(3-((1-(2-hydroxy-2-methylpropyl)piperidin-4-yl)amino)pyridin-2-yl)-5,7-dimethoxyquinazolin-4(3H)-one (0.029 g, 72%) as yellow solid: mp 220-221° C.; $^1$H NMR (400 MHz, DMSO-d$_6$) δ 10.79 (s, 1H), 9.41 (d, J=7.8 Hz, 1H), 7.93 (dd, J=3.7, 1.8 Hz, 1H), 7.35-7.42 (m, 2H), 6.72 (d, J=1.95 Hz, 1H), 6.60 (d, J=1.95 Hz, 1H), 4.08 (s, 1H), 3.93 (s, 3H), 3.87 (s, 3H), 3.59-3.69 (m, 1H), 2.76-2.86 (m, 2H), 2.53-2.57 (m, 2H), 2.24 (s, 2H), 1.91-2.01 (m, 2H), 1.56-1.67 (m, 2H), 1.10 (s, 6H); ESI MS m/z 454 [M+H]$^+$.

Example 60: 2-(3-((1-(2-hydroxypropanoyl)piperidin-4-yl)amino)pyridin-2-yl)-5,7-dimethoxyquinazolin-4(3H)-one

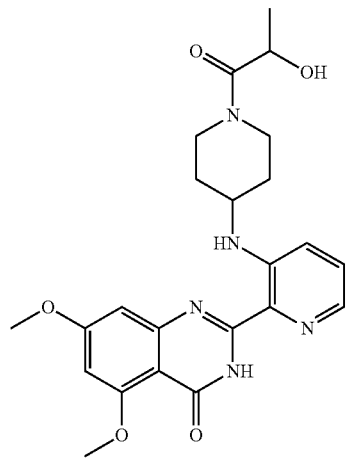 [SMILES: COc1cc(OC)c2c(=O)[nH]c(-c3ncccc3NC3CCN(C(=O)C(C)O)CC3)nc2c1]

N,N'-Dicyclohexylcarbodiimide (0.113 g, 0.55 mmol) and 1-hydroxy-1H-benzotriazole (0.074 g, 0.55 mmol) were added to a solution of 2-hydroxypropanoic acid (0.058 g, 0.55 mmol; 85% in water) in DMF (15 mL) at rt. The reaction was stirred for 1 h and then 5,7-dimethoxy-2-(3-(piperidin-4-ylamino)pyridin-2-yl)quinazolin-4(3H)-one (0.070 g, 0.18 mmol) was added. The reaction was stirred 18 h at rt. After that time the reaction was concentrated under reduced pressure and the product was purified by prep. HPLC to give 2-(3-((1-(2-hydroxypropanoyl)piperidin-4-yl)amino)pyridin-2-yl)-5,7-dimethoxyquinazolin-4(3H)-one (0.010 g, 12%) as yellow solid: mp 290-291° C.; $^1$H NMR (400 MHz, DMSO-d$_6$) δ 10.75 (s, 1H), 9.44 (d, J=7.0 Hz, 1H), 7.95-7.97 (m, 1H), 7.40-7.49 (m, 2H), 6.67 (s, 1H), 6.60 (d, 1H), 4.84-4.96 (m, 1H), 4.41-4.54 (m, 1H), 4.00-4.19 (m, 1H), 3.91 (s, 3H), 3.87 (s, 3H), 3.38-3.44 (m, 1H), 3.05-3.26 (m, 2H), 1.96-2.13 (m, 2H), 1.44-1.70 (m, 2H), 1.20 (d, J=6.25 Hz, 3H); ESI MS m/z 452 [M+H]$^+$.

Example 61: 2-(3-((1-Isopropylpiperidin-4-yl)amino)pyridin-2-yl)-5-methoxy-7-((4-methoxybenzyl)amino)quinazolin-4(3H)-one

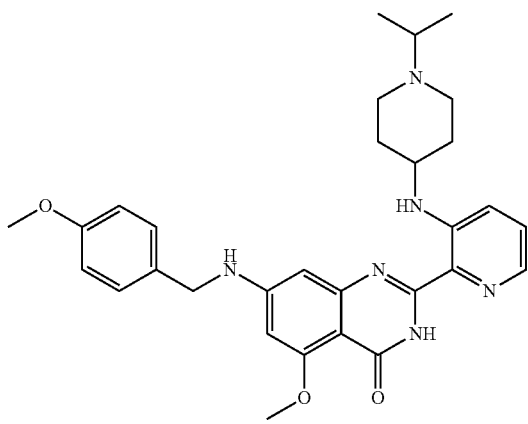 [SMILES: COc1ccc(CNc2cc(OC)c3c(=O)[nH]c(-c4ncccc4NC4CCN(C(C)C)CC4)nc3c2)cc1]

A solution of 3-bromopicolinaldehyde (5.00 g, 27 mmol), ethylene glycol (6.0 mL, 108 mmol) and p-toluenesulfonic acid monohydrate (0.256 g, 1.35 mmol) in anhydrous toluene (120 mL) was heated to reflux for 16 h with azeotropic removal of water using a Dean-Stark apparatus. After that time the reaction was cooled to rt and diluted with ethyl acetate (100 mL). The organic phase was separated, washed with 5% aq. $Na_2CO_3$ (120 mL), sat. NaCl (100 mL), dried ($Na_2SO_4$) and concentrated under reduced pressure to give 3-bromo-2-(1,3-dioxolan-2-yl)pyridine (5.36 g, 87%) as a brown oil: $^1$H NMR (CDCl$_3$) δ 8.60 (d, J=3.5 Hz, 1H), 7.86-7.93 (m, 1H), 7.18 (dd, J=8.2, 4.7 Hz, 1H), 6.31 (s, 1H), 4.26-4.34 (m, 2H), 4.08-4.15 (m, 2H).

Tris(dibenzylideneacetone)dipalladium (0.092 g, 0.10 mmol) was added to a de-gassed solution of 3-bromo-2-(1,3-dioxolan-2-yl)pyridine (1.15 g, 5.00 mmol), 1-isopropylpiperidin-4-amine (1.03 mL, 6.50 mmol), sodium-tert-butoxide (0.865 g, 9.00 mmol) and 2,2'-bis(diphenylphosphino)-1,1'-binaphthyl (0.187 g, 0.30 mmol) in toluene (10 mL). The mixture was de-gassed again and heated at 110° C. with stirring for 3 h under nitrogen. After that time the mixture was cooled to rt, filtered through celite, and concentrated under reduced pressure. The product was purified by flash column chromatography (silica gel, 97:3 dichloromethane/methanol then 97:3 dichloromethane/7N ammonia in methanol) to give 2-(1,3-dioxolan-2-yl)-N-(1-isopropylpiperidin-4-yl)pyridin-3-amine (1.342 g, 92%) as a brown oil: $^1$H NMR (CDCl$_3$) δ 7.89 (dd, J=4.7, 1.2 Hz, 1H), 7.10 (dd, J=8.4, 4.5 Hz, 1H), 6.96 (d, J=7.8 Hz, 1H), 5.79 (s, 1H), 5.10 (d, J=7.8 Hz, 1H), 4.10-4.18 (m, 2H), 4.02-4.10 (m, 2H), 3.24-3.38 (m, 1H), 2.69-2.87 (m, 2H), 2.26-2.38 (m, 2H), 1.99-2.11 (m, 2H), 1.46-1.59 (m, 2H), 1.06 (d, J=6.6 Hz, 6H).

A solution of 2-(1,3-dioxolan-2-yl)-N-(1-isopropylpiperidin-4-yl)pyridin-3-amine (1.32 g, 4.53 mmol) and 2 N aqueous HCl (10 mL) was stirred at rt for 16 h. After that time the reaction was concentrated under reduced pressure and dried to give 3-((1-isopropylpiperidin-4-yl)amino)picolinaldehyde dihydrochloride (4.53 g). The aldehyde was dissolved in N,N-dimethylacetamide (20 mL) and 2-amino-4,6-difluorobenzamide (0.64 g, 3.70 mmol) was added followed by NaHSO$_3$ (58.5 wt %, 1.01 g, 5.55 mmol) and p-toluenesulfonic acid monohydrate (0.14 g, 0.74 mmol). The reaction was heated at 130° C. with stirring for 16 h. After that time the mixture was cooled to rt, concentrated under reduced pressure and diluted with water (100 mL). The resulting precipitate was collected by filtration, washed with water and dried. The product was purified by flash column chromatography (silica gel, 97:3 dichloromethane/methanol) to give 5,7-difluoro-2-(3-((1-isopropylpiperidin-4-yl)amino)pyridin-2-yl)quinazolin-4(3H)-one (0.705 g, 48%) as yellow solid: $^1$H NMR (CDCl$_3$) δ 11.16 (br s, 1H), 9.35 (d, J=7.8 Hz, 1H), 7.90 (dd, J=4.3, 1.2 Hz, 1H), 7.23-7.31 (m, 1H), 7.05-7.19 (m, 2H), 6.80-6.93 (m, 1H), 3.47-3.58 (m, 1H), 2.84-2.94 (m, 2H), 2.74-2.84 (m, 1H), 2.35-2.48 (m, 2H), 2.08-2.20 (m, 2H), 1.67-1.79 (m, 2H), 1.09 (d, J=6.6 Hz, 6H); ESI MS m/z 400 [M+H]$^+$.

A solution of sodium methoxide in methanol (25 wt %, 2.3 mL, 10.6 mmol) was added to a suspension of 5,7-difluoro-2-(3-((1-isopropylpiperidin-4-yl)amino)pyridin-2-yl)quinazolin-4(3H)-one (0.703 g, 1.76 mmol) in anhydrous DMF (10 mL). The reaction was stirred at rt for 16 h under nitrogen. After that time 2N HCl was added to quench the reaction and adjust the reaction pH to about 2. The reaction was then made strongly basic with aq. Na$_2$CO$_3$ solution. The resulting precipitate was collected by filtration, washed with water and dried. The product was purified by flash column chromatography (silica gel, 97:3 dichloromethane/methanol) to give 7-fluoro-2-(3-((1-isopropylpiperidin-4-yl)amino)pyridin-2-yl)-5-methoxyquinazolin-4(3H)-one (0.765 g, >99%) as yellow solid: $^1$H NMR (DMSO-d$_6$) δ 10.96 (br s, 1H), 9.28 (d, J=7.4 Hz, 1H), 7.93 (dd, J=3.5, 2.0 Hz, 1H), 7.34-7.44 (m, 2H), 6.94-7.08 (m, 2H), 3.90 (s, 3H), 3.52-3.65 (m, 1H), 2.68-2.79 (m, 3H), 2.33-2.45 (m, 2H), 1.93-2.03 (m, 2H), 1.53-1.67 (m, 2H), 0.99 (d, J=6.3 Hz, 6H); ESI MS m/z 412 [M+H]$^+$.

A suspension of 7-fluoro-2-(3-((1-isopropylpiperidin-4-yl)amino)pyridin-2-yl)-5-methoxyquinazolin-4(3H)-one (0.412 g, 1.00 mmol)) and 4-methoxybenzylamine (0.78 mL, 6.00 mmol) in DMSO (5 mL) was heated at 100° C. with stirring for 24 h. After that time the reaction was cooled to rt and diluted with water (50 mL). The resulting precipitate was collected by filtration, washed with water and dried. The product was triturated with diethyl ether and then purified by flash column chromatography (silica gel, 97:3 dichloromethane/methanol then 97:3 dichloromethane/7N ammonia in methanol) to give 2-(3-((1-isopropylpiperidin-4-yl)amino)pyridin-2-yl)-5-methoxy-7-((4-methoxybenzyl)amino)quinazolin-4(3H)-one (0.230 g, 43%) as yellow solid: mp 220-222° C.; $^1$H NMR (DMSO-d$_6$) δ 10.37 (br s, 1H), 9.52 (d, J=7.8 Hz, 1H), 7.84-7.93 (m, 1H), 7.30-7.43 (m, 4H), 7.26 (t, J=5.7 Hz, 1H), 6.87-6.99 (m, 2H), 6.31 (d, J=2.0 Hz, 1H), 6.22-6.29 (m, 1H), 4.32 (d, J=5.7 Hz, 2H), 3.77 (s, 3H), 3.73 (s, 3H), 3.53 (br. s, 1H), 2.68-2.80 (m, 3H), 2.32-2.42 (m, 2H), 1.92-2.03 (m, 2H), 1.43-1.57 (m, 2H), 0.99 (d, J=6.6 Hz, 6H); ESI MS m/z 529 [M+H]$^+$.

Example 62: 2-[5-(2-Hydroxyethoxy)-3-(1-isopropylpiperidin-4-ylamino)pyridin-2-yl]-5,7-dimethoxyquinazolin-4(3H)-one

Example 63: cis-4-((2-(5,7-Dimethoxy-4-oxo-3,4-dihydroquinazolin-2-yl)pyridin-3-yl)amino)-N-isopropylcyclohexane-1-carboxamide

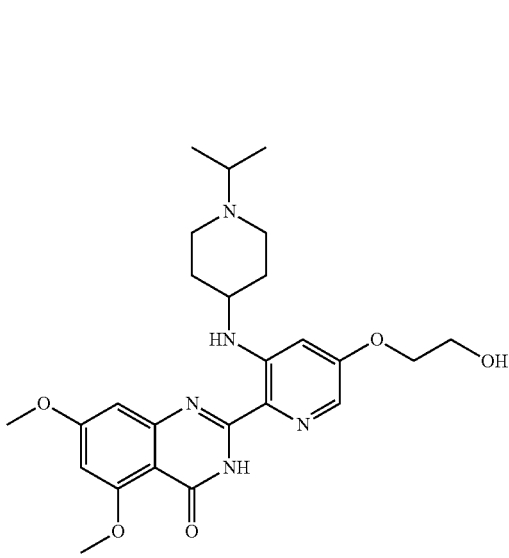 [SMILES: COc1cc(OC)c2c(=O)[nH]c(-c3ncc(OCCO)cc3NC3CCN(C(C)C)CC3)nc2c1]

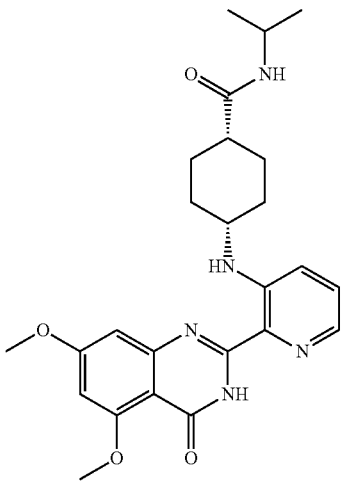 [SMILES: COc1cc(OC)c2c(=O)[nH]c(-c3ncccc3N[C@H]3CC[C@@H](C(=O)NC(C)C)CC3)nc2c1]

A solution of 2-[5-(2-(tert-butyldimethylsilyloxy)ethoxy]-3-fluoropyridin-2-yl)-5,7-dimethoxyquinazolin-4(3H)-one (0.476 g, 1.0 mmol) and 1-isopropyl-4-aminopiperidine (0.711 g, 5 mmol) in anhydrous acetonitrile (5 mL) was heated to reflux with stirring for 26 h. After that time the reaction was cooled to rt and concentrated under reduced pressure. The solids were treated with chloroform (25 mL) and the resulting mixture was filtered, washed with sat. NaHCO$_3$ (15 mL), dried (MgSO$_4$) and concentrated under reduced pressure. The product was purified by flash column chromatography (silica gel, 95:5 dichloromethane/methanol) followed by recrystallization from chloroform/diethyl ether to give 2-[5-(2-Hydroxyethoxy)-3-(1-isopropylpiperidin-4-ylamino)pyridin-2-yl]-5,7-dimethoxyquinazolin-4(3H)-one (0.292 g, 60%) as a yellow solid: mp 231-233° C.; $^1$H NMR (400 MHz, CDCl$_3$) δ 10.67 (br s, 1H), 9.56 (d, J=7.2 Hz, 1H), 7.62 (d, J=2.4 Hz, 1H), 6.59 (d, J=2.4 Hz, 1H), 6.50 (d, J=2.0 Hz, 1H), 6.42 (d, J=2.0 Hz, 1H), 4.19 (t, J=4.4 Hz, 2H), 4.02 (t, J=4.4 Hz, 2H), 3.97 (s, 3H), 3.93 (s, 3H), 3.40 (br s, 1H), 2.93-2.90 (m, 2H), 2.81-2.77 (m, 1H), 2.44-2.42 (m, 2H), 2.14-2.11 (m, 2H), 1.79-1.74 (m, 2H), 1.10 (d, J=6.4 Hz, 6H); ESI MS m/z 484 [M+H]$^+$.

Lithium bis(trimethylsilyl)amide (1 M in THF, 10.0 mL, 10.0 mmol) was added to a stirred suspension of 2-(3-fluoropyridin-2-yl)-5,7-dimethoxyquinazolin-4(3H)-one (0.500 g, 1.66 mmol) and cis-4-amino-N-(propan-2-yl)cyclohexanecarboxamide hydrochloride (1.10 g, 5.0 mmol) in anhydrous THF (15 mL). After the addition was complete, the reaction was heated to reflux with stirring for 2 h. After that time a second portion of lithium bis(trimethylsilyl)amide (1 M in THF, 5.0 mL, 5.0 mmol) was added and reflux with stirring was continued for an additional 18 h. After that time the reaction was cooled to rt, diluted with saturated aqueous NH$_4$Cl (3 mL), concentrated under reduced pressure and the product was purified by flash column chromatography (silica gel, 98:2 dichloromethane/methanol) to give cis-4-((2-(5,7-dimethoxy-4-oxo-3,4-dihydroquinazolin-2-yl)pyridin-3-yl)amino)-N-isopropylcyclohexane-1-carboxamide (0.120 g, 16%) as a light yellow solid: mp 256-257° C.; $^1$H NMR (400 MHz, CDCl$_3$) δ 10.93 (br s, 1H), 9.74 (d, J=8.2 Hz, 1H), 7.89 (d, J=4.3 Hz, 1H), 7.23 (dd, J=8.6, 4.3 Hz, 1H), 7.10 (d, J=8.6 Hz, 1H), 6.95 (d, J=2.3 Hz, 1H), 6.46 (d, J=2.3 Hz, 1H), 5.23 (d, J=7.0 Hz, 1H), 4.00-4.09 (m, 1H), 3.98 (s, 6H), 3.84-3.94 (m, 1H), 2.12-2.24 (m, 1H), 1.93-2.08 (m, 4H), 1.81-1.91 (m, 2H), 1.65-1.79 (m, 2H), 1.09 (d, J=6.6 Hz, 6H); ESI MS m/z 464 [M+H]$^+$.

Example 64: 2-[5-(2-Hydroxyethoxy)-3-(1-isobutyroylpiperidin-4-ylamino)pyridin-2-yl]-5,7-dimethoxyquinazolin-4(3H)-one

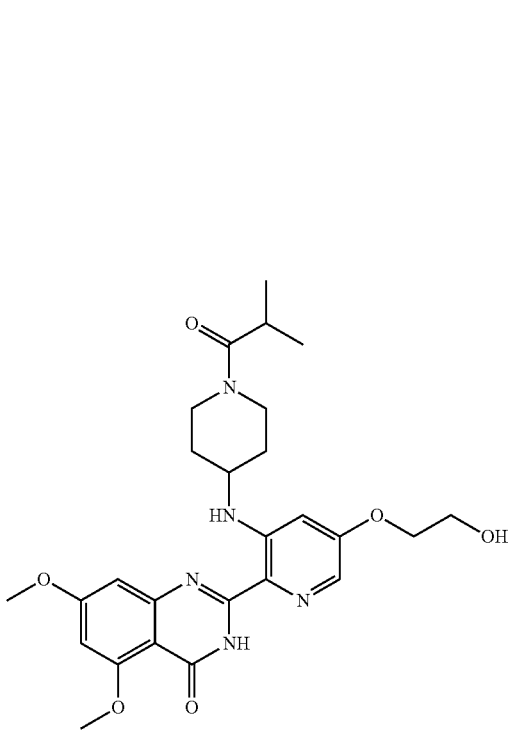 [SMILES: COc1cc(OC)c2c(=O)[nH]c(-c3ncc(OCCO)cc3NC3CCN(C(=O)C(C)C)CC3)nc2c1]

A mixture of 2-[5-(2-(tert-butyldimethylsilyloxy)ethoxy]-3-fluoropyridin-2-yl)-5,7-dimethoxyquinazolin-4(3H)-one (0.476 g, 1.0 mmol), 1-isobutyroyl-4-aminopiperidine hydrochloride (1.034 g, 5.0 mmol) and $K_2CO_3$ (1.11 g, 8.0 mmol) in anhydrous DMSO (10 mL) was heated to 96° C. with stirring for 26 h. After that time the reaction was cooled to rt, diluted with chloroform (100 mL), washed with water (5×10 mL), dried ($MgSO_4$) and concentrated under reduced pressure. The oily product was triturated (diethyl ether, (5×10 mL) to give a solid product that was purified by flash column chromatography (silica gel, 98:2 chloroform/methanol) to give 2-[5-(2-hydroxyethoxy)-3-(1-isobutyroylpiperidin-4-ylamino)pyridin-2-yl]-5,7-dimethoxyquinazolin-4(3H)-one (0.172 g, 34%) as a yellow solid: mp 173-176° C.; $^1$H NMR (400 MHz, $CDCl_3$) δ 10.66 (br s, 1H), 9.65 (d, J=6.8 Hz, 1H), 7.65 (d, J=2.4 Hz, 1H), 6.52 (s, 2H), 6.43 (d, J=2.4 Hz, 1H), 4.13-4.28 (m, 1H), 4.22-4.20 (m, 2H), 4.05-4.03 (m, 2H), 3.98 (s, 3H), 3.93 (s, 3H), 3.90-3.86 (m, 1H), 3.66-3.63 (m, 1H), 3.41-3.28 (m, 2H), 2.88-2.82 (m, 1H), 2.34 (t, J=6.4 Hz, 1H), 2.12 (br s, 2H), 1.72-1.58 (m, 2H), 1.16 (d, J=7.2 Hz, 6H); ESI MS m/z 512 [M+H]$^+$.

Example 65: 7-amino-2-(3-((1-Isopropylpiperidin-4-yl)amino)pyridin-2-yl)-5-methoxyquinazolin-4(3H)-one

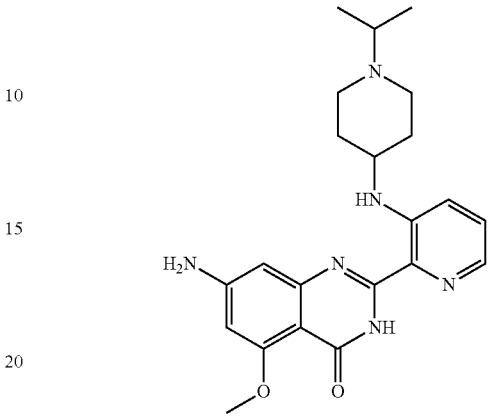

A solution of 2-(3-((1-isopropylpiperidin-4-yl)amino)pyridin-2-yl)-5-methoxy-7-((4-methoxybenzyl)amino)quinazolin-4(3H)-one (0.200 g, 0.37 mmol) and trifluroacetic acid (2 mL) in dichloromethane (18 mL) was stirred at rt for 48 h. After this time the reaction was concentrated under reduced pressure, diluted with water (20 mL) and made basic with sat. $Na_2CO_3$. The precipitated solids were collected by filtration, washed with water and dried. The product was purified by flash column chromatography (silica gel, 97:3 dichloromethane/methanol then 97:3 dichloromethane/7N ammonia in methanol) to give 7-amino-2-(3-((1-isopropylpiperidin-4-yl)amino)pyridin-2-yl)-5-methoxyquinazolin-4(3H)-one (0.023 g, 15%) as yellow solid: $^1$H NMR (DMSO-$d_6$) δ 10.72 (s, 1H), 8.74 (d, J=7.8 Hz, 1H), 7.99 (t, J=2.7 Hz, 1H), 7.44 (d, J=2.7 Hz, 2H), 6.24 (s, 1H), 5.92 (br s, 2H), 4.41 (s, 1H), 3.72 (s, 3H), 3.40-3.52 (m, 1H), 2.62-2.77 (m, 2H), 2.57 (sept, J=6.3 Hz 1H), 2.14-2.29 (m, 2H), 1.91-2.04 (m, 2H), 1.27-1.38 (m, 2H), 0.84 (d, J=6.3 Hz, 6H); ESI MS m/z 409 [M+H]$^+$.

Example 66: 2-{3-(1-Isopropylpiperidin-4-ylamino)-5-[2-(pyrrolidin-1-yl)ethoxy]pyridin-2-yl}-5,7-dimethoxyquinazolin-4(3H)-one

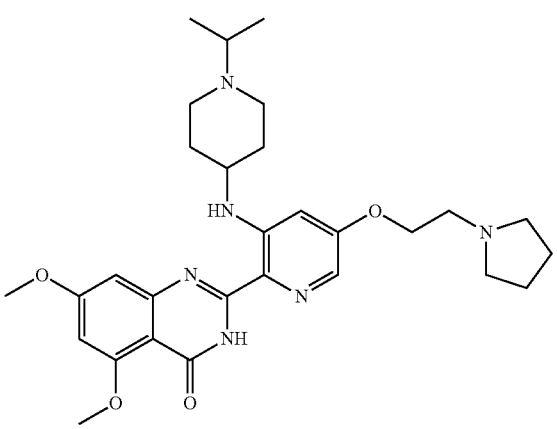 [SMILES: COc1cc(OC)c2c(=O)[nH]c(-c3ncc(OCCN4CCCC4)cc3NC3CCN(C(C)C)CC3)nc2c1]

Carbon tetrabromide (1.33 g, 4.0 mmol) and triphenylphosphine (1.10 g, 4.2 mmol) were added to a stirred suspension of 2-[5-(2-hydroxyethoxy)-3-(1-isopropylpiperidin-4-ylamino)pyridin-2-yl]-5,7-dimethoxyquinazolin-4(3H)-one (0.967 g, 2.0 mmol) in dichloromethane (60 mL). The reaction was stirred for 2 h at rt. After that time the reaction was concentrated under reduced pressure. The residue was suspended in anhydrous DMSO (10 mL) and pyrrolidine (7.11 g, 100 mmol) was added. The reaction mixture was heated to 80° C. with stirring for 14 h. After that time the reaction was cooled to rt, diluted with chloroform (100 mL), washed with sat. NaHCO$_3$ (20 mL), water (4×20 mL), dried (MgSO$_4$) and concentrated under reduced pressure. The product was purified by flash column chromatography (silica gel, 90:10 chloroform/methanol) followed by trituration (diethyl ether) to give 2-{3-(1-isopropylpiperidin-4-ylamino)-5-[2-(pyrrolidin-1-yl)ethoxy]pyridin-2-yl}-5,7-dimethoxyquinazolin-4(3H)-one (0.520 g, 48%) as a yellow solid: mp 166-169° C.; $^1$H NMR (400 MHz, CDCl$_3$) δ 10.69 (br s, 1H), 9.57 (d, J=7.2 Hz, 1H), 7.64 (d, J=2.4 Hz, 1H), 6.60 (d, J=2.0 Hz, 1H), 6.54 (d, J=2.0 Hz, 1H), 6.41 (d, J=2.4 Hz, 1H), 4.21 (t, J=5.6 Hz, 2H), 3.97 (s, 3H), 3.93 (s, 3H), 3.45 (br s, 1H), 2.97-2.93 (m, 3H), 2.84-2.80 (m, 1H), 2.67 (br s, 4H), 2.46-2.44 (m, 2H), 2.17-2.15 (m, 2H), 1.86-1.77 (m, 6H), 1.12 (d, J=6.4 Hz, 6H); ESI MS m/z 537 [M+H]$^+$.

Example 67: 2-{5-[2-(Isopropylamino)ethoxy]-3-(1-isopropylpiperidin-4-ylamino)pyridin-2-yl}-5,7-dimethoxyquinazolin-4(3H)-one

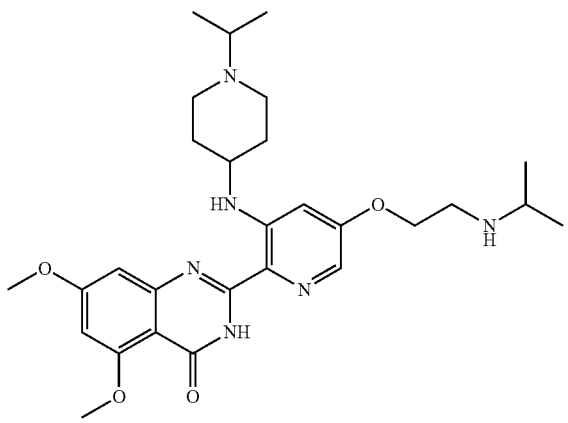 [SMILES: COc1cc(OC)c2c(=O)[nH]c(-c3ncc(OCCNC(C)C)cc3NC3CCN(C(C)C)CC3)nc2c1]

Carbon tetrabromide (1.79 g, 5.4 mmol) and triphenylphosphine (1.49 g, 5.7 mmol) were added to a stirred suspension of 2-[5-(2-hydroxyethoxy)-3-(1-isopropylpiperidin-4-ylamino)pyridin-2-yl]-5,7-dimethoxyquinazolin-4(3H)-one (1.303 g, 2.7 mmol) in dichloromethane (80 mL). The reaction was stirred for 2 h at rt and was then concentrated under reduced pressure. The residue was suspended in anhydrous DMSO (10 mL) and isopropylamine (7.98 g, 135 mmol) was added. The reaction mixture was heated to 60° C. with stirring for 18 h. After that time the reaction was cooled to rt, diluted with chloroform (100 mL), washed with sat. NaHCO$_3$ (20 mL), water (4×20 mL), dried (MgSO$_4$) and concentrated under reduced pressure. The product was purified by flash column chromatography (silica gel, 90:10 chloroform/methanol) followed by recrystallization from chloroform/diethyl ether to give 2-{5-[2-(isopropylamino)ethoxy]-3-(1-isopropylpiperidin-4-ylamino)pyridin-2-yl}-5,7-dimethoxyquinazolin-4(3H)-one (0.742 g, 52%) as a yellow solid: mp 178-181° C.; $^1$H NMR (400 MHz, CDCl$_3$) δ 9.58 (d, J=8.0 Hz, 1H), 7.63 (d, J=1.6 Hz, 1H), 6.60 (d, J=1.6 Hz, 1H), 6.51 (d, J=2.2 Hz, 1H), 6.42 (d, J=2.2 Hz, 1H), 4.17 (t, J=5.2 Hz, 2H), 3.97 (s, 3H), 3.93 (s, 3H), 3.45 (br s, 1H), 3.05 (t, J=5.2 Hz, 2H), 2.94-2.79 (m, 4H), 2.48-2.44 (m, 2H), 2.17-2.13 (m, 2H), 1.80-1.76 (m, 2H), 1.14-1.10 (m, 12H); ESI MS m/z 525 [M+H]$^+$.

Example 68: 2-(3-((1-(1-Hydroxy-2-methylpropan-2-yl)piperidin-4-yl)amino)pyridin-2-yl)-5,7-dimethoxyquinazolin-4(3H)-one

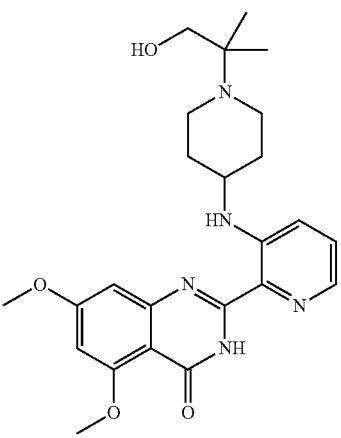 [SMILES: COc1cc(OC)c2c(=O)[nH]c(-c3ncccc3NC3CCN(C(C)(C)CO)CC3)nc2c1]

A solution of tert-butyl piperidin-4-ylcarbamate (5.0 g, 25 mmol), ethyl 2-bromo-2-methylpropanoate (7.30 g, 37 mmol) and potassium carbonate (8.60 g, 62 mmol) in anhydrous acetonitrile (80 mL) was heated to reflux for 17 h. After that time the reaction was cooled to rt, filtered and concentrated under reduced pressure. The product was purified by flash column chromatography (silica gel, 80:20 hexanes/ethyl acetate to 60:40 hexanes/ethyl acetate) to give ethyl 2-(4-((tert-butoxycarbonyl)amino)piperidin-1-yl)-2-methylpropanoate (3.20 g, 41%) as a white solid: $^1$H NMR (400 MHz, CDCl$_3$) δ 4.40 (br s, 1H), 4.18 (q, J=6.8 Hz, 2H), 3.44 (br s, 1H), 2.84-2.92 (m, 2H), 2.27 (td, J=11.5, 2.3 Hz, 2H), 1.87-1.96 (m, 2H), 1.44 (s, 9H), 1.34-1.49 (m, 2H), 1.30 (s, 6H), 1.24-1.29 (m, 3H); ESI MS m/z 315 [M+H]$^+$.

A solution of diisobutylaluminum hydride (1M in toluene, 36 mL, 36 mmol) was slowly added to a vigorously stirred solution of ethyl 2-(4-((tert-butoxycarbonyl)amino) piperidin-1-yl)-2-methylpropanoate (2.80 g, 8.9 mmol) in anhydrous dichloromethane (120 mL) at −78° C. The reaction was stirred at −78° C. for 15 min and then warmed to 0° C. and stirred an additional 45 min. After this time the reaction was quenched by addition of saturated aqueous NH$_4$Cl (40 mL). The resulting mixture was diluted with ethyl acetate (150 mL) and chloroform (150 mL), dried (MgSO$_4$), concentrated under reduced pressure and dried in vacuum to give tert-butyl (1-(1-hydroxy-2-methylpropan-2-yl)piperidin-4-yl)carbamate (2.17 g, 89%) as a white solid: $^1$H NMR (400 MHz, CDCl$_3$) δ 4.46 (br s, 1H), 3.39-3.55 (m, 1H), 3.35 (s, 2H), 2.85-2.97 (m, 2H), 2.22-2.38 (m, 2H), 1.94-2.05 (m, 2H), 1.44 (s, 9H), 1.36-1.51 (m, 2H), 1.05 (s, 6H); ESI MS m/z 273 [M+H]$^+$.

Concentrated HCl (3.3 mL, 39.8 mmol) was added slowly to a stirred solution of tert-butyl (1-(1-hydroxy-2-methylpropan-2-yl)piperidin-4-yl)carbamate (2.17 g, 7.97 mmol) in methanol (50 mL). The reaction mixture was then stirred at rt for 17 h. After that time the reaction was concentrated under reduced pressure, triturated with diethyl ether and dried to give 2-(4-aminopiperidin-1-yl)-2-methylpropan-1-ol dihydrochloride (1.71 g, 87%) as a white solid: $^1$H NMR (400 MHz, DMSO-d$_6$) δ 9.64 (t, J=9.0 Hz, 1H), 8.49 (br s, 3H), 5.78 (br s, 1H), 3.55 (s, 2H), 3.39-3.55 (m, 2H), 3.19-3.37 (m, 1H); 3.00-3.15 (m, 2H), 1.93-2.20 (m, 4H), 1.27 (s, 6H); ESI MS m/z 173 [M+H]$^+$.

A mixture of 2-(3-fluoropyridin-2-yl)-5,7-dimethoxyquinazolin-4(3H)-one (0.300 g, 0.99 mmol), 2-(4-aminopiperidin-1-yl)-2-methylpropan-1-ol dihydrochloride (0.624 g, 2.54 mmol) and potassium carbonate (1.38 g, 9.96 mmol) in anhydrous DMF (15 mL) was heated at 100° C. for 40 h. After that time the reaction was cooled to rt and concentrated under reduced pressure. Water (50 mL) was added and the resulting suspension was stirred at rt for 20 min. The precipitated solid was collected by filtration and air-dried. The product was purified by flash column chromatography (silica gel, 99:1 dichloromethane/7N ammonia in methanol to 97:3 dichloromethane/7N ammonia in methanol) to give 2-(3-((1-(1-hydroxy-2-methylpropan-2-yl)piperidin-4-yl)amino)pyridin-2-yl)-5,7-dimethoxyquinazolin-4(3H)-one (0.218 g, 48%) as a yellow solid: mp 223-225° C.; $^1$H NMR (400 MHz, DMSO-d$_6$) δ 10.78 (s, 1H), 9.37 (d, J=7.0 Hz, 1H), 7.92 (d, J=2.7 Hz, 1H), 7.30-7.44 (m, 2H), 6.71 (d, J=2.15 Hz, 1H), 6.59 (d, J=2.15 Hz, 1H), 4.23 (t, J=4.7 Hz, 1H), 3.93 (s, 3H), 3.86 (s, 3H), 3.60 (br s, 1H), 3.29 (d, J=4.7 Hz, 2H), 2.79-2.90 (m, 2H), 2.46-2.57 (m, 2H), 1.92-2.03 (m, 2H), 1.52-1.66 (m, 2H), 0.97 (s, 6H); ESI MS m/z 454 [M+H]$^+$.

Example 69: 7-(Ethylamino)-2-(3-((1-isopropylpiperidin-4-yl)amino)pyridin-2-yl)-5-methoxyquinazolin-4(3H)-one

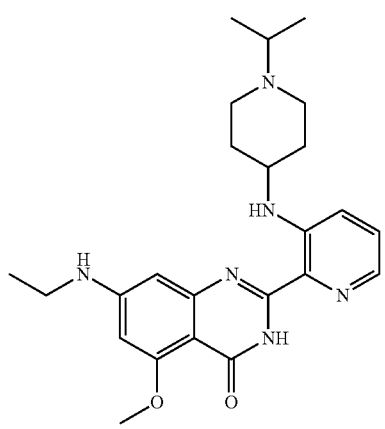 [SMILES: CCNc1cc(OC)c2c(=O)[nH]c(-c3ncccc3NC3CCN(C(C)C)CC3)nc2c1]

Ethylamine (2.0 M solution in THF, 10 mL, 20.0 mmol) was added to a suspension of 7-fluoro-2-(3-((1-isopropylpiperidin-4-yl)amino)pyridin-2-yl)-5-methoxyquinazolin-4(3H)-one (0.284 g, 0.69 mmol) in DMSO (5 mL). The reaction heated under microwave conditions at 100° C. with stirring for 10 h. After that time the reaction was cooled to rt, concentrated under reduced pressure and diluted with water (50 mL). The resulting precipitate was collected by filtration, washed with water and dried. The product was purified by flash column chromatography (silica gel, 97:3 chloroform/methanol then 97:3 chloroform/7N ammonia in methanol) to give 7-(ethylamino)-2-(3-((1-isopropylpiperidin-4-yl)amino)pyridin-2-yl)-5-methoxyquinazolin-4(3H)-one (0.106 g, 35%) as yellow solid: mp 219-221° C.; $^1$H NMR (400 MHz, CDCl$_3$) δ 10.73 (s, 1H), 9.62 (d, J=7.4 Hz, 1H), 7.87 (dd, J=3.9, 1.2 Hz, 1H), 7.20 (dd, J=8.6, 4.3 Hz, 1H), 7.08 (d, J=8.2 Hz, 1H), 6.32 (d, J=2.0 Hz, 1H), 6.08 (d, J=2.0 Hz, 1H), 4.10-4.19 (m, 1H), 3.95 (s, 3H), 3.41-3.56 (m, 1H), 3.23-3.36 (m, 2H), 2.85-2.97 (m, 2H), 2.71-2.84 (m, 1H), 2.38-2.47 (m, 2H), 2.07-2.19 (m, 2H), 1.67-1.82 (m, 2H), 1.34 (t, J=7.2 Hz, 3H), 1.10 (d, J=6.6 Hz, 6H); ESI MS m/z 437 [M+H]$^+$.

Example 70: Inhibition of Tetra-Acetylated Histone H4 Binding Individual BET Bromodomains Proteins were cloned and overexpressed with a N-terminal 6×His tag, then purified by nickel affinity followed by size exclusion chromatography. Briefly. E. coli BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein is pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 and BET bromodomains was confirmed by a Time Resolved Fluorescence Resonance Energy Transfer (TR-FRET) method. N-terminally His-tagged bromodomains (200 nM) and biotinylated tetra-acetylated histone H4 peptide (25-50 nM, Millipore) were incubated in the presence of Europium Cryptate-labeled streptavidin (Cisbio Cat. #610SAKLB) and XL665-labeled monoclonal anti-His antibody (Cisbio Cat. #61HISXLB) in a white 96 well microtiter plate (Greiner). For inhibition assays, serially diluted test compound was added to these reactions in a 0.2% final concentration of DMSO. Final buffer concentrations were 30 mM HEPES pH 7.4, 30 mM NaCl, 0.3 mM CHAPS, 20 mM phosphate pH 7.0, 320 mM KF, 0.08% BSA). After a 2-h incubation at room temperature, the fluorescence by FRET was measured at 665 and 620 nm by a SynergyH4 plate reader (Biotek). Illustrative results with the first bromodomain of Brd4 are shown below. The binding inhibitory activity was shown by a decrease in 665 nm fluorescence relative to 620 nm. IC$_{50}$ values were determined from a dose response curve.

Compounds with an IC$_{50}$ value less than 30 μM were deemed to be active.

TABLE 2

Inhibition of Tetra-acetylated Histone H4 Binding to Brd4 bromodomain 1 (BRD4(1) as Measured by FRET

| Example Number | FRET activity BRD4(1) | Example Number | FRET activity BRD4(1) | Example Number | FRET activity BRD4(1) | Example Number | FRET activity BRD4(1) |
|---|---|---|---|---|---|---|---|
| 1 | Active | 2 | Active | 3 | Active | 4 | Active |
| 5 | Not Active | 6 | Active | 7 | Active | 8 | Active |

TABLE 2-continued

Inhibition of Tetra-acetylated Histone H4 Binding to Brd4 bromodomain 1 (BRD4(1)) as Measured by FRET

| Example Number | FRET activity BRD4(1) | Example Number | FRET activity BRD4(1) | Example Number | FRET activity BRD4(1) | Example Number | FRET activity BRD4(1) |
|---|---|---|---|---|---|---|---|
| 9 | Active | 10 | Active | 11 | Active | 12 | Active |
| 13 | Active | 14 | Active | 15 | Active | 16 | Active |
| 17 | Active | 18 | Active | 19 | Active | 20 | Active |
| 21 | Active | 22 | Active | 23 | Active | 24 | Active |
| 25 | Active | 26 | Active | 27 | Active | 28 | Active |
| 29 | Active | 30 | Active | 31 | Active | 32 | Active |
| 33 | Not Active | 34 | Active | 35 | Active | 36 | Active |
| 37 | Active | 38 | Not Active | 39 | Active | 40 | Active |
| 41 | Active | 42 | Active | 43 | Active | 44 | Active |
| 45 | Active | 46 | Active | 47 | Active | 48 | Active |
| 49 | Active | 50 | Active | 51 | Active | 52 | Active |
| 53 | Active | 54 | Active | 55 | Active | 56 | Active |
| 57 | Active | 58 | Active | 59 | Active | 60 | Active |
| 61 | Active | 62 | Active | 63 | Active | 64 | Active |
| 65 | Active | 66 | Active | 67 | Active | 68 | Active |
| 69 | Active | — | — | — | — | — | — |

Example 71: Inhibition of c-Myc Expression in Cancer Cell Lines

MV4-11 cells ($2.5 \times 10^4$ cells) were plated in 96 well U-bottom plates with test compound or DMSO (0.1%), and incubated for 3 h at 37° C. Cells were then harvested by centrifugation, lysed, and mRNA was isolated using the mRNA catcher plus kit (Invitrogen). Reverse transcription of the mRNA and duplex amplification of the c-myc and cyclophilin cDNAs was performed using the RNA Ultrasense kit (Invitrogen) and a ViiA7 real-time PCR machine (Applied Biosystems). $IC_{50}$ values were determined from a dose response curve.

an additional 3-4 h. The absorbance was taken at 490 nm in a spectrophotometer and the percentage of proliferation relative to DMSO-treated cells was calculated after correction from the blank well. $IC_{50}$ were calculated using the GraphPad Prism software.

Compounds with an $IC_{50}$ value less than 30 μM were deemed to be active.

TABLE 3

Inhibition of c-myc Activity in Human AML MV4-11 cells

| Example Number | c-myc activity (IC50 <30 μM) | Example Number | c-myc activity (IC50 <30 μM) | Example Number | c-myc activity (IC50 <30 μM) | Example Number | c-myc activity (IC50 <30 μM) |
|---|---|---|---|---|---|---|---|
| 1 | Active | 3 | Active | 7 | Active | 8 | Active |
| 9 | Not Active | 13 | Not Active | 14 | Not Active | 15 | Active |
| 16 | Active | 17 | Active | 18 | Active | 19 | Active |
| 20 | Active | 21 | Active | 22 | Active | 23 | Not Active |
| 26 | Active | 28 | Active | 30 | Not Active | 31 | Not Active |
| 32 | Active | 36 | Active | 37 | Active | 39 | Active |
| 42 | Active | 45 | Not Active | 46 | Active | 47 | Not Active |
| 48 | Active | 51 | Active | 52 | Active | 55 | Active |
| 56 | Active | 57 | Active | 59 | Active | 60 | Active |
| 61 | Active | 62 | Active | 63 | Not Active | 64 | Active |
| 66 | Active | 67 | Active | 69 | Active | — | — |

Example 72: Inhibition of Cell Proliferation in Cancer Cell Lines

MV4-11 cells: 96-well plates were seeded with $5 \times 10^4$ cells per well of exponentially growing human AML MV-4-11 (CRL-9591) cells and immediately treated with two-fold dilutions of test compounds, ranging from 30 μM to 0.2 μM. Triplicate wells were used for each concentration, as well as a media only and three DMSO control wells. The cells and compounds were incubated at 37° C., 5% $CO_2$ for 72 h before adding 20 μl of the CellTiter Aqueous One Solution (Promega) to each well and incubating at 37° C., 5% $CO_2$ for

TABLE 4

Inhibition of Cell Proliferation in Human AML MV-4-11 cells

| Example Number | Cell Proliferation activity (IC50 <30 μM) | Example Number | Cell Proliferation activity (IC50 <30 μM) | Example Number | Cell Proliferation activity (IC50 <30 μM) |
|---|---|---|---|---|---|
| 1 | Active | 3 | Active | 7 | Active |
| 8 | Active | 9 | Not Active | 14 | Not Active |
| 15 | Active | 16 | Active | 18 | Active |
| 19 | Active | 20 | Active | 21 | Active |

TABLE 4-continued

Inhibition of Cell Proliferation in Human AML MV-4-11 cells

| Example Number | Cell Proliferation activity (IC50 <30 μM) | Example Number | Cell Proliferation activity (IC50 <30 μM) | Example Number | Cell Proliferation activity (IC50 <30 μM) |
|---|---|---|---|---|---|
| 22 | Active | 23 | Not Active | 26 | Not Active |
| 28 | Active | 30 | Active | 31 | Not Active |
| 32 | Active | 36 | Active | 37 | Active |
| 39 | Active | 42 | Active | 45 | Not Active |
| 46 | Active | 47 | Not Active | 48 | Active |
| 51 | Active | 52 | Not Active | 55 | Active |
| 56 | Active | 57 | Not Active | 59 | Active |
| 60 | Active | 61 | Active | 62 | Active |

TABLE 4-continued

Inhibition of Cell Proliferation in Human AML MV-4-11 cells

| Example Number | Cell Proliferation activity (IC50 <30 μM) | Example Number | Cell Proliferation activity (IC50 <30 μM) | Example Number | Cell Proliferation activity (IC50 <30 μM) |
|---|---|---|---|---|---|
| 63 | Not Active | 64 | Active | 66 | Active |
| 67 | Active | 69 | Active | — | — |

Example 73: Inhibition of hIL-6 mRNA Transcription

In this example, hIL-6 mRNA in tissue culture cells was quantitated to measure the transcriptional inhibition of hIL-6 when treated with a compound of the present disclosure.

A human leukemic monocyte lymphoma cell line (U937) was plated ($3.2 \times 10^4$ cells per well) in a 96-well plate in 100 μL RPMI-1640 containing 10% FBS and penicillin/streptomycin, and differentiated into macrophages for 3 days in 60 ng/mL PMA (phorbol-13-myristate-12-acetate) at 37° C. in 5% $CO_2$ prior to the addition of the compound of interest. The cells were pretreated for 1 h with the test compound prior to stimulation with 1 ug/mL lipopolysaccharide from *Escherichia coli*. The cells were incubated at 37° C. for 3 h before the cells were harvested. At time of harvest, the spent media was removed from the cells and the cells were rinsed in 200 μL PBS. Cell lysis solution (70 μL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hIL-6 to an internal control, prior to determining the fold induction of each unknown sample, relative to the control.

Compounds with an $IC_{50}$ value less than 30 μM were deemed to be active.

TABLE 5

Inhibition of hIL-6 mRNA Transcription

| Example Number | IL-6 activity (IC50 <30 μM) | Example Number | IL-6 activity (IC50 <30 μM) | Example Number | IL-6 activity (IC50 <30 μM) | Example Number | IL-6 activity (IC50 <30 μM) |
|---|---|---|---|---|---|---|---|
| 1 | Active | 3 | Active | 7 | Active | 8 | Active |
| 14 | Not Active | 15 | Not Active | 16 | Not Active | 18 | Active |
| 19 | Active | 20 | Active | 21 | Not Active | 22 | Active |
| 23 | Not Active | 25 | Active | 26 | Active | 28 | Active |
| 30 | Not Active | 31 | Active | 32 | Active | 36 | Active |
| 37 | Active | 39 | Active | 45 | Active | 46 | Active |
| 47 | Active | 48 | Active | 50 | Active | 51 | Active |
| 52 | Active | 55 | Active | 56 | Active | 57 | Active |
| 59 | Not Active | 60 | Active | 62 | Not Active | 63 | Not Active |
| 64 | Active | 66 | Not Active | 67 | Not Active | 69 | Active |

Example 74: Inhibition of IL-17 mRNA Transcription

In this example, hIL-17 mRNA in human peripheral blood mononuclear cells was quantitated to measure the transcriptional inhibition of hIL-17 when treated with a compound of the invention.

Human peripheral blood mononuclear cells were plated ($2.0 \times 10^5$ cells per well) in a 96-well plate in 45 μL OpTimizer T Cell expansion media containing 20 ng/ml IL-2 and penicillin/streptomycin. The cells were treated with the test compound (45 μL at 2× concentration), and then the cells were incubated at 37° C. for 1 h before addition of 10× stock OKT3 antibody at 10 ug/ml in media. Cells were incubated at 37° C. for 6 h before the cells were harvested. At time of harvest, cells were centrifuged (800 rpm, 5 min). Spent media was removed and cell lysis solution (70 μL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative RT-PCR reaction, using components of the Ultra Sense Kit together with Applied Biosystems primer-probe mixes. Real-time PCR data was analyzed, normalizing the Ct values for hIL-17 to an internal control, prior to determining the fold induction of each unknown sample, relative to the control.

Compounds with an $IC_{50}$ value less than 30 µM were deemed to be active.

TABLE 6

Inhibition of hIL-17 mRNA Transcription

| Example | IL-17 activity (IC50 <30 µM) |
|---|---|
| Example 19 | Active |

Example 75: Inhibition of hVCAM mRNA Transcription

In this example, hVCAMmRNA in tissue culture cells is quantitated to measure the transcriptional inhibition of hVCAM when treated with a compound of the present disclosure.

Human umbilical vein endothelial cells (HUVECs) are plated in a 96-well plate (4.0×10 cells/well) in 100 µL EGM media and incubated for 24 h prior to the addition of the compound of interest. The cells are pretreated for 1 h with the test compound prior to stimulation with tumor necrosis factor-α. The cells are incubated for an additional 24 h before the cells are harvested. At time of harvest, the spent media is removed from the HUVECs and rinsed in 200 µL PBS. Cell lysis solution (70 µL) is then added the cells in each well and incubated for ~5-10 min at room temperature, to allow for complete cell lysis and detachment. mRNA is then prepared using the "mRNA Catcher PLUS plate" (Invitrogen), according to the protocol supplied. After the last wash, as much wash buffer as possible is aspirated without allowing the wells to dry. Elution buffer (E3, 70 µL) is then added to each well. mRNA is then eluted by incubating the mRNA Catcher PLUS plate with elution buffer for 5 min at 68° C. and then immediately placing the plate on ice.

The eluted mRNA so isolated is then used in a one-step quantitative real-time PCR reaction, using components of the Ultra Sense Kit together with Applied Biosystems primer-probe mixes. Real-time PCR data is analyzed, normalizing the Ct values for hVCAM to an internal control, prior to determining the fold induction of each unknown sample, relative to the control.

Compounds with an $IC_{50}$ value less than 30 µM are deemed to be active.

Example 76: Inhibition of hMCP-1 mRNA Transcription

In this example, hMCP-1 mRNA in human peripheral blood mononuclear cells is quantitated to measure the transcriptional inhibition of hMCP-1 when treated with a compound of the present disclosure.

Human Peripheral Blood Mononuclear Cells are plated (1.0×10$^5$ cells per well) in a 96-well plate in 45 µL RPMI-1640 containing 10% FBS and penicillin/streptomycin. The cells are treated with the test compound (45 µL, at 2× concentration), and then the cells are incubated at 37° C. for 3 h before the cells are harvested. At time of harvest, cells are transferred to V-bottom plates and centrifuged (800 rpm, 5 min). Spent media is removed and cell lysis solution (70 µL) is added to the cells in each well and incubated for 5-10 min at room temperature, to allow for complete cell lysis and detachment. mRNA is then prepared using the "mRNA Catcher PLUS plate" (Invitrogen), according to the protocol supplied. After the last wash, as much wash buffer as possible is aspirated without allowing the wells to dry. Elution buffer (E3, 70 µL) is then added to each well. mRNA is then eluted by incubating the mRNA Catcher PLUS plate with Elution Buffer for 5 min at 68° C. and then immediately placing the plate on ice.

The eluted mRNA isolated is then used in a one-step quantitative real-time PCR reaction, using components of the Ultra Sense Kit together with Applied Biosystems primer-probe mixes. Real-time PCR data is analyzed, normalizing the Ct values for hMCP-1 to an internal control, prior to determining the fold induction of each unknown sample, relative to the control.

Compounds with an $IC_{50}$ value less than 30 µM are deemed to be active.

Example 77: Up-Regulation of hApoA-1 mRNA Transcription

In this example, ApoA-I mRNA in tissue culture cells was quantitated to measure the transcriptional up-regulation of ApoA-I when treated with a compound of the present disclosure.

Huh7 cells (2.5×10$^5$ per well) were plated in a 96-well plate using 100 µL DMEM per well, (Gibco DMEM supplemented with penicillin/streptomycin and 10% FBS), 24 h before the addition of the compound of interest. After 48 h treatment, the spent media was removed from the Huh-7 cells and placed on ice (for immediate use) or at −80° C. (for future use) with the "LDH cytotoxicity assay Kit II" from Abcam. The cells remaining in the plate were rinsed with 100 µL PBS.

Then 85 µL of cell lysis solution was added to each well and incubated for 5-10 min at room temperature, to allow for complete cell lysis and detachment. mRNA was then prepared using the "mRNA Catcher PLUS plate" from Life Technologies, according to the protocol supplied. After the last wash, as much wash buffer as possible was aspirated without allowing the wells to dry. Elution Buffer (E3, 80 µL) was then added to each well. mRNA was then eluted by incubating the mRNA Catcher PLUS plate with Elution Buffer for 5 min at 68° C., and then 1 min at 4° C. Catcher plates with mRNA eluted were kept on ice for use or stored at −80° C.

The eluted mRNA isolated was then used in a one-step real-time PCR reaction, using components of the Ultra Sense Kit together with Life Technologies primer-probe mixes. Real-time PCR data was analyzed, using the Ct values, to determine the fold induction of each unknown sample, relative to the control (that is, relative to the control for each independent DMSO concentration).

Compounds with an $EC_{170}$ value less than 30 µM were deemed to be active.

TABLE 8

Up-regulation of hApoA-1 mRNA Transcription.

| Example Number | ApoA-1 activity ($EC_{170}$ <30 μM) | Example Number | ApoA-1 activity ($EC_{170}$ <30 μM) | Example Number | ApoA-1 activity ($EC_{170}$ <30 μM) | Example Number | ApoA-1 activity ($EC_{170}$ <30 μM) |
|---|---|---|---|---|---|---|---|
| 1 | Active | 20 | Active | 25 | Active | 32 | Active |
| 36 | Active | — | — | — | — | — | — |

Examples 78: In Vivo Efficacy in Athymic Nude Mouse Strain of an Acute Myeloid Leukemia Xenograft Model Using MV4-11 Cells MV4-11 cells (ATCC) are grown under standard cell culture conditions and (NCr) nu/nu fisol strain of female mice age 6-7 weeks are injected with $5 \times 10^6$ cells/animal in 100 μL PBS+100 μL Matrigel in the lower left abdominal flank. By approximately day 18 after MV4-11 cells injection, mice are randomized based on tumor volume (L×W×H)/2) of average ~120 mm³. Mice are dosed orally with compound at 75 mg/kg b.i.d and 120 mg/kg b.i.d in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Example 79: Evaluation of Target Engagement

MV4-11 cells (ATCC) are grown under standard cell culture conditions and (NCr) nu/nu fisol strain of female mice age 6-7 weeks were injected with $5 \times 10^6$ cells/animal in 100 μL PBS+100 μL Matrigel in the lower left abdominal flank. By approximately day 28 after MV4-11 cells injection, mice are randomized based on tumor volume (L×W×H)/2) of average ~500 mm³. Mice are dosed orally with compound in EA006 formulation at 10 mL/kg body weight dose volume and tumors harvested 6 hrs post dose for Bcl2 and c-myc gene expression analysis as PD biomarkers.

Example 80: In Vivo Efficacy in Mouse Endotoxemia Model Assay

Sub lethal doses of Endotoxin (*E. Coli* bacterial lipopolysaccharide) are administered to animals to produce a generalized inflammatory response which is monitored by increases in secreted cytokines. Compounds are administered to C57/Bl6 mice at T=4 hours orally at 75 mg/kg dose to evaluate inhibition in IL-6 and IL-17 and MCP-1 cytokines post 3-h challenge with lipopolysaccharide (LPS) at T=0 hours at 0.5 mg/kg dose intraperitoneally.

Example 81: In Vivo Efficacy in Rat Collagen-Induced Arthritis

Rat collagen-induced arthritis is an experimental model of polyarthritis that has been widely used for preclinical testing of numerous anti-arthritic agents. Following administration of collagen, this model establishes a measurable polyarticular inflammation, marked cartilage destruction in association with pannus formation and mild to moderate bone resorption and periosteal bone proliferation. In this model, collagen is administered to female Lewis strain of rats on Day 1 and 7 of study and dosed with compounds from Day 11 to Day 17. Test compounds are evaluated to assess the potential to inhibit the inflammation (including paw swelling), cartilage destruction and bone resorption in arthritic rats, using a model in which the treatment is administered after the disease has been established.

Example 82: In Vivo Efficacy in Experimental Autoimmune Encephalomyelitis (EAE) Model of MS Experimental autoimmune encephalomyelitis (EAE) is a T-cell-mediated autoimmune disease of the CNS which shares many clinical and histopathological features with human multiple sclerosis (MS). EAE is the most commonly used animal model of MS. T cells of both Th1 and Th17 lineage have been shown to induce EAE. Cytokines IL-23, IL-6 and IL-17, which are either critical for Th1 and Th17 differentiation or produced by these T cells, play a critical and non-redundant role in EAE development. Therefore, drugs targeting production of these cytokines are likely to have therapeutic potential in treatment of MS.

Compounds of Formula I or Formula Ia are administered to EAE mice to access anti-inflammatory activity. In this model, EAE is induced by $MOG_{35-55}$/CFA immunization and pertussis toxin injection in female C57Bl/6 mice.

Example 83: Ex Vivo Effects on T Cell Function from Splenocyte and Lymphocyte Cultures Stimulated with External MOG Stimulation Mice are immunized with MOG/CFA and simultaneously treated with the compound for 11 days on a b.i.d regimen. Inguinal Lymph node and spleen are harvested and cultures set up with external MOG stimulation for 72 hours. Supernatants from these cultures are analyzed for Th1, Th2 and Th17 cytokines using a Cytometric Bead Array assay.

Example 84: In Vivo Efficacy in Athymic Nude Mouse Strain of Multiple Myeloma Xenograft Model Using MM1.s Cells MM1.s cells (ATCC) are grown under standard cell culture conditions and (NCr) nu/nu fisol strain of female mice age 6-7 weeks are injected with $10 \times 10^6$ cells/animal in 100 μL PBS+100 μL Matrigel in the lower left abdominal flank. By approximately day 21 after MM1.s cells injection, mice are randomized based on tumor volume (L×W×H)/2) of average ~120 mm³. Mice are dosed orally with compound at 75 mg/kg b.i.d in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A compound of Formula I:

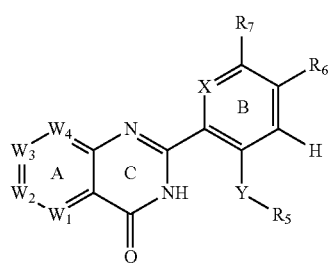

Formula I or a stereoisomer, tautomer, or pharmaceutically acceptable salt thereof,
wherein:
  $W_1$ is selected from N and $CR_1$;
  $W_2$ is selected from N and $CR_2$;
  $W_3$ is selected from N and $CR_3$;
  $W_4$ is selected from N and $CR_4$;
  X is selected from N and CH;
  Y is selected from —S(O)—, —NH—, —NHCH$_2$—, —NHCH$_2$CH$_2$—, and —NHCH$_2$CH$_2$CH$_2$—,
    wherein if Y is —NH—, —NHCH$_2$—, —NHCH$_2$CH$_2$—, or —NHCH$_2$CH$_2$CH$_2$—, then the nitrogen is attached to the B ring, and one or more hydrogens may be optionally substituted with alkyl($C_1$-$C_3$), halogen, hydroxyl, or amino;
  $R_1$, $R_2$, $R_3$, and $R_4$ are independently selected from hydrogen, alkyl, alkenyl, alkynyl, alkoxy, amino, aryloxy, aryl, hydroxyl, and halogen,
    wherein each alkyl and alkoxy may be optionally substituted with hydroxyl, amino, or halogen,
    wherein each aryl and aryloxy may be optionally substituted with halogen, alkoxy, or amino, and
    wherein two adjacent substituents selected from $R_1$, $R_2$, $R_3$, and $R_4$ may be connected in a 5- or 6-membered ring to form a bicyclic carbocycle or bicyclic heterocycle;
  $R_5$ is selected from amino and 5- and 6-membered carbocycles and heterocycles;
  $R_6$ is selected from hydrogen, alkoxy, alkyl, halogen, aminoalkyl, and thioalkyl; and
  $R_7$ is selected from hydrogen, alkyl, alkoxy, thioalkyl, aminoalkyl, and halogen.

2. The compound of claim 1, wherein the compound is a compound of Formula Ia:

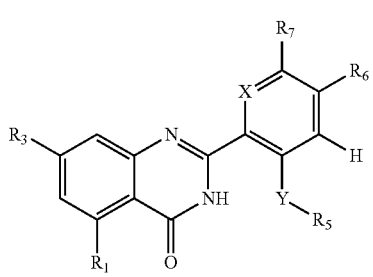

Formula Ia or a stereoisomer, tautomer, or pharmaceutically acceptable salt thereof,
wherein:
  X is selected from N and CH;
  Y is selected from —S(O)—, —NH—, —NHCH$_2$—, —NHCH$_2$CH$_2$—, and —NHCH$_2$CH$_2$CH$_2$—,
    wherein if Y is —NH—, —NHCH$_2$—, —NHCH$_2$CH$_2$—, or —NHCH$_2$CH$_2$CH$_2$—, then the nitrogen is attached to the B ring, and one or more hydrogens may be optionally substituted with alkyl($C_1$-$C_3$), halogen, hydroxyl, or amino;
  $R_1$ and $R_3$ are independently selected from hydrogen, alkyl, alkenyl, alkynyl, alkoxy, amino, aryloxy, aryl, hydroxyl, and halogen,
    wherein each alkyl and alkoxy may be optionally substituted with hydroxyl, amino, or halogen,
    wherein each aryl and aryloxy may be optionally substituted with halogen, alkoxy, or amino;
  $R_5$ is selected from amino and 5- and 6-membered carbocycles and heterocycles;
    wherein the 5- and 6-membered carbocycles and heterocycles are selected from:

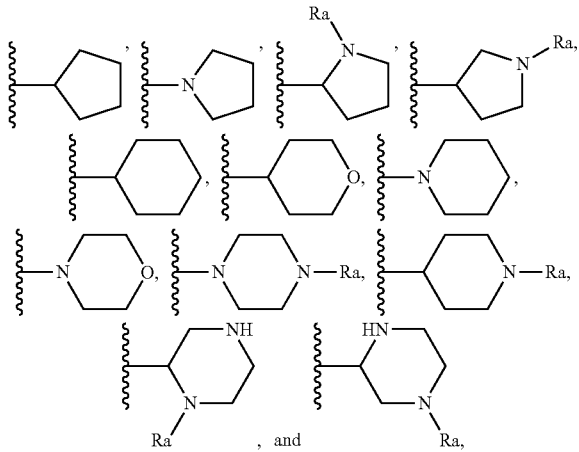

wherein the 5- and 6- membered carbocycles and heterocycles may be optionally substituted with halogen, amino, alkyl($C_1$-$C_6$), or alkoxy($C_1$-$C_6$);
and wherein Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$— amino, and —CH$_2$CH$_2$C(Me)$_2$OH;

R$_6$ is selected from hydrogen, alkoxy, alkyl, halogen, aminoalkyl, and thioalkyl; and R$_7$ is selected from hydrogen, alkyl, alkoxy, thioalkyl, aminoalkyl, and halogen.

3. The compound of claim 2, wherein X is N.

4. The compound of claim 2, wherein R$_1$ and R$_3$ are each independently an alkoxy group.

5. The compound of claim 4, wherein R$_1$ and R$_3$ are each independently selected from methoxy, ethoxy, isopropoxy, and propoxy.

6. The compound of claim 5, wherein R$_1$ and R$_3$ are each methoxy.

7. The compound of claim 2, wherein R$_1$ is methoxy and R$_3$ is amino.

8. The compound of claim 2, wherein Y is selected from —NH—, —NHCH$_2$—, —NHCH$_2$CH$_2$—, and —NHCH$_2$CH$_2$CH$_2$—, wherein the nitrogen attached to the B ring, and wherein one or more hydrogens may be optionally substituted with F, Me, or Cl.

9. The compound of claim 8, wherein Y is —NH—.

10. The compound of claim 2, wherein R$_5$ is selected from —NHRa and 5- and 6-membered carbocycles and heterocycles;

wherein the 5- and 6-membered carbocycles and heterocycles are selected from:

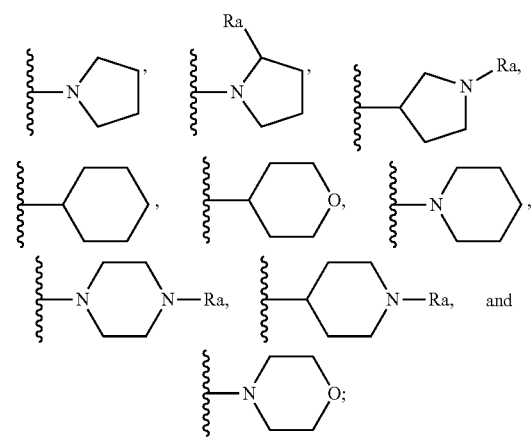

wherein the 5- and 6- membered carbocycles and heterocycles may be optionally substituted with halogen, amino, amide, alkyl(C$_1$-C$_6$), or alkoxy(C$_1$-C$_6$);

and wherein Ra is selected from hydrogen, methyl, ethyl, propyl, isopropyl, t-butyl, —C(O)Me, —C(O)Pr, —C(O)iPr, benzyl, —C(O)CF$_3$, —C(O)-tBu, —C(O)NHiPr, —C(O)NMe$_2$, —C(O)NHEt, —C(O)NH$_2$, —C(O)CH(OH)CH$_3$, —C(O)C(O)OMe, —CF$_3$, —CH$_2$CH$_2$OH, —CH$_2$CH$_2$-amino, and —CH$_2$CH$_2$C(Me)$_2$OH.

11. The compound of claim 2, wherein R$_6$ is selected from hydrogen, methyl, and methoxy.

12. The compound of claim 2, wherein R$_6$ is selected from groups of Formula II:

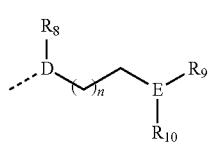

Formula II wherein:

D is selected from O, N, and S;

E is selected from O and N;

R$_9$ is selected from hydrogen and alkyl,
wherein R$_8$ is present only if D is N;

R$_9$ and R$_{10}$ are independently selected from hydrogen, alkyl, and cycloalkyl,
wherein only one of R$_9$ and R$_{10}$ is present if E is O;

R$_9$ and R$_{10}$ may be connected to form a carbocycle or a heterocycle containing one or more heteroatoms; and n is selected from 1, 2, and 3.

13. The compound of claim 11, wherein R$_6$ is selected from:

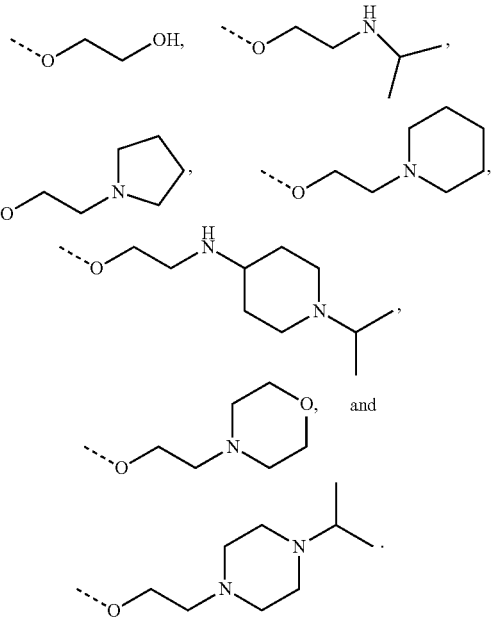

14. The compound of claim 2, wherein:

R$_1$ and R$_3$ are each alkoxy;

Y is selected from —NH—, —NHCH$_2$—, —NHCH$_2$CH$_2$—, and —NHCH$_2$CH$_2$CH$_2$—,
wherein the nitrogen is attached to the B ring;

R$_5$ is selected from —NHRa and 5- and 6-membered carbocycles and heterocycles, wherein the 5- and 6-membered carbocycles and heterocycles are selected from:

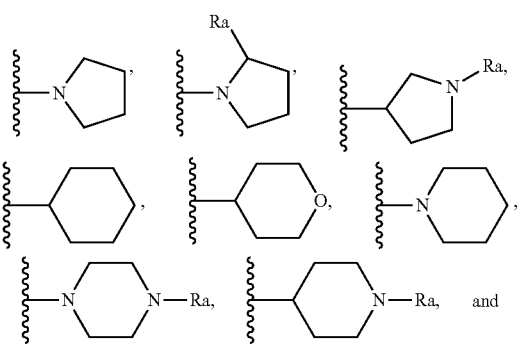

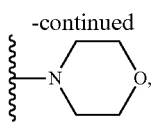

wherein Ra is selected from hydrogen, methyl, ethyl, propyl, isopropyl, t-butyl, —C(O)Me, —C(O)Pr, —C(O)iPr, benzyl, —C(O)CF₃, —C(O)-tBu, —C(O)NHiPr, —C(O)NMe₂, —C(O)NHEt, —C(O)NH₂, —C(O)CH(OH)CH₃, —C(O)C(O)OMe, —CF₃, —CH₂CH₂OH, —CH₂CH₂amino, and —CH₂CH₂C(Me)₂OH; and R₆ is selected from hydrogen, methyl, and alkoxy, wherein the alkoxy is optionally substituted with hydroxyl or amino.

15. The compound of claim 2, wherein:

R₁ is alkoxy;

R₃ is amino;

Y is selected from —NH—, —NHCH₂—, —NHCH₂CH₂—, and —NHCH₂CH₂CH₂—,
wherein the nitrogen is attached to the B ring;

R₅ is selected from—NHRa and 5- and 6-membered carbocycles and heterocycles, wherein the 5- and 6-membered carbocycles and heterocycles are selected from:

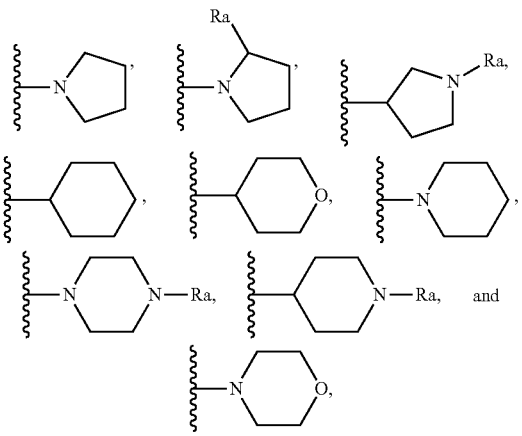

wherein Ra is selected from hydrogen, methyl, ethyl, propyl, isopropyl, t-butyl, —C(O)Me, —C(O)Pr, —C(O)iPr, benzyl, —C(O)CF₃, —C(O)-tBu, —C(O)NHiPr, —C(O)NMe₂, —C(O)NHEt, —C(O)NH₂, —C(O)CH(OH)CH₃, —C(O)C(O)OMe, —CF₃, —CH₂CH₂OH, —CH₂CH₂amino, and —CH₂CH₂C(Me)₂OH; and R₆ is selected from hydrogen, methyl, and alkoxy, wherein the alkoxy is optionally substituted with hydroxyl or amino.

16. A compound selected from:

5,7-Dimethoxy-2-(4-methoxy-2-((1-methylpiperidin-4-yl)amino)phenyl)-quinazolin-4(3H)-one;

5,7-Dimethoxy-2-(4-methoxy-2-(4-methylpiperazine-1-carbonyl)phenyl) quinazolin-4(3H)-one;

2-(2-((1-isopropylpiperidin-4-yl)amino)-4-methoxyphenyl)-5,7-dimethoxyquinazolin-4(3H)-one;

5,7-Dimethoxy-2-(4-methoxy-2-(((1-methylpyrrolidin-3-yl)amino)phenyl)quinazolin-4(3H)-one;

5,7-Dimethoxy-2-(4-methoxy-2-(methyl(1-methylpiperidin-4-yl)amino)phenyl) quinazolin-4(3H)-one;

5,7-Dimethoxy-2-(4-methoxy-2-(((1-methylpiperidin-4-yl)methyl)amino)phenyl) quinazolin-4(3H)-one;

5,7-Dimethoxy-2-(4-methoxy-2-(((1-methylpyrrolidin-3-yl)methyl)amino)phenyl)-quinazolin-4(3H)-one;

2-(2-((2-(Isopropylamino)ethyl)amino)-4-methoxyphenyl)-5, 7-dimethoxyquinazolin-4(3H)-one;

5,7-dimethoxy-2-(4-Methoxy-2-((tetrahydro-2H-pyran-4-yl)amino)-phenyl)quinazolin-4(3H)-one;

2-(2-((1-Isopropylpiperidin-4-yl)amino)phenyl)-5,7-dimethoxyquinazolin-4(3H)-one;

5,7-Dimethoxy-2-(4-methoxy-2-((2-(pyrrolidin-1-yl)ethyl)amino)phenyl)quinazolin-4(3H)-one;

5,7-Dimethoxy-2-(4-methoxy-2-((2-(piperidin-1-yl)ethyl)amino)-phenyl)quinazolin-4(3H)-one;

5,7-Dimethoxy-2-(4-methoxy-2-((3-morpholinopropyl)amino)-phenyl)quinazolin-4(3H)-one;

5,7-Dimethoxy-2-(4-methoxy-2-((2-morpholinoethyl)amino)phenyl)-quinazolin-4(3H)-one;

5,7-Dimethoxy-2-(4-methoxy-2-((3-(pyrrolidin-1-yl)propyl)amino)phenyl)quinazolin-4(3H)-one;

2-(2-(((1-Isopropylpyrrolidin-3-yl)methyl)amino)-4-methoxyphenyl)-5,7-dimethoxyquinazolin-4(3H)-one;

2-(2-(((1-Isopropylpyrrolidin-2-yl)methyl)amino)-4-methoxyphenyl)-5,7-dimethoxyquinazolin-4(3H)-one;

2-(3-((1-Isopropylpiperidin-4-yl)amino)pyridin-2-yl)-5, 7-dimethoxyquinazolin-4(3H)-one;

2-(2-((1-Isobutyrylpiperidin-4-yl)amino)-4-methoxyphenyl)-5,7-dimethoxyquinazolin-4(3H)-one;

2-(2-((3-(Isopropylamino)propyl)amino)-4-methoxyphenyl)-5,7-dimethoxyquinazolin-4(3H)-one;

5,7-Dimethoxy-2-(4-methoxy-2-(3-(methylpiperazin-1-yl)propyl)amino)-phenylquinazolin-4(3H)-one;

2-(2-((2-(4-Isopropylpiperazin-1-yl)ethyl)amino)-4-methoxyphenyl)-5,7-dimethoxyquinazolin-4(3H)-one;

5,7-Dimethoxy-2-[4-methoxy-2-(1-methylpiperidin-4-ylsulfinyl)phenyl]quinazolin-4(3H)-one;

5,7-Dimethoxy-2-(4-methoxy-2-((2-(piperazin-1-yl)ethyl)amino)phenyl)quinazolin-4(3H)-one;

5,7-Dimethoxy-2-(4-methoxy-2-((2-(4-methylpiperazin-1-yl)ethyl)amino)phenyl)-quinazolin-4(3H)-one;

2-(2-((1-Isopropylpiperidin-4-yl)amino)-5-methoxyphenyl)-5,7-dimethoxyquinazolin-4(3H)-one;

2-(3-((1-Isopropylpiperidin-4-yl)amino)phenyl)-5,7-dimethoxyquinazolin-4(3H)-one;

5,7-Dimethoxy-2-(4-methoxy-2-[3-(piperazin-1-yl)propylamino]phenyl)quinazolin-4(3H)-one;

2-(2-((4,4-Dimethylcyclohexyl)amino)-4-methoxyphenyl)-5,7-dimethoxyquinazolin-4(3H)-one;

2-(3-((1-Isopropylpiperidin-4-yl)amino)-5-methoxypyridin-2-yl)-5,7-dimethoxyquinazolin-4(3H)-one;

2-(2-((trans-4-(2-Hydroxypropan-2-yl)cyclohexyl)amino)-4-methoxyphenyl)-5,7-dimethoxyquinazolin-4(3H)-one;

2-(3-((1-Isobutyrylpiperidin-4-yl)amino)-5-methoxypyridin-2-yl)-5,7-dimethoxyquinazolin-4(3H)-one;

2-(4-Chloro-2-((1-isopropylpiperidin-4-yl)amino)phenyl)-5,7-dimethoxyquinazolin-4(3H)-one;

2-(4-Chloro-2-((1-isobutyrylpiperidin-4-yl)amino)phenyl)-5,7-dimethoxyquinazolin-4(3H)-one;

2-(2-((1-Benzylpiperidin-4-yl)amino)-4-methoxyphenyl)-5,7-dimethoxyquinazolin-4(3H)-one;

2-(-((1-Isobutyrylpiperidin-4-yl)amino)pyridin-2-yl)-5, 7-dimethoxyquinazolin-4(3H)-one;

2-(3-((1-Acetylpiperidin-4-yl)amino)pyridine-2-yl)-5,7-dimethoxyquinazolin-4(3H)-one;

N-(cis-4-((2-(5,7-Dimethoxy-4-oxo-3,4-dihydroquinazolin-2-yl)-5-methoxypyridin-3-yl)amino)cyclohexyl)isobutyramide;

2-(2-((1-Acetylpiperidin-4-yl)amino)-4-methoxyphenyl)-5,7-dimethoxyquinazolin-4(3H)-one;

5,7-Dimethoxy-2-(5-methoxy-3-((1-methylpiperidin-4-yl)amino)pyridin-2-yl)quinazolin-4(3H)-one;

5,7-Dimethoxy-2-(3-(((1-methylpyrrolidin-3-yl)methyl)amino)pyridin-2-yl)quinazolin-4(3H)-one;

4-((2-(5,7-Dimethoxy-4-oxo-3,4-dihydroquinazolin-2-yl)pyridin-3-yl)amino)-N,N-dimethylpiperidine-1-carboxamide;

2-(3-((3-(Isopropylamino)propyl)amino)pyridin-2-yl)-5,7-dimethoxyquinazolin-4(3H)-one;

5,7-Dimethoxy-2-(3-((1-methylpiperidin-4-yl)amino)pyridine-2-yl)quinazolin-4(3H)-one;

cis-4-((2-(5,7-Dimethoxy-4-oxo-3,4-dihydroquinazolin-2-yl)-5-methoxypyridin-3-yl)amino)-N-isopropylcyclohexane-1-carboxamide;

5,7-Dimethoxy-2-(3-((1-(2,2,2-trifluoroacetyl)piperidin-4-yl)amino)pyridin-2-yl)quinazolin-4(3H)-one;

4-((2-(5,7-Dimethoxy-4-oxo-3,4-dihydroquinazolin-2-yl)pyridin-3-yl)amino)-N-isopropylpiperidine-1-carboxamide;

5,7-Dimethoxy-2-(3-((1-pivaloylpiperidin-4-yl)amino)pyridin-2-yl)quinazolin-4(3H)-one;

5,7-Dimethoxy-2-(3-((2-morpholinoethyl)amino)pyridine-2-yl)quinazolin-4(3H)-one;

2-(3-((1-Isopropylpiperidin-4-yl)amino)-5-(2-((1-isopropylpiperidin-4-yl)amino)ethoxy)pyridin-2-yl)-5,7-dimethoxyquinazolin-4(3H)-one;

2-(4-((2-(5,7-Dimethoxy-4-oxo-3,4-dihydroquinazolin-2-yl)pyridin-3-yl)amino)piperidin-1-yl)-N,N-dimethyl-2-oxoacetamide;

4-((2-(5,7-dimethoxy-4-oxo-3,4-dihydroquinazolin-2-yl)pyridin-3-yl)amino)-N-ethylpiperidine-1-carboxamide;

cis-4-((2-(5,7-Dimethoxy-4-oxo-3,4-dihydroquinazolin-2-yl)pyridin-3-yl)amino)-N,N-dimethylcyclohexane-1-carboxamide;

4-((2-(5, 7-Dimethoxy-4-oxo-3,4-dihydroquinazolin-2-yl)pyridin-3-yl)amino)piperidine-1-carboxamide;

Methyl-2-(4-((2-(5,7-dimethoxy-4-oxo-3,4-dihydroquinazolin-2-yl)pyridin-3-yl)amino)piperidin-1-yl)-2-oxoacetate;

N-(2-((2-(5, 7-Dimethoxy-4-oxo-3,4-dihydroquinazolin-2-yl)pyridin-3-yl)amino)ethyl)isobutyramide;

N-(3-((2-(5, 7-Dimethoxy-4-oxo-3,4-dihydroquinazolin-2-yl)pyridin-3-yl)amino)propyl)isobutyramide;

2-(3-((1-Isopropylpiperidin-4-yl)amino)pyridin-2-yl)-5-methoxypyrido[3,4-d]pyrimidin-4(3H)-one;

2-(3-((1-(2-Hydroxy-2-methylpropyl)piperidin-4-yl)amino)pyridin-2-yl)-5,7-dimethoxyquinazolin-4(3H)-one;

2-(3-((1-(2-hydroxypropanoyl)piperidin-4-yl)amino)pyridin-2-yl)-5,7-dimethoxyquinazolin-4(3H)-one;

2-(3-((1-Isopropylpiperidin-4-yl)amino)pyridin-2-yl)-5-methoxy-7-((4-methoxybenzyl)amino)quinazolin-4(3H)-one;

2-[5-(2-Hydroxyethoxy)-3-(1-isopropylpiperidin-4-ylamino)pyridin-2-yl]-5,7-dimethoxyquinazolin-4(3H)-one;

cis-4-((2-(5,7-Dimethoxy-4-oxo-3,4-dihydroquinazolin-2-yl)pyridin-3-yl)amino)-N-isopropylcyclohexane-1-carboxamide;

2-[5-(2-Hydroxyethoxy)-3-(1-isobutyroylpiperidin-4-ylamino)pyridin-2-yl]-5,7-dimethoxyquinazolin-4(3H)-one;

7-amino-2-(3-((1-Isopropylpiperidin-4-yl)amino)pyridin-2-yl)-5-methoxyquinazolin-4(3H)-one;

2-{3-(1-Isopropylpiperidin-4-ylamino)-5-[2-(pyrrolidin-1-yl)ethoxy]pyridin-2-yl}-5,7-dimethoxyquinazolin-4(3H)-one;

2-{5-[2-(Isopropylamino)ethoxy]-3-(1-isopropylpiperidin-4-ylamino)pyridin-2-yl}-5,7-dimethoxyquinazolin-4(3H)-one;

2-(3-((1-(1-Hydroxy-2-methylpropan-2-yl)piperidin-4-yl)amino)pyridin-2-yl)-5,7-dimethoxyquinazolin-4(3H)-one; and 7-(Ethylamino)-2-(3-((1-isopropylpiperidin-4-yl)amino)pyridin-2-yl)-5-methoxyquinazolin-4(3H)-one; and stereoisomers, tautomers, and pharmaceutically acceptable salts thereof.

17. A pharmaceutical composition comprising the compound of claim 2, or a stereoisomer, tautomer, or pharmaceutically acceptable salt thereof, and a pharmaceutically acceptable carrier.

18. A pharmaceutical composition comprising the compound of claim 1, or a stereoisomer, tautomer, or pharmaceutically acceptable salt thereof, and a pharmaceutically acceptable carrier.

19. A pharmaceutical composition comprising the compound of claim 16, or a stereoisomer, tautomer, or pharmaceutically acceptable salt thereof, and a pharmaceutically acceptable carder.

\* \* \* \* \*

UNITED STATES PATENT AND TRADEMARK OFFICE
CERTIFICATE OF CORRECTION

PATENT NO.        : 9,855,271 B2
APPLICATION NO.   : 14/908898
DATED             : January 2, 2018
INVENTOR(S)       : John Frederick Quinn et al.

Page 1 of 1

It is certified that error appears in the above-identified patent and that said Letters Patent is hereby corrected as shown below:

Claim 2, Column 116, Line 60, "halogen, amino, alkyl($C_1$-$C_6$), or alkoxy($C_1$-$C_6$);" should read --halogen, amino, amide, alkyl($C_1$-$C_6$), or alkoxy($C_1$-$C_6$);--.

Claim 12, Column 118, Line 4, "$R_9$ is selected from hydrogen and alkyl," should read --$R_8$ is selected from hydrogen and alkyl,--.

Claim 19, Column 122, Line 48, "acceptable carder." should read --acceptable carrier.--.

Signed and Sealed this
Tenth Day of April, 2018

Andrei Iancu
*Director of the United States Patent and Trademark Office*